(12) United States Patent
Buhrlage et al.

(10) Patent No.: US 11,136,409 B2
(45) Date of Patent: Oct. 5, 2021

(54) COMPOSITIONS AND METHODS FOR IDENTIFICATION, ASSESSMENT, PREVENTION, AND TREATMENT OF AML USING USP10 BIOMARKERS AND MODULATORS

(71) Applicant: Dana-Farber Cancer Institute, Inc., Boston, MA (US)

(72) Inventors: Sara Buhrlage, Somerville, MA (US); Ellen Weisberg, Chelmsford, MA (US); James D. Griffin, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 21 days.

(21) Appl. No.: 16/331,712

(22) PCT Filed: Sep. 20, 2017

(86) PCT No.: PCT/US2017/052506
§ 371 (c)(1),
(2) Date: Mar. 8, 2019

(87) PCT Pub. No.: WO2018/057618
PCT Pub. Date: Mar. 29, 2018

(65) Prior Publication Data
US 2019/0202929 A1 Jul. 4, 2019

Related U.S. Application Data

(60) Provisional application No. 62/397,100, filed on Sep. 20, 2016.

(51) Int. Cl.
| | | |
|---|---|---|
| *A61P 31/00* | (2006.01) | |
| *C07K 16/30* | (2006.01) | |
| *A61P 35/02* | (2006.01) | |
| *C12Q 1/6886* | (2018.01) | |
| *G01N 33/50* | (2006.01) | |
| *G01N 33/574* | (2006.01) | |
| *A01K 67/027* | (2006.01) | |
| *C12Q 1/02* | (2006.01) | |
| *C12Q 1/6806* | (2018.01) | |
| *C12Q 1/6841* | (2018.01) | |
| *C12Q 1/6851* | (2018.01) | |
| *C12Q 1/686* | (2018.01) | |
| *A61K 45/06* | (2006.01) | |

(52) U.S. Cl.
CPC ...... *C07K 16/3061* (2013.01); *A01K 67/0271* (2013.01); *A61P 31/00* (2018.01); *A61P 35/02* (2018.01); *C12Q 1/025* (2013.01); *C12Q 1/6806* (2013.01); *C12Q 1/686* (2013.01); *C12Q 1/6841* (2013.01); *C12Q 1/6851* (2013.01); *C12Q 1/6886* (2013.01); *G01N 33/50* (2013.01); *G01N 33/57426* (2013.01); *A01K 2267/0331* (2013.01); *A61K 45/06* (2013.01); *C12Q 2600/106* (2013.01); *C12Q 2600/158* (2013.01); *G01N 2800/52* (2013.01)

(58) Field of Classification Search
CPC .................................................. C07K 16/3061
USPC ............................................................ 514/1
See application file for complete search history.

(56) References Cited

U.S. PATENT DOCUMENTS

| | | | |
|---|---|---|---|
| 2009/0004173 A1 | 1/2009 | Evans et al. | |
| 2009/0215793 A1* | 8/2009 | Michelson | A61K 31/4425 |
| | | | 514/253.07 |

FOREIGN PATENT DOCUMENTS

| | | |
|---|---|---|
| WO | WO-2009/091547 A1 | 7/2009 |
| WO | WO-2014/107209 A2 | 7/2014 |
| WO | WO-2015/060922 A1 | 4/2015 |
| WO | WO-2015/069935 A1 | 5/2015 |

OTHER PUBLICATIONS

Jiangqiao etal (Frontiers in Immunology, 2020, 11, article 506275, 1-15).*
Bosman et al (Blood, 2014, 124(20): 3130-3140).*
International Search Report and Written Opinion for International Application No. PCT/US2017/052506 dated Jan. 18, 2018.
Mistry et al. "Small-Molecule Inhibitors of USP1 Target ID1 Degradation in Leukemic Cells," Mol Cancer Ther, 12(12):2651-2662 (2013).
Noguera et al. "Nucleophosmin/B26 regulates PTEN through interaction with HAUSP in acute myeloid leukemia," Leukemia 27(5):1037-1043 (2013).
D'Arcy et al, "Deubiquitinase inhibition as a cancer therapeutic strategy," Pharmacology and Therapeutics, 147:32-54 (2014).
DeVine et al., "Targeting the ubiquitin-mediated proteasome degradation of the p53 for cancer therapy," Current Pharmaceutical Design, 19(18):3248-3262 (2013).
Extended European Search Report for EP Application No. DF20610PCTEP dated Jun. 12, 2020.
Maat et al., "Identification of USP7 as druggable target in non-canonical PRC.1 for human leukemias," Experimental Hematology, 44(9) (2016).
Kazi et al., "Suppressor of cytokine signaling 2 (SOCS2) associates with FLT3 and negatively regulates downstream signaling," Molecular Oncology, 7(3):693-703 (2013).

(Continued)

*Primary Examiner* — Sean E Aeder
(74) *Attorney, Agent, or Firm* — Foley Hoag LLP

(57) ABSTRACT

The present invention is based, in part, on the identification of novel USP10 biomarkers and modulators, and methods of use thereof, for identifying, assessing, preventing, and treating AML.

8 Claims, 47 Drawing Sheets
Specification includes a Sequence Listing.

(56) References Cited

OTHER PUBLICATIONS

Reece et al., "A novel regulator (USP10) of p53: Implications for tumor suppression and therapeutic targeting," Cancer Biology & Therapy, 9(8):583-584 (2010).
Tang et al., "Gene copy-number alterations: A cost-benefit analysis," Cell, 152(3):394-405 (2013).

\* cited by examiner

A

B

C

D

E

F

A

B

A a) USP10i-1 suppresses growth of Ba/F3-FLT3-ITD cells with the effect being partially IL3 rescueable; c) USP10i-1 inhibits proliferation of FLT3-ITD mutant AML cell lines more potently than wt or null lines; d) USP10i-1 leads to increased ubiquitination of FLT3 and loss of protein levels.

USP10 KD phenocopies the cellular effects of USP10i-1 a) 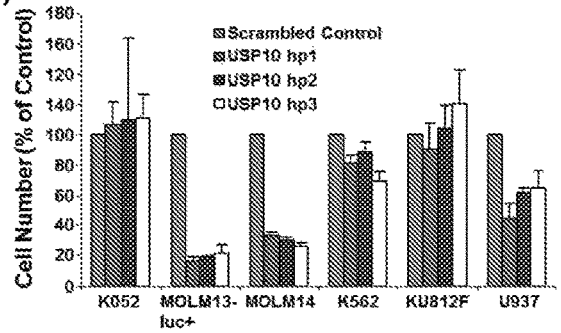
b) 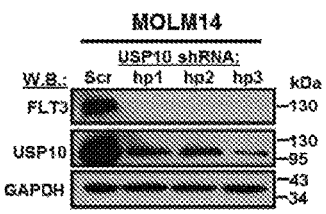

a) USP10 KD suppresses growth of FLT3 mutant but not wild-type AML cell lines
b) USP10 KD results in loss of FLT3 protein

USP10 stabilizes mutant FLT3, cont'd

A distinct USP10 inhibitor chemotype mimics the USP10i-1 phenotype and USP10 is in complex with mutant FLT3 a) 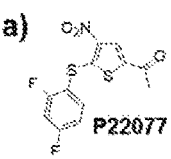
P22077

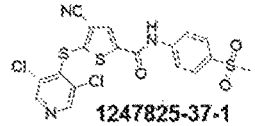
1247825-37-1 b) 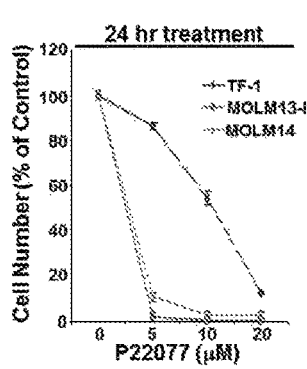

c) 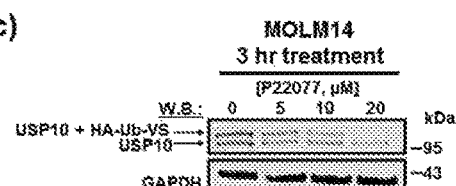

d) 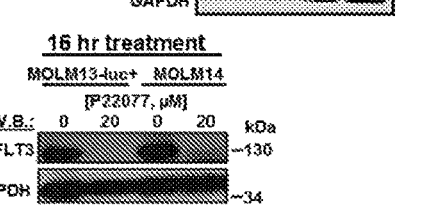

e) 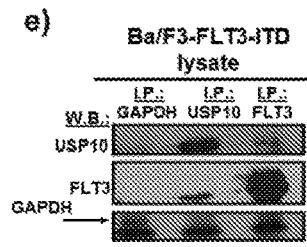

a) Structures of USP7/10 inhibitors P22077 and 1247825-37-1
b) P22077 blocks proliferation of FLT3-ITD mutant cell lines MOLM13-luc+ and MOLM14 but not control line TF-1
c) P22077 binds USP10 in MOLM14 cells
d) P22077 promotes loss of FLT3 in mutant expressing cells
e) USP10 and FLT3-ITD co-IP

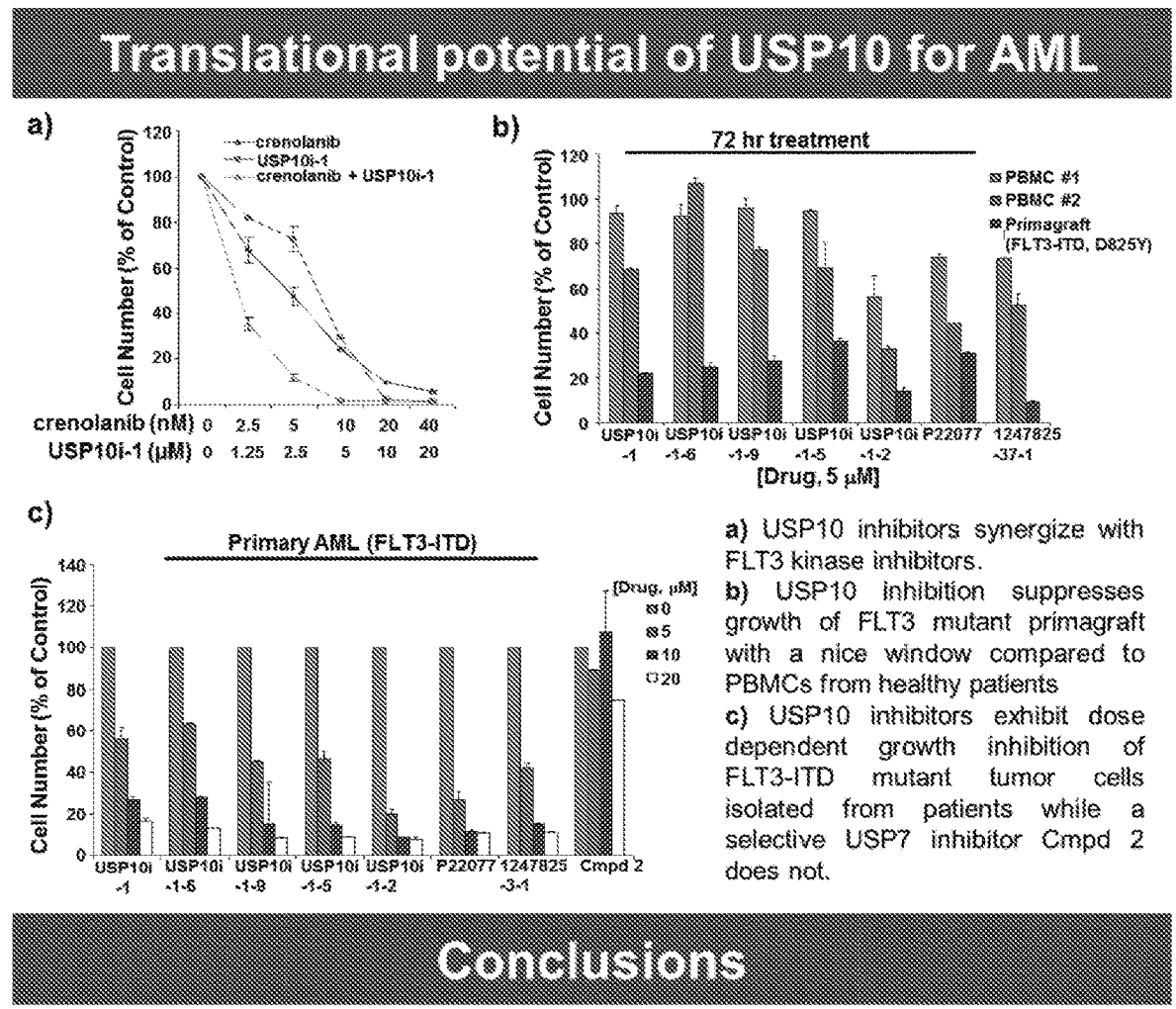

We introduce USP10 as a critical effector enzyme of tumor growth and survival in FLT3-ITD mutant-positive AML, resulting from its deubiquitination and stabilization of this mutant driver protein. Furthermore, we identified two chemical classes of USP10 inhibitor that promote degradation of mutant FLT3 and confer an anti-proliferative effect in FLT3 mutant-positive AML cell lines and primary patient samples. Overall, these studies indicate that therapeutic targeting of USP10 has potent suppressive effects on FLT3-ITD positive AML including kinase inhibitor resistant FLT3 mutants and warrants further investigation as an alternative treatment strategy for this disease.

COMPOSITIONS AND METHODS FOR IDENTIFICATION, ASSESSMENT, PREVENTION, AND TREATMENT OF AML USING USP10 BIOMARKERS AND MODULATORS

CROSS-REFERENCE TO RELATED APPLICATIONS

This application is the U.S. national phase of International Patent Application No. PCT/US2017/052506, filed on 20 Sep. 2017, which claims the benefit of priority to U.S. Provisional Application Ser. No. 62/397,100, filed on 20 Sep. 2016, the entire contents of each of said applications are incorporated herein in their entirety by this reference.

BACKGROUND OF THE INVENTION

Acute myeloid leukemia (AML) is the most common type of acute leukemia in adults. Overall, the survival with current chemotherapy is only 20-40%, declining steadily with advancing age. Sequencing studies have shown that the number of oncogenes per AML genome is relatively small compared to epithelial tumors, with most patients having 2-10 identifiable mutations. Mutations typically involve genes that regulate hematopoietic differentiation, alter chromatin structure, or induce proliferation and inhibit apoptosis. The most common genetic alteration overall involves the FMS-like tyrosine kinase 3 (FLT3), a gene whose normal function is in controlling hematopoiesis. In normal cells, in response to binding of FLT3 ligand to the FLT3 extracellular domain, FLT3 homodimerizes, autophosphorylates and activates downstream effectors involved in apoptosis, proliferation and differentiation of hematopoietic cells. Consistent with the main function of FLT3 being regulation of hematopoiesis, FLT3 knockout mice are viable but have hematological abnormalities.

Approximately 30% of AML patients have mutations that constitutively activate the FLT3 gene. The most common type of FLT3 mutation results in tandem duplications within the juxtamembrane domain, observed in 20-25% of AML patients (internal tandem duplication, ITD), associated with markedly decreased survival (Levis (2013) *ASH Edu. Book* 2013:220-226). An additional 7% of patients have point mutations within the "activation loop" of FLT3, making FLT3 the most commonly mutated gene in this disease (Levis (2013) *ASH Edu. Book* 2013:220-226).

A number of FLT3 kinase domain inhibitors, including SU11248, SU5416, CEP-701 and PKC412 (midostaurin), have been shown to induce partial, and usually brief, remissions in clinical trials of relapsed AML patients when administered as single agents (Weisberg et al. (2009) *Drug Resist. Updates* 12:81-89). In a large trial in newly diagnosed patients, however, midostaurin was shown to increase survival when combined with standard chemotherapy. This trial (RATIFY (CALGB 10603)) enrolled 717 AML patients with FLT3 mutations, randomized between midostaurin and placebo. Overall survival was increased in the midostaurin arm compared to the placebo arm (74.7 months vs. 26.0 months; p=0.007) (Stone et al. (2015) "The Multi-Kinase Inhibitor Midostaurin (M) Prolongs Survival Compared with Placebo (P) in Combination with Daunorubicin (D)/Cytarabine (C) Induction (ind), High-Dose C Consolidation (consol) and As Maintenance (maint) Therapy in Newly Diagnosed Acute Myeloid Leukemia (AML) Patients (pts) Age 18-60 with FLT3 Mutations (muts): An International Prospective Randomized (rand) P-Controlled Double-Blind Trial (CALGB 10603/RATIFY [Alliance])" ASH 57th Annual Meeting & Exposition, Plenary; Program: General Sessions; Session: Plenary Scientific Session (6 Dec. 2015)). This study in particular supports the notion that inhibition of FLT3 may be important, at least in patients with mutations in the FLT3 gene. As is true for other receptor tyrosine kinases, there is ongoing synthesis and degradation of FLT3, which is thought to be accelerated by ligand binding. However, the details of receptor homeostasis in AML are not well studied. Since drug resistance develops in some patients with newly diagnosed AML and virtually all patients with advanced disease, additional strategies to target FLT3 would be of value. Accordingly, there is a great need to identify new cancer-related targets and biomarkers useful for the identification, assessment, prevention, and treatment of cancer, such as AML.

SUMMARY OF THE INVENTION

The present invention is based, at least in part, on the discovery that treatment approaches focusing on FLT3 degradation as opposed to or in addition to kinase inhibition are useful for treating cancers driven by FLT3. For example, FLT3, the most commonly mutated gene in AML, is associated with a poor prognosis. FLT3 kinase inhibitors display significant clinical activity against acute myeloblastic leukemia (AML) with activating FLT3 mutations. However, drug resistance often develops rapidly. In model systems, drug treatment leads to a compensatory increase in FLT3 protein, which may contribute to clinical drug resistance. It has been determined herein that genetic knockdown (KD) or pharmacological inhibition of the deubiquitylating enzyme, USP10, which directly interacts with FLT3, causes FLT3 degradation and reduces FLT3 mutant-positive AML cell survival. These results identify USP10 as a new FLT3 regulator, and provide an alternative and complementary therapy for AML. Importantly, the results demonstrate stabilization of an AML mutant driver protein by a deubiquitylating (DUB) enzyme. The methods of the present invention can simultaneously block both enzymatic and scaffolding functions of FLT3, and block compensatory increases in FLT3 protein or resistant point mutations associated with some kinase inhibitors.

In one aspect, a method of treating a subject afflicted with acute myeloblastic leukemia (AML) is provided, comprising administering to the subject an agent that inhibits the copy number, amount, and/or activity of at least one USP10 biomarker, thereby treating the subject afflicted with the AML, optionally wherein the at least one USP10 biomarker is selected from the group of USP10 biomarkers listed in Table 1.

Numerous embodiments are further provided that can be applied to any aspect of the present invention and/or combined with any other embodiment described herein. For example, in one embodiment, the agent is administered in a pharmaceutically acceptable formulation. In another embodiment, the agent directly binds the at least one biomarker, optionally wherein the at least one USP10 biomarker is selected from the group of USP10 biomarkers listed in Table 1. In still another embodiment, the at least one USP10 biomarker is human USP10 or an ortholog thereof. In yet another embodiment, the method further comprises administering at least one additional anti-cancer agents, optionally wherein the at least one additional anti-cancer agent inhibits the copy number, amount, and/or activity of at least one biomarker listed in Table 2.

In another aspect, a method of inhibiting hyperproliferative growth of AML cells is provided, the method comprising contacting the AML cells with an agent that inhibits the copy number, amount, and/or activity of at least one USP10 biomarker, thereby inhibiting hyperproliferative growth of the AML cells, optionally wherein the at least one USP10 biomarker is selected from the group of USP10 biomarkers listed in Table 1.

As described above, numerous embodiments are further provided that can be applied to any aspect of the present invention and/or combined with any other embodiment described herein. For example, in one embodiment, the step of contacting occurs in vivo, ex vivo, or in vitro, optionally wherein the AML cells die. In another embodiment, the agent is administered in a pharmaceutically acceptable formulation. In still another embodiment, the agent directly binds the at least one biomarker, optionally wherein the USP10 biomarker is selected from the group of USP10 biomarkers listed in Table 1. In yet another embodiment, the at least one USP10 biomarker is human USP10 or an ortholog thereof. In another embodiment, the method further comprises administering at least one additional anti-cancer agents, optionally wherein the at least one additional anti-cancer agent inhibits the copy number, amount, and/or activity of at least one biomarker listed in Table 2.

In still another aspect, a method of determining whether a subject afflicted with AML or at risk for developing AML, would benefit from USP10 inhibitor therapy is provided, the method comprising: a) obtaining a biological sample from the subject; b) determining the copy number, amount, and/or activity of at least one USP10 biomarker, optionally wherein the at least one USP10 biomarker is selected from the group consisting of USP10 biomarkers listed in Table 1, in a subject sample; c) determining the copy number, amount, and/or activity of the at least one USP10 biomarker in a control; and d) comparing the copy number, amount, and/or activity of the at least one USP10 biomarker detected in steps b) and c), wherein the presence of, or a significant increase in the copy number, amount, and/or activity of, the at least one USP10 biomarker in the subject sample relative to the control copy number, amount, and/or activity of the at least one USP10 biomarker indicates that the subject afflicted with the AML or at risk for developing the AML would benefit from USP10 inhibitor therapy. In one embodiment, the method further comprises recommending, prescribing, or administering USP10 inhibitor therapy if the AML is determined to benefit from USP10 inhibitor therapy. In another embodiment, the method further comprises recommending, prescribing, or administering anti-AML therapy other than USP10 inhibitor therapy if the AML is determined to not benefit from USP10 inhibitor therapy. In still another embodiment, the anti-AML therapy is selected from the group consisting of targeted therapy, chemotherapy, radiation therapy, and/or hormonal therapy. In yet another embodiment, the control sample is determined from a cancerous or non-cancerous sample from either the patient or a member of the same species to which the patient belongs. In another embodiment, the control sample comprises cells. In still another embodiment, the method further comprises determining responsiveness to USP10 inhibitor therapy measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In yet another aspect, a method of assessing the efficacy of an agent for treating AML in a subject is provided, comprising: a) detecting in a first subject sample and maintained in the presence of the agent the copy number, amount or activity of at least one USP10 biomarker, optionally wherein the USP10 biomarker is selected from the group of USP10 biomarkers listed in Table 1; b) detecting the copy number, amount, and/or activity of the at least one USP10 biomarker in a second subject sample and maintained in the absence of the test compound; and c) comparing the copy number, amount, and/or activity of the at least one USP10 biomarker from steps a) and b), wherein a significantly increased copy number, amount, and/or activity of the at least one USP10 biomarker in the first subject sample relative to the second subject sample, indicates that the agent treats the AML in the subject.

In another aspect, a method of monitoring the progression of AML in a subject is provided, comprising: a) detecting in a subject sample at a first point in time the copy number, amount, and/or activity of at least one USP10 biomarker, optionally wherein the USP10 biomarker is selected from the group of USP10 biomarkers listed in Table 1; b) repeating step a) during at least one subsequent point in time after administration of a therapeutic agent; and c) comparing the copy number, amount, and/or activity detected in steps a) and b), wherein a significantly increased copy number, amount, and/or activity of the at least one USP10 biomarker in the first subject sample relative to at least one subsequent subject sample, indicates that the agent treats the AML in the subject. In one embodiment, between the first point in time and the subsequent point in time, the subject has undergone treatment, completed treatment, and/or is in remission for the AML. In another embodiment, the subject has undergone USP10 inhibitor therapy between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of AML. In another embodiment, the first and/or at least one subsequent sample is a portion of a single sample or pooled samples obtained from the subject.

In still another aspect, a cell-based method for identifying an agent that modulates hyperproliferative growth of AML cells and/or AML cell death is provided, the method comprising: a) contacting a cell expressing at least one USP10 biomarker, optionally wherein the USP10 biomarker is selected from the group of USP10 biomarkers listed in Table 1, with a test agent; and b) determining the effect of the test agent on the copy number, level of expression, or level of activity of the at least one USP10 biomarker to thereby identify an agent that that modulates hyperproliferative growth of AML cells and/or AML cell death. In one embodiment, said cells are isolated from an animal model of AML. In still another embodiment, said cells are from a subject afflicted with AML. In yet another embodiment, said cells are unresponsive to USP10 inhibitor therapy. In another embodiment, the step of contacting occurs in vivo, ex vivo, or in vitro, optionally wherein the agent inhibits hyperproliferative growth of AML cells and/or promotes AML cell death. In still another embodiment, the method further comprises determining the ability of the test agent to bind to the at least one USP10 biomarker before or after determining the effect of the test agent on the copy number, level of expression, or level of activity of the at least one USP10 biomarker, optionally wherein the agent inhibits hyperproliferative growth of AML cells and/or promotes AML cell death. In yet another embodiment, the sample comprises cells, cell lines, histological slides, paraffin embedded tissue, fresh frozen tissue, fresh tissue, biopsies, blood, plasma, serum, buccal scrape, saliva, cerebrospinal fluid, urine, stool, mucus, or bone marrow, obtained from the subject.

In yet another aspect, a cell-free method for identifying an agent that inhibits hyperproliferative growth of AML cells and/or promotes AML cell death is provided, the method comprising: a) determining the effect of a test agent on the amount or activity of at least one USP10 biomarker, optionally wherein the USP10 biomarker is selected from the group of USP10 biomarkers listed in Table 1, contacted with a test agent; b) determining the amount or activity of the at least one USP10 biomarker maintained in the absence of the test agent; and c) comparing the amount and/or activity of the at least one USP10 biomarker from steps a) and b), wherein a significantly decreased amount, and/or activity of the at least one USP10 biomarker in step a) relative to step b), identifies the test agent as an agent that inhibits hyperproliferative growth of AML cells and/or promotes AML cell death. In one embodiment, the method further comprises determining the ability of the test agent to bind to the at least one USP10 biomarker before or after determining the effect of the test agent on the amount or activity of the at least one USP10 biomarker. In another embodiment, the method further comprises contacting an AML cell expressing the at least one USP10 biomarker with the test agent to confirm the ability of the test agent to inhibit hyperproliferative growth of AML cells and/or promote AML cell death.

As described above, numerous embodiments are further provided that can be applied to any aspect of the present invention and/or combined with any other embodiment described herein. For example, in one embodiment, the copy number is assessed by microarray, quantitative PCR (qPCR), high-throughput sequencing, comparative genomic hybridization (CGH), or fluorescent in situ hybridization (FISH). In another embodiment, the amount of the at least one USP10 biomarker is assessed by detecting the presence in the samples of a polynucleotide molecule encoding the biomarker or a portion of said polynucleotide molecule. In still another embodiment, the polynucleotide molecule is an mRNA, cDNA, or functional variants or fragments thereof. In yet another embodiment, the step of detecting further comprises amplifying the polynucleotide molecule. In another embodiment, the amount of the at least one biomarker is assessed by annealing a nucleic acid probe with the sample of the polynucleotide encoding the one or more biomarkers or a portion of said polynucleotide molecule under stringent hybridization conditions. In still another embodiment, the amount of the at least one biomarker is assessed by detecting the presence a polypeptide of the at least one USP10 biomarker. In yet another embodiment, the presence of said polypeptide is detected using a reagent which specifically binds with said polypeptide. In another embodiment, the reagent is selected from the group consisting of an antibody, an antibody derivative, and an antibody fragment. In still another embodiment, the activity of the at least one USP10 biomarker is assessed by determining the magnitude of modulation of the activity or expression level of at least one downstream target of the at least one USP10 biomarker. In yet another embodiment, the at least one downstream target of the at least one USP10 biomarker is a human FLT3 or an ortholog thereof. In another embodiment, the human FLT3 or an ortholog thereof is at least one human FLT3 selected from the group consisting of biomarkers listed in Table 2.

In some embodiments, the USP10 inhibitor therapy or test agent is an inhibitor selected from the group consisting of a small molecule, antisense nucleic acid, interfering RNA, shRNA, siRNA, miRNA, piwiRNA, aptamer, ribozyme, genome editing, dominant-negative protein binding partner, and combinations thereof. In yet another embodiment, the USP10 inhibitor therapy or test agent is a small molecule. In another embodiment, the small molecule is selected from the group consisting of small molecules listed in FIGS. 1-22 and Table 8. In still another embodiment, the USP10 inhibitor therapy or test agent is identified in a high-throughput screen. In yet another embodiment, the USP10 inhibitor therapy or test agent also inhibits the activity or expression level of USP7. In another embodiment, the USP10 inhibitor therapy or test agent does not inhibit the activity or expression level of p53. In still another embodiment, the at least one USP10 biomarker is 2, 3, 4, 5, 6, 7, 8, 9, 10, or more USP10 biomarkers. In yet another embodiment, the USP10 inhibitor therapy or test agent modulates the activity or expression level of at least one downstream target of USP10. In another embodiment, the activity or expression level of the at least one downstream target of USP10 is decreased. In still another embodiment, the at least one downstream target of USP10 is a human FLT3 or an ortholog thereof. In yet another embodiment, the human FLT3 or an ortholog thereof is at least one human FLT3 selected from the group consisting of biomarkers listed in Table 2. In another embodiment, the AML is adult AML or pediatric AML. In still another embodiment, the subject is a mammal, such as an animal model of AML or a human.

Figure 1A:
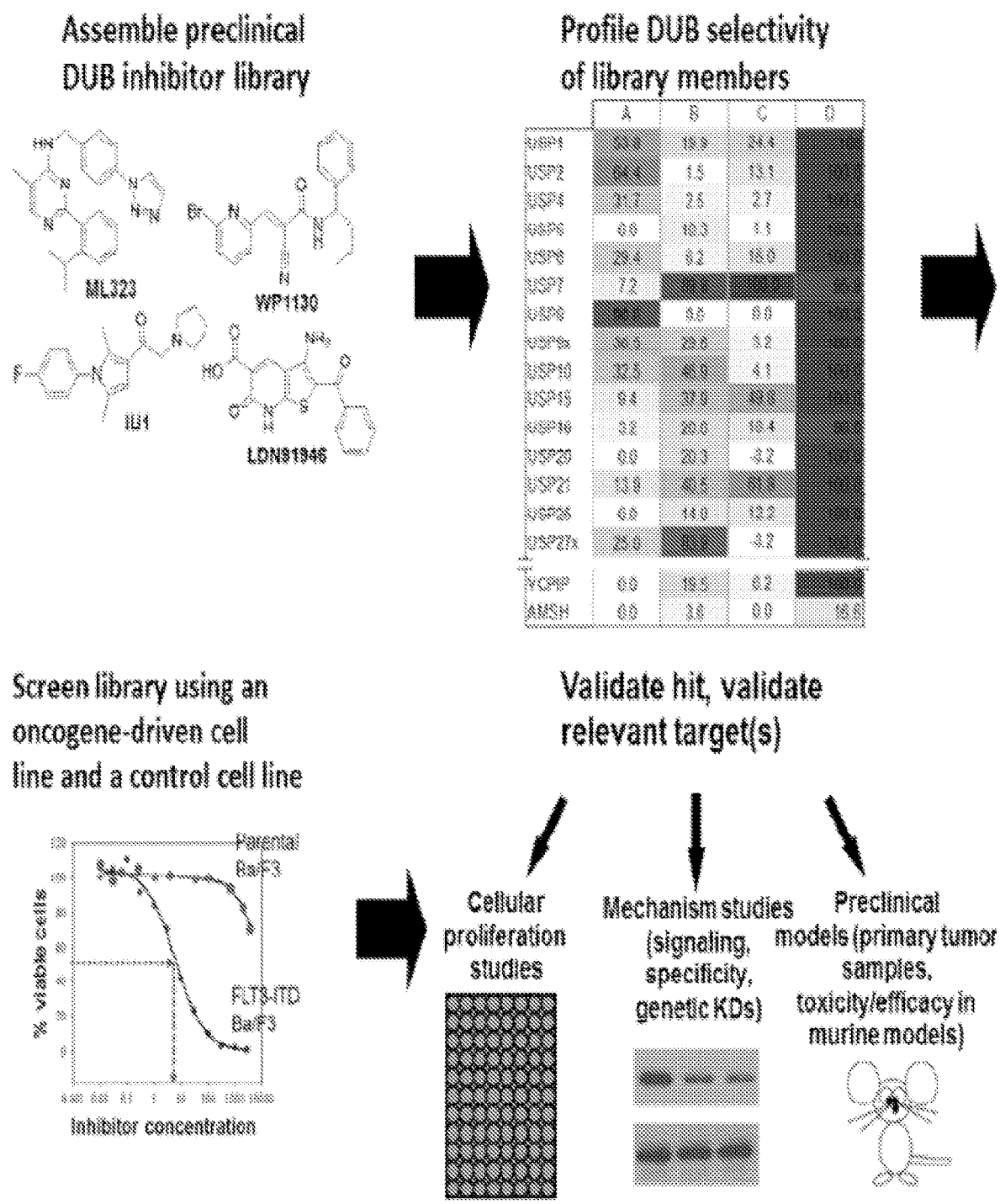
FIG. 1 includes 10 panels, identified as panels A, B, C, D, E, F, G, H, I, and J, which show the effects of HBX19818 on mutant FLT3-expressing cells. Panel A shows the screening strategy for identification of novel regulators of mutant FLT3. Panel B shows the chemical structure of HBX19818, which was identified in a screen of DUB inhibitors using a screening concentration of 5 µM and being able to effectively kill mutant FLT3-expressing cells. Panels C-D show the effects of HBX19818 on Ba/F3-FLT3-ITD (Panel C) and Ba/F3-D835Y (Panel D) cells cultured in the absence or presence of 20% WEHI-conditioned media (used as a source of IL-3) following 72 hr of treatment. Panel E shows the effects of HBX19818 on Ba/F3-FLT3-ITD and Ba/F3-D835Y cells after approximately 22 hr treatment. Panels F and G shows the effects of HBX19818 on FLT3 protein expression in Ba/F3-FLT3-ITD cells (Panel F) and Ba/F3-D835Y cells (Panel G). Panel H shows the effect of HBX19818 on FLT3 protein levels in Ba/F3-wtFLT3 cells. Panel I shows analysis of proliferation of HBX19818-treated mutant FLT3-positive MV4,11, MOLM13-luc+ and MOLM14 cells, as compared to null FLT3 or wt FLT3-expressing leukemia cells at a concentration of 20 µM following 24 hours of treatment. Panel J shows mitochondrial priming in AML cell lines treated with HBX19818. Mitochondrial priming was detected by measuring cytochrome c release in response to Bim peptide at 14 h (hours) post drug exposure. The % change in priming=priming of DMSO treated cells-priming of drug treated cells. The immunoblots shown herein are representative of 1-2 additional studies for which similar results were observed.
Figure 1:
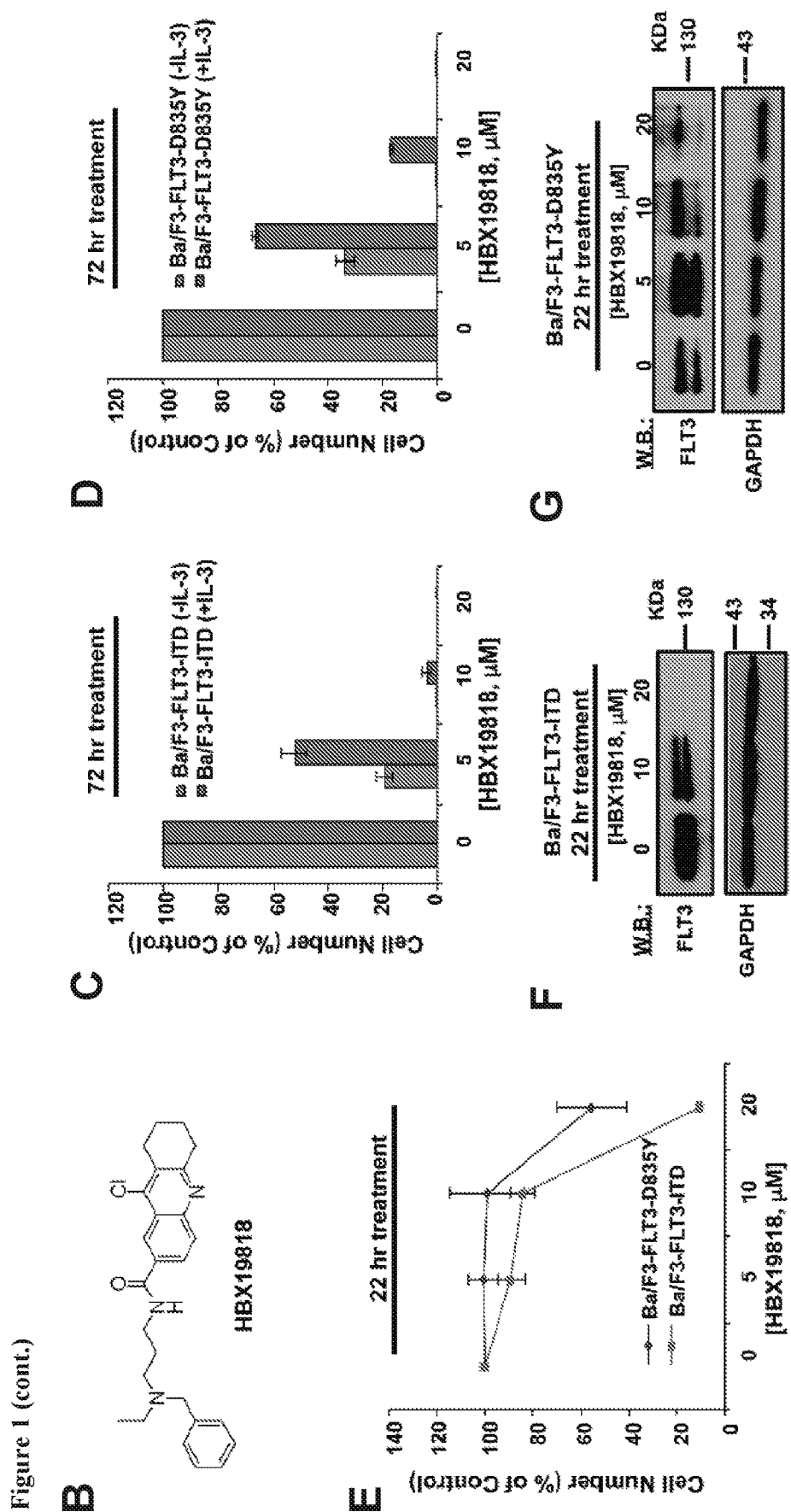
Figure 1:
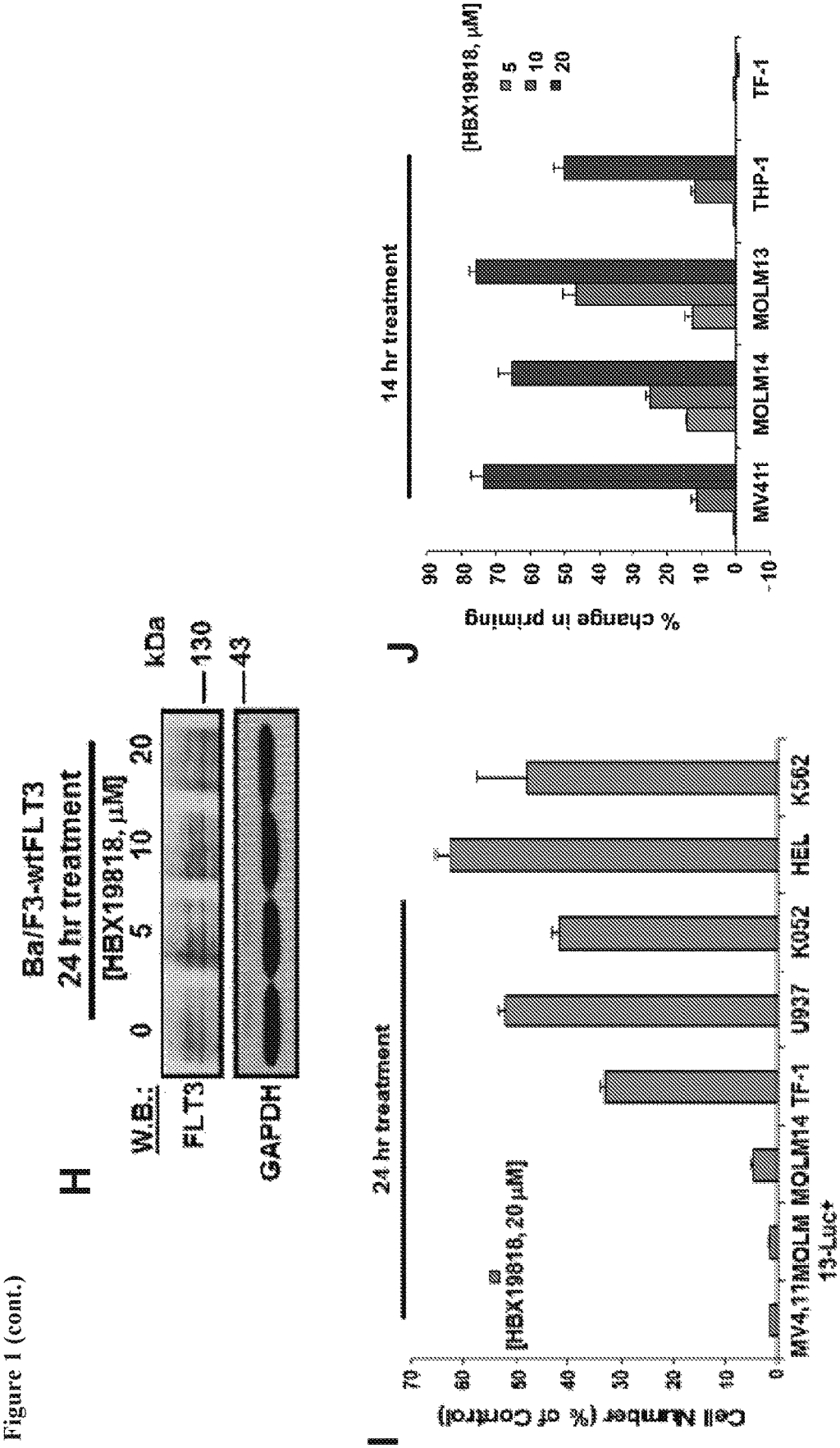

Note that for every figure containing a histogram, the bars from left to right for each discreet measurement correspond to the figure boxes from top to bottom in the figure legend as indicated. In addition, for every figure referring to a compound using numeric value, the numeric value refers to a compound name as follows:
compound 1 is C598-0466; compound 2 is C598-0468;
compound 3 is C598-0515;
compound 4 is C598-0563; compound 5 is C598-0571;
compound 6 is C598-0646;
compound 7 is C673-0105.

DETAILED DESCRIPTION OF THE INVENTION

FLT3 kinase inhibitors display significant clinical activity against acute myeloblastic leukemia (AML) with activating FLT3 mutations. However, drug resistance often develops rapidly. In model systems, drug treatment leads to a compensatory increase in FLT3 protein, which may contribute to clinical drug resistance. It has been determined herein that the deubiquitylating (DUB) enzyme, USP10, is a FLT3 regulator (e.g., a stabilizer of FLT3 activating mutants that drive AML) and that focusing on FLT3 degradation by modulating USP10, as opposed to focusing on FLT3 kinase inhibition, can treat AML. For example, it is demonstrated herein that genetic knockdown (KD) or pharmacological inhibition of USP10, which directly interacts with FLT3, to cause FLT3 degradation and reduce FLT3 mutant-positive AML cell survival. Inhibiting or blocking the activity of activating mutant FLT3 that drives AML by promoting its degradation, such as by inhibiting or blocking USP10, is believed to be more efficacious than solely inhibiting or blocking the FLT3 kinase activity, since such degradation, either alone or in combination with FLT3 kinase activity inhibition or blockade, can simultaneously inhibit or block both enzymatic and scaffolding functions of FLT3, and compensatory increases in FLT3 protein or resistant point mutations associated with some kinase inhibitors can be curbed.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal and/or amount of the biomarker, if the amount of the biomarker is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal and/or control amount if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control amount of the biomarker. Such significant modulation values can be applied to any metric described herein, such as altered level of expression, altered activity, changes in cancer cell hyperproliferative growth, changes in cancer cell death, changes in biomarker inhibition, changes in test agent binding, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subject not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al.

(1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of anti-AML therapy (e.g., USP10 inhibitor therapy) effects. Biomarkers can include, without limitation, nucleic acids (e.g., genomic nucleic acids and/or transcribed nucleic acids) and proteins, particularly those involved shown in Table 1. Many biomarkers listed in Table 1 are also useful as therapeutic targets. In one embodiment, such targets are USP10 members shown in Table 1 and/or Flt3 members shown in Table 2.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of oncogenes, such as FLT3 having mutations that activate FLT3 kinase activity. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer is acute myeloblastic leukemia (AML). The AML can be adult AML, pediatric AML, or both. Acute myeloid leukemia (AML), also known as acute myelogenous leukemia, acute myeloblastic leukemia, acute granulocytic leukemia or acute nonlymphocytic leukemia, is a fast-growing form of cancer of the blood and bone marrow characterized by fatigue, shortness of breath, easy bruising and bleeding, and increased risk of infection. AML is the most common type of acute leukemia. It occurs when the bone marrow begins to make blasts, cells that have not yet completely matured. These blasts normally develop into white blood cells. However, in AML, these cells do not develop and are unable to ward off infections. In AML, the bone marrow may also make abnormal red blood cells and platelets. The number of these abnormal cells increases rapidly, and the abnormal (leukemia) cells begin to crowd out the normal white blood cells, red blood cells and platelets that the body needs. AML involves higher percentages of dedifferentiated and undifferentiated cells, including more blasts (myeloblasts, monoblasts, and megakaryoblasts) than other leukemias. AML subtypes are classified based on the cell type from which the leukemia develops. The eight common AML subtypes include myeloblastic (M0) on special analysis, myeloblastic (M1) without maturation, myeloblastic (M2) with maturation, promyeloctic (M3), myelomonocytic (M4), monocytic (M5), erythroleukemia (M6), and megakaryocytic. Generally, the standard of care of treating AML is initial treatment with chemotherapy aimed at inducing a remission, although additional chemotherapy or a hematopoietic stem cell transplant may follow.

The early signs of AML are often vague and nonspecific, and may be similar to those of influenza or other common illnesses. Some generalized symptoms include fever, fatigue, weight loss or loss of appetite, shortness of breath, anemia, easy bruising or bleeding, petechiae (flat, pin-head sized spots under the skin caused by bleeding), bone and joint pain, and persistent or frequent infections. Enlargement of the spleen may occur in AML, but it is typically mild and asymptomatic. Lymph node swelling is rare in AML, in contrast to acute lymphoblastic leukemia. The skin is involved about 10% of the time in the form of leukemia cutis. Rarely, Sweet's syndrome, a paraneoplastic inflammation of the skin, can occur with AML. Some people with AML may experience swelling of the gums because of infiltration of leukemic cells into the gum tissue. Rarely, the first sign of leukemia may be the development of a solid leukemic mass or tumor outside of the bone marrow, called a chloroma. The first clue to a diagnosis of AML is typically an abnormal result on a complete blood count. While an excess of abnormal white blood cells (leukocytosis) is a common finding, and leukemic blasts are sometimes seen, AML can also present with isolated decreases in platelets, red blood cells, or even with a low white blood cell count (leukopenia). While a presumptive diagnosis of AML can be made by examination of the peripheral blood smear when there are circulating leukemic blasts, a definitive diagnosis usually requires an adequate bone marrow aspiration and biopsy. Marrow or blood is examined under light microscopy, as well as flow cytometry, to diagnose the presence of leukemia, to differentiate AML from other types of leukemia (e.g. acute lymphoblastic leukemia—ALL), and to classify the subtype of disease. A sample of marrow or blood is typically also tested for chromosomal abnormalities by routine cytogenetics or fluorescent in situ hybridization. Genetic studies may also be performed to look for specific mutations in genes, such as FLT3, nucleophosmin, and KIT, which may influence the outcome of the disease. Cytochemical stains on blood and bone marrow smears are helpful in the distinction of AML from ALL, and in subclassification of AML. The combination of a myeloperoxidase or Sudan black stain and a nonspecific esterase stain will provide the desired information in most cases. The myeloperoxidase or Sudan black reactions are most useful in establishing the identity of AML and distinguishing it from ALL. The nonspecific esterase stain is used to identify a monocytic component in AMLs and to distinguish a poorly differentiated monoblastic leukemia from ALL.

The two most commonly used classification schemata for AML are the older French-American-British (FAB) system and the newer World Health Organization (WHO) system. According to the widely used WHO criteria, the diagnosis of AML is established by demonstrating involvement of more than 20% of the blood and/or bone marrow by leukemic myeloblasts, except in the three best prognosis forms of AML with recurrent genetic abnormalities (t(8; 21), inv(16), and t(15; 17)) in which the presence of the genetic abnormality is diagnostic irrespective of blast percent. The French-American-British (FAB) classification involves a blast percentage of at least 30% in bone marrow (BM) or peripheral blood (PB) for the diagnosis of AML. AML must be carefully differentiated from "preleukemic" conditions such as myelodysplastic or myeloproliferative syndromes, which are treated differently. Fluorescent in situ hybridization performed on blood or bone marrow is often used for diagnosis since it can identify the chromosomal translocation [t(15; 17)(q22;q12);] (PML/RARA fusion protein oncogene) that characterizes APL, which is different from AML.

The term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide anti-cancer therapy (e.g., USP10 inhibitor therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "FLT3" refers to Fms-related tyrosine kinase 3, as a cytokine receptor which belongs to the receptor tyrosine kinase class III, and is alternatively known as "Fms-Related Tyrosine Kinase 3," "stem cell tyrosine kinase 1," "Fms-Like Tyrosine Kinase 3," "FL cytokine receptor," "CD135," "CD135 Antigen," "EC 2.7.10.1," "EC 2.7.10," "FLK-2," "STK1," "growth factor receptor tyrosine kinase Type III," "fetal liver kinase 2," and "receptor-type tyrosine-protein kinase FLT3." Somatic mutations that lead to constitutive activation of FLT3 are frequent in AML patients. These mutations fall into two classes, the most common being in-frame internal tandem duplications of variable length in the juxtamembrane region that disrupt the normal regulation of the kinase activity. Likewise, point mutations in the activation loop of the kinase domain can result in a constitutively activated kinase.

Nucleic acid and amino acid sequence for FLT3 nucleic acids and protein are known in the art and are publicly available in the GenBank database maintained by the U.S. National Center for Biotechnology Information. For example, human FLT3 nucleic acid sequences are well-known and include, for example, NM_004119.2 (variant 1, representing the shorter transcript and encoding the protein) and NR_130706.1 (variant 2, which contains an alternate internal exon compared to variant 1. Variant 2 is non-coding because the use of the 5'-most expected translational start codon as used in variant 1 renders the transcript a candidate for nonsense-mediated mRNA decay (NMD). Additional Flt3 human sequences include, without limitation, XM_017020486.1, XM_017020489.1, XM_017020487.1, XM_017020488.1, XM_011535015.2, XM_011535017.2, and XM_011535018.2. Human FLT3 amino acid sequences are well-known and include, for example, NP 004110.2 (variant 1, as above), XP 016875975.1, XP_016875978.1, XP_016875976.1, XP_016875977.1, XP_011533317.1, XP_011533319.1, and XP_011533320.1.

Nucleic acid and amino acid sequence for FLT3 orthologs in other species are also well-known and include, for example, chimpanzee (*Pan troglodytes*) FLT3 (XM_509601.5 and XP_509601.2), rhesus monkey (*Macaca mulatta*) FLT3 (XM_015120801.1 and XP_014976287.1, XM_015120802.1 and XP_014976288.1, XM_001117913.2 and XP_001117913.1, XM_015120803.1 and XP_014976289.1), dog (*Canis lupus familiaris*) FLT3 (NM 001020811.1 and NP 001018647.1, XM_005635382.2 and XP_005635439.1, XM_014107333.1 and XP_013962808.1, XM_014107331.1 and XP_013962806.1, XM_014107332.1 and XP_013962807.1), cattle (*Bos taurus*) FLT3 (XM_010810805.2 and XP_010809107.2, XM_015465697.1 and XP_015321183.1), house mouse (*Mus musculus*) FLT3 (NM 010229.2 and NP 034359.2, XM_006504805.3 and XP_006504868.1, XM_006504804.3 and XP_006504867.1), Norway rat (*Rattus norvegicus*) FLT3 (NM 001100822.2 and NP 001094292.1), chicken (*Gallus gallus*) FLT3 (XM_015278776.1 and XP_015134262.1, XM_003640612.3 and XP_003640660.2), tropical clawed frog (*Xenopus tropicalis*) FLT3 (XM_012957932.2 and XP_012813386.1), and zebrafish (*Danio rerio*) FLT3 (XM_001921725.4 and XP_001921760.2). In addition, FLT3 inhibitors are well-known in the art and include, without limitation, sunitinib, sorafenib, midostaurin (PKC412), lestaurtinib (CEP-701), tandautinib (MLN518), quizartinib (AC220), and KW-2449 (Wiernik et al. (2010) *Clin. Adv. Hematol. Oncol.* 8:429-437). Similarly, anti-FLT3 detection agents are well-known in the art and include, without limitation, antibodies OAAF00442 (Aviva Systems Biology), 8F2 (Cell Signaling Technology), ab66035 (Abcam), PE A2F10 (eBioscience) (Ju et al. (2011) *Hybridoma* 30:61-67; Piloto et al. (2005) *Cancer Res.* 65:1514-1522)).

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICO S, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

"Anti-immune checkpoint" therapy refers to the use of agents that inhibit immune checkpoint nucleic acids and/or proteins. Immune checkpoints share the common function of providing inhibitory signals that suppress immune response and inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy). Numerous immune checkpoint inhibitors are known and publicly available including, for example, Keytruda® (pembrolizumab; anti-PD-1 antibody), Opdivo® (nivolumab; anti-PD-1 antibody), Tecentriq® (atezolizumab; anti-PD-L1 antibody), durvalumab (anti-PD-L1 antibody), and the like.

The term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" or "deficient" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein, is inhibited if it is decreased as compared to a reference state, such as a control like a wild-type state. For example, USP10 activity of a USP10 protein that is contacted with a USP10 inhibitor is inhibited or deficient if the stability of FLT3 kinase is decreased due to contact with the USP10 inhibitor, in comparison to the USP10 protein not contacted with the USP10 inhibitor. Similarly, kinase activity of a mutant FLT3 kinase is inhibited or deficient if the kinase activity is decreased due to the mutation and/or contact with the inhibitor, in comparison to the wild-type FLT3 kinase and/or the mutant FLT3 kinase not contacted with the inhibitor. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized.

An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy.

The "normal" level of expression of a biomarker is the level of expression of the biomarker in cells of a subject, e.g., a human patient, not afflicted with a cancer. An "overexpression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

Such "significance" levels can also be applied to any other measured parameter described herein, such as for expression, inhibition, cytotoxicity, cell growth, and the like.

The term "P53" refers to the well-known tumor suppressor, p53 (see, for example, Meek (2015) Biochem J. 469: 325-346; Ballinger et al. (2015) Curr. Opin. Oncol. 27:332-337; Amelio and Melino (2015) Trends Biochem. Sci. 40:425-434; Saha et al. (2014) Prog. Biophys. Mol. Biol. 117:250-263; Tchelebit et al. (2014) Subcell. Biochem. 85:133-159; Yeudall (2014) Subcell. Biochem. 85:105-117; Santoro et al. (2014) Subcell. Biochem. 85:91-103; Girardini et al. (2014) Subcell. Biochem. 85:41-70; Soussi et al. (2014) Hum. Mutat. 35:766-778; Leroy et al. (2014) Hum. Mutat. 35:756-765; Leory et al. (2014) Hum. Mutat. 35:672-688; Nguyen et al. (2014) Hum. Mutat. 35:738-755; Bertheau et al. (2013) Breast 22:S27-S29; Brachova et al. (2013) Int. J. Mol. Sci. 14:19257-19275; Carvajal and Manfredi (2013) EMBO Rep. 14:414-421; Tornesello et al. (2013) Gynecol. Oncol. 128:442-448; Lehmann and Pietenpol (2012) J. Clin. Oncol. 30:3648-3650; Bellini et al. (2012) J Biomed. Biotechnol. 2012:891961; Li et al. (2012) Biochim. Biophys. Acta. 1819:684-687; and Naccarati et al. (2012) Mutagenesis 27:211-218). The gene encoding the p53 protein is highly conserved among vertebrates and is mutated to cause deficiency of p53 protein function in greater than 50% of human cancers (Surget et al. (2013) OncoTargets Therapy 7:57-68). In humans, the p53 gene, which is located at 17p13.1, encodes at least 15 protein isoforms. The protein structure of the p53 protein is well-known and is characterized by certain domains. For example, in one embodiment, wild-type functional human p53 comprises:

1) an acidic N-terminus transcription-activation domain (TAD), also known as activation domain 1 (AD1), which activates transcription factors (e.g., residues 1-42). The N-terminus contains two complementary transcriptional activation domains, with a major one at residues 1-42 and a minor one at residues 55-75, specifically involved in the regulation of several pro-apoptotic genes (Venot et al. (1998) EMBO J. 17:4668-4679);

2) activation domain 2 (AD2), which is important for apoptotic activity (e.g., residues 43-63);

3) proline rich domain, which is important for the apoptotic activity of p53 by nuclear exportation via MAPK (e.g., residues 64-92);

4) central DNA-binding core domain (DBD), which contains one zinc atom and several arginine amino acids (e.g., residues 102-292). This region is responsible for binding the p53 co-repressor LMO3 (Larsen et al. (2010) Biochem. Biophys. Res. Commun. 392:252-257;

5) nuclear localization signaling domain (e.g., residues 316-325);

6) homo-oligomerization domain (OD) (e.g., residues 307-355). Tetramerization is essential for the activity of p53 in vivo; and 7) a C-terminal domain involved in downregulation of DNA binding of the central domain (e.g., residues 356-393) (Harms et al. (2005) Mol. Cell. Biol. 25:2014-2030).

Mutations that make p53 deficient in cancer usually occur in the DBD. Most of these mutations destroy the ability of the protein to bind to its target DNA sequences, and thus prevents transcriptional activation of these genes. As such, mutations in the DBD are recessive loss-of-function mutations. Molecules of p53 with mutations in the OD dimerize with wild-type p53, and prevent them from activating transcription. Therefore, OD mutations have a dominant negative effect on the function of p53. Mutations in p53 nucleic acids that either do not encode functional p53 protein or p53 protein having reduced function (collectively, p53 deficiency) are well-known in the art, as described above, and can be generated by any number of well-known types of mutation including, for example, a missense mutation (base change that alters the encoded amino acid), a nonsense mutation (base change that alters the encoded amino acid to a premature stop codon), a frameshift mutation (base addition or loss in a manner that is not a multiple of 3), an insertion mutation (any base addition, large or small in number, that alters the function of the encoded protein), a deletion mutation (any base deletion, large or small in number, that alters the function of the encoded protein), or a rearrangement mutation (any alteration, large or small, that alters the function of the encoded protein while retaining the starting amount of bases). In some embodiments, mutations can be combined, such as when rearrangements are accompanied by additions and/or deletions, or multiple missense mutations are combined. In some embodiments, the mutation is a genetic null (any mutation that completes ablates the function of the encoded protein) that arises in the germline, somatically, or both. This description of mutation types applies to any marker described herein.

Assays for determining p53 activity, or reduction thereof, are well-known and commercially available (see, for example, Qiagen Cignal® p53 reporter kit, Active Motif® TransAM® p53 reporter kit; Cayman Chemical p53 transcription factor assay kit item number 600020, Genecopoeia™ TF-Detect™ human p53 activity assay kit; Hiraki et al. (2015) Cell Chem. Biol. 22:1206-1216; Flaman et al. (1995) Proc. Natl. Acad. Sci. USA 92:3963-3967 (1995); and Kovvali et al. (2001) Nucl. Acids Res. 29:e28).

Nucleic acid and amino acid sequences for p53 nucleic acids and protein are known in the art and are publicly available in the GenBank database maintained by the U.S. National Center for Biotechnology Information. For example, human p53 nucleic acid and amino acid sequences are well-known and include, for example, NM_000546.5 (variant 1) and NP_000537.3 (isoform a); NM_001126112.2 (variant 2) and NP_001119584.1 (isoform a); NM_001126114.2 (variant 3) and NP_001119586.1 (isoform b); NM_001126113.2 (variant 4) and NP_001119585.1 (isoform c); NM_001126115.1 (variant 5) and NP_001119587.1 (isoform d); NM_001126116.1 (variant 6) and NP_001119588.1 (isoform e); NM_001126117.1 (variant 7) and NP_001119589.1 (isoform f); NM_001126118.1 (variant 8) and NP_001119590.1 (isoform g); NM_001276695.1 (variant 9) and NP_001263624.1 (isoform h); NM_001276696.1 (variant 10) and NP_001263625.1 (isoform i); NM_001276697.1 (variant 10) and NP_001263626.1 (isoform j); NM_001276698.1 (variant 11) and NP_001263627.1 (isoform k); NM_001276699.1 (variant 12) and NP_001263628.1 (isoform 1); NM_001276760.1 (variant 13) and NP_001263689.1 (isoform g); and NM_001276761.1 (variant 14) and NP_001263690.1 (isoform g). Nucleic acid and amino acid sequences of p53 orthologs in other species are also well-known and include, for example, mouse p53 (NM_001127233.1, NP_001120705.1, NM_011640.3, and NP_035770.2), chimpanzee p53 (XM_001172077.4 and XP_001172077.2), monkey p53 (NM_001047151.2 and NP_001040616.1), dog p53 (NM_001003210.1 and NP_001003210.1), cow p53 (NM_174201.2 and NP_776626.1), frog p53 (NM_001001903.1 and NP_001001903.1), and zebrafish p53 (NM_001271820.1, NP_001258749.1, NM_131327.3, and NP_571402.1). It is to be noted that the term can further be used to refer to any combination of features described herein regarding p53. For example, any combination of class, sequence composition, percentage identify, sequence length, domain structure, functional activity, etc. can be used to describe p53 as used according to the present invention.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as one or more USP10 inhibitors alone or in combination with one or more FLT3 inhibitors, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to anti-cancer therapy, such as USP10 inhibitor therapy (e.g., USP10 inhibitors either alone or in combination with FLT3 inhibitors). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular anti-cancer therapy (e.g., USP10 inhibitors either alone or in combination with FLT3 inhibitors) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to anti-cancer therapy (e.g., USP10 inhibitors either alone or in combination with FLT3 inhibitors)" relates to any response of the hyperproliferative disorder (e.g., cancer) to an anti-cancer therapy (e.g., USP10 inhibitors either alone or in combination with FLT3 inhibitors), preferably to a change in cancer cell numbers, tumor mass, and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multidrug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

In addition to RNAi, genome editing can be used to modulate the copy number or genetic sequence of a biomarker of interest, such as constitutive or induced knockout or mutation of a USP10 biomarker of interest. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "selective inhibition" or "selectively inhibit" as applied to a biologically active agent refers to the agent's ability to selectively reduce the target signaling activity as compared to off-target signaling activity, via direct or interact interaction with the target. For example, an agent that selectively inhibits USP10 over another deubiquitylating (DUB) enzyme, such as USP7, has an activity against USP10 that is at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 2× (times) more than the compound's activity against the comparison protein (e.g., at least about 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, 10000×, or greater, or any range in between, inclusive). Such metrics are typically expressed in terms of relative amounts of agent required to reduce activity by half.

In particular, USP7/HAUSP (herpes virus-associated USP) is well known in the art (Reverdy et al. (2012) *Chem. Biol.* 19:567-477) as a 135 kDa protein in the USP family of DUB enzymes. In addition to a DUB domain, USP7 also contains an N-terminal TRAF-like MATH domain (Zapata et al. (2001) *J. Biol. Chem.* 276:24242-24252) and a C-terminal domain that contains at least five ubiquitin-like domains (Faesen et al. (2011)*Mol. Cell* 44:147-159). This protein is produced ubiquitously and is highly conserved in eukaryotes (see, for example, human USP7 nucleic acid and protein sequences well-known in the art and publicly available under accession numbers NM_001286457.1 and NP_001273386.1; NM_001286458.1 and NP_001273387.1; NM_001321858.1 and NP_001308787.1; and NM_003470.2 and NP_003461.2). USP7 is primarily a nuclear protein and localizes to a subset of PML bodies (Everett et al. (1999) *J Virol.* 73:417-426; Muratani et al. (2002) *Nat. Cell Biol.* 4:106-110). At the molecular level, by virtue of its deubiquitinating activity, USP7 has been shown to regulate the steady-state level of several poly-ubiquitinated substrates. For example, USP7 alters the level of the p53 and p16$^{INK4a}$ tumor suppressors through Mdm2 stabilization and Bmi1/Mel18 stabilization, respectively (Cummins et al. (2004) Nature 428; Li et al. (2004) *Mol. Cell* 13:8790-896; Maertens et al. (2010) *EMBO J.* 29:2553-2565). USP7 binding to p53 was recently shown to be regulated by TSPYL5, a protein potentially involved in breast oncogenesis through its competition with p53 for binding to the same region of USP7 (Epping et al. (2011) *Nat. Cell Biol.* 13:102-108). Additional proteins involved in genomic integrity and regulation, such as the DNMT1 DNA methylase and the claspin adaptor, are also stabilized by USP7 (Du et al. (2010) *Sci. Signal.* 3:ra80; Faustrup et al. (2009) *J. Cell Biol.* 184:13-19). USP7 has also been shown to regulate the cellular compartmentalization of several mono-ubiquitinated substrates by deubiquitination. In this respect, the PTEN and FOXO4 tumor suppressors are inactivated by USP7-induced nuclear export (Song et al. (2008) *Nature* 455:813-817; van der Horst et al. (2006) *Nat. Cell Biol.* 8:1064-1073). USP7 overexpression has also been reported in human prostate cancer and was directly associated with tumor aggressiveness (Song et al. (2008) *Nature* 455:813-817). Previous in vivo data also underlined the involvement of USP7 in cancer cell proliferation (Becker et al. (2008) *Cell Cycle* 7:7-10). USP10-selective and USP7-selective agents are known (see, for example, exemplary agents listed in Table 8, D'Arcy et al. (2015) *Pharmacol. Ther.* 147:32-54, and others described herein).

TABLE 8

| Reported Target | Compound ID | Structure | Reference |
|---|---|---|---|
| USP2 & USP7 | NSC632839 | 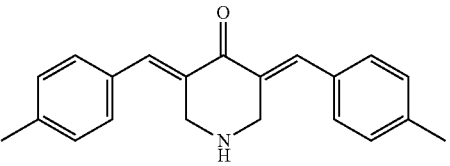<br>O=C(/C(CNC/1)=C/C2=CC=C(C)C=C2)C1=C\C3=CC=C(C)C=C3 | Nicholson B, et al. Protein Sci, 2008, 17(6), 1035-1043. |
| USP7 | HBX19818 | 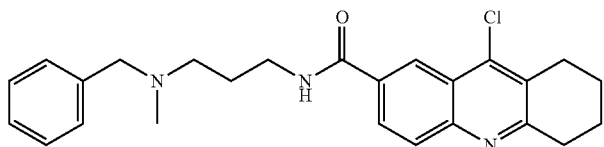<br>CN(CCCNC(C1=CC=C(N=C(CCCC2)C2=C3Cl)C3=Cl)=O)CC4=CC=CC=C4 | Reverdy, C., Conrath, S., Lopez, Planquette, C., Atmanene, C., Collura, V., Harpon, J., Battaglia, V., Vivat, V., Sippl, W., and Colland, F. (2012) *Chemistry & biology* 19, 467-477 |
|  | HBX41108 | 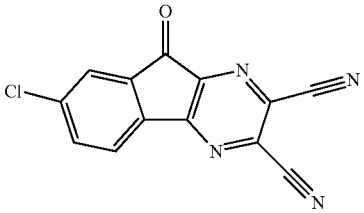<br>O=C1C2=CC(C1)=CC=C2C3=C1N=C(C#N)C(C#N)=N3 | Colombo, M., et al. (2010). "Synthesis and biological evaluation of 9-oxo-9H-indeno[1,2-b pyrazine-2,3-dicarbonitrile analogues as potential inhibitors of deubiquitinating enzymes." *ChemMedChem* 5(4): 552-558. |
|  | Spongi-acidin A | 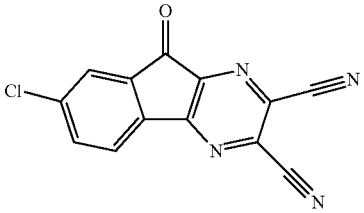<br>O=C1C2=CC(C1)=CC=C2C3=C1N=C(C#N)C(C#N)=N3 | Yamaguchi, M., et al. (2013). "Spongiacidin C, a pyrrole alkaloid from the marine sponge Stylissa massa, functions as a USP7 inhibitor." Bioorg Med Chem Lett 23(13): 3884-3886. |
|  | Petro-quinones | 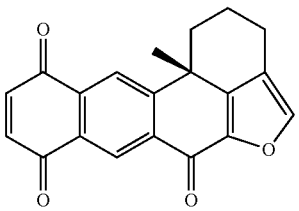<br>O=C(C1=C2[C@@]3(C)CCCC2=CO1)C(C3=C4)=CC5=C4C(C=CC5=O)=O | Tanokashira, N., et. al. (2016). "Petroquinones: trimeric and dimeric xestoquinone derivatives isolated from the marine sponge *Petrosia alfiani.*" *Tetrahedron* 72 (35): 5530-5540. |
|  | Compound 2 | 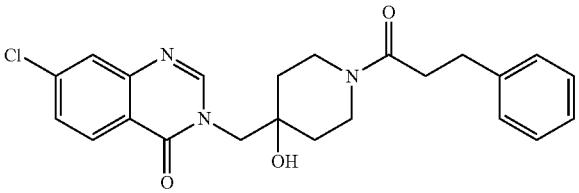<br>O=C1N(CC2(O)CCN(C(CCC3=CC=CC=C3)=O)CC2)C=NC4=CCC(Cl)=CC=C41 | Compound 2 - WO2013030218; Analogs - WO20160185785, WO20160185786, WO2016126926, WO2016126929, WO2016126935. |

TABLE 8-continued

| Reported Target | Compound ID | Structure | Reference |
|---|---|---|---|
| USP7 & USP8 | HY50736/ Compound 16 | N#CCC1=NC2=C(N=C1C#N)/C(C3=CC=CC=C32)=N/OCC4=CC=CC=C4 | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| | HY-50737A | CCO/N=C1C2=CC=CC=C2C3=C\1N=C(C(C#N)C(C#N)=N3 | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| USP7 & USP47 | P5091 | ClC1=C(Cl)C=CC=C1SC2=C([N+]([O-])=O)C=C(C(C)=O)S2 | Chauhan D, et al. Cancer Cell, 2012, 22(3), 345-358. |
| | P22077 | FC1=CC=C(SC2=C([N+]([O-])=O)C=C(C(C)=O)S2)C(F)=C1 | Tian X, et al. Assay Drug Dev Technol, 2011, 9(2), 165-173. Ritorto, M. S. et al. Screening of DUB activity and specificity by MALDI-TOF mass spectrometry. Nature communications 5, 4763, doi:10.1038/ncomms 5763 (2014). |

TABLE 8-continued

| Reported Target | Compound ID | Structure | Reference |
|---|---|---|---|
| | 1247825-37-1 | 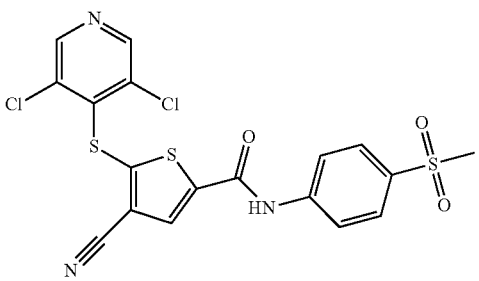<br>O=C(CNC1=CC=C(S(=O)(C)=C1)C2=CC(C#N)=C(SC3=C(Cl)C=NC=C3Cl)S2 | Weinstock, J., Wu, J., Cao, P., Kingsbury, W. D., McDermott, J. L., Kodrasov, M. P., McKelvey, D. M., Suresh Kumar, K. G., Goldenberg, S. J., Mattern, M. R., and Nicholson, B. (2012) *ACS medicinal chemistry letters* 3, 789-792 |
| USP10 & USP13 | Spautin-1 | 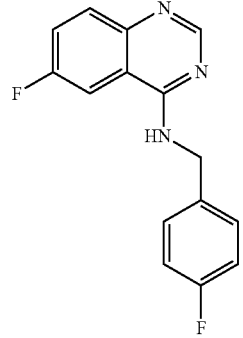<br>FC1=CC=C(N=CN=C2NCC3=CC=C(F)C=C3)C2=C1 | Liu, J., Xia, H., Kim, M., Xu, L., Li, Y., Zhang, L., Cai, Y., Norberg, H. V., Zhang, T., Furuya, T., Jin, M., Zhu, Z., Wang, H., Yu, J., Hao, Y., Choi, A., Ke, H., Ma, D., and Yuan, J. (2011) *Cell* 147, 223-234 |

The term "sensitize" means to alter cancer cells or tumor cells in a way that allows for more effective treatment of the associated cancer with a cancer therapy (e.g., USP10 inhibitors either alone or in combination with FLT3 inhibitors; chemotherapeutic; and/or radiation therapy). In some embodiments, normal cells are not affected to an extent that causes the normal cells to be unduly injured by the anticancer therapy (e.g., USP10 inhibitors either alone or in combination with FLT3 inhibitors). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more therapeutic agents, such as two or more USP10 inhibitors, a USP10 inhibitor and a FLT3 inhibitor, USP10 inhibitors either alone or in combination with FLT3 inhibitors, and the like, can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. Cancer cell death can be promoted by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in cancer cell numbers and/or a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

The term "USP10" refers to Ubiquitin Specific Peptidase 10, as a member of the ubiquitin-specific protease family of cysteine proteases and is alternatively known as "Ubiquitin-Specific-Processing Protease 10," "Ubiquitin Specific Protease 10," "Deubiquitinating Enzyme 10," "Ubiquitin Thioesterase 10," "Ubiquitin Thiolesterase 10," "Ubiquitin carboxyl-terminal hydrolase 10," "EC 3.4.19.12," "KIAA0190," "UBPO," and "UBPO 3." In general, USP10 contains an Ataxin-2 C-terminal domain and a deubiquitylating enzyme (DUB) domain. USP10 belongs to the largest family of DUB enzymes referred to as the ubiquitin specific protease (USP) family. This family is comprised of 56 cysteine protease members that are most well known for their ability to remove post-translational ubiquitin tags that mark substrates for proteosomal degradation thereby resulting in stabilization of the substrate. The reported substrates of USP10 include Beclin 1 (Liu et al. (2011) Cell 147:223-234), CFTR (Bomberger et al. (2009) J. Biol. Chem. 284: 18778-18789), and p53 (Yuan et al. (2010) Cell 140:384-396). USP10 is ubiquitously expressed and, as is true for many DUBs, may have diverse functions depending of the cellular context. For example, USP10 functions as a cofactor of the DNA-bound androgen receptor complex, and is inhibited by Ras-GAP SH3 domain binding protein (G3BP) in the Ras-GTPase pathway (Faus et al. (2005) *Mol. Cell Endocrinol.* 245:138-146; Soncini et al. (2001) *Oncogene* 20:3869-3879).

Nucleic acid and amino acid sequence for USP10 nucleic acids and protein are well-known in the art and are publicly available in the GenBank database maintained by the U.S. National Center for Biotechnology Information. For example, human USP10 nucleic acid sequences are well-known and include, for example, NM_001272075.1 (variant 1, representing the longest transcript and encoding the longest isoform 1) and NM_005153.2 (variant 2, which lacks an alternate exon in the 5' end compared to variant 1). Isoform 2 encoded by variant 2 has a shorter and distinct N-terminus compared to isoform 1). In addition, NR_073577 (transcript variant 3), lacks three alternate internal exons as compared to variant 1. This variant is non-coding due to the presence of an upstream ORF that is predicted to interfere with translation of the longest ORF. Translation of the upstream ORF renders the transcript a candidate for nonsense-mediated mRNA decay (NMD). NR_073578.1 (transcript variant 4), lacks four alternate internal exons, compared to variant 1. This variant is represented as non-coding due to the presence of two upstream ORFs that are predicted to interfere with translation of the longest ORF; translation of either of the upstream ORFs renders the transcript a candidate for nonsense-mediated mRNA decay (NMD)), and predicted sequences XM_017023869.1, XM_017023864.1, XM_011523441.1, XM_011523440.1, XM_017023868.1, XM_011523443.1, XM_017023863.1, XM_006721332.1, XM_017023867.1, XM_017023865.1, and XM_017023866.1. Human FLT3 amino acid sequences are well-known and include, for example, NP_001259004.1 (isoform 1), NP_005144.2 (isoform 2) and predicted sequences XP_016879358.1, XP_016879353.1, XP_011521743.1, XP_011521742.1, XP_016879357.1, XP_011521745.1, XP_016879352.1, XP_006721395.1, XP_016879356.1, XP_016879354.1 and XP_0168793551

Nucleic acid and amino acid sequence for USP10 orthologs in other species are also well-known and include, for example, chimpanzee (*Pan troglodytes*) USP10 (XM_016930295.1 and XP_016785784.1, XM_009431337.2 and XP_009429612.2); rhesus monkey (*Macaca mulatta*) USP10 (1XM_015126723.1 and XP_014982209.1, XM_015126724.1 and XP_014982210.1); dog (*Canis lupus familiaris*) USP10 (XM_005620883.1 and XP_005620940.1); cattle (*Bos taurus*) USP10 (BC142223.1 and AAI42224.1); mouse (*Mus musculus*) USP10 (NM_001310630.1 and NP_001297559.1, NM_009462.2 and NP_033488.1, XM_006530845.3 and XP_006530908.1, XM_006530846.3 and XP_006530909.1); rat (*Rattus norvegicus*) USP10 (NM_001034146.1 and NP_001029318.1, XM_008772609.2 and XP_008770831.1, XM_008772610.2 and XP_008770832.1, BC105892.1 and AA105893.1); chicken (*Gallus gallus*) USP10 (NM_001006130.1 and NP_001006130.1, AJ720400.1 and CAG32059.1); tropical clawed frog (*Xenopus tropicalis*) USP10 (NM_001006760.1 and NP_001006761.1, XM_012960855.2 and XP_012816309.2, XM_018092993.1 and XP_017948482.1, BC075544.1 and AAH75544.1, CR855702.2 and CAJ83514.1); and zebrafish (*Danio rerio*) USP10 (XM_005169052.3 and XP_005169109.1, XM_005169051.3 and XP_005169108.1, XM_680529.8 and XP_685621.5).

Inhibitors of USP10 are also well-known in the art and include, spautin-1 (specific and potent autophagy inhibitor-1), a derivative of MBCQ that binds to USP10 and inhibits deubiquitinase activity. Various anti-USP10 antibodies are commercially available recognizing the N-terminus, C-terminus, or internal region of USP10.

USP10 variants and mutations are also well-known and include, for example, a T-to-A substitution at position 42 of SEQ ID NO: 4 which, when combined with an S-to-A substitution at position 337 of SEQ ID NO: 4, abolishes its phosphorylation by Ataxia telangiectasia mutated (ATM) (Yuan et al., 2010); a T-to-E substitution at position 42 of SEQ ID NO: 4 which, when combined with an S-to-D substitution at position 337 of SEQ ID NO: 4, results in a Phospho-mimetic mutant that translocates to the nucleus in absence of genotoxic stress (Yuan et al., 2010); a C-to-A substitution at position 424 of SEQ ID NO: 4 which abolishes its de-ubiquitinating activity (Soncini et al., 2001). Similarly, acetylation at position 2 of SEQ ID NO: 4 and phosphorylation at positions 24, 42, 100, 211, 226, 321, 337, 365, 370, 547, 563, and 576 of SEQ ID NO: 4 (Bian, et al., J. Proteomics 96:253-262(2014) Olsen et al., (2010). *Sci. Signal.* 3:RA3-RA3; Yuan et al., 2010), is knownto occur. Post-translation, USP10 is phosphorylated by ATM following DNA damage, leading to stablization and translocation it to the nucleus (Yuan et al., 2010). USP10 can be deubiquitinated by USP13 (Liu et al., 2011).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention and related biomarkers (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

Representative sequences of the biomarkers described above are presented below in Tables 1 and 2. It is to be noted that the terms described above can further be used to refer to any combination of features described herein regarding the biomarkers. For example, any combination of sequence composition, percentage identify, sequence length, domain structure, functional activity, etc. can be used to describe a biomarker of the present invention.

TABLE 1

```
SEQ ID NO: 1 Human USP10 cDNA sequence (transcript variant 1)
(NM_001272075.1)
    1    ctccccgcgc cccgcggcgc gcggccagtg cgcaggcgcg gcggccgatg cgagtgtgta 61    tgtgcgggcg agaagatggc ggcggcgggg gaagcagcgt gagcagccgg aggatcgcgg 121    agtcccaatg aaacgggcag ccatggccct ccacagcccg cagctcctgg gccatgatcc 181    cattttcatc agatgacttg agaacccaga agctctacca gcactgccat tctgtcccgt 241    cttgaaacat catgccctgg ttgccctctc ctggaatagg gcagtatatt tttggagatt 301    ttagccctga tgaattcaat caattctttg tgactcctcg atcttcagtt gagcttcctc 361    catacagtgg aacagttctg tgtggcacac aggctgtgga taaactacct gatggacaag 421    aatatcagag aattgagttt ggtgtcgatg aagtcattga acccagtgac actttgccga 481    gaaccccag ctacagtatt tcaagcacac tgaaccctca ggcccctgaa tttattctcg 541    gttgtacagc ttccaaaata acccctgatg gtatcactaa agaagcaagc tatggctcca 601    tcgactgcca gtacccaggc tctgccctcg ctttggatgg aagttctaat gtggaggcgg 661    aagttttgga aaatgatggt gtctcaggtg gtcttggaca aagggagcgt aaaaagaaga 721    aaaagcggcc acctggatat tacagctatt tgaaagatgg tggcgatgat agtatctcca 781    cagaagccct ggtcaatggc catgccaatt cagcagtccc gaacagtgtc agtgcagagg 841    atgcagaatt tatgggtgac atgccccgt cagttacgcc caggacttgt aacagccccc 901    agaactccac agactctgtc agtgacattg tgcctgacag tcctttcccc ggagcactcg 961    gcagtgacac caggactgca gggcagccag agggggggccc cggggctgat tttggtcagt 1021    cctgcttccc tgcagaggct ggcagagaca ccctgtcaag gacagctggg gctcagccct 1081    gcgttggtac cgatactact gaaaaccttg gagttgctaa tggacaaata cttgaatcct 1141    cgggtgaggg cacagctacc aacgggggtgg agttgcacac cacggaaagc atagacttgg 1201    acccaaccaa acccgagagt gcatcacctc ctgctgacgg cacgggctct gcatcaggca 1261    cccttcctgt cagccagccc aagtcctggg ccagcctctt tcatgattct aagccctctt 1321    cctcctcgcc ggtggcctat gtggaaacta agtattcccc tcccgccata tctcccctgg 1381    tttctgaaaa gcaggttgaa gtcaaagaag ggcttgttcc ggtttcagag gatcctgtag 1441    ccataaagat tgcagagttg ctggagaatg taaccctaat ccataaacca gtgtcgttgc 1501    aaccccgtgg gctgatcaat aaagggaact ggtgctacat taatgctaca ctgcaggcat 1561    tggttgcttg cccgccgatg taccacctga tgaagttcat tcctctgtat tccaaagtgc 1621    aaaggccttg tacgtcaaca cccatgatag acagctttgt tcggctaatg aatgagttca 1681    ctaatatgcc agtacctcca aaaccccgac aagctcttgg agataaaatc gtgagggata 1741    ttcgccctgg agctgccttt gagcccacat atatttacag actcctgaca gttaacaagt 1801    caagcctgtc tgaaaagggt cgacaagaag atgctgagga atacttaggc ttcattctaa
```

TABLE 1-continued

```
1861    atggacttca tgaggaaatg ttgaacctaa agaagcttct ctcaccaagt aatgaaaaac
1921    ttacgatttc caacggcccc aaaaaccact cggtcaatga agaagagcag gaagaacaag
1981    gtgaaggaag cgaggatgaa tgggaacaag tgggcccccg gaacaagact tccgtcaccc
2041    gccaggcgga ttttgttcag actccaatca ccggcatttt tggtggacac atcaggtctg
2101    tggtttacca gcagagttca aaagaatctg ccactttgca gccattttc acgttgcagt
2161    tggatatcca gtcagacaag atacgcacag tccaggatgc actggagagc ttggtggcaa
2221    gagaatctgt ccaaggttat accacaaaaa ccaaacaaga ggttgagata agtcgaagag
2281    tgactctgga aaaactccct cctgtcctcg tgctgcacct gaaacgattc gtttatgaga
2341    agactggtgg gtgccagaag cttatcaaaa atattgaata tcctgtggac ttggaaatta
2401    gtaaagaact gctttctcca ggggttaaaa ataagaattt taaatgccac cgaacctatc
2461    ggctctttgc agtggtctac catcacggca acagtgcgac gggcggccat tacactacag
2521    acgtcttcca gatcggtctg aatggctggc tgcgcatcga tgaccagaca gtcaaggtga
2581    tcaaccagta ccaggtggtg aaaccaactg ctgaacgcac agcctacctc ctgtattacc
2641    gccgagtgga cctgctgtaa accctgtgtg cgctgtgtgt gcgcccagtg cccgcttcgt
2701    aggacaccac ctcacactca cttcccgcct ctctttagtg gctctttaga gagaaactct
2761    ttctcccttt gcaaaaatgg gctagaatga aaggagatg ccttggggtt cgtgcacaac
2821    acagcttctg ttgactctaa cttccaaatc aaaatcattt ggttgaaaca gactgttgct
2881    tgattttaga aaatacacaa aaacccatat ttctgaaata atgctgattc ctgagataag
2941    aaagtggatt tgatccccag tctcattgct tagtagaata atcctgcac cagcaacaac
3001    acttgtaaat ttgtgaaaat gaattttatc tttccttaaa aagaaattt tttaatccat
3061    cacactttc ttccctaccc tttagttttt gataaatgat aaaaatgagc cagttatcaa
3121    agaagaacta gttcttactt caaaagaaaa ataaacataa aaataagtt gctggttcct
3181    aacaggaaaa attttaataa ttgtactgag agaaactgct tacgtacaca ttgcagatca
3241    aatatttgga gttaaaatgt tagtctacat agatgggtga ttgtaacttt attgccatta
3301    aaagatttca aattgcattc atgcttctgt gtacacataa tgaaaaatgg gcaaataatg
3361    aagatctctc cttcagtctg ctctgtttaa ttctgctgtc tgctcttctc taatgctgcg
3421    tccctaattg tacacagttt agtgatatct aggagtataa agttgtcgcc catcaataaa
3481    aatcacaaag ttggtttaaa aaaaaaaaaa aaaaaaaaa
```

SEQ ID NO: 2 Human USP10 amino acid (isoform 1) (NP_001259004.1)
```
  1    mpwlpspgig qyifgdfspd efnqffvtpr ssvelppysg tvlcgtqavd klpdgqeyqr
 61    iefgvdevie psdtlprtps ysisstlnpq apefilgcta skitpdgitk easygsidcq
121    ypgsalaldg ssnveaevle ndgvsgglgq rerkkkkkrp pgyysylkdg gddsisteal
181    vnghansavp nsysaedaef mgdmppsvtp rtcnspqnst dsysdivpds pfpgalgsdt
241    rtagqpeggp gadfgqscfp aeagrdtlsr tagaqpcvgt dttenlgvan gqilessgeg
301    tatngvelht tesidldptk pesasppadg tgsasgtlpv sqpkswaslf hdskpssssp
361    vayvetkysp paisplvsek qvevkeglvp vsedpvaiki aellenvtli hkpvslqprg
421    linkgnwcyi natlqalvac ppmyhlmkfi plyskvqrpc tstpmidsfv rlmneftnmp
481    vppkprqalg dkivrdirpg aafeptyiyr lltvnkssls ekgrqedaee ylgfilnglh
541    eemlnlkkll spsnekltis ngpknhsvne eeqeqgegs edeweqvgpr nktsvtrqad
601    fvqtpitgif gghirsvvyq qsskesatlq pfftlqldiq sdkirtvqda leslvaresv
```

TABLE 1-continued

```
661  qgyttktkqe veisrrvtle klppvlvlhl krfvyektgg cqklikniey pvdleiskel
721  lspgvknknf kchrtyrlfa vvyhhgnsat gghyttdvfq iglngwlrid dqtvkvinqy
781  qvvkptaert ayllyyrrvd ll
```

SEQ ID NO: 3 Human USP10 cDNA (transcript variant 2) (NM_005153.2)
```
   1 ctccccgcgc cccgcggcgc gcggccagtg cgcaggcgcg gcggccgatg cgagtgtgta
  61 tgtgcgggcg agaagatggc ggcggcgggg gaagcagcgt gagcagccgg aggatcgcgg
 121 agtcccaatg aaacgggcag ccatggccct ccacagcccg cagtatattt ttggagattt
 181 tagccctgat gaattcaatc aattctttgt gactcctcga tcttcagttg agcttcctcc
 241 atacagtgga acagttctgt gtggcacaca ggctgtggat aaactacctg atggacaaga
 301 atatcagaga attgagtttg gtgtcgatga agtcattgaa cccagtgaca ctttgccgag
 361 aaccccccagc tacagtattt caagcacact gaaccctcag gcccctgaat ttattctcgg
 421 ttgtacagct tccaaaataa cccctgatgg tatcactaaa gaagcaagct atggctccat
 481 cgactgccag tacccaggct ctgccctcgc tttggatgga agttctaatg tggaggcgga
 541 agttttggaa atgatggtg tctcaggtgg tcttggacaa agggagcgta aaaagaagaa
 601 aaagcggcca cctggatatt acagctattt gaaagatggt ggcgatgata gtatctccac
 661 agaagccctg gtcaatggcc atgccaattc agcagtcccg aacagtgtca gtgcagagga
 721 tgcagaattt atgggtgaca tgccccgtc agttacgccc aggacttgta cagcccca
 781 gaactccaca gactctgtca gtgacattgt gcctgacagt cctttccccg gagcactcgg
 841 cagtgacacc aggactgcag ggcagccaga gggggggcccc ggggctgatt ttggtcagtc
 901 ctgcttccct gcagaggctg gcagagacac cctgtcaagg acagctgggg ctcagccctg
 961 cgttggtacc gatactactg aaaaccttgg agttgctaat ggacaaatac ttgaatcctc
1021 gggtgagggc acagctacca acgggggtgga gttgcacacc acggaaagca tagacttgga
1081 cccaaccaaa cccgagagtg catcacctcc tgctgacggc acgggctctg catcaggcac
1141 ccttcctgtc agccagccca gtcctgggc cagcctcttt catgattcta gccctcttc
1201 ctcctcgccg gtggcctatg tggaaactaa gtattcccct cccgccatat ctccctggt
1261 ttctgaaaag caggttgaag tcaaagaagg gcttgttccg gtttcagagg atcctgtagc
1321 cataaagatt gcagagttgc tggagaatgt aaccctaatc cataaaccag tgtcgttgca
1381 accccgtggg ctgatcaata aagggaactg gtgctacatt aatgctacac tgcaggcatt
1441 ggttgcttgc ccgccgatgt accacctgat gaagttcatt cctctgtatt ccaaagtgca
1501 aaggccttgt acgtcaacac ccatgataga cagctttgtt cggctaatga atgagttcac
1561 taatatgcca gtacctccaa aaccccgaca gctcttgga gataaaatcg tgagggatat
1621 tcgccctgga gctgcctttg agccacata tatttacaga ctcctgacag ttaacaagtc
1681 aagcctgtct gaaaagggtc gacaagaaga tgctgaggaa tacttaggct tcattctaaa
1741 tggacttcat gaggaaatgt tgaacctaaa gaagcttctc tcaccaagta atgaaaaact
1801 tacgatttcc aacgccccca aaaaccactc ggtcaatgaa gaagagcagg aagaacaagg
1861 tgaaggaagc gaggatgaat gggaacaagt gggcccccgg aacaagactt ccgtcacccg
1921 ccaggcggat tttgttcaga ctccaatcac cggcattttt ggtggacaca tcaggtctgt
1981 ggtttaccag cagagttcaa aagaatctgc cactttgcag ccattttca cgttgcagtt
2041 ggatatccag tcagacaaga tacgcacagt ccaggatgca ctggagagct tggtggcaag
2101 agaatctgtc caaggttata ccacaaaaac caaacaagag gttgagataa gtcgaagagt
2161 gactctggaa aaactccctc ctgtcctcgt gctgcacctg aaacgattcg tttatgagaa
```

TABLE 1-continued

```
2221    gactggtggg tgccagaagc ttatcaaaaa tattgaatat cctgtggact tggaaattag
2281    taaagaactg ctttctccag gggttaaaaa taagaatttt aaatgccacc gaacctatcg
2341    gctctttgca gtggtctacc atcacggcaa cagtgcgacg ggcggccatt acactacaga
2401    cgtcttccag atcggtctga atggctggct gcgcatcgat gaccagacag tcaaggtgat
2461    caaccagtac caggtggtga aaccaactgc tgaacgcaca gcctacctcc tgtattaccg
2521    ccgagtggac ctgctgtaaa ccctgtgtgc gctgtgtgtg cgcccagtgc ccgcttcgta
2581    ggacaccacc tcacactcac ttcccgcctc tctttagtgg ctctttagag agaaactctt
2641    tctccctttg caaaaatggg ctagaatgaa aaggagatgc cttggggttc gtgcacaaca
2701    cagcttctgt tgactctaac ttccaaatca aaatcatttg gttgaaacag actgttgctt
2761    gattttagaa aatacacaaa aacccatatt tctgaaataa tgctgattcc tgagataaga
2821    aagtggattt gatcccccagt ctcattgctt agtagaataa atcctgcacc agcaacaaca
2881    cttgtaaatt tgtgaaaatg aatttatct ttccttaaaa aagaaatttt ttaatccatc
2941    acactttcct tccctaccct ttagttttg ataaatgata aaaatgagcc agttatcaaa
3001    gaagaactag ttcttacttc aaaagaaaaa taaacataaa aataagttg ctggttccta
3061    acaggaaaaa ttttaataat tgtactgaga gaaactgctt acgtacacat tgcagatcaa
3121    atatttggag ttaaaatgtt agtctacata gatgggtgat tgtaacttta ttgccattaa
3181    aagatttcaa attgcattca tgcttctgtg tacacataat gaaaaatggg caaataatga
3241    agatctctcc ttcagtctgc tctgtttaat tctgctgtct gctcttctct aatgctgcgt
3301    ccctaattgt acacagttta gtgatatcta ggagtataaa gttgtcgccc atcaataaaa
3361    atcacaaagt tggtttaaaa aaaaaaaaaa aaaaaaaaa
```

SEQ ID NO: 4 Human USP10 amino acid (isoform 2) (NP_005144.2)
```
  1    malhspqyif gdfspdefnq ffvtprssve lppysgtvlc gtqavdklpd gqeyqriefg
 61    vdeviepsdt lprtpsysis stlnpqapef ilgctaskit pdgitkeasy gsidcqypgs
121    alaldgssnv eaevlendgv ssglgqrerk kkkkrppgyy sylkdggdds istealvngh
181    ansavpnsvs aedaefmgdm ppsvtprtcn spqnstdsvs divpdspfpg algsdtrtag
241    qpeggpgadf gqscfpaeag rdtlsrtaga qpcvgtdtte nlgvangqil essgegtatn
301    gvelhttesi dldptkpesa sppadgtgsa sgtlpvsqpk swaslfhdsk psssspvayv
361    etkysppais plvsekqvev keglvpvsed pvaikiaell envtlihkpv slqprglink
421    gnwcyinatl qalvacppmy hlmkfiplys kvqrpctstp midsfvrlmn eftnmpvppk
481    prqalgdkiv rdirpgaafe ptyiyrlltv nksslsekgr qedaeeylgf ilnglheeml
541    nlkkllspsn ekltisngpk nhsvneeeqe eqgegsedew eqvgprnkts vtrqadfvqt
601    pitgifgghi rsvvyqqssk esatlqpfft lqldiqsdki rtvqdalesl varesvqgyt
661    tktkqeveis rrvtleklpp vlvlhlkrfv yektggcqkl iknieypvdl eiskellspg
721    vknknfkchr tyrlfavvyh hgnsatgghy ttdvfqigln gwlriddqtv kvinqyqvvk
781    ptaertayll yyrrvdll
```

SEQ ID NO: 5 Human USP10 cDNA (transcript variant 3) (NR_073577.1)
```
  1    ctccccgcgc cccgcggcgc gcggccagtg cgcaggcgcg gcggccgatg cgagtgtgta
 61    tgtgcgggcg agaagatggc ggcggcgggg gaagcagcgt gagcagccgg aggatcgcgg
121    agtcccaatg aaacgggcag ccatggccct ccacagcccg cagtatattt ttggagattt
181    tagccctgat gaattcaatc aattctttgt gactcctcga tcttcagttg agagttgctg
241    gagaatgtaa ccctaatcca taaaccagtg tcgttgcaac cccgtgggct gatcaataaa
```

TABLE 1-continued

```
 301  gggaactggt gctacattaa tgctacactg caggcattgg ttgcttgccc gccgatgtac
 361  cacctgatga agttcattcc tctgtattcc aaagtgcaaa ggccttgtac gtcaacaccc
 421  atgatagaca gctttgttcg gctaatgaat gagttcacta atatgccagt acctccaaaa
 481  ccccgacaag ctcttggaga taaaatcgtg agggatattc gccctggagc tgcctttgag
 541  cccacatata tttacagact cctgacagtt aacaagtcaa gcctgtctga aaagggtcga
 601  caagaagatg ctgaggaata cttaggcttc attctaaatg gacttcatga ggaaatgttg
 661  aacctaaaga agcttctctc accaagtaat gaaaaactta cgatttccaa cggcccccaaa
 721  aaccactcgg tcaatgaaga agagcaggaa gaacaaggtg aaggaagcga ggatgaatgg
 781  gaacaagtgg gcccccggaa caagacttcc gtcacccgcc aggcggattt tgttcagact
 841  ccaatcaccg gcattttgg tggacacatc aggtctgtgg tttaccagca gagttcaaaa
 901  gaatctgcca ctttgcagcc attttcacg ttgcagttgg atatccagtc agacaagata
 961  cgcacagtcc aggatgcact ggagagcttg gtggcaagag aatctgtcca aggttatacc
1021  acaaaaacca acaagaggt tgagataagt cgaagagtga ctctggaaaa actccctcct
1081  gtcctcgtgc tgcacctgaa acgattcgtt tatgagaaga ctggtgggtg ccagaagctt
1141  atcaaaaata ttgaatatcc tgtggacttg gaaattagta aagaactgct ttctccaggg
1201  gttaaaaata agaattttaa atgccaccga acctatcggc tctttgcagt ggtctaccat
1261  cacggcaaca gtgcgacggg cggccattac actacagacg tcttccagat cggtctgaat
1321  ggctggctgc gcatcgatga ccagacagtc aaggtgatca accagtacca ggtggtgaaa
1381  ccaactgctg aacgcacagc ctacctcctg tattaccgcc gagtggacct gctgtaaacc
1441  ctgtgtgcgc tgtgtgtgcg cccagtgccc gcttcgtagg acaccacctc acactcactt
1501  cccgcctctc tttagtggct ctttagagag aaactctttc tccctttgca aaaatgggct
1561  agaatgaaaa ggagatgcct tggggttcgt gcacaacaca gcttctgttg actctaactt
1621  ccaaatcaaa atcatttggt tgaaacagac tgttgcttga ttttagaaaa tacacaaaaa
1681  cccatatttc tgaaataatg ctgattcctg agataagaaa gtggatttga tccccagtct
1741  cattgcttag tagaataaat cctgcaccag caacaacact tgtaaatttg tgaaaatgaa
1801  ttttatcttt ccttaaaaaa gaaattttt aatccatcac acttttcttc cctaccttt
1861  agtttttgat aaatgataaa aatgagccag ttatcaaaga gaactagtt cttacttcaa
1921  aagaaaaata aacataaaaa ataagttgct ggttcctaac aggaaaaatt ttaataattg
1981  tactgagaga aactgcttac gtacacattg cagatcaaat atttggagtt aaaatgttag
2041  tctacataga tgggtgattg taactttatt gccattaaaa gatttcaaat tgcattcatg
2101  cttctgtgta cacataatga aaaatgggca aataatgaag atctctcctt cagtctgctc
2161  tgtttaattc tgctgtctgc tcttctctaa tgctgcgtcc ctaattgtac acagtttagt
2221  gatatctagg agtataaagt tgtcgcccat caataaaaat cacaaagttg gtttaaaaaa
2281  aaaaaaaaaa aaaaaaa
```

SEQ ID NO: 6 Human USP10 cDNA (transcript variant 4) (NR_073578.1)
```
   1  ctccccgcgc cccgcggcgc gcggccagtg cgcaggcgcg gcggccgatg cgagtgtgta
  61  tgtgcgggcg agaagatggc ggcggcgggg gaagcagcgt gagcagccgg aggatcgcgg
 121  agtcccaatg aaacgggcag ccatggccct ccacagcccg cagtatattt ttggagattt
 181  tagccctgat gaattcaatc aattctttgt gactcctcga tcttcagttg aggacaagaa
 241  tatcagagaa ttgagtttgg tgtcgatgaa gtcattgaac ccagtgacac tttgccgaga
```

TABLE 1-continued

| | | | | | |
|---|---|---|---|---|---|
| 301 | accccccagct | acagtatttc | aagcacactg | aaccctcagg | ccctgaatt | tattctcggt |
| 361 | tgtacagctt | ccaaaataac | ccctgatggt | atcactaaag | aagcaagcta | tggctccatc |
| 421 | gactgccagt | acccaggctc | tgccctcgct | ttggatggaa | gttctaatgt | ggaggcggaa |
| 481 | gttttggaaa | atgatggtgt | ctcaggtggt | cttggacaaa | gggagcgtaa | aagaagaaa |
| 541 | aagcggccac | ctggatatta | cagctatttg | aaagatggtg | gcgatgatag | tatctccaca |
| 601 | gaagccctgg | tcaatggcca | tgccaattca | gcagtcccga | acagtgtcag | tgcagaggat |
| 661 | gcagaattta | tgggtgacat | gccccgtca | gttacgccca | ggacttgtaa | cagcccccag |
| 721 | aactccacag | actctgtcag | tgacattgtg | cctgacagtc | ctttccccgg | agcactcggc |
| 781 | agtgacacca | ggactgcagg | gcagccagag | ggggccccg | ggctgattt | tggtcagtcc |
| 841 | tgcttccctg | cagaggctgg | cagagacacc | ctgtcaagga | cagctgggc | tcagccctgc |
| 901 | gttggtaccg | atactactga | aaaccttgga | gttgctaatg | acaaatact | tgaatcctcg |
| 961 | ggtgagggca | cagctaccaa | cggggtggag | ttgcacacca | cggaaagcat | agacttggac |
| 1021 | ccaaccaaac | ccgagagtgc | atcacctcct | gctgacggca | cgggctctgc | atcaggcacc |
| 1081 | cttcctgtca | gccagcccaa | gtcctgggcc | agcctctttc | atgattctaa | gccctcttcc |
| 1141 | tcctcgccgg | tggcctatgt | ggaaactaag | tattcccctc | ccgccatatc | tccctggtt |
| 1201 | tctgaaaagc | aggttgaagt | caaagaaggg | cttgttccgg | tttcagagga | tcctgtagcc |
| 1261 | ataaagattg | cagtgttcgg | ctaatgaatg | agttcactaa | tatgccagta | cctccaaaac |
| 1321 | cccgacaagc | tcttggagat | aaaatcgtga | gggatattcg | ccctggagct | gcctttgagc |
| 1381 | ccacatatat | ttacagactc | ctgacagtta | acaagtcaag | cctgtctgaa | aagggtcgac |
| 1441 | aagaagatgc | tgaggaatac | ttaggcttca | ttctaaatgg | acttcatgag | gaaatgttga |
| 1501 | acctaaagaa | gcttctctca | ccaagtaatg | aaaaacttac | gatttccaac | ggccccaaaa |
| 1561 | accactcggt | caatgaagaa | gagcaggaag | aacaaggtga | aggaagcgag | gatgaatggg |
| 1621 | aacaagtggg | cccccggaac | aagacttccg | tcacccgcca | ggcggatttt | gttcagactc |
| 1681 | caatcaccgg | cattttggt | ggacacatca | ggtctgtggt | ttaccagcag | agttcaaaag |
| 1741 | aatctgccac | tttgcagcca | tttttcacgt | tgcagttgga | tatccagtca | gacaagatac |
| 1801 | gcacagtcca | ggatgcactg | gagagcttgg | tggcaagaga | atctgtccaa | ggttatacca |
| 1861 | caaaaccaa | acaagaggtt | gagataagtc | gaagagtgac | tctggaaaaa | ctccctcctg |
| 1921 | tcctcgtgct | gcacctgaaa | cgattcgttt | atgagaagac | tggtgggtgc | agaagctta |
| 1981 | tcaaaaatat | tgaatatcct | gtggacttgg | aaattagtaa | agaactgctt | tctccagggg |
| 2041 | ttaaaaataa | gaattttaaa | tgccaccgaa | cctatcggct | ctttgcagtg | gtctaccatc |
| 2101 | acggcaacag | tgcgacgggc | ggccattaca | ctacagacgt | cttccagatc | ggtctgaatg |
| 2161 | gctggctgcg | catcgatgac | cagacagtca | aggtgatcaa | ccagtaccag | gtggtgaaac |
| 2221 | caactgctga | acgcacagcc | tacctcctgt | attaccgccg | agtggacctg | ctgtaaaccc |
| 2281 | tgtgtgcgct | gtgtgtgcgc | ccagtgcccg | cttcgtagga | caccacctca | cactcacttc |
| 2341 | ccgcctctct | ttagtggctc | tttagagaga | aactcttct | ccttttgcaa | aaatgggcta |
| 2401 | gaatgaaaag | gagatgcctt | ggggttcgtg | cacaacacag | cttctgttga | ctctaacttc |
| 2461 | caaatcaaaa | tcatttggtt | gaaacagact | gttgcttgat | tttagaaaat | acacaaaaac |
| 2521 | ccatatttct | gaaataatgc | tgattcctga | gataagaaag | tggatttgat | ccccagtctc |
| 2581 | attgcttagt | agaataaatc | ctgcaccagc | aacaacactt | gtaaattgt | gaaaatgaat |
| 2641 | tttatctttc | cttaaaaaag | aaattttta | atccatcaca | cttttcttcc | ctacccttta |

TABLE 1-continued

| | | | | | |
|---|---|---|---|---|---|
| 2701 | gtttttgata | aatgataaaa | atgagccagt | tatcaaagaa | gaactagttc ttacttcaaa |
| 2761 | agaaaaataa | acataaaaaa | taagttgctg | gttcctaaca | ggaaaaattt taataattgt |
| 2821 | actgagagaa | actgcttacg | tacacattgc | agatcaaata | tttggagtta aaatgttagt |
| 2881 | ctacatagat | gggtgattgt | aactttattg | ccattaaaag | atttcaaatt gcattcatgc |
| 2941 | ttctgtgtac | acataatgaa | aaatgggcaa | ataatgaaga | tctctccttc agtctgctct |
| 3001 | gtttaattct | gctgtctgct | cttctctaat | gctgcgtccc | taattgtaca cagtttagtg |
| 3061 | atatctagga | gtataaagtt | gtcgcccatc | aataaaaatc | acaagttgg tttaaaaaaa |
| 3121 | aaaaaaaaaa | aaaaaa | | | |

*Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

TABLE 2

SEQ ID NO: 7 Human FLT3 mRNA sequence (transcript variant 1; NM_0041192)

| | | | | | |
|---|---|---|---|---|---|
| 1 | acctgcagcg | cgaggcgcgc | cgctccaggc | ggcatcgcag | ggctgggccg gcgcggcctg |
| 61 | gggaccccgg | gctccggagg | ccatgccggc | gttggcgcgc | gacggcggcc agctgccgct |
| 121 | gctcgttgtt | ttttctgcaa | tgatatttgg | gactattaca | aatcaagatc tgcctgtgat |
| 181 | caagtgtgtt | ttaatcaatc | ataagaacaa | tgattcatca | gtggggaagt catcatcata |
| 241 | tcccatggta | tcagaatccc | cggaagacct | cggtgtgcg | ttgagacccc agagctcagg |
| 301 | gacagtgtac | gaagctgccg | ctgtggaagt | ggatgtatct | gcttccatca cactgcaagt |
| 361 | gctggtcgac | gccccaggga | acatttcctg | tctctgggtc | tttaagcaca gctccctgaa |
| 421 | ttgccagcca | catttttgatt | tacaaaacag | aggagttgtt | tccatggtca ttttgaaaat |
| 481 | gacagaaacc | caagctggag | aatacctact | ttttattcag | agtgaagcta ccaattacac |
| 541 | aatattgttt | acagtgagta | taagaaatac | cctgctttac | acattaagaa gaccttactt |
| 601 | tagaaaaatg | gaaaccagg | acgccctggt | ctgcatatct | gagagcgttc cagagccgat |
| 661 | cgtggaatgg | gtgctttgcg | attcacaggg | ggaaagctgt | aaagaagaa gtccagctgt |
| 721 | tgttaaaaag | gaggaaaaag | tgcttcatga | attatttggg | acggacataa ggtgctgtgc |
| 781 | cagaaatgaa | ctgggcaggg | aatgcaccag | gctgttcaca | atagatctaa atcaaactcc |
| 841 | tcagaccaca | ttgccacaat | tatttcttaa | agtagggaa | cccttatgga taaggtgcaa |
| 901 | agctgttcat | gtgaaccatg | gattcgggct | cacctgggaa | ttagaaaaca aagcactcga |
| 961 | ggagggcaac | tactttgaga | tgagtaccta | ttcaacaaac | agaactatga tacggattct |
| 1021 | gtttgcttt | gtatcatcag | tggcaagaaa | cgcaccgga | tactacactt gttcctcttc |
| 1081 | aaagcatccc | agtcaatcag | ctttggttac | catcgtagaa | aagggattta aaatgctac |
| 1141 | caattcaagt | gaagattatg | aaattgacca | atatgaagag | ttttgttttt ctgtcaggtt |
| 1201 | taaagcctac | ccacaaatca | gatgtacgtg | gaccttctct | cgaaaatcat tccttgtga |
| 1261 | gcaaaaggggt | cttgataacg | gatacagcat | atccaagttt | tgcaatcata gcaccagcc |
| 1321 | aggagaatat | atattccatg | cagaaaatga | tgatgcccaa | tttaccaaaa tgttcacgct |
| 1381 | gaatataaga | aggaaacctc | aagtgctcgc | agaagcatcg | gcaagtcagg cgtcctgttt |
| 1441 | ctcggatgga | tacccattac | catcttggac | ctggaagaag | tgttcagaca gtctcccaa |

TABLE 2-continued

```
1501  ctgcacagaa gagatcacag aaggagtctg aatagaaag gctaacagaa aagtgtttgg
1561  acagtgggtg tcgagcagta ctctaaacat gagtgaagcc ataaaagggt tcctggtcaa
1621  gtgctgtgca tacaattccc ttggcacatc ttgtgagacg atccttttaa actctccagg
1681  cccttccct ttcatccaag acaacatctc attctatgca acaattggtg tttgtctcct
1741  cttcattgtc gttttaaccc tgctaatttg tcacaagtac aaaaagcaat ttaggtatga
1801  aagccagcta cagatggtac aggtgaccgg ctcctcagat aatgagtact tctacgttga
1861  tttcagagaa tatgaatatg atctcaaatg ggagtttcca agagaaaatt tagagtttgg
1921  gaaggtacta ggatcaggtg cttttggaaa agtgatgaac gcaacagctt atggaattag
1981  caaaacagga gtctcaatcc aggttgccgt caaatgctg aagaaaaag cagacagctc
2041  tgaaagagag gcactcatgt cagaactcaa gatgatgacc cagctgggaa gccacgagaa
2101  tattgtgaac ctgctggggg cgtgcacact gtcaggacca atttacttga ttttgaata
2161  ctgttgctat ggtgatcttc tcaactatct aagaagtaaa agagaaaat tcacaggac
2221  ttggacagag attttcaagg aacacaattt cagttttac cccacttcc aatcacatcc
2281  aaattccagc atgcctggtt caagagaagt tcagatacac ccggactcgg atcaaatctc
2341  agggcttcat gggaattcat ttcactctga agatgaaatt gaatatgaaa accaaaaaag
2401  gctggaagaa gaggaggact tgaatgtgct tacatttgaa gatcttcttt gctttgcata
2461  tcaagttgcc aaaggaatgg aatttctgga atttaagtcg tgtgttcaca gagacctggc
2521  cgccaggaac gtgcttgtca cccacgggaa agtggtgaag atatgtgact ttggattggc
2581  tcgagatatc atgagtgatt ccaactatgt tgtcaggggc aatgcccgtc tgcctgtaaa
2641  atggatggcc cccgaaagcc tgtttgaagg catctacacc attaagagtg atgtctggtc
2701  atatggaata ttactgtggg aaatcttctc acttggtgtg aatccttacc ctggcattcc
2761  ggttgatgct aacttctaca aactgattca aaatggattt aaaatggatc agccatttta
2821  tgctacagaa gaaatataca ttataatgca atcctgctgg gcttttgact caaggaaacg
2881  gccatcctc cctaatttga cttcgttttt aggatgtcag ctggcagatg cagaagaagc
2941  gatgtatcag aatgtggatg gccgtgtttc ggaatgtcct cacacctacc aaaacaggcg
3001  acctttcagc agagagatgg atttggggct actctctccg caggctcagg tcgaagattc
3061  gtagaggaac aatttagttt taaggacttc atccctccac ctatccctaa caggctgtag
3121  attaccaaaa caagattaat ttcatcacta aaagaaaatc tattatcaac tgctgcttca
3181  ccagacttt ctctagaagc tgtctgcgtt tactcttgtt ttcaaaggga cttttgtaaa
3241  atcaaatcat cctgtcacaa ggcaggagga gctgataatg aactttattg gagcattgat
3301  ctgcatccaa ggccttctca ggctggcttg agtgaattgt gtacctgaag tacagtatat
3361  tcttgtaaat acataaaaca aaagcatttt gctaaggaga agctaatatg atttttaag
3421  tctatgtttt aaaataatat gtaaattttt cagctattta gtgatatatt ttatgggtgg
3481  gaataaaatt tctactacag aattgcccat tattgaatta tttacatggt ataattaggg
3541  caagtcttaa ctggagttca cgaaccccct gaaattgtgc acccatagcc acctacacat
3601  tccttccaga gcacgtgtgc ttttacccca agatacaagg aatgtgtagg cagctatggt
3661  tgtcacagcc taagatttct gcaacaacag gggttgtatt ggggggaagtt tataatgaat
3721  aggtgttcta ccataaagag taatacatca cctagacact ttggcggcct tcccagactc
3781  agggccagtc agaagtaaca tggaggatta gtattttcaa taaagttact cttgtcccca
3841  caaaaaaa
```

TABLE 2-continued

SEQ ID NO: 8 Human FLT3 amino acid sequence (transcript variant 1;
NP_004110.2)
```
   1  mpalardggq  lpllvvfsam  ifgtitnqdl  pvikcvlinh  knndssvgks  ssypmvsesp
  61  edlgcalrpq  ssgtvyeaaa  vevdvsasit  lqvlvdapgn  isclwvfkhs  slncqphfdl
 121  qnrgvvsmvi  lkmtetqage  yllfiqseat  nytilftvsi  rntllytlrr  pyfrkmenqd
 181  alvcisesvp  epivewvlcd  sqgesckees  pavvkkeekv  lhelfgtdir  ccarnelgre
 241  ctrlftidln  qtpqttlpql  flkvgeplwi  rckavhvnhg  fgltwelenk  aleegnyfem
 301  stystnrtmi  rilfafvssv  arndtgyytc  ssskhpsqsa  lvtivekgfi  natnssedye
 361  idqyeefcfs  vrfkaypqir  ctwtfsrksf  pceqkgldng  ysiskfcnhk  hqpgeyifha
 421  enddaqftkm  ftlnirrkpq  vlaeasasqa  scfsdgyplp  swtwkkcsdk  spncteeite
 481  gvwnrkanrk  vfgqwvssst  lnmseaikgf  lvkccaynsl  gtscetilln  spgpfpfiqd
 541  nisfyatigv  cllfivvltl  lichkykkqf  ryesqlqmvq  vtgssdneyf  yvdfreyeyd
 601  lkwefprenl  efgkvlgsga  fgkvmnatay  gisktgvsiq  vavkmlkeka  dssserealms
 661  elkmmtqlgs  henivnllga  ctlsgpiyli  feyccygdll  nylrskrekf  hrtwteifke
 721  hnfsfyptfq  shpnssmpgs  revqihpdsd  qisglhgnsf  hsedeieyen  qkrleeeedl
 781  nvltfedllc  fayqvakgme  flefkscvhr  dlaarnvlvt  hgkvvkicdf  glardimsds
 841  nyvvrgnarl  pvkwmapesl  fegiytiksd  vwsygillwe  ifslgvnpyp  gipvdanfyk
 901  liqngfkmdq  pfyateeiyi  imqscwafds  rkrpsfpnlt  sflgcqlada  eeamyqnvdg
 961  rvsecphtyq  nrrpfsremd  lgllspqaqv  eds
```
SEQ ID NO: 9 Human FLT3 mRNA sequence (transcript variant 2 (non-coding);
NR_130706.1)
```
    1  acctgcagcg  cgaggcgcgc  cgctccaggc  ggcatcgcag  ggctgggccg  gcgcggcctg
   61  gggaccccgg  gctccggagg  ccatgccggc  gttggcgcgc  gacggcggcc  agctgccgct
  121  gctcgttgtt  ttttctgcaa  tgatatttgg  gactattaca  aatcaagatc  tgcctgtgat
  181  caagtgtgtt  ttaatcaatc  ataagaacaa  tgattcatca  gtggggaagt  catcatcata
  241  tccatggta   tcagaatccc  cggaagacct  cgggtgtgcg  ttgagacccc  agagctcagg
  301  gacagtgtac  gaagctgccg  ctgtggaagt  ggatgtatct  gcttccatca  cactgcaagt
  361  gctggtcgac  gccccaggga  acatttcctg  tctctgggtc  tttaagcaca  gctccctgaa
  421  ttgccagcca  cattttgatt  tacaaaacag  aggagttgtt  tccatggtca  ttttgaaaat
  481  gacagaaacc  caagctggag  aatacctact  ttttattcag  agtgaagcta  ccaattacac
  541  aatattgttt  acagtgagta  taagaaatac  cctgctttac  acattaagaa  gaccttactt
  601  tagaaaaatg  gaaaaccagg  acgccctggt  ctgcatatct  gagagcgttc  cagagccgat
  661  cgtggaatgg  gtgctttgcg  attcacaggg  ggaaagctgt  aaagaagaaa  gtccagctgt
  721  tgttaaaaag  gaggaaaaag  tgcttcatga  attatttggg  acggacataa  ggtgctgtgc
  781  cagaaatgaa  ctgggcaggg  aatgcaccag  gctgttcaca  atagatctaa  atcaaactcc
  841  tcagaccaca  ttgccacaat  tatttcttaa  agtaggggaa  cccttatgga  taaggtgcaa
  901  agctgttcat  gtgaaccatg  gattcgggct  cacctgggaa  ttagaaaaca  aagcactcga
  961  ggagggcaac  tactttgaga  tgagtaccta  ttcaacaaac  agaactatga  tacggattct
 1021  gtttgctttt  gtatcatcag  tggcaagaaa  cgacaccgga  tactacactt  gttcctcttc
 1081  aaagcatccc  agtcaatcag  ctttggttac  catcgtagaa  aagggattta  taatgctac
 1141  caattcaagt  gaagattatg  aaattgacca  atatgaagag  ttttgttttt  ctgtcaggtt
 1201  taaagcctac  ccacaaatca  gatgtacgtg  gaccttctct  cgaaaatcat  tccttgtga
```

TABLE 2-continued

```
1261  gcaaaagggt cttgataacg gatacagcat atccaagttt tgcaatcata agcaccagcc
1321  aggagaatat atattccatg cagaaaatga tgatgcccaa tttaccaaaa tgttcacgct
1381  gaatataaga aggaaacctc aagtgctcgc agaagcatcg gcaagtcagg cgtcctgttt
1441  ctcggatgga tacccattac catcttggac ctggaagaag tgttcagaca agtctcccaa
1501  ctgcacagaa gagatcacag aaggagtctg aatagaaag gctaacagaa aagtgtttgg
1561  acagtgggtg tcgagcagta ctctaaacat gagtgaagcc ataaaagggt tcctggtcaa
1621  gtgctgtgca tacaattccc ttggcacatc ttgtgagacg atccttttaa actctccagg
1681  ccccttccct ttcatccaag acaacatctc attctatgca acaattggtg tttgtctcct
1741  cttcattgtc gttttaaccc tgctaatttg tcacaagtac aaaaagcaat ttaggtatga
1801  aagccagcta cagatggtac aggtgaccgg ctcctcagat aatgagtact tctacgttga
1861  tttcagagaa tatgaatatg atctcaaatg ggagtttcca agagaaaatt tagagtttgg
1921  gaaggtacta ggatcaggtg cttttggaaa agtgatgaac gcaacagctt atggaattag
1981  caaaacagga gtctcaatcc aggttgccgt caaaatgctg aaagaaaaag cagacagctc
2041  tgaaagagag gcactcatgt cagaactcaa gatgatgacc cagctgggaa gccacgagaa
2101  tattgtgaac ctgctggggg cgtgcacact gtcaggacca atttacttga tttttgaata
2161  ctgttgctat ggtgatcttc tcaactatct aagaagtaaa agagaaaaat tcacaggac
2221  ttggacagag attttcaagg aacacaattt cagtttttac cccactttcc aatcacatcc
2281  aaattccagt aaaaagaaat gagctttaca aaggcaaact ggaaaaaaga aggatggtga
2341  aacgcttacg ggactctcgg gaagatctgt attatgtgag ggaaagtggg ctgagttcag
2401  aaaccaaaga atgagatcga tcatgcctgg ttcaagagaa gttcagatac acccggactc
2461  ggatcaaatc tcagggcttc atgggaattc atttcactct gaagatgaaa ttgaatatga
2521  aaaccaaaaa aggctggaag aagaggagga cttgaatgtg cttacatttg aagatcttct
2581  ttgctttgca tatcaagttg ccaaaggaat ggaatttctg gaatttaagt cgtgtgttca
2641  cagagacctg gccgccagga acgtgcttgt cacccacggg aaagtggtga agatatgtga
2701  ctttggattg gctcgagata tcatgagtga ttccaactat gttgtcaggg caatgcccg
2761  tctgcctgta aaatggatgg ccccgaaag cctgtttgaa ggcatctaca ccattaagag
2821  tgatgtctgg tcatatggaa tattactgtg ggaaatcttc tcacttggtg tgaatcctta
2881  ccctggcatt ccggttgatg ctaacttcta caaactgatt caaaatggat ttaaaatgga
2941  tcagccattt tatgctacag aagaaatata cattataatg caatcctgct gggcttttga
3001  ctcaaggaaa cggccatcct tccctaattt gacttcgttt ttaggatgtc agctggcaga
3061  tgcagaagaa gcgatgtatc agaatgtgga tggccgtgtt tcggaatgtc ctcacaccta
3121  ccaaaacagg cgacctttca gcagagagat ggatttgggg ctactctctc cgcaggctca
3181  ggtcgaagat tcgtagagga acaatttagt tttaaggact tcatccctcc acctatccct
3241  aacaggctgt agattaccaa aacaagatta atttcatcac taaaagaaaa tctattatca
3301  actgctgctt caccagactt ttctctagaa gctgtctgcg tttactcttg ttttcaaagg
3361  gacttttgta aaatcaaatc atcctgtcac aaggcaggag gagctgataa tgaactttat
3421  tggagcattg atctgcatcc aaggccttct caggctggct tgagtgaatt gtgtacctga
3481  agtacagtat attcttgtaa atacataaaa caaaagcatt tgctaagga gaagctaata
3541  tgattttta agtctatgtt ttaaaataat atgtaaattt tcagctatt tagtgatata
3601  ttttatgggt gggaataaaa tttctactac agaattgccc attattgaat tatttacatg
```

TABLE 2-continued

```
3661    gtataattag ggcaagtctt aactggagtt cacgaacccc ctgaaattgt gcacccatag 3721    ccacctacac attccttcca gagcacgtgt gcttttaccc caagatacaa ggaatgtgta 3781    ggcagctatg gttgtcacag cctaagattt ctgcaacaac aggggttgta ttgggggaag 3841    tttataatga ataggtgttc taccataaag agtaatacat cacctagaca ctttggcggc 3901    cttcccagac tcagggccag tcagaagtaa catggaggat tagtattttc aataaagtta 3961    ctcttgtccc cacaaaaaaa
```

*Included in Table 2 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 2, or a portion thereof Such nucleic acid molecules can have a function of the full-length nucleic acid as described further herein.
*Included in Table 2 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 2, or a portion thereof. Such polypeptides can have a function of the full-length polypeptide as described further herein.
*Included in Table 2 are FLT3 mutants described below and/or in the Examples, particularly activating mutations that enhance FLT3 kinase activity to drive cancer, which are well-known. Such mutants include, for example, a Y-to-F substitution at position 589 of SEQ ID NO: 8, which reduces phosphorylation in response to ligand binding and abolishes activation of STAT5A, but has no effect on the phosphorylation of the constitutively activated mutant kinase variants (Kiyoi et al. (1998) Leukemia 12:1333-1337; Rocnik et al. (2006) Blood 108:1339-1345; Heiss et al., (2006) Blood 108:1542-1550); a Y-to-F substitution at position 591 of SEQ ID NO: 8, which abolishes activation of STAT5A but has no significant effect on tyrosine phosphorylation (Kiyoi et at., 1998; Rocnik et al., 2006); a Y-to-F substitution at position 599 of SEQ ID NO: 8, which abolishes its interaction with PTPN11/SHP2 and phosphorylation of PTPN11/SHP2 (Heiss et al., 2006); and a K-to-A substitution at position 644 of SEQ ID NO: 8, which abolishes its kinase activity.

The potential amino acid modifications of FLT3 are also well known and include, for example, disulfide bonds at positions 35/65, 103/114, 199/206, 232/241, 272/330, 368/407, and 381/392 of SEQ ID NO: 8, glycosylations at positions of 43, 100, 151, 306, 323, 351, 354, 473, 502, and 541 of SEQ ID NO: Band phosphorylation at positions 572, 574, 589, 591, 599, 726, 759, 768, 793, 842, 955, 969, and 993 of SEQ ID NO: 8 (Verstraete et al. (2011) Blood 118:60-68; Heiss et al., 2006; Arora et al. (2011) J. Biol. Chem. 286:10918-10929; Razumovskaya et al. (2009) Exp. Hematol. 37:979-989; Schmidt-Arras et al. (2005) Mol. Cell Biol. 25:3690-3703; Rocnik et al., 2006; Oppermann et al. (2009) Mol. Cell Proteomics 8:1751-1764).

Post-translational modifications for FLT3 include, for example, N-glycosylation with complex N-glycans with sialic acid (Schmidt-Arras et al., 2005; Arora et al., 2011; Verstraete et al., 2011), autophosphorylation on several tyrosine residues in response to FLT3LG binding (which also increases phosphorylation of mutant kinases that are constitutively activated), dephosphorylation by PTPRJ/DEP-1, PTPN1, PTPN6/SHP-1, and to a lesser degree by PTPN12 (dephosphorylation is important for FLT3 export from the endoplasmic reticulum and location at the cell membrane), and rapid ubiquitination by UBE2L6 and the E3 ubiquitin-protein ligase SIAH1 after autophosphorylation, leading to its proteasomal degradation (Buchwald et al. (2010) Leukemia 24:1412-1421; Arora et al., 2011).

Natural variants of human FLT3 amino acid sequence include, for example, a D-to-G variant at position 7, a V-to-A variant at position 158, a V-to-M variant at position 194, a T-to-M variant at position 227, a D-to-N variant at position 324, a D-to-V variant at position 358, a I-to-L variant at position 417, a V-to-I variant at position 557, a D-to-E, D-to-H, D-to-N, D-to-V, or D-to-Y variant at position 835, and a I-to-M variant at position 836 of SEQ ID NO: 8. Among these, the variants at position 835 was found in acute lymphoblastic leukemia patients and in acute myelogenous leukemia patients, where somatic mutations lead to constitutively activated FLT3 (Yamamoto et al. (2001) Blood 97:2434-2439; Taketani et al., (2004) Blood 103: 1085-1088; Abu-Duhier et al. (2001) Br. 1 Haematol 113: 983-988). The variant at position 836 was also found in acute lymphoblastic leukemia patients (Taketani et al., 2004).

Mutations in FLT3 have been found in patients with acute myeloid leukemia (AML). Although approximately 30% of AML patients harbor some form of FLT3 mutation, the clinical significance one of these genetic lesions in any given patient varies according to the nature of the mutation and the context in which it occurs. In general, FLT3 mutations can be divided into 2 categories: (1) internal tandem duplications (FLT3/ITD mutations) in or near the juxtamembrane domain of the receptor and (2) point mutations resulting in single amino acid substitutions occurring within the activation loop of the tyrosine kinase domain (FLT3/TKD mutations, e.g., on position 835 and/or 836 of SEQ ID NO: 8). In-frame internal tandem duplication (ITD) mutations of exons 14-15 have been noted in 15-30% of cases of AML. This elongates the juxtamembrane segment of flt-3 resulting in its dimerization and constitutive activation (Yokota et al., (1997) Leukemia 11:1605-1609). Such ITD mutations occur across FAB types and are particularly frequent in M3. They primarily occur in "intermediate risk" patients and are more frequent in adults than in children (Gilliland and Griffine, (2002) Blood 100:1532-1542). ITD mutations of FLT3 have been shown to be an independent poor prognostic factor in several studies (Schnittger et al., (2002) Blood 100:59-66; Thiede et al., (2002) Blood 99:4326-4335) and mutation status can delineate a "poor risk" group from a previously homogeneous "intermediate risk" group. Biallelic mutations are noted in approximately 10% and are associated with an even poorer outcome.

Additionally, point mutation of codon 835 of FLT3 has been reported in 7-8% of cases of de novo AML (Yamamoto et al., 2001). This mutation results in up-regulation of the function of the kinase domain, the prognostic significance of which is controversial. Such mutations have also been found in ALL associated with cytogenetic hyperdiploidy or abnormalities of MLL (Stubbs et al., (2008) *Leukemia* 22:66-77) as well as in myeloid sarcoma (Ansari-Lari et al., (2004) *Br. J. Haematol.* 126:785-791). Increasing numbers of tyrosine kinase domain mutations at other codons are being reported (Smith et al., (2005) *Br. J. Haematol.* 128:318-323). Reviews on, e.g., the association of FLT3 mutations with acute myeloid leukemia (e.g., with abnormal bone marrow eosinophils inv(16)(p13q22) or t(16; 16)(p13;q22), with t(8; 21)(q22;q22) translocation, and with or without maturation), acute biphenotypic leukemia, minimally differentiated acute myeloblastic leukemia, precursor B-cell acute lymphoblastic leukemia, and precursor T-cell acute lymphoblastic leukemia can be found on the website of Orphanet (with reference codes ORPHA98829, 102724, 98837, 98834, 98833, 98832, 99860, 99861, etc.).

II. Subjects

In one embodiment, the subject for whom cancer treatment is administered or who is predicted likelihood of efficacy of an anti-cancer therapy (e.g., at least one USP10 inhibitor, either alone or in combination with at least one FLT3 inhibitor) is determined, is a mammal (e.g., mouse, rat, primate, non-human mammal, domestic animal such as dog, cat, cow, horse), and is preferably a human.

In another embodiment of the methods of the invention, the subject has not undergone treatment, such as chemotherapy, radiation therapy, targeted therapy, and/or anti-cancer therapy (e.g., at least one USP10 inhibitor, either alone or in combination with at least one FLT3 inhibitor). In still another embodiment, the subject has undergone treatment, such as chemotherapy, radiation therapy, targeted therapy, and/or anti-cancer therapy (e.g., at least one USP10 inhibitor, either alone or in combination with at least one FLT3 inhibitor).

In certain embodiments, the subject has had surgery to remove cancerous or precancerous tissue, such as by blood compartment purification. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the invention can be used to determine the responsiveness to anti-cancer therapy (e.g., at least one USP10 inhibitor, either alone or in combination with at least one FLT3 inhibitor) of many different cancers in subjects such as those described above. In one embodiment, the cancers are hematologic cancers, such as leukemia. In another embodiment, the cancers are solid tumors, such as lung cancer, melanoma, and/or renal cell carcinoma. In another embodiment, the cancer is an epithelial cancer such as, but not limited to, brain cancer (e.g., glioblastomas), bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer.

III. Sample Collection, Preparation and Separation

In some embodiments, biomarker presence, absence, amount, and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples, such as the normal copy number, amount, or activity of a biomarker in the cell or tissue type of a member of the same species as from which the test sample was obtained or a non-diseased cell or tissue from the subject from which the test samples was obtained. As described herein, a "pre-determined" biomarker amount and/or activity measurement(s) may be a biomarker amount and/or activity measurement(s) used to, by way of example only, evaluate a subject that may be selected for treatment, evaluate a response to an anti-cancer therapy (e.g., at least one USP10 inhibitor, either alone or in combination with at least one FLT3 inhibitor), and/or evaluate a response to a combination anti-cancer therapy (e.g., at least one USP10 inhibitor, either alone or in combination with at least one FLT3 inhibitor, plus anti-immunoinhibitory therapy). A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., biomarker expression normalized to the expression of a housekeeping gene, or gene expression at various time points).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid molecule of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein.

A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci*, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198: 1056; Ike et al., 1983 *Nucleic Acid Res.* 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors for use in the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells)

include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number and/or Genomic Nucleic Acid Mutations

Methods of evaluating the copy number and/or genomic nucleic acid status (e.g., mutations) of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. In some embodiments, the dereased copy number of at least one biomarker listed in Table 1 is predictive of better outcome of USP10 inhibitor therapy (e.g., at least one USP10 inhibitor, either alone or in combination with at least one FLT3 inhibitor). A copy number of at least 3, 4, 5, 6, 7, 8, 9, or 10 of at least one biomarker listed in Table 1 is predictive of likely responsive to USP10 inhibitor therapy (e.g., at least one USP10 inhibitor, either alone or in combination with at least one FLT3 inhibitor).

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radio-isotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Biomarker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) *Curr. Top. Dev. Biol.* 36, 245 and Jena et al. (1996) *J. Immunol. Methods* 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences.

In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-cancer therapy (e.g., USP10 inhibitor therapy). Any method known in the art for detecting polypeptides can be used. Such methods include, but are not limited to, immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and MA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I) carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M, or $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify sequences or agents that affect translation of iron-sulfur cluster biosynthesis-related genes.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of anti-cancer therapy (e.g., at least one USP10 inhibitor, either alone or in combination with at least one FLT3 inhibitor) is predicted according to biomarker presence, absence, amount and/or activity associated with a cancer (e.g., cancer) in a subject according to the methods described herein. In one embodiment, such anti-cancer therapy (e.g., at least one USP10 inhibitor, either alone or in combination with at least one FLT3 inhibitor) or combinations of therapies (e.g., at least one USP10 inhibitor, either alone or in combination with at least one FLT3 inhibitor, and anti-immunoinhibitory therapies) can be administered to a desired subject or once a subject is indicated as being a likely responder to anti-cancer therapy (e.g., at least one USP10 inhibitor, either alone or in combination with at least one FLT3 inhibitor). In another embodiment, such anti-cancer therapy (e.g., at least one USP10 inhibitor, either alone or in combination with at least one FLT3 inhibitor) can be avoided once a subject is indicated as not being a likely responder to the anti-cancer therapy (e.g., at least one USP10 inhibitor, either alone or in combination with at least one FLT3 inhibitor) and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with or without anti-cancer therapy (e.g., at least one USP10 inhibitor, either alone or in combination with at least one FLT3 inhibitor).

The USP10 and exemplary agents useful for inhibiting the USP10, or other biomarkers described herein, have been described above.

The term "targeted therapy" refers to administration of agents that selectively interact with a chosen biomolecule to thereby treat cancer. For example, targeted therapy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-cancer therapy (e.g., at least one USP10 inhibitor, either alone or in combination with at least one FLT3 inhibitor) may vary according to the particular USP10 inhibitor agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to an anti-cancer therapy (e.g., at least one USP10 inhibitor, either alone or in combination with at least one FLT3 inhibitor), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., J. Clin. Oncol. (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular USP10 inhibitor therapeutic regimen is at least 25%, 30%, 35%, 40%, 45%, 50%, 55%, 60%, 65%, 70%, 75%, 80%, 85%, or more.

Additional criteria for evaluating the response to anti-cancer therapy (e.g., at least one USP10 inhibitor, either alone or in combination with at least one FLT3 inhibitor) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular USP10 inhibitor therapeutic regimen can be administered to a population of subjects and the outcome can be correlated to biomarker measurements that were determined prior to administration of any anti-cancer therapy (e.g., at least one USP10 inhibitor, either alone or in combination with at least one FLT3 inhibitor). The outcome measurement may be pathologic response to therapy given in the neoadjuvant setting. Alternatively, outcome measures, such as overall survival and disease-free survival can be monitored over a period of time for subjects following anti-cancer therapy (e.g., at least one USP10 inhibitor, either alone or in combination with at least one FLT3 inhibitor) for whom biomarker measurement values are known. In certain embodiments, the same doses of USP10 inhibitor agents are administered to each subject. In related embodiments, the doses administered are standard doses known in the art for USP10 inhibitor agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-cancer therapy (e.g., at least one USP10 inhibitor, either alone or in combination with at least one FLT3 inhibitor) can be determined using methods such as those described in the Examples section.

5. Further Uses and Methods of the Present Invention

The compositions described herein can be used in a variety of diagnostic, prognostic, and therapeutic applications regarding biomarkers described herein, such as those listed in Tables 1 and 2. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays. In one embodiment, the assays provide a method for identifying whether a cancer is likely to respond to anti-cancer therapy (e.g., at least one USP10 inhibitor, either alone or in combination with at least one FLT3 inhibitor) and/or whether an agent can inhibit the growth of or kill a cancer cell that is unlikely to respond to anti-cancer therapy (e.g., at least one USP10 inhibitor, either alone or in combination with at least one FLT3 inhibitor).

In one embodiment, the invention relates to assays for screening test agents which bind to, or modulate the biological activity of, at least one biomarker listed in Table 1 and/or Table 2. In one embodiment, a method for identifying such an agent entails determining the ability of the agent to modulate, e.g. inhibit, the at least one biomarker listed in Table 1 and/or Table 2.

In one embodiment, an assay is a cell-free or cell-based assay, comprising contacting at least one biomarker listed in Table 1 and/or Table 2, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1 and/or Table 2, with a test agent, and determining the ability of the test agent to modulate the ability of the biomarker to regulate USP10 and/or FLT3, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C or $^3$H, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the USP10.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the presence, absence, amount, and/or activity level of a biomarker described herein, such as those listed in Table 1, in the context of a biological sample (e.g., blood, serum, cells, or tissue) to thereby determine whether an individual afflicted with a cancer is likely to respond to anti-cancer therapy (e.g., at least one USP10 inhibitor, either alone or in combination with at least one FLT3 inhibitor), whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Table 1 and/or Table 2.

Another aspect of the present invention pertains to monitoring the influence of agents (e.g., drugs, compounds, and small nucleic acid-based molecules) on the expression or activity of a biomarker listed in Table 1 and/or Table 2. These and other agents are described in further detail in the following sections.

The skilled artisan will also appreciate that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to anti-cancer therapy (e.g., at least one USP10 inhibitor, either alone or in combination with at least one FLT3 inhibitor). In some embodiments, the present invention is useful for classifying a sample (e.g., from a subject) as associated with or at risk for responding to or not responding to anti-cancer therapy (e.g., at least one USP10 inhibitor, either alone or in combination with at least one FLT3 inhibitor) using a statistical algorithm and/or empirical data (e.g., the amount or activity of at least one biomarker listed in Table 1 and/or Table 2).

An exemplary method for detecting the amount or activity of a biomarker listed in Table 1 and/or Table 2, and thus useful for classifying whether a sample is likely or unlikely to respond to anti-cancer therapy (e.g., at least one USP10 inhibitor, either alone or in combination with at least one FLT3 inhibitor) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-cancer therapy (e.g., at least one USP10 inhibitor, either alone or in combination with at least one FLT3 inhibitor) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to anti-cancer therapy (e.g., at least one USP10 inhibitor, either alone or in combination with at least one FLT3 inhibitor), a biological sample from the subject during remission, or a biological sample from the subject during treatment for developing a cancer progressing despite anti-cancer therapy (e.g., at least one USP10 inhibitor, either alone or in combination with at least one FLT3 inhibitor).

d. Prognostic Assays

The diagnostic methods described herein can furthermore be utilized to identify subjects having or at risk of developing a cancer that is likely or unlikely to be responsive to anti-cancer therapy (e.g., at least one USP10 inhibitor, either alone or in combination with at least one FLT3 inhibitor). The assays described herein, such as the preceding diagnostic assays or the following assays, can be utilized to identify a subject having or at risk of developing a disorder associated with a misregulation of the amount or activity of at least one biomarker described in, for example, Table 1 and/or Table 2, such as in cancer. Alternatively, the prognostic assays can be utilized to identify a subject having or at risk for developing a disorder associated with a misregulation of the at least one biomarker described in Table 1 and/or Table 2, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect of the invention pertains to methods of modulating the expression or activity of one or more biomarkers described herein (e.g., those listed in Table 1, Table 2, and the Examples, or fragments thereof,) for therapeutic purposes. The biomarkers of the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods of the invention involve contacting a cell with one or more biomarkers of the invention, including one or more biomarkers of the invention, including one or more biomarkers listed in Table 1, Table 2, and the Examples, or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Table 1, Table 2, and the Examples, or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1 or 2 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. *The Physicians' Desk Reference* (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1: Materials and Methods for Examples 2-8 a. Cell Lines and Cell Culture

FLT3-ITD- or FLT3-D835Y-containing MSCV retroviruses were transfected into the IL-3-dependent murine hematopoietic cell line Ba/F3 as previously described (Kelly et al., 2002). Nomo-1, P31-FUJ, and NB4 were obtained from Dr. Gary Gilliland. MV4, 11 cells were obtained from Dr. Anthony Letai. Hel, K562, THP, U937, TF-1 and K052 cells were purchased from the American Type Culture Collection (ATCC) (Manassas, Va., USA). The human AML-derived, FLT3-ITD-expressing line, MOLM14 (Matsuo et al., 1997), was provided to us by Dr. Scott Armstrong, Dana Farber Cancer Institute (DFCI), Boston, Mass. The human AML-derived, FLT3-ITD-expressing cell line, MOLM-13 (DSMZ (German Resource Centre for Biological Material), was engineered to express luciferase fused to neomycin phosphotransferase (pMMP-LucNeo) by transduction with a VSVG-pseudotyped retrovirus as previously described (Armstrong et al., 2003). All cell lines used in this study were cultured with 5% $CO_2$ at 37° C., at a concentration of $2\times10^5$ to $5\times10^5$ in RPMI (Mediatech, Inc., Herndon, Va.) with 10% fetal bovine serum (FBS) and supplemented with 2% L-glutamine and 1% penicillin/streptomycin. Exceptions include TF-1 and OCI-AML5 cells, which were cultured in RPMI media with 10% FBS and supplemented with 2% L-glutamine and 1% pen/strep and human GM-CSF (2 ng/mL). Parental Ba/F3 cells were cultured in RPMI with 10% FBS and supplemented with 2% L-glutamine and 1% penicillin/streptomcyin, as well as 15% WEHI (as a source of IL-3). Cell lines were submitted for cell line authentication and were authenticated within 6 months of manuscript preparation through cell line short tandem repeat (STR) profiling (DDC Medical, Fairfield, Ohio and Molecular Diagnostics Laboratory, Dana Farber Cancer Institute). All cell lines tested matched ≥80% with lines listed in the ATCC or DSMZ Cell Line Bank STR. All cell lines were confirmed to be virus- and *Mycoplasma*-free. PBMCs were generously provided by Dr. Steven Treon and Dr. Guang Yang.

b. Chemical Compounds and Biologic Reagents

DUB inhibitors, HBX19818, P22077 and 1247825-37-1, were purchased from Medchem Express and dissolved in DMSO to obtain a 10 mM stock solution. HBX19818 analogs were purchased from ChemDiv and dissolved in DMSO to obtain a 10 mM stock solution. Serial dilutions were then made, to obtain final dilutions for cellular assays with a final concentration of DMSO not exceeding 0.1%.

c. Labeling with HA-Ubiquitin-Vinylmethylsulfone (HA-Ub-VS)

MOLM14 cells were treated for three hours with P22077 and Ba/F3-FLT3-ITD cells were treated for 7 hours with HBX-19818. Cells were harvested, washed with PBS, and lysed in 1% NP-40, 10% glycerol, 2% sodium orthovanadate, and HALT protease inhibitor cocktail (ThermoFisher). Lysate was diluted to 50 ug in 30 uL lysis buffer with 1% DTT and incubated on ice for 15 minutes. 0.25 ug HA-Ub-VS was added, and the sample was gently rocked at room temperature for 30 minutes, then denatured with LDS sample buffer. 12 ug lysate was separated by SDS-PAGE, transferred to a nitrocellulose membrane, blocked in milk, and treated with a USP10 antibody ((D7A5) (rabbit, #8501) (Cell Signaling, Danvers, Mass.). After washing, the membrane was treated with a 780-nm IRdye goat anti-rabbit IgG (Licor) and imaged using an Odyssey scanner (Licor).

d. Quantitative Real-Time Polymerase Chain Reaction (qPCR)

Ba/F3 cells were treated with the indicated compounds for 23 hours, then harvested and washed with PBS. mRNA was extracted using the RNEasy® Mini Kit (Qiagen) and converted to cDNA using SuperScript® III reverse transcriptase (ThermoFisher) and a SimpliAmp™ thermal cycler (ThermoFisher). Real-time PCR was carried out in a 96-well plate using TaqMan® probes and an Applied Biosystems® 7500 FAST Real-Time PCR system (ThermoFisher). Relative gene expression was calculated by comparison to a GAPDH reference probe.

e. Chloroquine Rescue

Cells were plated in 24-well plates and 25 uM chloroquine was added. After 60 minutes, the indicated concentration of HBX-19818 or P22077 was added. After 3 or 7 hours for P22077 or HBX-19818, respectively, cells were harvested, washed with 1×PBS, and lysed. Thirty ug lysate was separated by SDS-PAGE, transferred to a nitrocellulose membrane, blocked in milk, and treated with a FLT3 antibody (Santa Cruz). After washing, the membrane was treated with a horseradish peroxidase-conjugated goat anti-rabbit IgG, incubated with Peirce ECL Western Blotting Substrate (ThermoFisher), and imaged in a dark room.

f. Ubiquitin AMC Assay

Protein expression and purification. A construct of human USP10 covering residues 376-798 in the pET28a vector was over-expressed in *E. coli* BL21 (DE3) in TB medium in the presence of 50 mg/ml of kanamycin. Cells were grown at 37° C. to an OD of 0.8, cooled to 17° C., induced with 500 μM isopropyl-1-thio-D-galactopyranoside, incubated overnight at 17° C., collected by centrifugation, and stored at −80° C. Cell pellets were sonicated in buffer A (50 mM HEPES (pH 7.5), 300 mM NaCl, 10% glycerol, 10 mM Imidazole, and 3 mM BME) and the resulting lysate was centrifuged at 30,000×g for 30 min. Ni-NTA beads (Qiagen) were mixed with lysate supernatant for 30 min and washed with buffer A. Beads were transferred to an FPLC-compatible column and the bound protein was washed with 15% buffer B (50 mM HEPES (pH 7.5), 300 mM NaCl, 10% glycerol, 300 mM Imidazole, and 3 mM BME) and eluted with 100% buffer B. Thrombin was added to the eluted protein and incubated at 4° C. overnight. The sample was then passed through a HiPrep 26/10 desalting column (GE Healthcare) pre-equilibrated with buffer A without imidazole, and the eluted protein was subjected to a second Ni-NTA step to remove His-tag and Thrombin. The eluent was concentrated and passed through a Superdex® 200 10/300GL column (GE Healthcare) in a buffer containing 20 mM HEPES (pH 7.5), 150 mM NaCl, and 1 mM DTT. Fractions were pooled, concentrated to 20 mg/ml, and frozen at −80° C.

In vitro USP10 activity assay. Recombinant USP10, residues 376-798, was tested for its activity in a Ubiquitin-AMC assay in presence or absence of inhibitors. For this assay, 10 nM USP10 were pre-incubated with different concentrations of inhibitors or DMSO as a control in 50 mM HEPES pH7.6, 0.5 mM EDTA, 11 uM ovalbumin, and 5 mM DTT. The reaction was incubated for 6 hours at room temperature prior to the addition of 2 uM Ubiquitin-AMC (Boston Biochem) substrate. The initial rate of the reaction was measured by collecting fluorescence data at one minute intervals over 30-minute period using a CLARIOstar® fluorescence plate reader at excitation and emission wavelength of 345 and 445 nm, respectively. The calculated initial rate values were plotted against inhibitor concentrations to determine $IC_{50}$ values.

g. Antibodies, Immunoblotting, and Immunoprecipitation

The following antibodies were purchased from Cell Signaling Technology (Danvers, Mass.): total AKT (rabbit, #9272) and total p44/42 MAPK (Erk1/2) (3A7) (mouse, #9107) were used at 1:1000 dilution. Anti-GAPDH (D16H-11) XP (R) (rabbit mAb, #5174) was used at 1:1000 dilution. Beclin-1 (rabbit, #3738) was used at 1:1000. USP10 (D7A5) (rabbit, #8501) was used at 1:1000 dilution. P53 (rabbit, #9282) was used at 1:1000 dilution. β-tubulin (rabbit, #2146s) was used 1:1000.

FLT3/Flk-2 (C-20) (sc-479) and Ub (P4D1) (mouse, sc-8017) were purchased from Santa Cruz Biotechnology, Inc. (Dallas, Tex.) and used at 1:1000 dilution for immunoblotting. Anti-pTyr (mouse, clone 4G10) was purchased from Upstate Biotechnology (Lake Placid, N.Y.) and was used at 1:1000 dilution. Anti-HAUSP/USP7 antibody (rabbit, ab4080) and anti-ubiquitin antibody (rabbit, ab7780) were purchased from Abcam (Cambridge, Mass.) and used at 1:1000 dilution.

Protein lysate preparation, immunoblotting, and immunoprecipitation were carried out as previously described in Weisberg et al. (2002) Cancer Cell 1:433-443.

h. PEI Transfection of 293T Cells

HEK 293T cells were cultured in DMEM containing 10% FBS, at 37° C. and in a 5% $CO_2$ incubator, and transfected using polyethylenimine (PEI) (Polysciences) according to the manufacturer's instructions. Ba/F3-FLT3-ITD and MOLM14 cells were maintained in RPMI 1640 medium containing 10% FBS, at 37° C. and in a 5% $CO_2$ incubator. For the endogenous ubiquitination assay, Ba/F3-FLT3-ITD or MOLM14 cells were treated with HBX19818 or P22077, or DMSO control, for 4 or 24 h at 0, 5, 10, or 20 μM. Cells were then collected and lysed. Immunoprecipitation was carried out using an anti-FLT3 antibody. Immunoblots were analyzed using anti-ubiquitin or anti-FLT3 antibodies.

i. Drug Combination Studies

For drug combination studies, cell viability was first determined using the Trypan Blue exclusion assay to quantify cells for cell seeding, and the CellTiter-Glo Luminescent Cell Viability assay (Promega, Madison, Wis.) was then implemented for proliferation studies. Single agents were added simultaneously at fixed ratios to cells. Cell viability was expressed as the function of growth affected (FA) drug-treated versus control cells; data were analyzed by Calcusyn software (Biosoft, Ferguson, M O and Cambridge, UK), which was utilized for synergy measurement and based on isobologram generation and the method of Chou-Talalay (1984) (REF). This method utilizes the median effect principle to quantify the effects of drug combinations to determine whether they give greater effects together than expected from a simple summation of their individual effects. After determining the ED50 or IC50 of each drug, combinations were studied where the concentrations were multiples, or fractions, of the ED/IC50. For the synergy studies described here, concentrations for each drug were used, alone and together, based on each drug's IC50 value (which is commonly used to select appropriate ratios for drug combinations). Specifically, concentrations of DUB inhibitor and kinase inhibitor were tested alone and combined as follows: 0.25× IC50, 0.5× IC50, IC50, 2× IC50, and 4× IC50. Calcusyn program-generated combination index (CI) values allow for a quantitative measurement of synergism, where synergism is defined by a CI<1, an additive effect is defined by a CI=1, and antagonism is defined by a CI>1. Statistical analysis is automatically part of the computations.

j. Knockdown (KD) of Genes by shRNA pLKO.1puro lentiviral shRNA vector particles against USP10 and USP7 were purchased from Sigma-Aldrich (St. Louis, Mo.). Cells were incubated with the viral particles in the presence of 8 μg/ml Polybrene® for 24 hours, and the cells were selected with 1-2 μg/ml puromycin for 72 hours. Following selection, cells were used for the studies described.

Repeat USP10 knockdown studies in MOLM14 cells: Viral particles were produced co-transfecting pLKO.1 containing shRNA or scramble (purchased from Sigma-Aldrich) together with psPAX2 (addgene #12260) and pMD2.G (addgene #12259), concentrated using LENTI-X concentrator (Clontech). MOLM14 cells were then infected in presence of 5 ug/ml polybrene and selection was started 48 h post infection using 1 ug/ml puromycin.

k. Dynamic BH3 Profiling (DBP)

To determine drug-induced changes in mitochondrial priming, dynamic BH3 profiling was performed as previously described in Montero et al. (2015) Cell 160:977-989 and Pan et al. (2014) Cancer Discov. 4:362-375. Briefly, $0.4 \times 10^6$ cells/well were exposed to drug treatment for 14 hours. At the end of incubation time, cells were washed in PBS, pelleted at 500×g for 5 min, and resuspended in MEB buffer. Fifteen μl of cell suspension was added to each well of 384 well plate containing 15 μl of MEB buffer containing 20 μg/mL digitonin and BH3 peptides at twice their final concentration, and the mixture was incubated for 60 min at 26° C. to allow mitochondrial depolarization. Peptide exposure was then terminated by adding 10 μl 4% formaldehyde in PBS for 15 min, followed by neutralization with N2 buffer (1.7M Tris, 1.25M glycine, pH 9.1) for 10 min. In order to determine cytochrome C levels, anti-cytochrome C clone 6H2.B4 conjugated to Alexa Fluor® 647 (BD Bioscience) was diluted 1:50 in 10× staining buffer (10% BSA, 2% Tween-20 and 0.02% sodium azide in PBS) and 10 μl of this antibody-containing buffer was added to each well for a final dilution of 1:400. Cells were stained overnight at 4° C. in dark and data were acquired on a BD LSRFortessa™ analyzer (BD Biosciences). Priming change (Δ) was calculated by comparing cytochrome C abundance in treated cells to that of DMSO-treated control cells.

l. Primagraft Study

All animal studies were performed according to protocols approved by the Dana-Farber Cancer Institute's Institutional Animal Care and Use Committee. Female NSG mice (6 weeks of age, Jackson Laboratories, Bar Harbor, Me.) were administered either vehicle (10% DMSO, +90% D5W IP QD) (n=3) or P22077, 15 mg/kg IP QD (dissolved in 10% DMSO, +90% D5W) (n=3) for a total of 21 days once leukemia burden reached the following levels as determined by percent double positive CD45+CD33+ cells in the peripheral blood: 2E #0 (vehicle) (3.07%), 2E #1 (vehicle) (0.34%), 2E #30 (vehicle) (1.63%), 2D #0 (P22077, 15 mg/kg) (4.68%), 2D #1 (P22077, 15 mg/kg) (1.5%), 2E #10 (P22077, 15 mg/kg) (0.29%). Mice were sacrificed on day 21 of treatment. Bone marrow was flushed from mouse femurs, and spleens and livers were dissected and preserved first in formalin, followed 24 hours later by preservation in 70% ethanol. P22077 at 15 mg/kg was generally well-tolerated for the 21-day treatment period with little change in weight (approximately 2-3 g on average loss for both vehicle-treated and P22077-treated; none of the mice were below 15% weight loss). All AML primagraft samples used in the studies described herein were obtained through the Public Repository of Xenografts (proxe.org).

m. Non-Invasive In Vivo Bioluminescence Study

All animal studies were performed according to protocols approved by the Dana-Farber Cancer Institute's Institutional Animal Care and Use Committee. Ba/F3-FLT3-ITD cells were transduced with a VSVG-pseudotyped retrovirus comprised of the firefly luciferase coding region (from pGL3-basic; Promega, Madison, Wis.) cloned into PMSCV puro (Clontech, Mountain View, Calif.). Cells were neomycin selected to produce the Ba/F3-FLT3-ITD (luc+) cell line. Bioluminescence imaging was carried out as previously described in Weisberg et al. (2005) Cancer Cell 7:129-141. Briefly, for administration to female NCR-nude mice (6-8 weeks of age; Taconic, N.Y.), virus- and Mycoplasma-free Ba/F3-FLT3-ITD-luc+ cells were washed and resuspended in 1×PBS and administered via IV tail vein injection (0.5× 10^6 cells/250 uL). A sample size of no less than 8 mice per treatment group was chosen to ensure statistical significance. Treatment was started 2 days after cell injection, anesthesized mice were imaged 2 days post IV-injection to generate a baseline used to establish treatment cohorts with matched tumor burden (mice were randomized and investigators were blinded to group allocation), and total body luminescence was measured as previously described in Armstrong et al. (2003) Cancer Cell 3:173-183. Mice were treated with vehicle (10% DMSO, +90% D5W IP QD) (n=5), P22077 (15 mg/kg IP QD) (n=6), or P22077 (50 mg/kg IP QD) (n=6) for the indicated times. Mice were treated with vehicle (10% DMSO in 90% [20%] HPBCD, IP BID) (n=8), P22077 (50 mg/kg, 10% DMSO in 90% [20%] HPBCD, IP BID) (n=8), P22077 (50 mg/kg, 10% NMP in 90% PEG300) for the indicated times. Note: One vehicle mouse that showed ≥10-fold lower leukemia burden than the other 7 vehicle mice in the vehicle treatment group across all time points was removed as an outlier from the final statistical analysis. One P22077 (PO, QD)-treated mouse died prematurely due to technical complications unrelated to treatment and consequently was not imaged with the other 7 mice from this treatment group.

For in vivo assessment of FLT3 protein levels in vehicle-treated and P22077-treated mice, 8 female NCR-nude mice (6-8 weeks of age; Taconic, N.Y.), were administered Ba/F3-FLT3-ITD-luc+ cells via tail vein injection as described above. Mice were imaged and randomized 2 days later to generate a baseline used to establish treatment cohorts with matched tumor burden. At this point, mice were treated with vehicle (10% DMSO in 90% [20%] HPBCD, IP BID) (n=4) or P22077 (50 mg/kg, 10% DMSO in 90% [20%] HPBCD, IP BID) (n=4) for a total of 4 days. Bone marrow cell suspensions were then analyzed for FLT3 levels by flow cytometry using a CD135-PE conjugated antibody (Cat. #IM2234U, Beckman Coulter, Marseille, France). Flow cytometry was carried out as previously described, according to standard protocols (Weisberg et al., 2011). Briefly, a FACS Fortessa™ flow cytometry machine equipped with FACSDiva™ analytical software was used for analyzing the percentage of FLT3-positive cells.

The statistical significance in bioluminescence between two groups was determined by using the two-tailed Student's t-test. A P<0.05 was considered to be statistically significant. The data had similar variance, and met the assumptions of the tests.

n. Flow Cytometry

Flow cytometry was carried out as previously described in Weisberg et al. (2011) PLoS One 6:e25351, according to standard protocols. Briefly, a BD FACSCanto™ flow cytometry machine equipped with BD FACSDiva™ analytical software was used for analyzing the percentage of FLT3-positive cells.

o. Proliferation Studies

The trypan blue exclusion assay has been previously described in Weisberg et al. (2002) Cancer Cell 1:433-443 and was used for quantification of cells prior to seeding for CellTiter-Glo® assays. The CellTiter-Glo® assay (Promega, Madison, Wis.) was used for proliferation studies and carried out according to manufacturer instructions. Cell viability is reported as percentage of control (untreated) cells, and error bars represent the standard error of the mean for each data point.

p. AML Patient Cells

Mononuclear cells were isolated from samples from AML patients identified as harboring mutant FLT3. Cells were tested in liquid culture (DMEM supplemented with 20% FBS) in the presence of different concentrations of single and combined agents. All blood and bone marrow samples from AML patients were obtained under approval of the Dana Farber Cancer Institute Institutional Review Board.

r. MALDI TOF DUB Assays

Thirty-one human DUBs were freshly diluted in the reaction buffer (40 mM Tris-HCl, pH 7.6, 5 mM DTT, 0.005% BSA) at different concentrations (see Table 10). Ubiquitin topoisomers (K63, K48, K11 and M1) were diluted to 0.2 µl/µg in dimer buffer (40 mM Tris-HCl, pH 7.6, 0.005% BSA) and used as substrates at a fixed concentration (1.5 µM). The enzymes were pre-incubated with the compounds for 30 min at room temperature at 10 µM final concentration. 0.48 µl of di-ubiquitin topoisomers were added to the reaction mixture to initiate the reaction. The reaction was sealed and incubated for 30 min at room temperature and stopped by adding TFA to a final concentration of 2% (v/v). 1.050 µl of each reaction was copied in a fresh plate and spiked with 0.15 µl of 16 µM $^{15}$N-ubiquitin as internal standard and mixed 1:1 with 2.5 DHAP matrix freshly prepared (7.6 mg of 2, 5 DHAP in 375 ml ethanol and 125 ml of an aqueous 12 mg/ml diammonium hydrogen citrate). Reaction and matrix were mixed and 200 nl of mixture was spotted in duplicate onto MTP AnchorChip 1,536 TF (600 mm anchor, Bruker Daltonics).

Mass spectrometry data was acquired on an UltrafleXtreme MALDI-TOF mass spectrometer (Bruker Daltonics) with Compass 1.3 control and processing software. The sample carrier was taught before each analysis to optimize and centre laser shooting. Internal calibration was performed before each analysis using the $^{15}$N-Ub peak [M+H]$^+$ average=8,569.3). Samples were analysed in automatic mode (AutoXecute, Bruker Daltonics). Ionization was achieved by a 2-kHz smartbeam-II solid state laser with a fixed initial laser power of 60% (laser attenuator offset 68%, range 30%) and detected by the FlashDetector at detector gain of ×10. Reflector mode was used with optimized voltages for reflector-1 (26.45 kV) and reflector-2 (13.40 kV), ion sources (IonSource-1: 25.0 kV, IonSource-2: 22.87 kV) and pulsed ion extraction (320 ns). An amount of 3,500 shots were summed up in "random walk" and with "large" smartbeam laser focus. Spectra were automatically calibrated on the $^{15}$N-Ub m/z and processed using smoothing (Savitzky-Golay algorithm) and baseline subtraction ('TopHat') for reproducible peak annotation on non-resolved isotope distributions: one cycle, 0.2 m/z for the width. For area calculation, the complete isotopic distribution was taken into account. An in-house made script was used to report—$^{15}$N and mono-ubiquitin areas; plotting of graphs, calculation of standard deviation and coefficient of variation (%) were processed in Microsoft Excel.

| Enzyme Dilution | | | |
|---|---|---|---|
| USP1 | USP2 | USP6 | OTUB2 |
| 240 ng/µl, K63 | 60 ng/µl, K63 | 3 ng/µl, K63 | 30 ng/µl, K63 |
| USP8 | USP5 | USP20 | OTUD1 |
| 144 ng/µl, K63 | 24 ng/µl, K63 | 60 ng/µl, K63 | 6 ng/µl, K63 |
| CYLD | OTUD5 | AMSH | AMSH-LP |
| 240 ng/µl, K63 | 300 ng/µl, K63 | 60 ng/µl, K63 | 24 ng/µl, K63 |
| USP7 | USP27x | Cezanne | USP21 |
| 30 ng/µl, K11 | 120 ng/µl, K11 | 12 ng/µl, K11 | 58.4 ng/µl, K11 |
| USP9x | USP28 | OTUD3 | USP25 |
| 170 ng/µl, K11 | 60 ng/µl, K11 | 60 ng/µl, K11 | 30 ng/µl, K11 |
| USP10 | USP36 | USP30 | Otplin |
| 240 ng/µl, K11 | 750 ng/µl, K11 | 430 ng/µl, K48 | 1.2 ng/µl, M1 |
| VCPIP* | A20 | TRABID | OTUB1 |
| 500 ng/µl, K48 | 60 ng/µl, K48 | 240 ng/µl, K48 | 300 ng/µl, K48 |
| USP4 | USP16 | USP15 | |
| 120 ng/µl, K48 | 60 ng/µl, K48 | 16 ng/µl, K48 | | s. Overexpression of USP10 Wild-Type and Mutant in MOLM14 Cells

FLAG-HA-USP10 was a gift from Wade Harper lab [Addgene (#22543)] (Sowa et al., 2009). This construct was used to create the corresponding USP10 catalytic dead construct (USP10 C424S) using site directed mutagenesis according to the manufacturer's instruction. Viral particles were produced co-transfecting USP10 WT, C424S or control vector together with GAG/POL and VSV-G containing vectors in 293T cells, and concentrated using LENTI-X concentrator (Clontech). MOLM14 cells were then infected in presence of 5 ug/ml polybrene and selection was started 48 h post infection using 1 ug/ml puromycin. Expression of exogenous USP10 was confirmed by HA blot.

Example 2: A Screen for DUB Inhibitors that Selectively Inhibit Growth of Mutant FLT3-Dependent AML and Induce Mutant FLT3 Degradation Identifies HBX19818

Figure 2A:
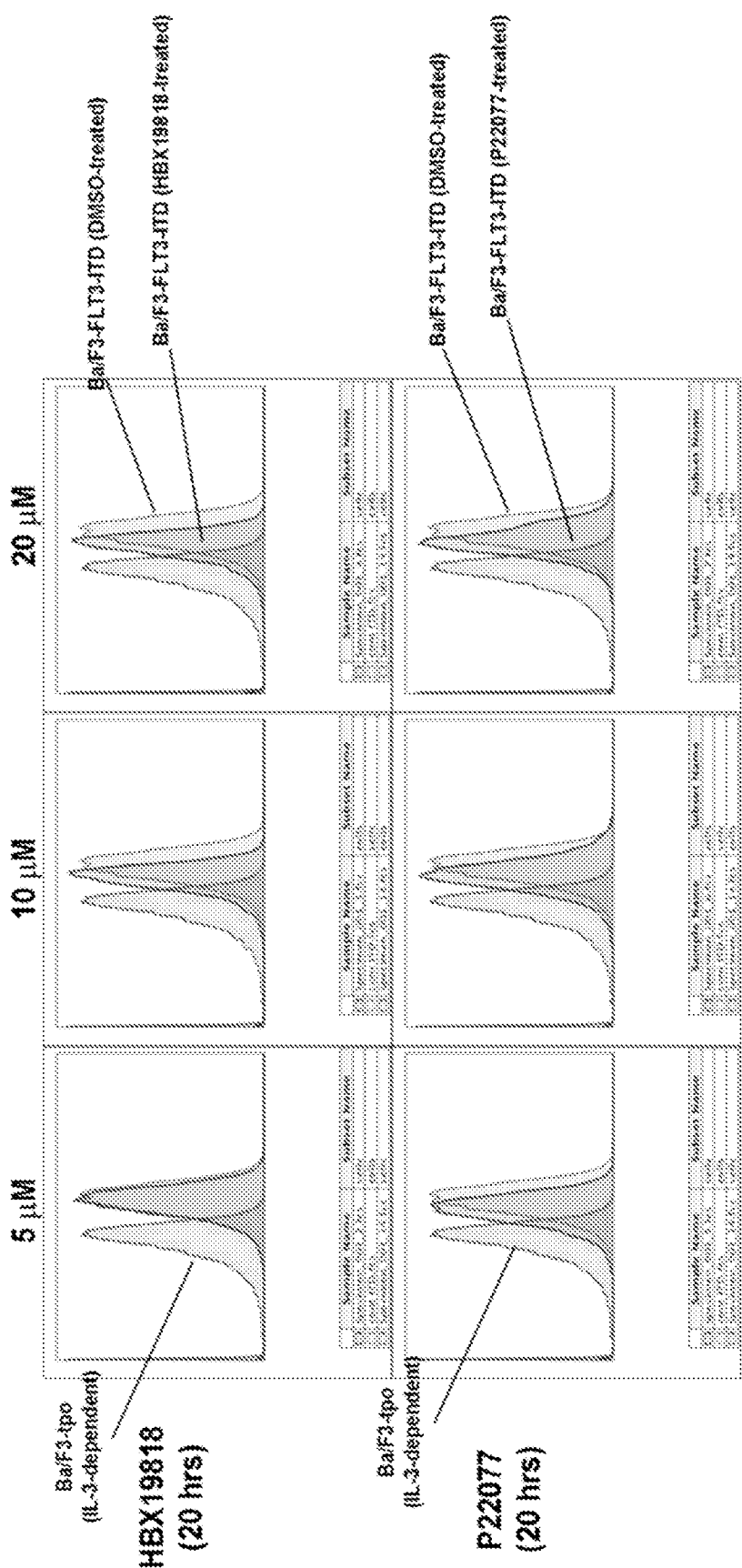
FIG. 2 includes 2 panels, identified as panels A and B, which show measurement of FLT3 levels following treatment of cells with USP10-targeting inhibitors. Panel A shows measurement of cell surface FLT3 expression following approximately 20 hr treatment of Ba/F3-FLT3-ITD cells with USP10-targeting inhibitors. C598-0466 is an analog of HBX19818. Ba/F3-tpo cells are growth factor-dependent Ba/F3 cells engineered to over-express the thrombopoietin (tpo) receptor. These cells express wt FLT3 and are used in this study as a control for comparison with oncogenic FLT3-over-expressing Ba/F3 cells. Panel B shows effect of P22077 on FLT3 protein levels in Ba/F3-wtFLT3 cells.

In order to identify novel targets and compounds that regulate protein homeostasis of oncogenic FLT3, a whole cell phenotypic screen of 29 reported small molecule DUB inhibitors (Table 10), which represents the majority of reported DUB inhibitors, annotated for inhibitory activity across a broad panel of DUBS (Ritorto et al. (2014) Nat. Commun. 5:4763), was performed using oncogene-dependent and control cell lines followed by hit validation and target deconvolution and translational studies (FIG. 1A). The compounds were evaluated for ability to selectively kill growth factor-independent Ba/F3 cells expressing FLT3-ITD and Ba/F3 cells expressing FLT3-D835Y over IL-3-dependent parental Ba/F3 cells. The top hit from the screen, HBX19818, a reported USP7 inhibitor (Reverdy et al. (2012) Chem. Biol. 19:467-477) (FIG. 1B; note that the ethyl group shown should be a methyl group, as shown in Table 8), inhibited proliferation of FLT3-ITD- and FLT3-D835Y-positive Ba/F3 cells with $EC_{50}$s in the single digit micromolar range following approximately 72 hours of treatment (FIGS. 1C-1D) and an approximate 2-fold therapeutic window compared to parental Ba/F3 cells. Inhibitory effects on the growth of Ba/F3-D835Y cells were observed to be more modest than for Ba/F3-FLT3-ITD cells, which is more evident following treatment of cells for approximately 22 hr (FIG. 1E). The anti-proliferative activity of HBX19818 correlated with loss of FLT3 protein in Ba/F3-FLT3-ITD cells at the same concentrations (FIG. 1F) and with a more modest loss of FLT3 protein in Ba/F3-D835Y cells (FIG. 1G). Consistent with these results, flow cytometry revealed loss of cell surface expression of FLT3 in Ba/F3-FLT3-ITD cells treated with HBX19818 (FIG. 2A). In contrast, FLT3 protein levels were unchanged in inhibitor-treated wild type FLT3-Ba/F3 cells (FIG. 1H and FIG. 2B). Owing to a lack of FLT3-D835Y-positive cell lines, subsequent studies focused on the FLT3-ITD mutation.

Effects of HBX19818 on FLT3 mutant-expressing cells were confirmed not to be unique to the Ba/F3 system. For example, HBX19818 also suppressed the growth of the FLT3-ITD positive AML cell lines, MOLM13-luc+, MOLM14, and MV4, 11 in a dose-dependent manner with concentrations in the same range (FIG. 1I and Table 3). The selectivity of HBX19818 toward mutant FLT3 was supported by the substantially higher sensitivity of the three mutant FLT3-expressing human AML lines to HBX19818 as compared to a panel of wild-type (wt) FLT3 or null FLT3-expressing human leukemia lines following 24 hours of treatment (FIG. 1I and Table 3). For instance, for HBX19818, $IC_{50}$s of 4.4, 9.6, and 8.1 µM were observed for MOLM13-luc+, MOLM14, and MV4,11, respectively, compared to $IC_{50}$s of 12.8, 20.7, 25.7, 16.6, and 18.5 for TF-1, U937, HEL, K052, and K562 cells, respectively (Table 3). Differences in drug responsiveness were sustained up to 72 hours of treatment. HBX19818 treatment led to increased priming of mutant FLT3-expressing cells for apoptosis (FIG. 1J). This priming significantly correlated with induction of apoptosis, and was stronger for MOLM13, MOLM14, and MV4, 11 cells than for wt FLT3-expressing THP cells or null FLT3-expressing TF-1 cells (FIGS. 3A-3D). Of note, mutant FLT3-expressing mouse and human cell lines tested were shown to pharmacologically respond to clinically tested FLT3 inhibitors, including midostaurin, AC220 (quizartinib), and crenolanib, with potencies similar to those reported for these compounds.

TABLE 3 h

Anti-proliferation IC50s (+/− SEM) calculated for 24 hr treatment of human AML cell lines with USP10-targeting inhibitors. MOLM13-luc+, MOLM14 and MV4,11 express FLT3-ITD, whereas other cells are FLT3 wt or FLT3 null

| 24 hr assay | MOLM13-luc+ | MOLM14 | MV4,11 | TF-1 | U937 | HEL |
|---|---|---|---|---|---|---|
| HBX19818 (IC50, µM) | 4.4 +/− 1.3 | 9.6 +/− 0.9 | 8.1 +/− 0.14 | 12.8 +/− 0.5 | 20.7 +/− 0.8 | 25.7 +/− 0.6 |
| C673-0105 (IC50, µM) | 7.9 +/− 2.7 | 10.1 +/− 0.6 | 7.5 +/− 0.5 | 12.5 +/− 2.5 | 16.2 +/− 0.8 | 34.4 +/− 1.6 |

TABLE 3 h-continued

Anti-proliferation IC50s (+/− SEM) calculated for 24 hr treatment of human AML
cell lines with USP10-targeting inhibitors. MOLM13-luc+, MOLM14 and MV4,11 express
FLT3-ITD, whereas other cells are FLT3 wt or FLT3 null

| | | | | | | |
|---|---|---|---|---|---|---|
| C598-0563 (IC50, μM) | 8.8 +/− 1.9 | 9.9 +/− 1.5 | 9.7 +/− 1.6 | 10.0 +/− 0 | 13.7 +/− 0.14 | 19.6 +/− 0.5 |
| C598-0466 (IC50, μM) | 2.9 +/− 1.3 | 5.2 +/− 0.5 | 4.1 +/− 0.07 | 10.7 +/− 1.2 | 12.9 +/− 0.5 | 16.8 +/− 0.9 |
| C598-0571 (IC50, μM) | 12.6 +/− 3.4 | 18.6 +/− 1.4 | 9.2 +/− 0 | 18.4 +/− 1.3 | 21.9 +/− 3 | 40.7 +/− 4.9 |
| P22077 (IC50, μM) | 0.4 +/− 0.4 | 0.8 +/− 0.5 | 2.9 +/− 0.2 | 10.2 +/− 0.1 | 2.1 +/− 0.1 | 6.9 +/− 0.3 |

| 24 hr assay | K052 | K562 | OCI-AML5 | P31 | NB4-luc+ | NOMO-1 |
|---|---|---|---|---|---|---|
| HBX19818 (IC50, μM) | 16.6 +/− 0 | 18.5 +/− 1.7 | 17.9 +/− 0.3 | 18.2 +/− 1.4 | 16.4 +/− 0.8 | 16.1 +/− 0.1 |
| C673-0105 (IC50, μM) | 23.5 +/− 2.1 | 23.7 +/− 3.7 | 19.5 +/− 2.2 | 29.0 +/− 3.4 | 24.5 +/− 2.5 | 12.7 +/− 0.6 |
| C598-0563 (IC50, μM) | 14.5 +/− 1.4 | 15.9 +/− 0.9 | 17.0 +/− 1.8 | 10.6 +/− 1.1 | 13.6 +/− 0.9 | 10.7 +/− 0.4 |
| C598-0466 (IC50, μM) | 11.6 +/− 1.2 | 13.3 +/− 1.4 | 8.6 +/− 0.14 | 13.9 +/− 2.1 | 10.2 +/− 1.1 | 8.3 +/− 0.1 |
| C598-0571 (IC50, μM) | 35.1 +/− 12.9 | 35.9 +/− 3.2 | 37.7 +/− 8.8 | 30.0 +/− 4.5 | 29.0 +/− 8.2 | 20.9 +/− 1.9 |
| P22077 (IC50, μM) | 5.7 +/− 0.4 | 10.6 +/− 1.2 | 5.3 +/− 0.1 | 0.4 +/− 0.4 | 3.2 +/− 0.7 | 5.5 +/− 0.2 |

Figure 4:
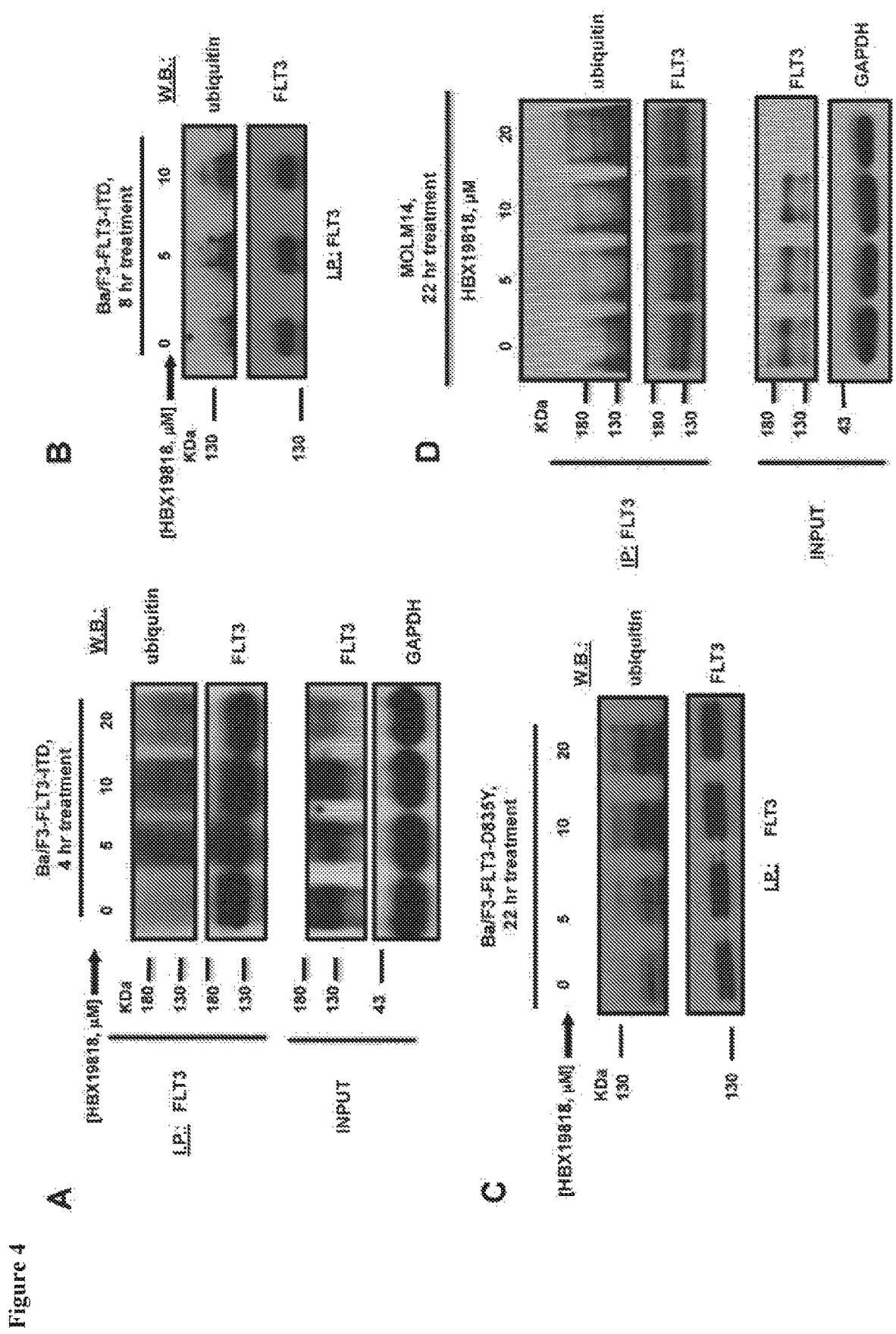
FIG. 4 includes 4 panels, identified as panels A, B, C, and D, which show that HBX19818 increases ubiquitination of mutant FLT3. Panel A shows an analysis of ubiquitination of FLT3-ITD following 4 hours of HBX19818 treatment. Panel B shows an analysis of ubiquitination of FLT3-ITD following 8 hours of HBX19818 treatment. Panel C shows an analysis of ubiquitination of FLT3-D835Y following 22 hours of HBX19818 treatment. Panel D shows an analysis of ubiquitination of FLT3 in MOLM14 cells following 22 hours of HBX19818 treatment.

In order to clarify whether the reduction in protein level is a consequence of ubiquitin-dependent degradation, inhibitor-mediated changes to mutant FLT3 ubiquitylation and rescue of protein loss with concurrent inhibition of degradation machinery were checked. Consistent with the degradation being ubiquitin-dependent, increased FLT3 ubiquitylation was observed for FLT3-ITD 4-8 hours after treatment with HBX19818 and the D835Y mutant 22 hours after compound treatment (FIGS. 4A-4C). These results are not unique to the Ba/F3 system. Similar findings with respect to increased FLT3 ubiquitination were observed in the FLT3-ITD-positive AML cancer cell line MOLM14 (FIG. 4D).

Figure 5:
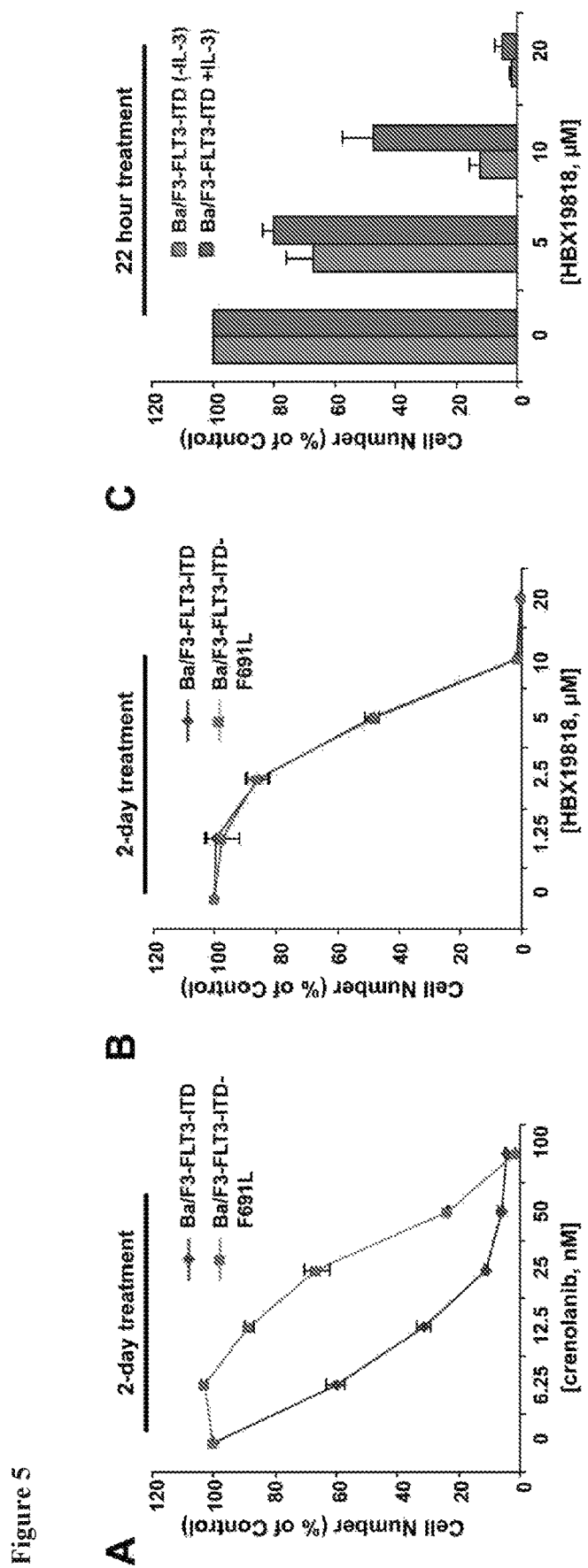
FIG. 5 includes 3 panels, identified as panels A, B, and C, which show the effects of HBX19818 on growth of cells expressing the crenolanib-resistant FLT3 F691L mutant. The results are from an approximately 2-day treatment of Ba/F3-FLT3-ITD cells or Ba/F3-FLT3-ITD-F691L cells with crenolanib (Panel A) or HBX19818 (Panel B). Panel C shows IL-3 rescue of Ba/F3-FLT3-ITD cells treated with HBX19818.

With data consistent with HBX19818 promoting loss of FLT3-ITD through an ubiquitin mediated degradation mechanism, it was next sought to confirm that this mechanism could be advantageous compared to kinase inhibition in terms of overriding drug resistance before investing in the identification and validation of the relevant DUB. Indeed, treatment of Ba/F3-FLT3-ITD cells co-expressing the tyrosine kinase domain point mutation, F691L, with the FLT3 kinase inhibitor, crenolanib, led to a rightward shift in the dose-response curve as compared to Ba/F3-FLT3-ITD (FIG. 5A), thereby validating resistance of the F691 point mutant to crenolanib (Smith et al. (2014) *Proc. Natl. Acad. Sci. U.S.A.* 111:5319-5324). In contrast, HBX19818 treatment was equipotent against both Ba/F3-FLT3-ITD-F691L cells and Ba/F3-FLT3-ITD cells (FIG. 5B) at concentrations that are partially IL-3 rescuable (FIG. 5C).

Figure 6:
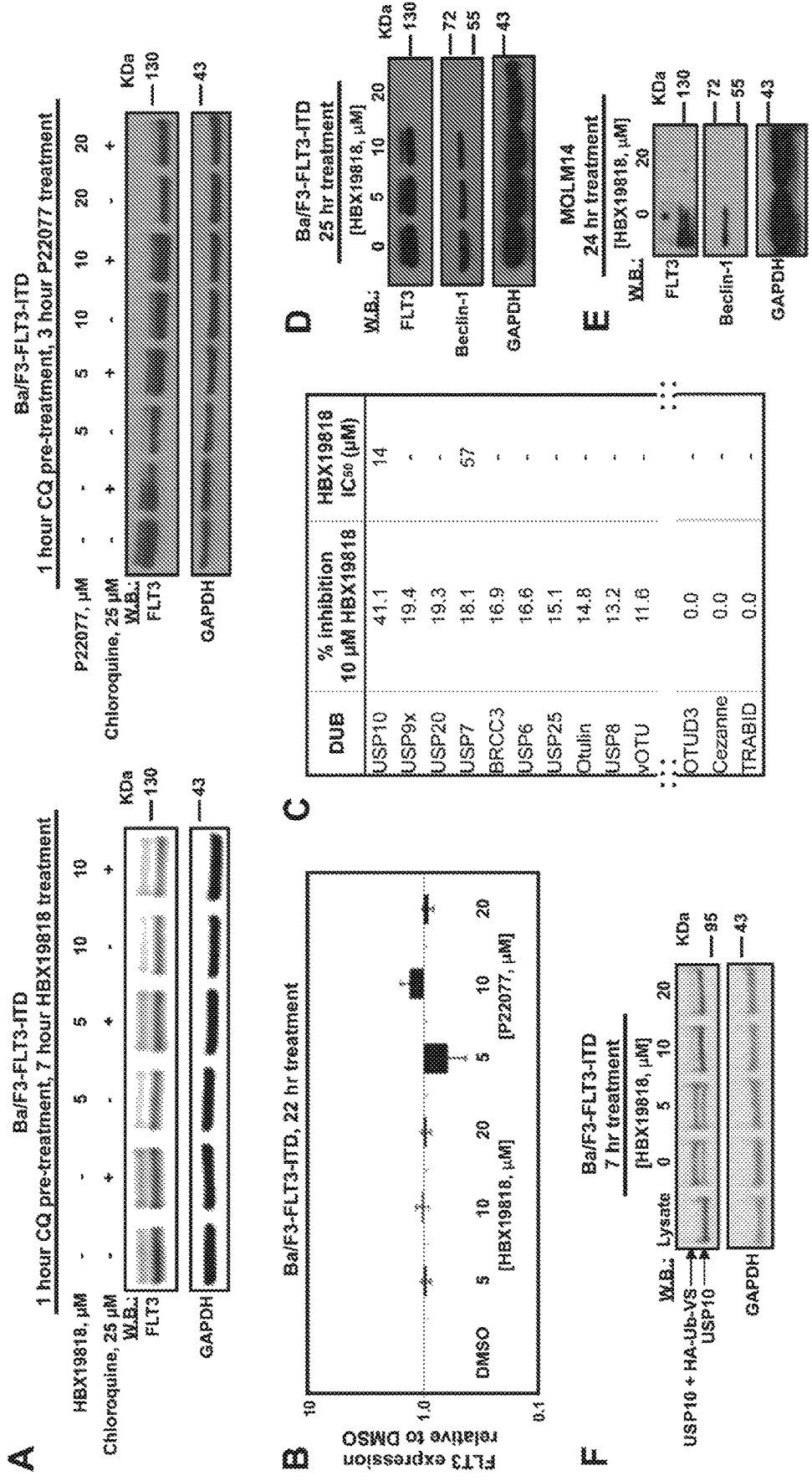
FIG. 6 includes 6 panels, identified as panels A, B, C, D, E, and F, which shows transcription-independent promotion of lysosomal degradation of mutant FLT3 and USP10 target engagement of HBX19818. Panel A shows the rescue of HBX19818- and P22077 (USP10-targeted chemokine)-treated Ba/F3-FLT3-ITD cells with the lysosome inhibitor, chloroquine (CQ). Panel B shows the effect of HBX19818 and P22077 on FLT3 transcription in Ba/F3-FLT3-ITD cells following 22 hours of treatment. FLT3 expression is shown relative to GAPDH expression. Panel C shows that DUB profiling data indicate HBX19818 shows the strongest activity against USP10. $IC_{50}$s were calculated using K11-diubiquitin as substrate. Panels D-E show analyses of FLT3 and Beclin-1 levels in HBX19818-treated Ba/F3-FLT3-ITD and MOLM14 cells. Panel F shows that HBX19818 binds USP10 in cells. Ba/F3-FLT3-ITD cells were treated with the indicated concentration of compound, lysed, and incubated with HA-Ub-VS.

Ubiquitin tags can encode either proteasomal or lysosomal degradation. FLT3 has been reported to undergo degradation by both pathways. It was determined that HBX19818-, as well as P22077-(another USP10-targeting inhibitor and described in further detail below), induced FLT3-ITD degradation is partially rescued by inhibition of the lysosome (FIG. 6A), and qPCR analysis confirmed the reduction in FLT3 levels occurred at the protein level only (FIG. 6B).

Example 3: USP10 Inhibitory Activity of HBX19818 Drives Degradation of FLT3-ITD HBX19818, as well as P222077 in Example 4, were reported to be two irreversible inhibitors of ubiquitin specific protease 7 (USP7), a deubiquitylating enzyme best known for its role in stabilization of MDM2 (Reverdy et al. (2012) *Chem. Biol.* 19:467-477; Chauhan et al. (2012) *Cancer Cell* 22:345-358). However, profiling of the compound in vitro against a panel of 33 recombinant DUB enzymes at a concentration of 10 μM using diubiquitin as substrate, identified USP10 as the most potently inhibited DUB (USP10 $IC_{50}$=14 μM) (Ritorto et al. (2014) *Nat. Commun.* 5:4763) (FIG. 6C). The profiling data further show that HBX19818 exhibits good DUBome selectivity, inhibiting no DUBs other than USP10 to an extent greater than 20% at a concentration of 10 μM (FIG. 6C). USP7 was inhibited with an $IC_{50}$ of 57 μM using the same assay. To further investigate USP10 as a potential target of HBX19818, levels of Beclin-1, an established substrate of USP10 (Liu et al. (2011) *Cell* 147:223-234), were analyzed in HBX19818-treated, mutant FLT3-expressing cells. Protein levels of Beclin-1 and FLT3 were strongly decreased in 20 μM HBX19818-treated Ba/F3-FLT3-ITD and MOLM14 cells, which suggests that USP10 may mediate the activity of HBX19818 and is consistent with DUBome profiling results for this compound (FIGS. 6D-6E). In addition, it was confirmed that HBX19818 binds USP10 in cells using establishing activity-based probe profiling methods (Altun et al. (2011) *Chem. Biol.* 18:1401-1412). USP10 in lysates from live cells treated with HBX19818 was blocked from labeling with an HA tagged ubiquitin probe modified to covalently label the active site cysteine of DUBs (HA-Ub-VS) with inhibitor concentrations in the low micromolar range (FIG. 6F).

Figure 7:
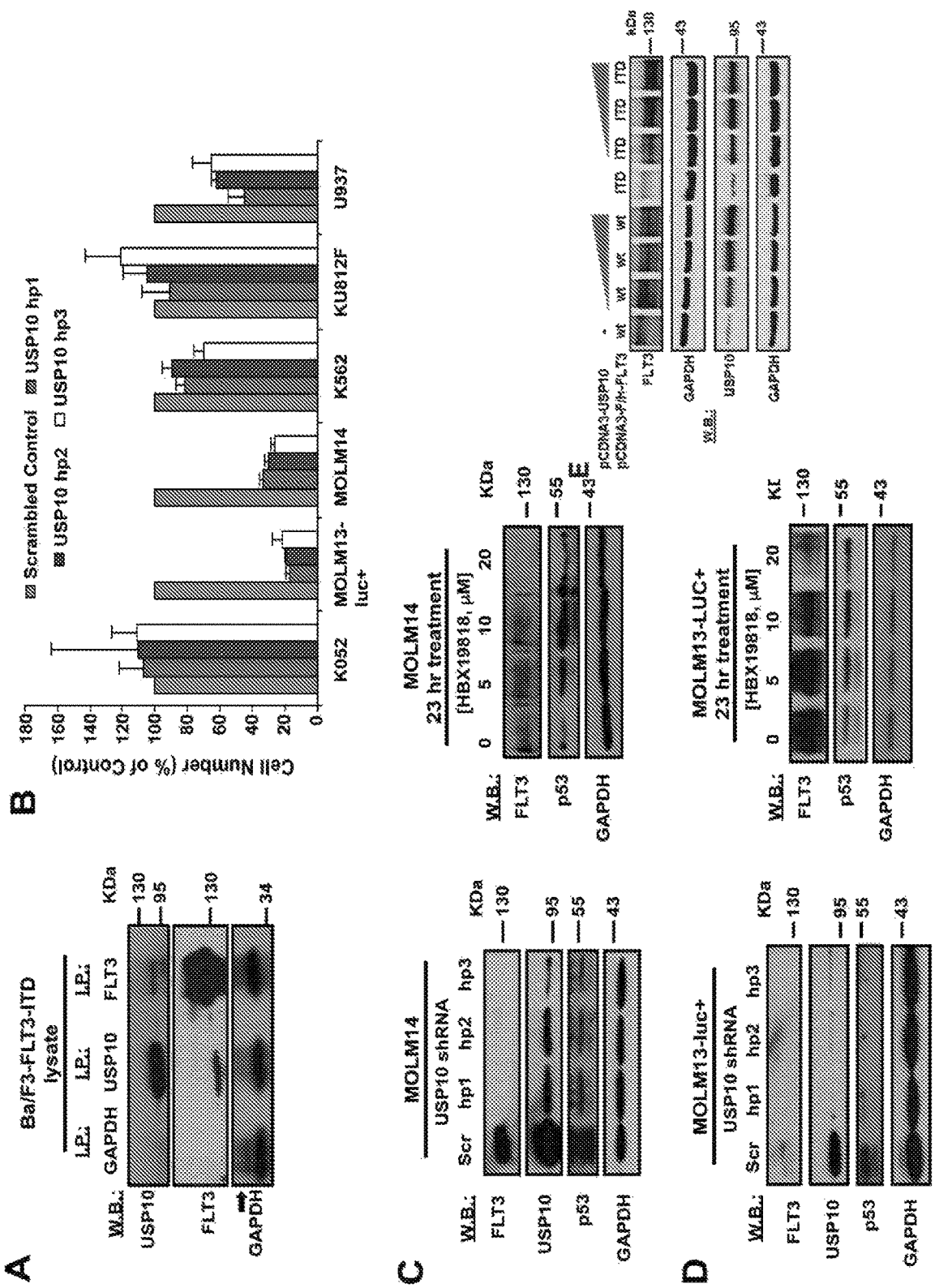
FIG. 7 includes 15 panels, identified as panels A, B, C, D, E, F, G, H, I, J, K, L, M, N, and O, which show the results of investigating USP10 as a mediator of FLT3 degradation induced by HBX19818. Panel A shows the association of endogenous USP10 with exogenously expressed FLT3-ITD in Ba/F3-FLT3-ITD cells. Panel B shows cell counts (Trypan Blue exclusion assay) determined following approximately 1 week after puromycin selection of USP10 shRNA-infected cells. Panels C-D show the effects of USP10 KD versus HBX19818 treatment, respectively, on FLT3 expression and p53 expression in MOLM14 cells (Panel C) and MOLM13-luc+ cells (Panel D). Panel E shows that USP10 stabilizes FLT3-ITD to a greater extent than wt FLT3 in transfected HEK 293T cells. Immunoblots shown are representative of three independent experiments for which similar results were observed. Panel F shows that HBX19818 and P22077 treatment leads to degradation of FLT3-ITD in transfected HEK 293T cells following 24 h treatment. Immunoblots shown are representative of three independent experiments for which similar results were observed. Panels G-I shows that HBX19818 shortens the half-life of FLT3-ITD to a greater extent than wt FLT3. The experiment in Panel G is representative of three independent experiments for which similar results were observed (the other two experiments shown in Panel H and Panel I). CHX=cycloheximide; F/H—Flag/HA. Panel J shows effects of USP10 KD on FLT3, AKT, and ERK1/2 protein levels in MOLM14 cells. Panels K-M show effects of USP10 KD on FLT3 expression in wt FLT3-expressing K562, KU812F, and U937 cells. Panel N shows analysis of FLT3 levels in MOLM14 cells overexpressing USP10 wt and catalytically inactive USP10, USP10C424S. Immunoblot shown is representative of 3 additional studies for which similar results were observed (Panel O). Panel O shows analysis of FLT3 levels in MOLM14 cells overexpressing USP10 wt and catalytically inactive, USP10C424S ("USP10 mut").
Figure 7:
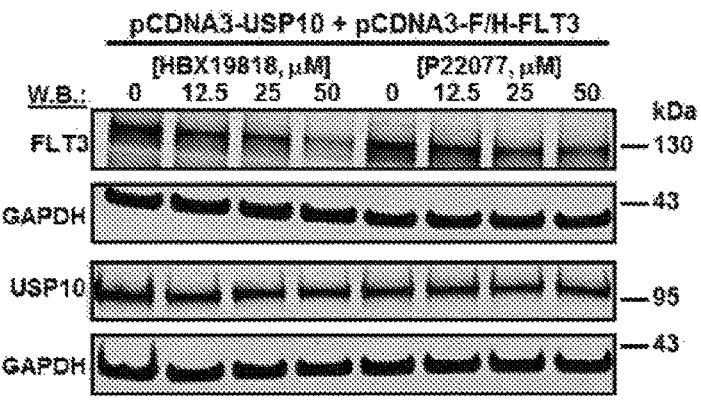
Figure 7:
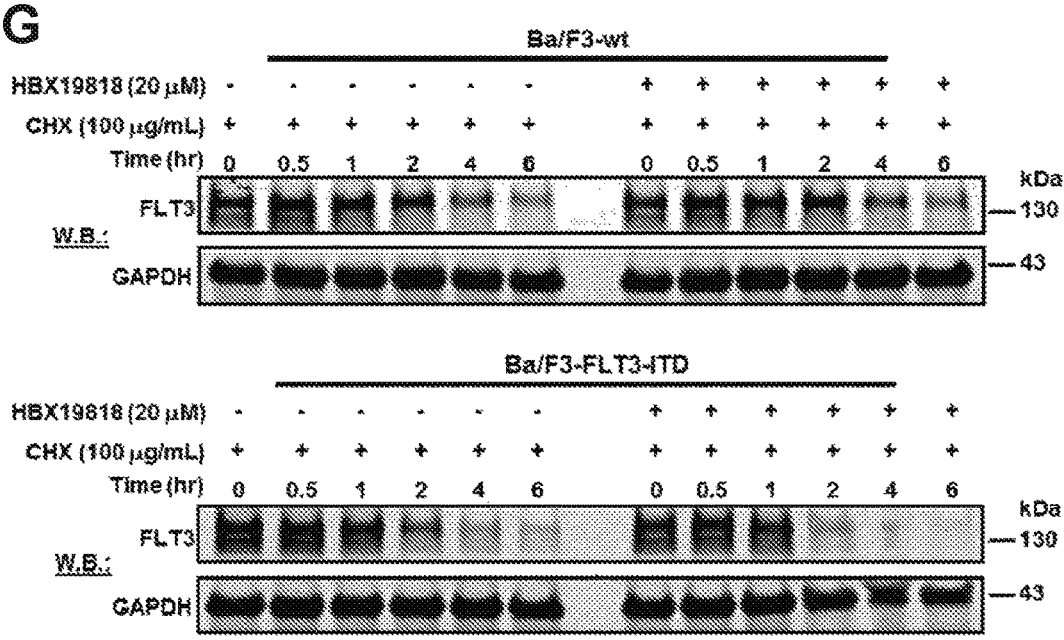
Figure 7:
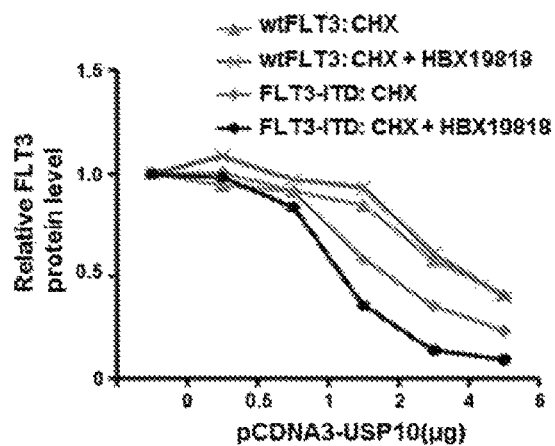
Figure 7:
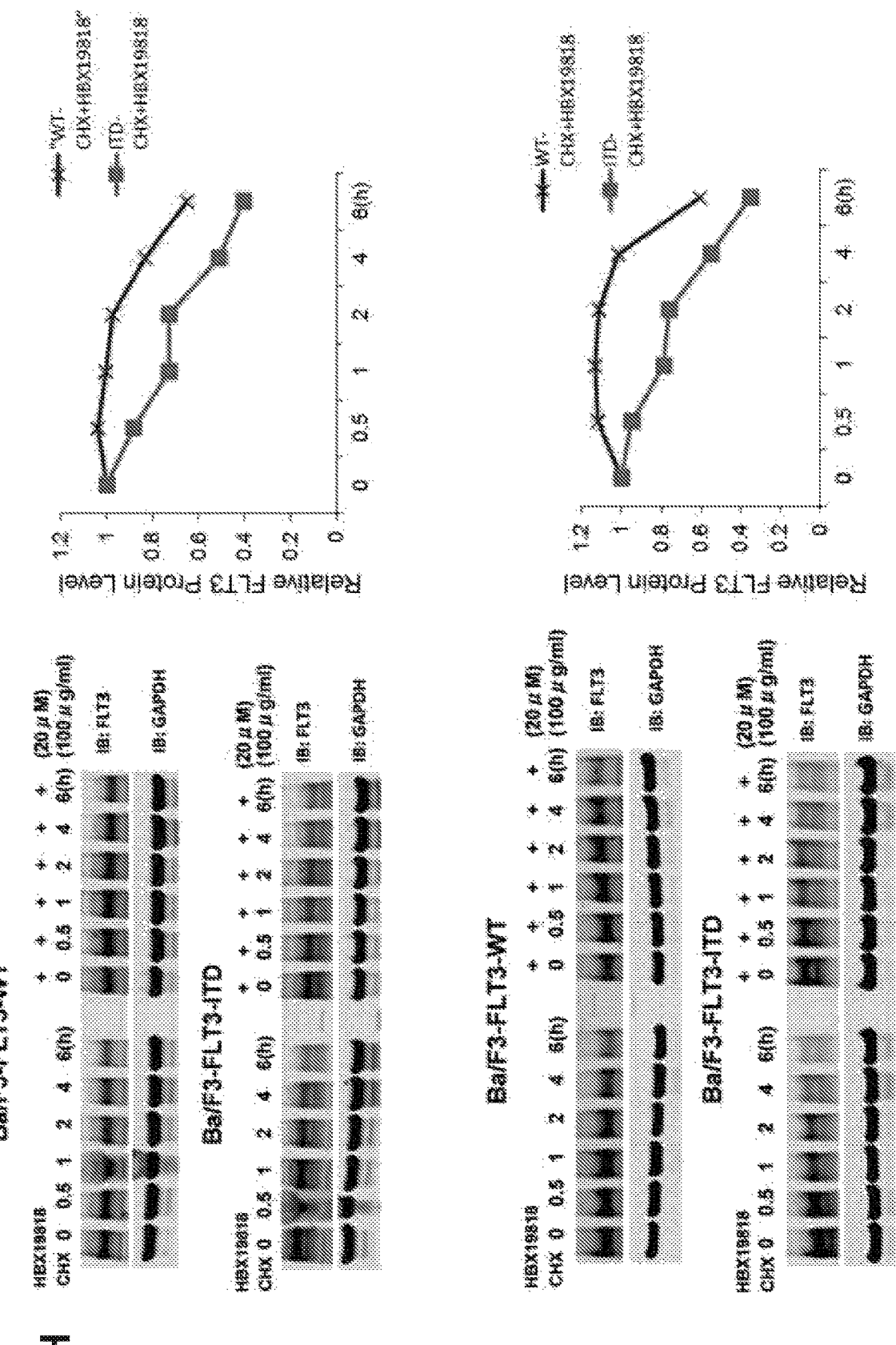
Figure 7:
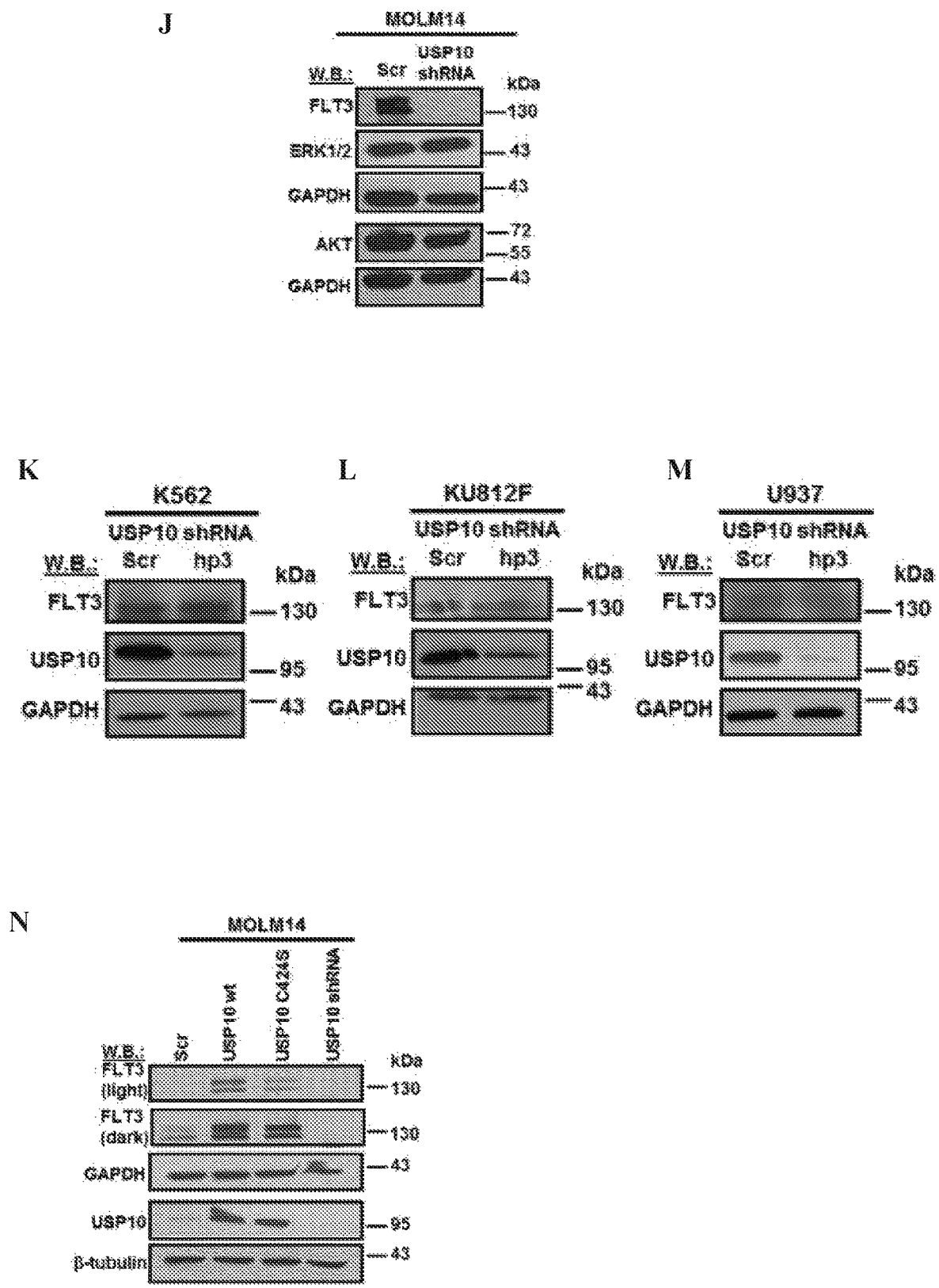
Figure 7:
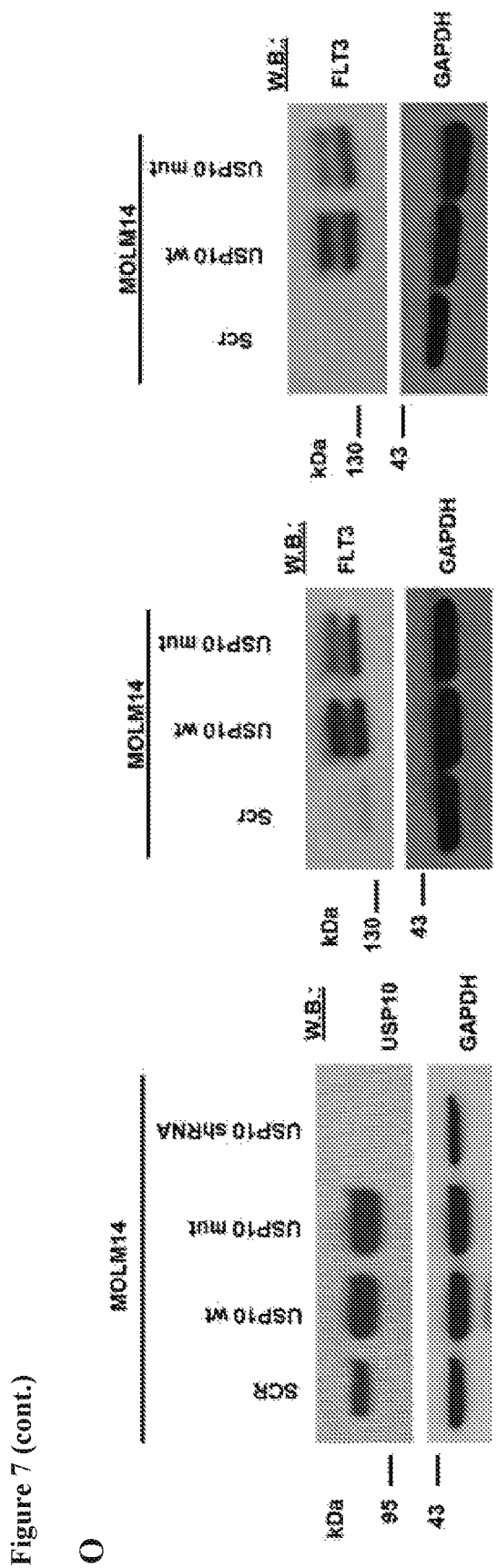
Figure 8:
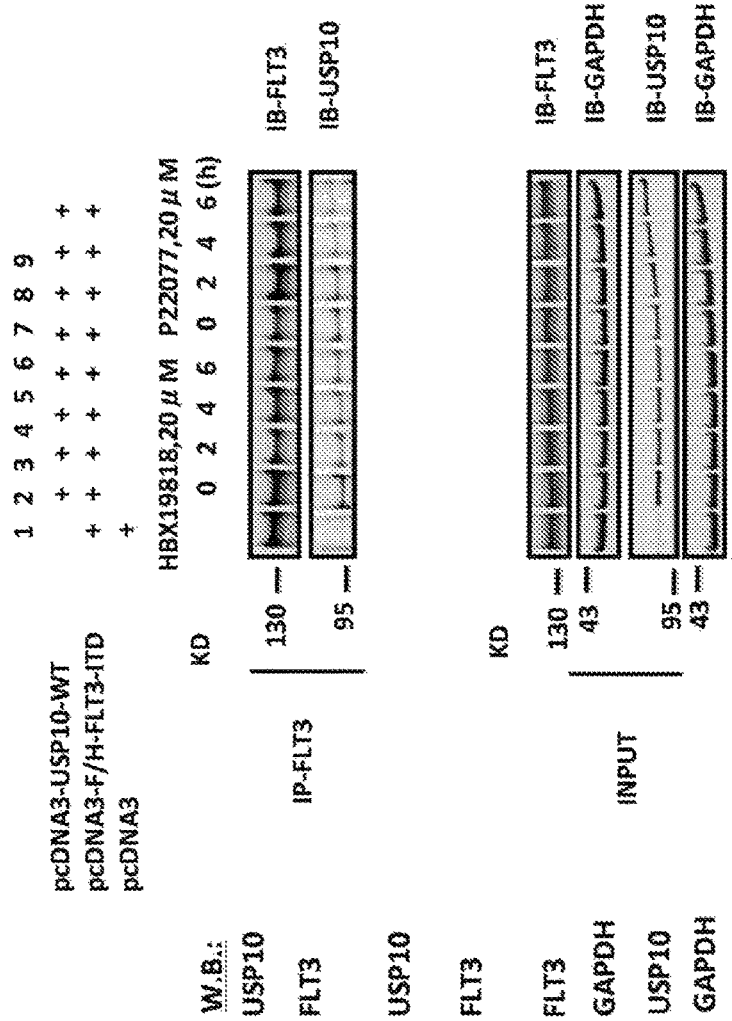
FIG. 8 includes 2 panels, identified as panels A, and B, which show the results of an investigation of FLT3 and USP10 association and DUB inhibitor-induced interference of FLT3-USP10 complex formation. Panel A shows the association of exogenously expressed USP10 with exogenously expressed wt FLT3 or FLT3-ITD in 293T cells transfected with PEI reagent. USP10-CS stands for the catalytically inactive mutant C424S. Panel B shows inhibition of the interaction of USP10 and FLT3 by HBX19818 and P22077 in 293T cells transfected with PEI reagent and made to over-express USP10 and FLT3. The first lane shown in this gel is the IP control for FLT3.
Figure 8:
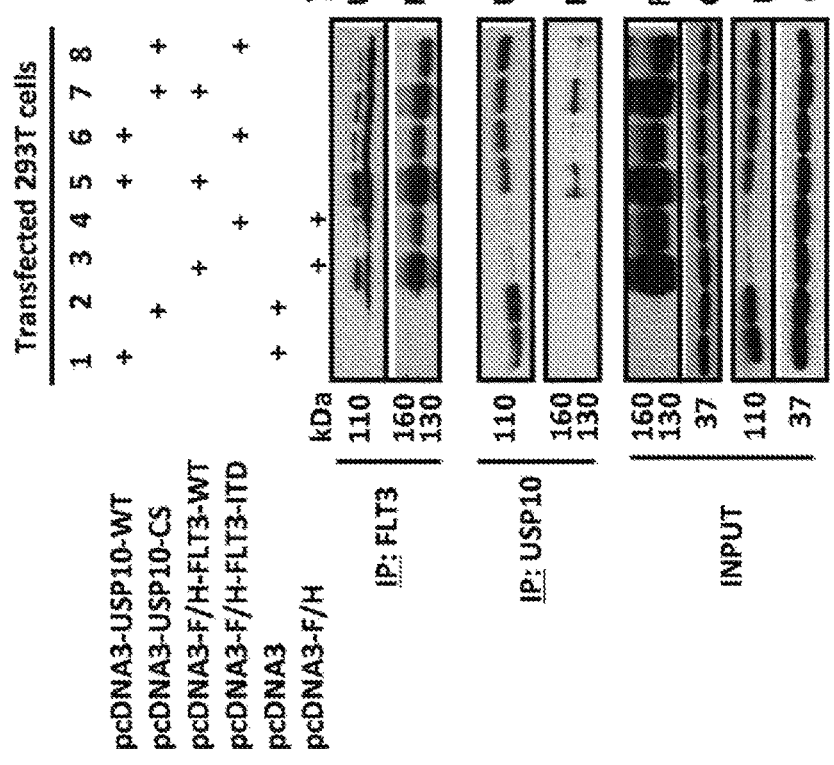

In order to investigate whether USP10 is the DUB that deubiquitylates FLT3, it was first examined whether USP10 and FLT3 are in a complex in FLT3 mutant cells. Robust co-immunoprecipitation of USP10 with FLT3 in FLT3-ITD Ba/F3 cells was observed and reverse co-immunoprecipitation studies confirmed the association of FLT3 with USP10 (FIG. 7A). In the converse experiment, increased expression of USP10 was observed to correlate with higher stabilization of FLT3-ITD protein than wt FLT3 protein in stably transfected MOLM14 and transiently transfected HEK 293T cells (FIGS. 7E, 7N, and 7O). It is important to note that, similar to oncogenic FLT3-driven AML cells, both HBX19818 and P22077 were able to induce degradation of FLT3 in HEK 293T cells, although approximately 2-fold higher concentrations were needed to replicate effects observed with both compounds in mutant FLT3-driven cells (FIG. 7F). Introduction of USP10 in which the catalytic cysteine has been replaced with serine, USP10C424S, into MOLM14 cells resulted in reduced stabilization of mutant FLT3 compared to wt confirming the importance of USP10 catalytic activity in regulating FLT3-ITD protein levels (FIG. 7N). Taken together, the SAR, KD and overexpression studies are in strong support of USP10 being the critical regulator of FLT3-ITD stability but do not address whether the impact is direct or indirect. It was then examined whether USP10 and FLT3 are in a complex in FLT3 mutant cells. It was observed that robust co-immunoprecipitation (co-I.P.) of USP10 with FLT3 in Ba/F3-FLT3-ITD cells, while reverse co-I.P. studies confirmed the association of FLT3 with USP10 (FIG. 7A). A similar interaction between USP10 and FLT3 (both wt and mutant) was demonstrated in 293T cells engineered to exogenously express these proteins (FIG. 8A). Importantly, HBX19818 at 2, 4, and 6 hours and the chemokine, P22077, at 4 and 6 hours were observed to block the interaction between USP10 and FLT3-ITD (FIG. 8B).

In order to clarify the potential role of USP10 in stabilization of mutant FLT3, USP10 knockdown (KD) was performed using three separate hairpins. Consistent with the anti-proliferation and degradation effects of HBX19818 being USP10-dependent, USP10 KD with each hairpin resulted in the robust degradation of FLT3-ITD, as well as substantial growth inhibition in FLT3-ITD-positive cells (MOLM13-luc+, MOLM14), as compared to the scrambled control hairpin (FIGS. 7B-7D, FIG. 10A). As was observed for HBX19818 and P22077, USP10 KD had little to no impact on signaling molecules, including AKT and ERK1/2, downstream of FLT3 (FIG. 7J). Effective USP10 KD by the same hairpins did not suppress growth of transformed human hematopoietic lines cell lines not driven by oncogenic FLT3 (K052, K562, KU812F, U937) (FIG. 7B and FIGS. 10B-E) and, similar to USP10-targeted small molecule inhibition, did not modulate wt FLT3 protein levels (FIG. 4K-M, 10B-D).

Figure 9:
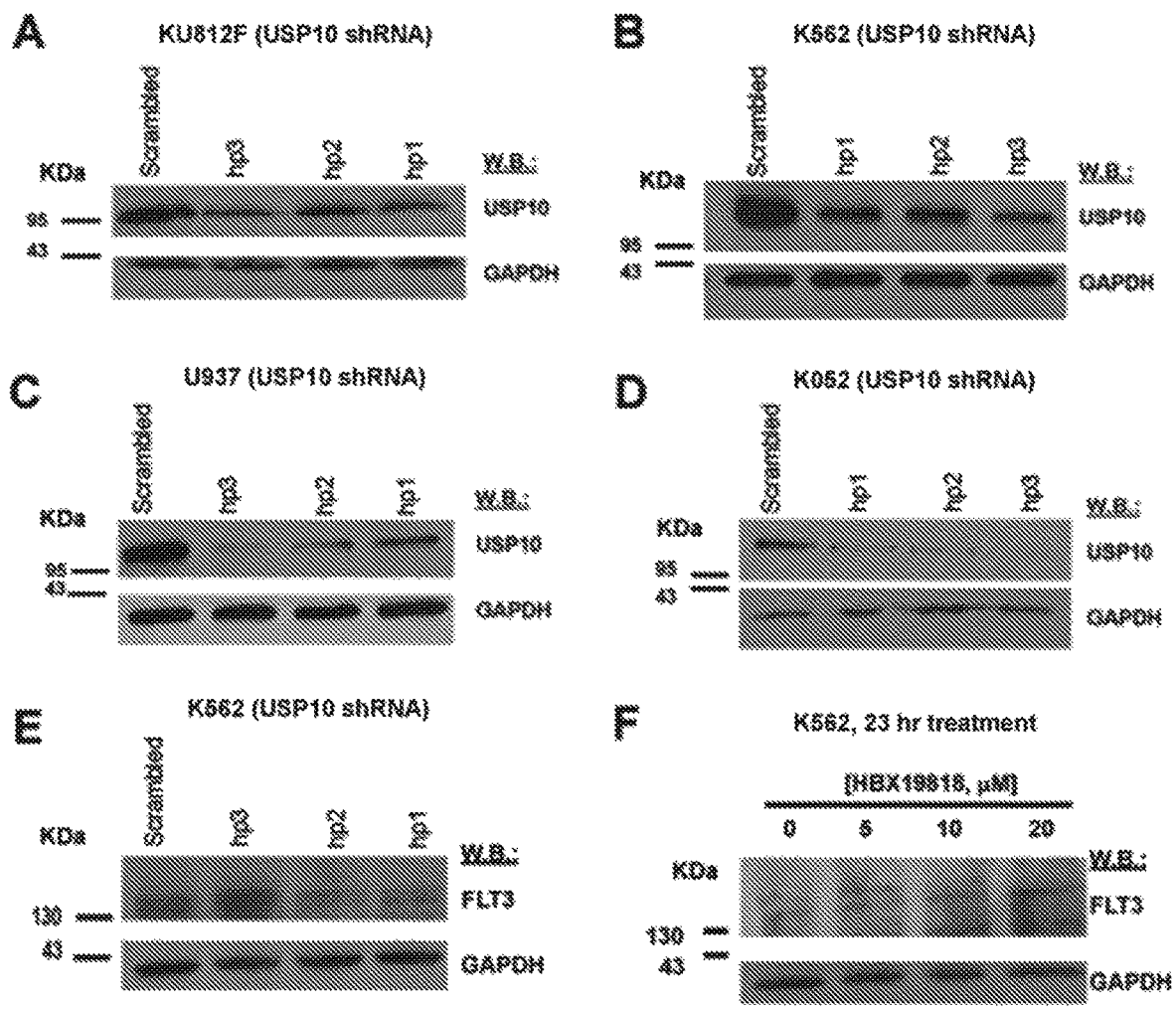
FIG. 9 includes 6 panels, identified as panels A, B, C, D, E, and F, which show the effect of USP10 KD in human leukemia cell lines not dependent on FLT3 for growth. Panels A-D show an analysis of USP10 gene KD efficiency. Panels E-F show the effect of USP10 KD or HBX19818 treatment on FLT3 expression in wt FLT3-expressing leukemia cells.
Figure 10:
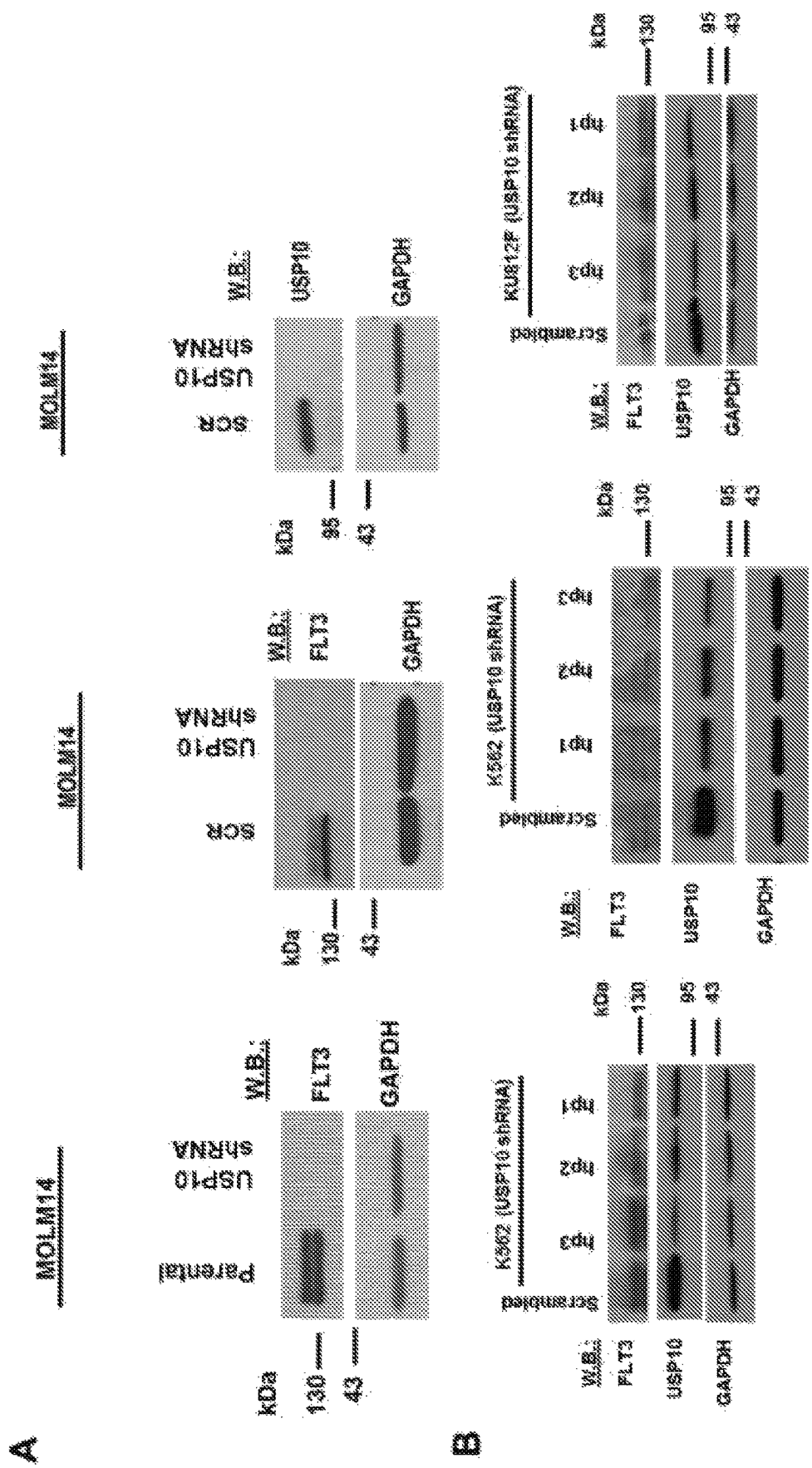
FIG. 10 includes 5 panels, identified as panels A, B, C, D, and E, which show effect of USP10 KD in human transformed hematopoietic cell lines expressing FLT3-ITD or wt FLT3. Panel A shows effects of USP10 KD on FLT3 expression in MOLM14 cells. Panels B-C shows analysis of USP10 gene KD efficiency and effect of USP10 KD on FLT3 expression in wt FLT3-expressing leukemia cells. Panel D shows analysis of USP10 gene KD efficiency in wt FLT3-expressing K062 cells. Panel E shows investigation of expression of USP10 and FLT3 in a panel of human transformed hematopoietic cell lines. Mutant FLT3-expressing lines are MOLM13, MOLM14, and MV411. The rest of the cell lines do not express mutant FLT3.
Figure 10C:
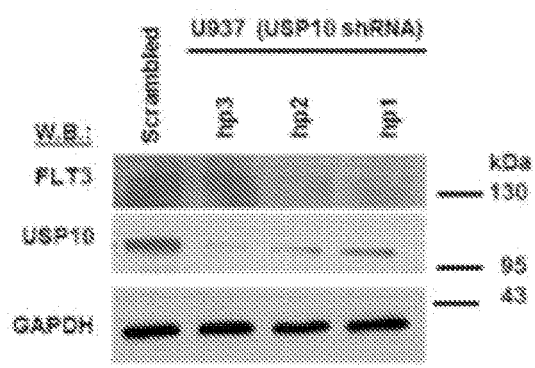
Figure 10D:
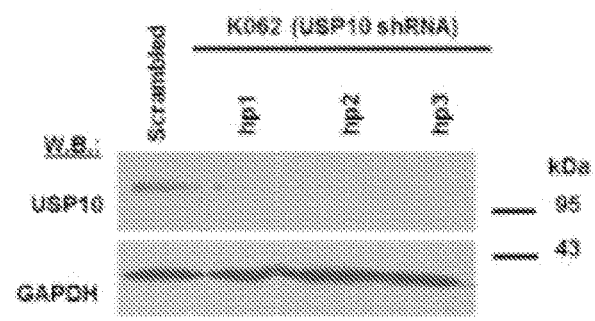
Figure 10E:
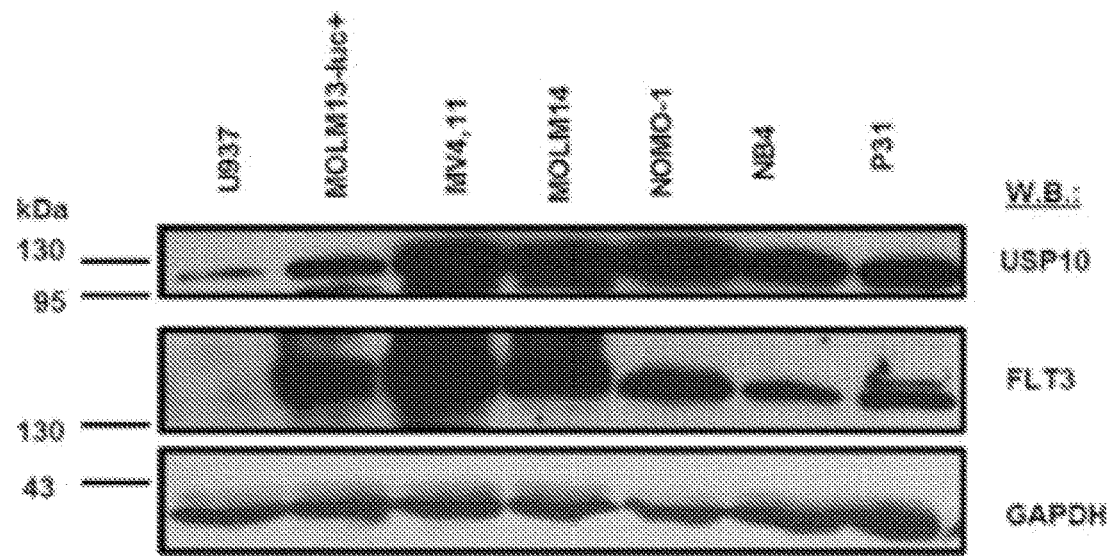

The observed differential impact on FLT3 wt and mutant protein with USP10 pharmacological inhibition and KD as well as enzyme overexpression, is consistent with reports that activated FLT3 is more prone to ubiquitin-mediated degradation (OSHIKAWA G., et. al., (2011) *J Biol Chem,* 286, 30263-73). The half-life of wt FLT3 and FLT3-ITD with and without over-expression of USP10 and in the absence and presence of HBX19818 was analyzed, to see if differences in protein stability might play a role in the differential responsiveness of the two proteins to DUB inhibitor treatment. In Ba/F3 cells, HBX19818 shortened the half-life of FLT3-ITD from 3-4 hr to around 2 hr, and was observed to shorten the half-life of FLT3-ITD to a greater extent than wt FLT3 (FIG. 7G-7I). Data are suggestive that this differential responsiveness to HBX19818 between wt FLT3 and FLT3-ITD may be due to modest differences in the inherent overall stability/half-life of these proteins. Similarly, HBX19818 strongly induced FLT3 degradation in these two cell lines at 20 μM (FIGS. 7C-7D). In contrast, effective USP10 KD by the same hairpins did not suppress growth of FLT3 wt cancer cells (e.g., K052, K562, KU812F, and U937; see FIGS. 7B and 9A-9D). Consistent with the minimal effects of HBX19818 on wt FLT3-expressing cell proliferation and FLT3 protein expression, USP10 KD in wt FLT3-expressing AML cell lines, U937 and K562, both of which have been characterized as expressing low levels of wt FLT3, did not change FLT3 protein levels (FIGS. 9E-9F). In addition, levels of USP10 were observed to be generally higher in cell lines expressing higher levels of FLT3, including MOLM14 and MV4,11, consistent with a stabilizing role for USP10 in FLT3 protein regulation (FIG. 10).

Figure 11:
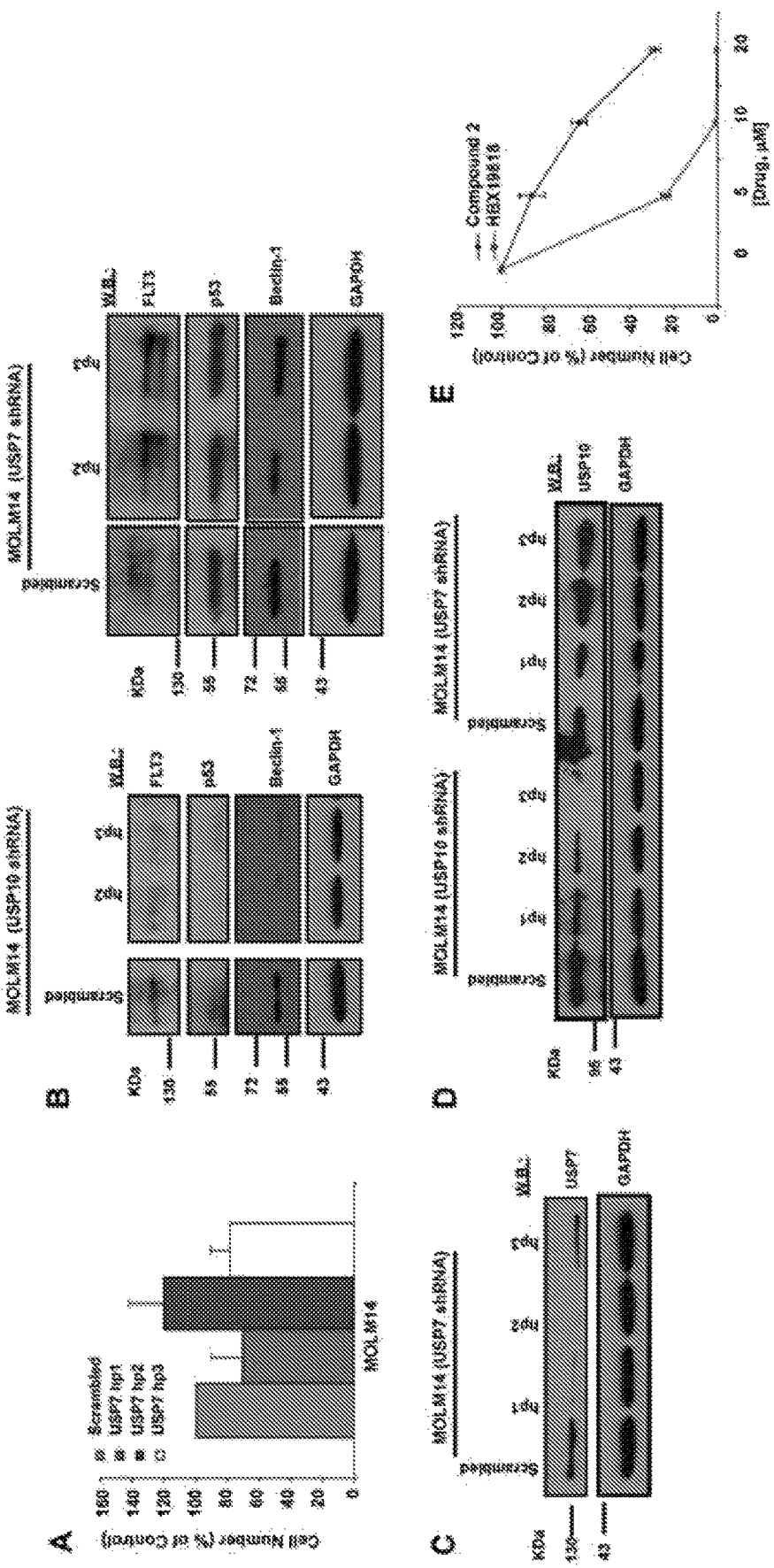
FIG. 11 includes 7 panels, identified as panels A, B, C, D, E, F, and G, which show the results of an investigation of USP7 as a potential mediator of FLT3 degradation induced by HBX19818. Panel A shows cell counts (Trypan Blue exclusion assay) determined approximately 9 days after puromycin selection of USP7 shRNA-infected MOLM14 cells. Panel B shows the results of a parallel investigation of the effects of USP10 KD and USP7 KD on FLT3, p53, and Beclin-1 expression in MOLM14 cells. Panel C shows validation of KD efficiency and analysis of expression of USP7 in USP7 shRNA-infected MOLM14 cells versus scrambled control cells. Panel D shows USP10 expression in USP10 shRNA-infected MOLM14 cells and USP7 shRNA-infected MOLM14 cells. Panel E shows the effects of HBX19818 versus Compound 2 on growth of Ba/F3-FLT3-ITD cells following approximately 72 hours of treatment. Panel F shows the results of an analysis of FLT3 protein levels in Ba/F3-FLT3-ITD cells treated with HBX19818 versus Compound 2. Panel G shows that Compound 2 selectively inhibits USP7 relative to a panel of DUB enzymes.
Figure 11F:
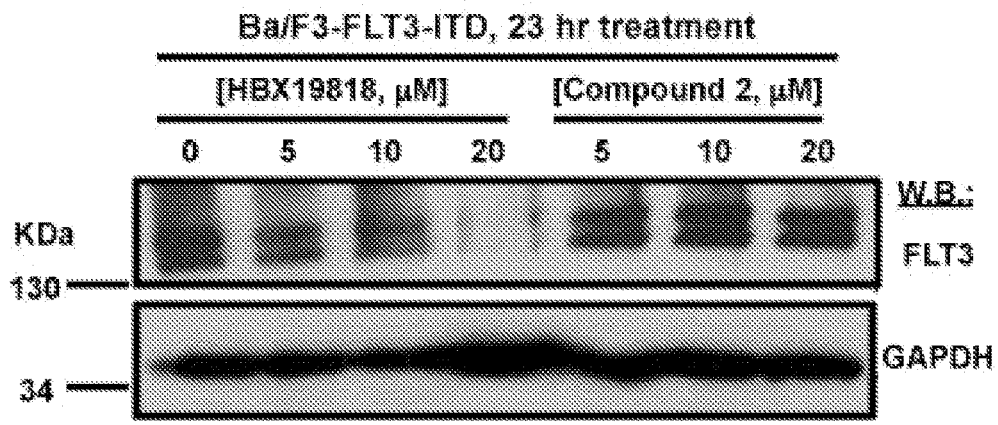
Figure 11G:
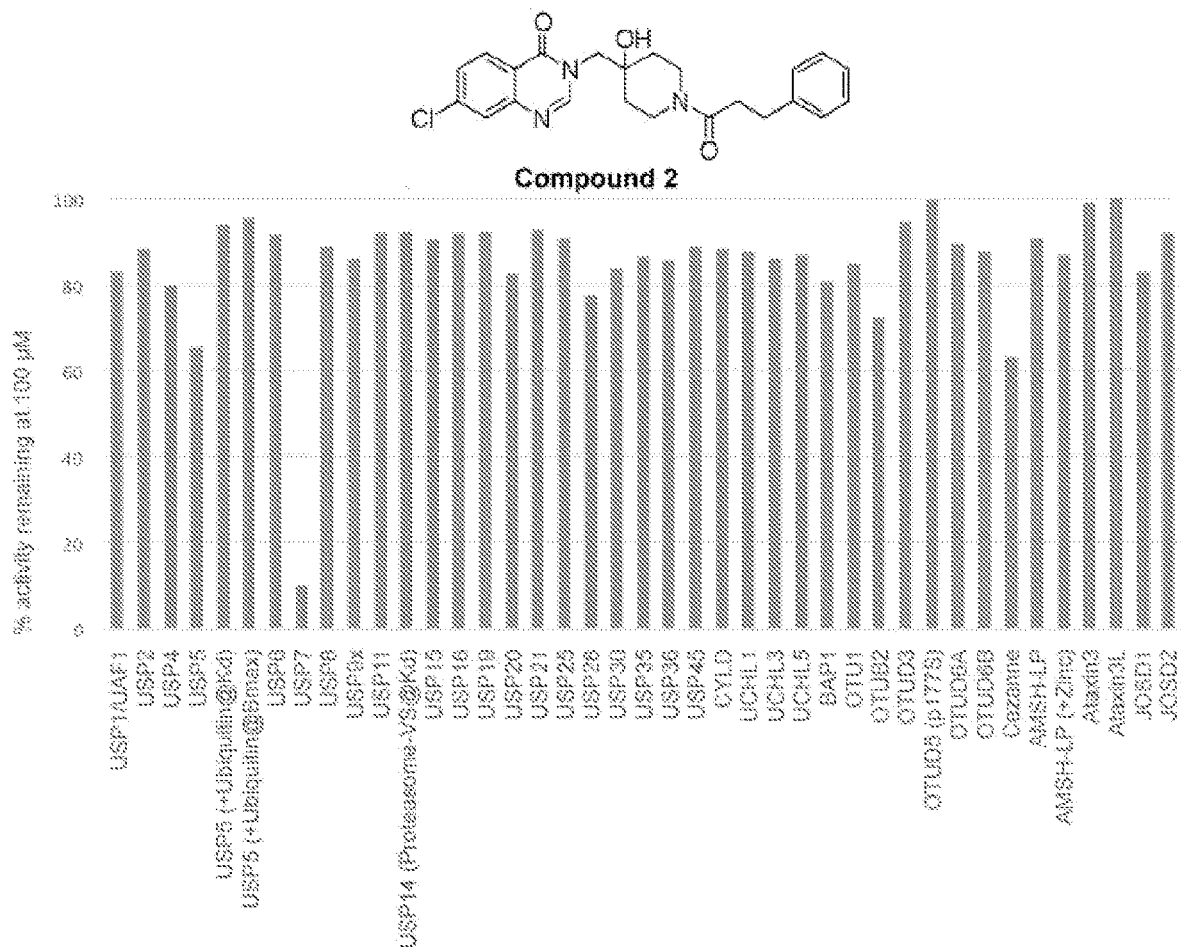

To elucidate whether USP7 may also contribute to mutant FLT3 degradation and growth inhibition of AML cells we knocked down USP7 using three separate hairpins. In contrast to USP10 KD, little to no change in FLT3 or Beclin-1 levels were observed in FLT3-ITD-expressing MOLM14 cells and transduction with the USP7 hairpins had little to no effect on cell viability as compared to the scrambled hairpin control (FIGS. 11A-11C). Importantly, USP7 KD was demonstrated to be selective, as levels of USP10, as expected, decreased in USP10 KD cells but remained unchanged in USP7 KD cells (FIG. 11D). Furthermore, pharmacological inhibition of USP7 using the selective USP7 inhibitor, Compound 2 (Kessler (2014) *Exp. Opin. Ther. Pat.* 24:597-602) (FIG. 11G), had little impact on cell viability and did not lead to reduced FLT3 levels in Ba/F3-FLT3 ITD cells at concentration up to 20 μM (FIGS. 11E-11G).

Figure 2A:
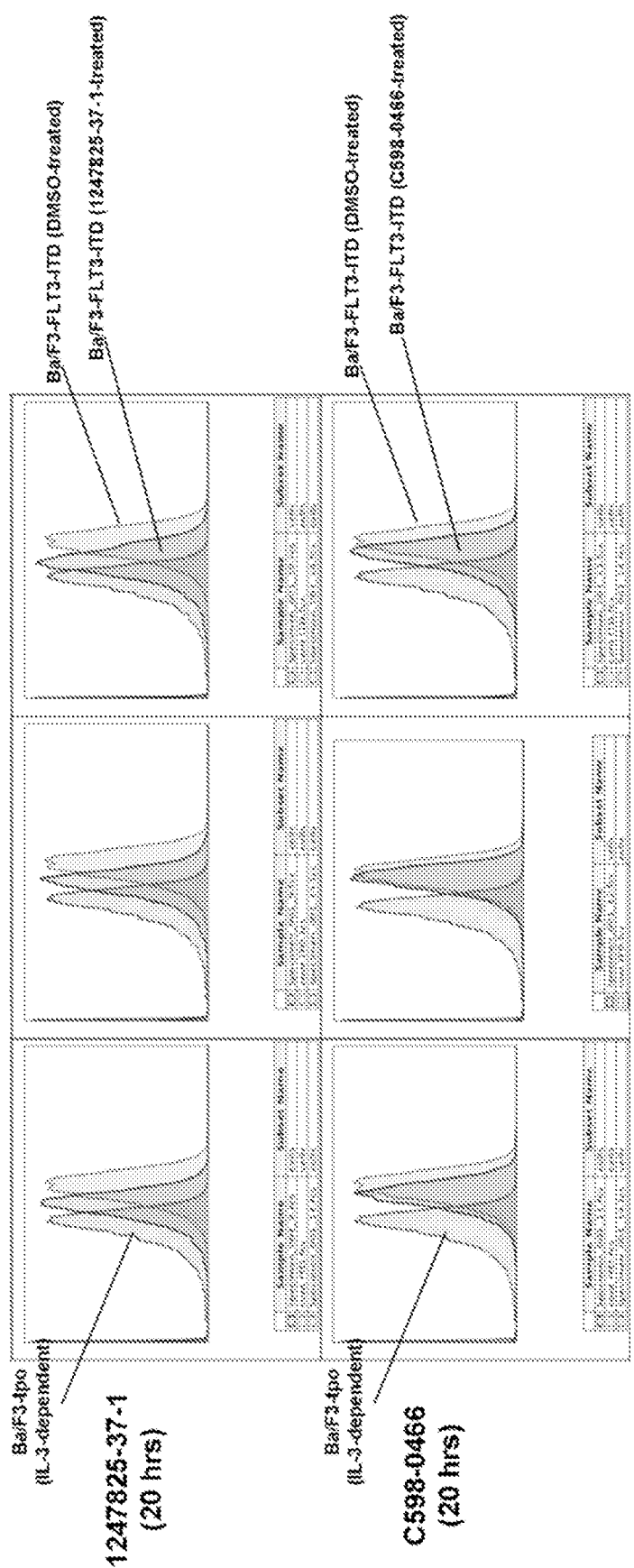
Figure 3:
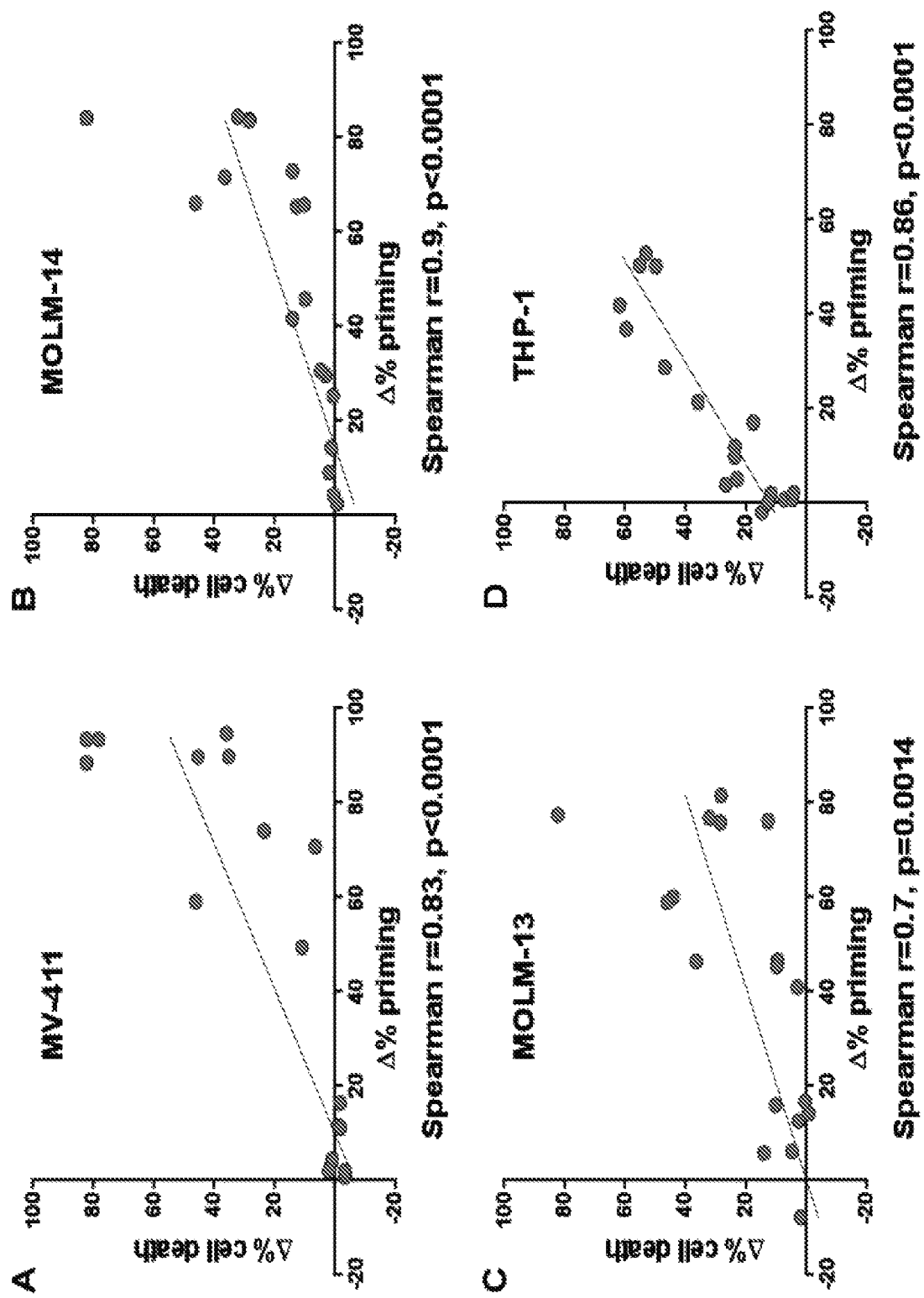
FIG. 3 includes 7 panels, identified as panels A, B, C, D, E, F, and G, which show that USP10-targeting inhibitors prime mutant FLT3-positive cells for apoptosis. Panels A-D show the correlation between priming and
n USP10 inhibitor-treated MV4, 11 cells (Panel A), MOLM-14 cells (Panel B), MOLM-13 cells (Panel C), and THP-1 cells (Panel D). Mitochondrial priming was detected by measuring cytochrome c release in response to Bim peptide at 14 h post-treatment. Cell death was determined by Annexin/PI staining at 72 h post-treatment. Panels E-G show mitochondrial priming in AML cell lines treated with C598-0105 (Panel E), C598-0571 (Panel F), and P22077 (Panel G). Mitochondrial priming was detected by measuring cytochrome c release in response to Bim peptide at 14 h post-drug exposure. A priming=priming of DMSO treated cells-priming of drug treated cells.
Figure 3:
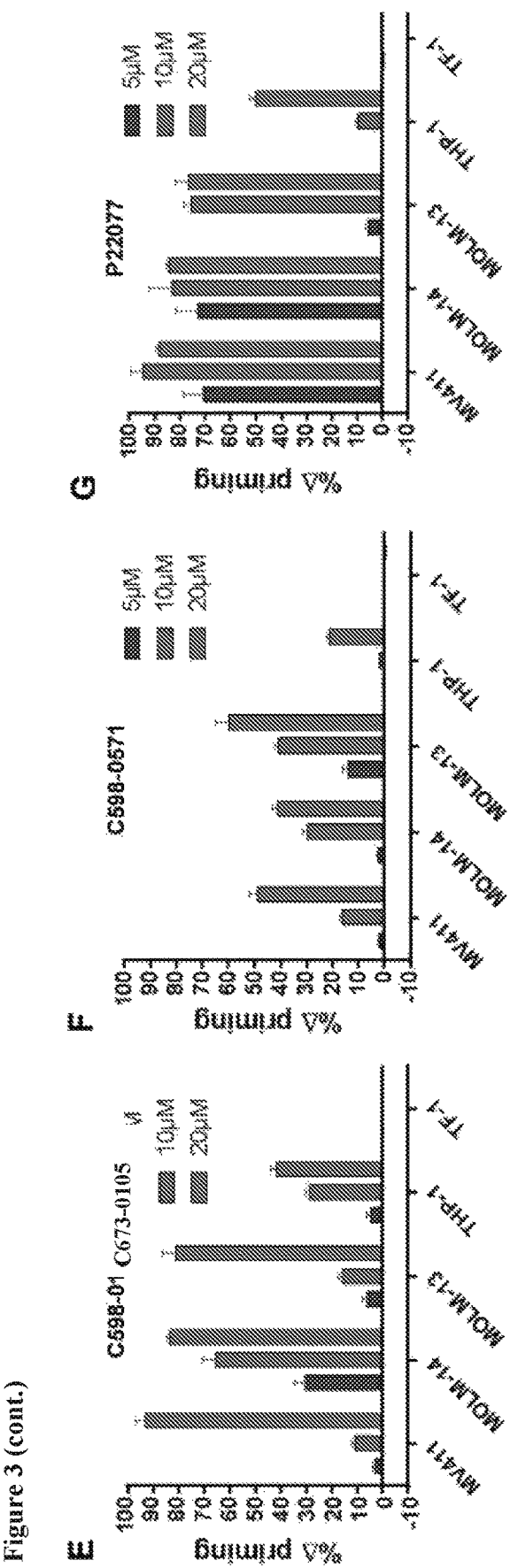
Figure 12:
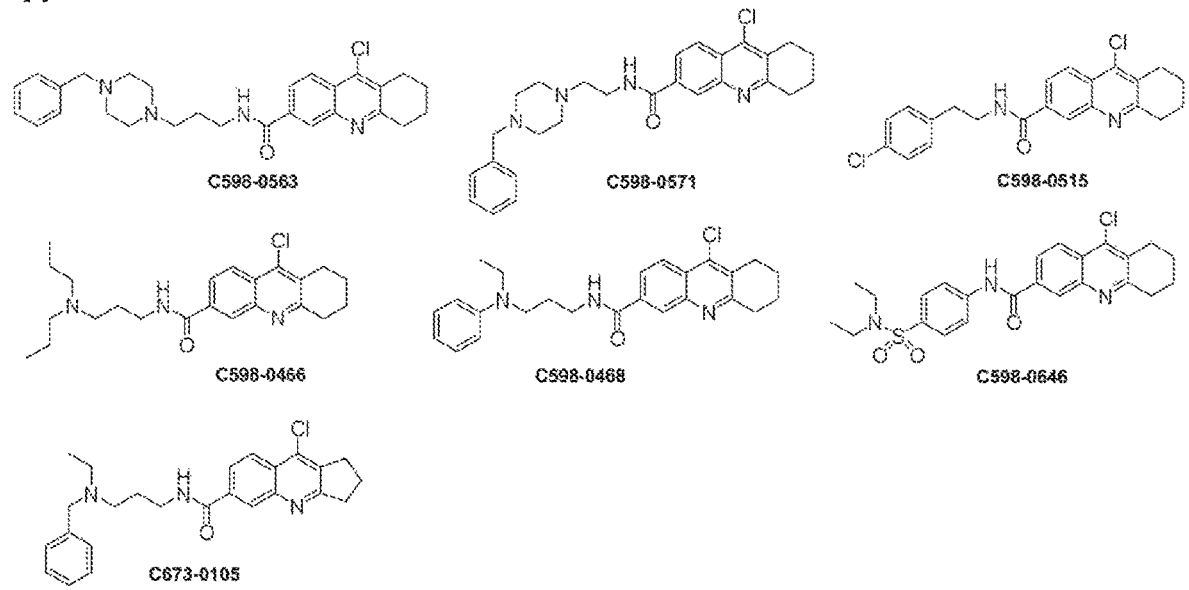
FIG. 12 includes 5 panels, identified as panels A, B, C, D, E, and F, which show the effects of P22077, HBX19818, and analogs on FLT3 or Beclin-1 levels in mutant FLT3-expressing cells. Panel A shows the chemical structures of HBX19818 analogs. Panel B-E show the results of an analysis of expression of FLT3 in Ba/F3-FLT3-ITD cells treated with C598-0571 (Panel B), C673-0105 (Panel C), C598-0515 (Panel D), or C598-0646 (Panel E) for approximately 25 hrs. Panel F shows the analysis of expression of Beclin-1 and FLT3 in Ba/F3-FLT3-ITD cells treated with 10 µM P22077.
Figure 12:
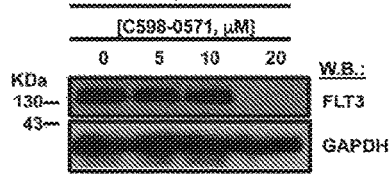
Figure 12:
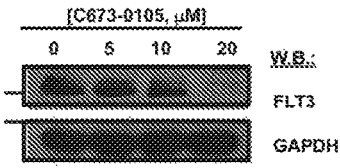
Figure 12:
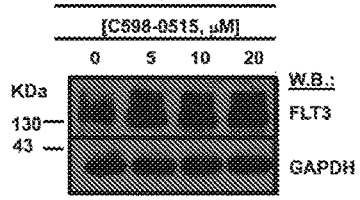
Figure 12:
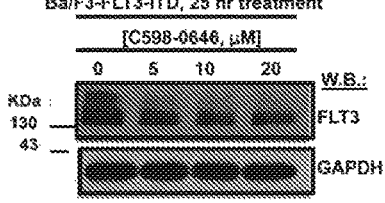
Figure 12:
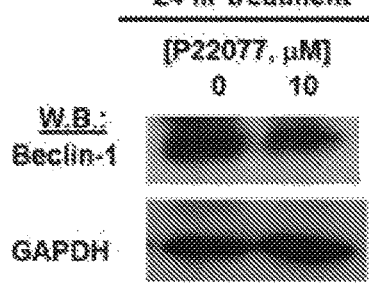
Figure 12:
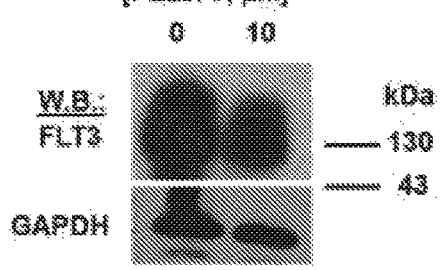
Figure 13:
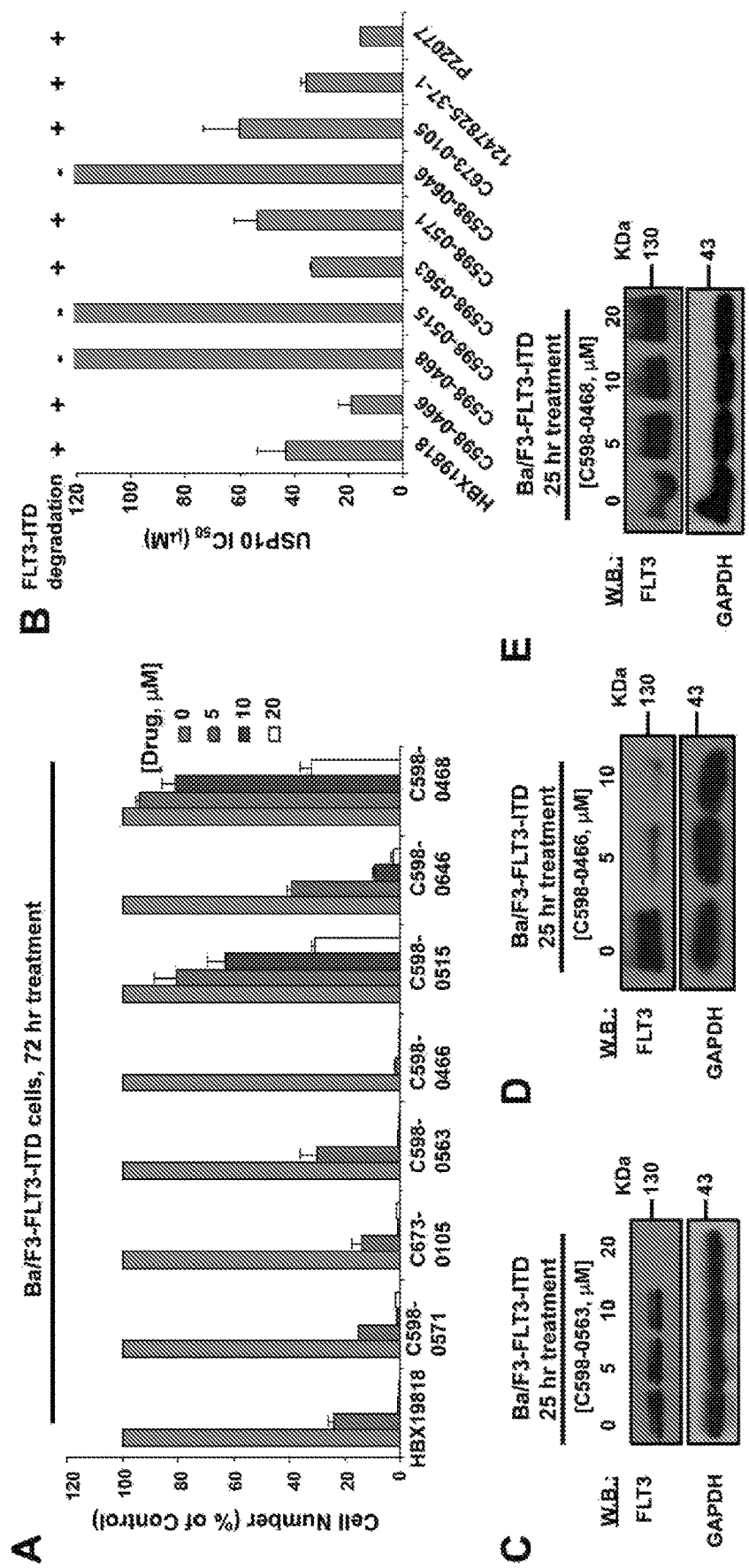
FIG. 13 includes 8 panels, identified as panels A, B, C, D, E, F, G, and H, which show targeted effects of HBX19818 and structural analogs of HBX19818 on growth of FLT3-ITD-driven cells. Panel A shows the effects of HBX19818 and structural analogs of HBX19818 on proliferation of Ba/F3-FLT3-ITD cells following approximately 72 hours of treatment. Panel B shows USP10 biochemical $IC_{50}$s of HBX19818, HBX19818 analogs, P22077, and 1247825-37-1 using Ub-AMC as substrate. Panel C-E show a comparison of effects of approximately 25 hours of treatment with C598-0563 (Panel C), C598-0466 (Panel D), or C598-0468 (Panel E) on FLT3 protein expression in Ba/F3-FLT3-ITD cells. Panel F shows the results of an analysis of proliferation of C598-0466-treated FLT3 null TF-1 cells versus FLT3-ITD-expressing MOLM13-luc+ and MOLM14 cells at 0, 5, 10, and 20 uM concentrations following 24 hours. Panel G-H show mitochondrial priming in AML cell lines treated with C598-0563 (Panel G) or C598-0466 (Panel H). Mitochondrial priming was detected by measuring cytochrome c release in response to Bim peptide at 14 h post drug exposure. Δ priming=priming of DMSO treated cells-priming of drug-treated cells.
Figure 13:
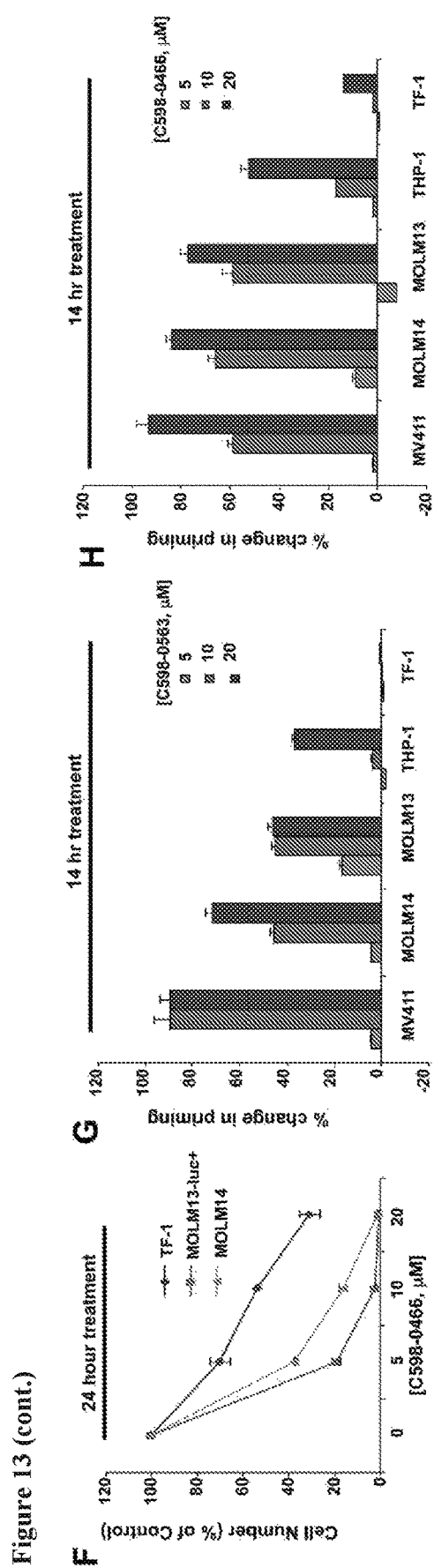

Next, seven HBX19818 analogs (chemical structures shown in FIG. 12A, their anti-proliferation $IC_{50}$s shown in Table 9) were acquire and their USP10 inhibitory activity was tested in a biochemical assay, impact on FLT3 protein levels, and anti-proliferative effects against Ba/F3-FLT3-ITD cells. Good correlation among these parameters was observed, supporting USP10 as the relevant target of HBX19818 (FIGS. 12B-12E and 13A-13E). For example, C598-0563, which inhibits USP10 comparably to HBX19818 (FIG. 13B), was observed to suppress cell growth and induce loss of FLT3 at similar concentrations (FIGS. 13A and 13C), whereas C673-0105, which inhibits USP10 comparably to HBX19818 (FIG. 13B) but no longer inhibits USP7 ($IC_{50}$>>100 μM, Table 9), had similar function as C598-0563 (FIGS. 12C and 13A). The more potent USP10 inhibitor, C598-0466 (FIG. 13B), has a lower anti-proliferation $EC_{50}$ and induces FLT3 degradation at lower concentrations (FIGS. 13A-13B and 13D). In contrast, C598-0468 exhibited little inhibition of USP10 in a purified enzyme assay ($IC_{50}$=>>100 μM), (FIG. 13B), a significantly right-shifted anti-proliferation curve and no effect on FLT3 levels at the same concentrations HBX19818 degraded FLT3 (FIGS. 13A and 13E). The more potent HBX19818 analog, C598-0466, maintained specificity for FLT3 mutant MOLM13, MOLM14, and MV4, 11 cell lines relative to the FLT3 null cell line, TF-1, and other leukemia lines not driven by FLT3 (FIG. 13F and Table 9), and led to a loss in cell surface FLT3 expression (FIG. 2). Also, similar to HBX19818, two analogs, 5 and 7, primed mutant FLT3-expressing cells more strongly than wt or null FLT3-expressing cells (FIGS. 3E-3F and 13G-13H). Taken together, the co-immunoprecipitation, hairpin KD, and SAR studies are in strong support of USP10 directly deubiquitylating FLT3-ITD.

Example 4: A Distinct USP10 Inhibitor Chemotype Mimics the HBX19818 Phenotype

Figure 14:
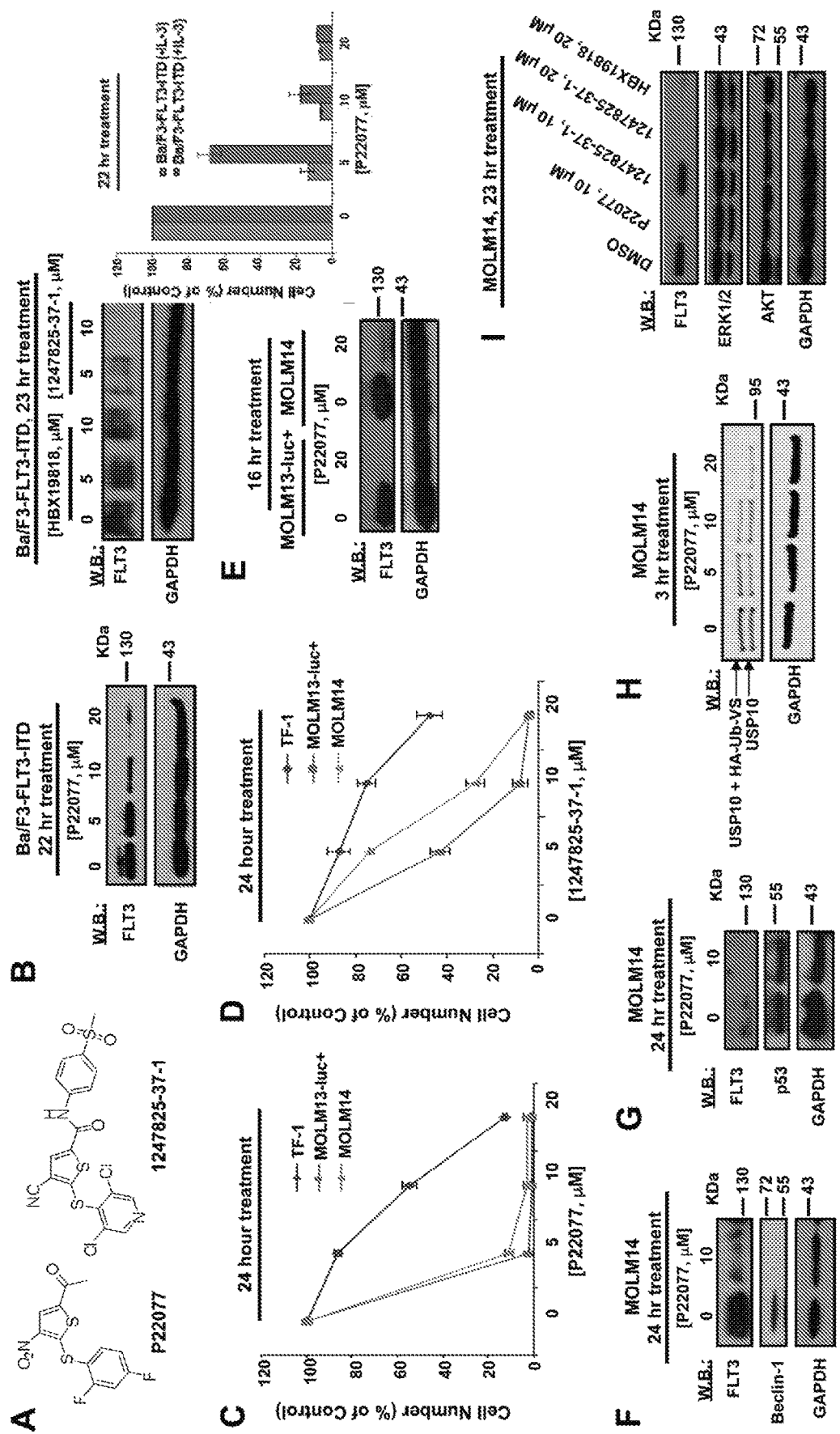
FIG. 14 includes 11 panels, identified as panels A, B, C, D, E, F, G, H, I, J, and K, which show the targeted effect of USP10 inhibitors, P22077 and 1247825-37-1, on FLT3-ITD-expressing AML cells. Panel A shows the chemical structure of P22077 and 1247825-37-1. Panel B shows the results of an analysis of FLT3 protein levels in Ba/F3-FLT3-ITD cells treated with P22077 and 1247825-37-1 for approximately 22-23 hours. HBX19818 is shown for comparison. Panels C-D show the effects of P22077 (Panel C) or 1247825-37-1 (Panel D) on growth of FLT3 null TF-1 versus FLT3 mutant MOLM13-luc+ and MOLM14 cells at 0, 5, 10, and 20 µM concentrations following approximately 24 hours of treatment. Panel E shows the results of an analysis of FLT3 protein levels in MOLM13-luc+ and MOLM14 cells treated with P22077 for approximately 16 hours. Panel F shows the results of an analysis of Beclin-1 levels in MOLM14 cells treated with P22077 for approximately 24 hours. Panel G shows the results of an analysis of p53 levels in MOLM14 cells treated with P22077 for approximately 24 hours. Panel H shows the results of a target engagement study (P22077, USP10). MOLM14 cells were treated with the indicated concentration of compound, lysed, and incubated with 0.25 ug HA-Ub-VS for 30 min at RT. The ability of P22077 to block USP10 labeling by HA-Ub-Vs indicates binding of the enzyme by inhibitor. Panel I shows the results of an analysis of FLT3, ERK1/ERK2, and AKT expression in MOLM14 cells treated with P22077, 1247825-37-1, or HBX19818 for approximately 23 hours. Panel J shows the effect of 1247825-31-1 on FLT3 versus AKT protein levels in MV4, 11 cells following approximately 23 hours of treatment. Panel K shows the effects of P22077 on Ba/F3-FLT3-ITD cells cultured in the absence or presence of 20% WEHI-conditioned media (used as a source of IL-3) following 22 hr of treatment. Error bars represent the standard deviation for samples set up in duplicate.
Figure 14:
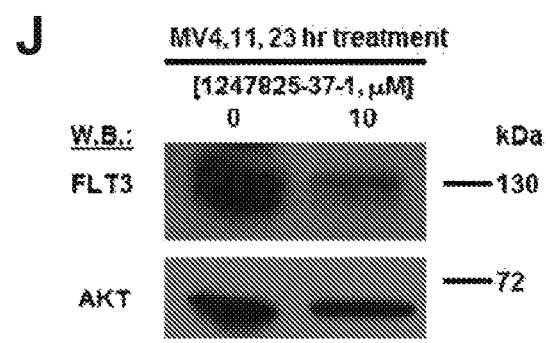
Figure 14:
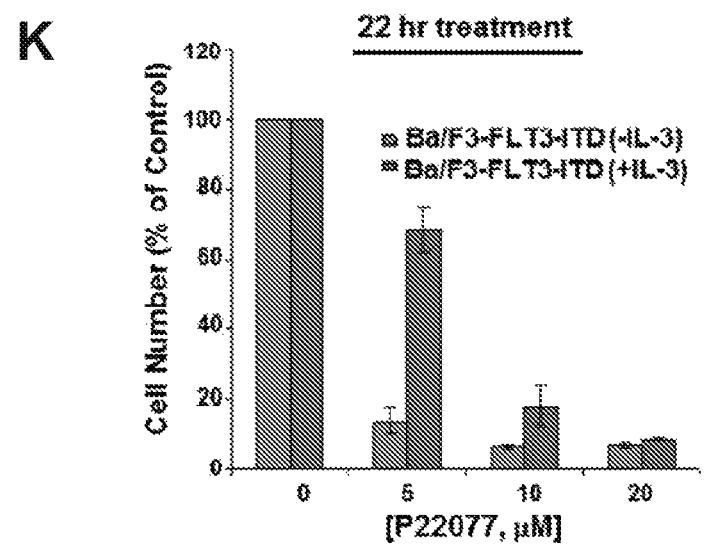
Figure 15:
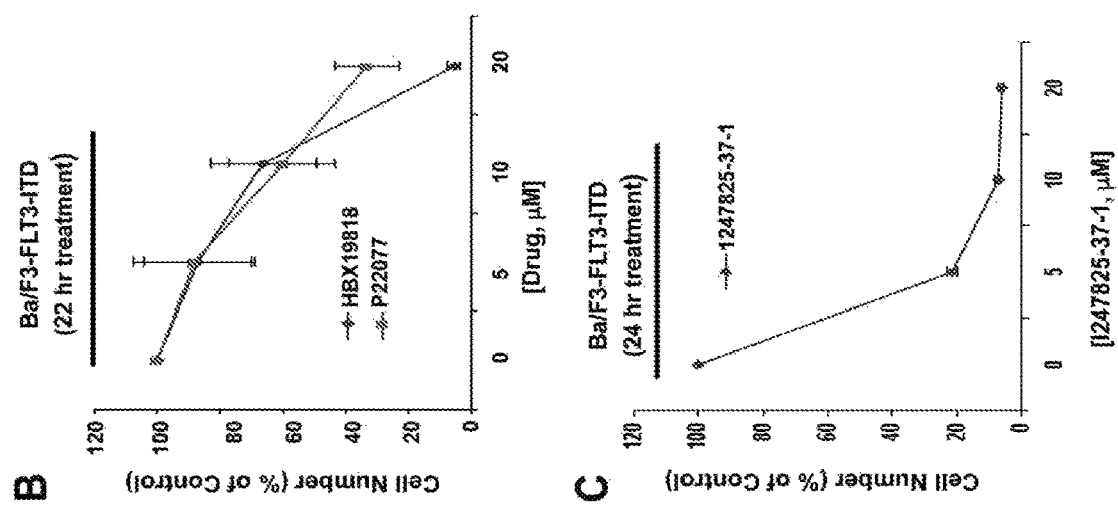
FIG. 15 includes 5 panels, identified as panels A, B, C, D, and E, which show characterization of chemotypes, P22077 and 1247825-37-1. Panel A shows the structures and selectivity profiling data for P22077 and 1247825-37-1. Panel B-E shows the effects of P22077 and 1247825-37-1 on the growth of mutant FLT3-expressing cells and targeting of USP10 by 1247825-37-1. Panels B-C show the effects of P22077, HBX19818, and 1247825-37-1 treatment on growth of Ba/F3-FLT3-ITD cells following approximately 22-24 hours. Panel D shows the effect of 1247825-37-1 versus Compound 2 on growth of MOLM13-luc+ and MOLM14 cells following approximately 72 hours of treatment. Panel E shows the results of a target engagement study (1247825-37-1, USP10) similar to that described in panel H of FIG. 14.
Figure 15:
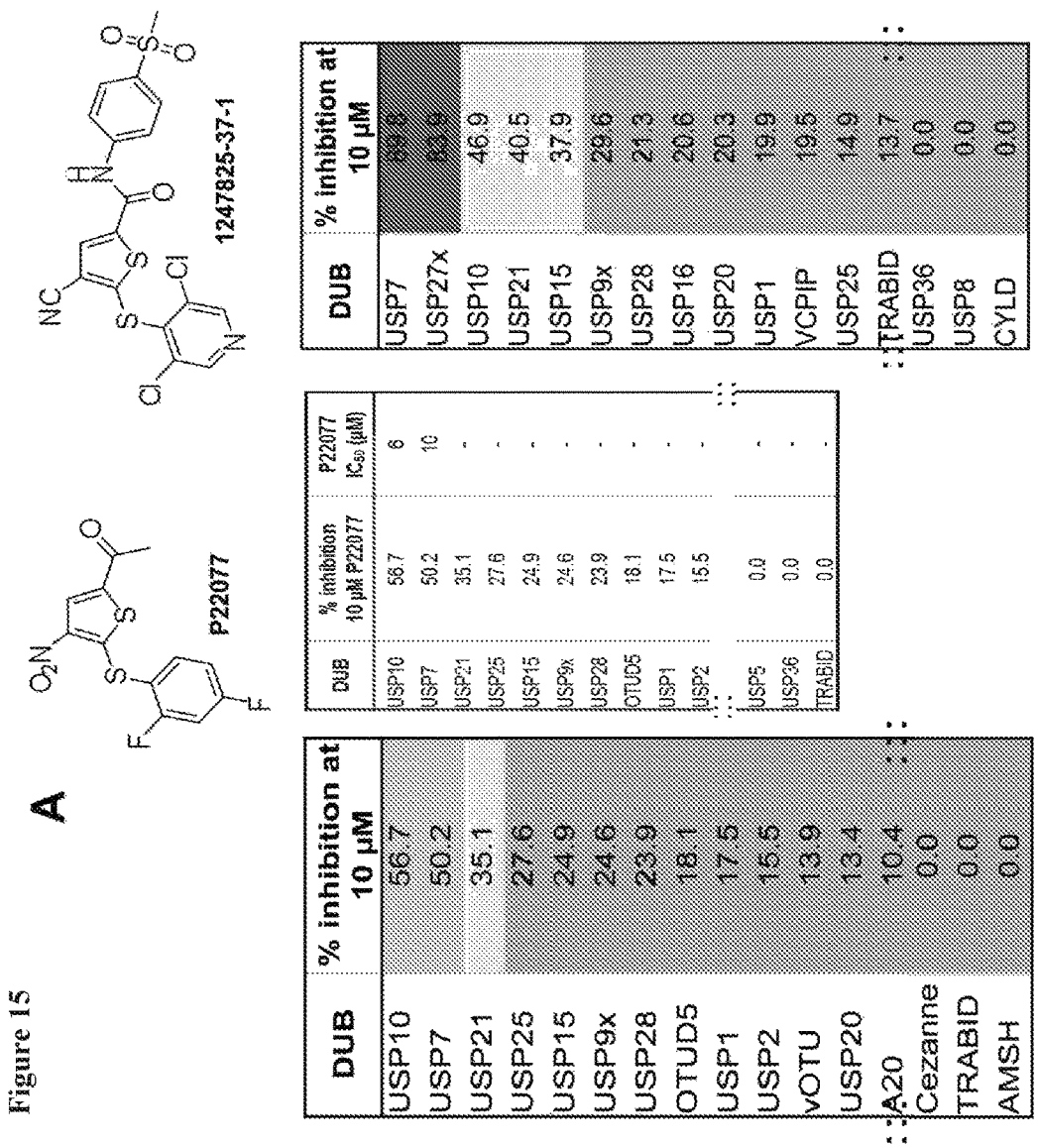
Figure 15:
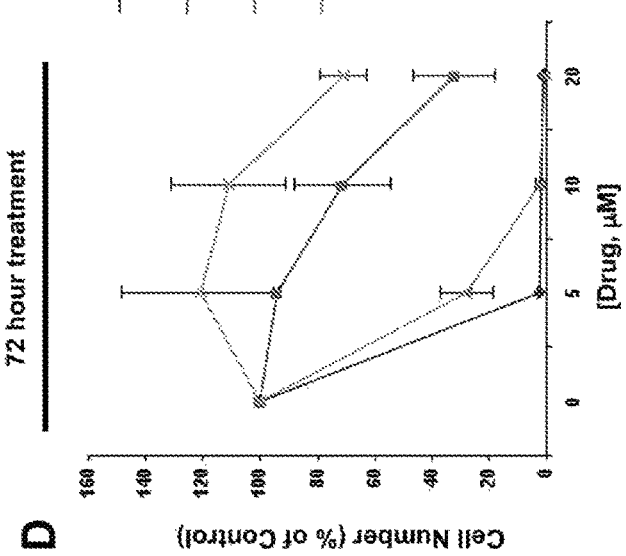

In order to further validate that the FLT3 degradation and anti-proliferative effects observed with HBX19818 treatment are a result of USP10 inhibition, it was sought to identify a distinct USP10 inhibitor chemotype and investigate whether the agent mimics the HBX19818 profile. In the screen as described in Example 1, it was also discovered that a thiophene-based DUB inhibitor series (Chauhan et al. (2012) *Cancer Cell* 22:345-358; Weinstock et al. (2012) *ACS Med. Chem. Lett.* 3:789-792), including members P22077 and 1247825-37-1 (structures in FIG. 14A), inhibits USP10 (Ritorto et al. (2014) *Nat. Commun.* 5:4763) and exhibits the same pattern of activity against FLT3-mutant cancer cell lines as HBX19818. Profiling of the compounds in vitro against a panel of 33 recombinant DUBs at a concentration of 10 µM, using diubiquitins as substrate, revealed potent USP10 inhibition for both compounds (FIG. 15A; showing P22077 inhibiting USP10 and USP7 with $IC_{50}$s of 6 µM and 10 µM, respectively). The biochemical $IC_{50}$s for P22077 and 1247825-37-1, using ubiquitin-AMC as substrate, were 15 µM and 36 µM, respectively (FIG. 13B). However, it should be noted that biochemical assays have revealed 1247825-37-1 to be characteristically more multi-targeted in nature than P22077, and thus this compound may be subject to off-target effects (FIG. 15A). Treatment of FLT3-ITD-positive Ba/F3, MOLM13-luc+ and MOLM14 cells with P22077 and 1247825-37-1 resulted in FLT3 and Beclin-1 degradation, which was similar to HBX19818, and reduced cell survival following 22-24 hours of treatment (FIGS. 14B-14G and 15B-15D). Beclin-1, like FLT3, was also strongly decreased in 10 µM P22077-treated MOLM14 cells (FIG. 14F) and partially degraded in Ba/F3-FLT3-ITD cells (FIG. 12F). It should be noted that although only validated as USP10 and USP7 inhibitors both HBX19818 and P22077 exhibit at least some degree of inhibitory activity against additional DUBs, and potentially non-DUB targets, which likely contributes to anti-proliferative effects observed at concentrations below where USP10 is well inhibited by compound. Both HBX19818 and P22077 suppressed the growth of the FLT3-ITD-positive AML cell lines, MOLM13-luc+, MOLM14, and MV4,11, in a dose-dependent manner with selectivity toward mutant FLT3-expressing cells versus wt or null FLT3-expressing cells (FIG. 1I, FIG. 14C, Table 3). It should be noted, however, that several human hematopoietic cell lines not driven by oncogenic FLT3 displayed relative sensitivity to P22077, which can likely be attributed to the multi-targeted nature of this agent. Similar to HBX19818, P22077 inhibited proliferation of FLT3-ITD- and FLT3-D835Y-positive Ba/F3 cells with EC50s in the single digit micromolar range following approximately 22 hours of treatment (FIG. 14 J). In addition, similar to HBX19818, it was confirmed that P22077 binds USP10 in cells using establishing activity-based probe profiling methods (Altun et al. (2011) *Chem. Biol.* 18:1401-1412). In particular, USP10 in lysates from live cells treated with P22077 or 1247825-37-1 was blocked from labeling with an HA tagged ubiquitin probe modified to in the low micromolar range (FIGS. 14H and 15E). Specifically, 1247825-37-1 was found as a second generation USP7 inhibitor, derived from P22077, which also inhibits USP10 (FIG. 13B and FIG. 15A) and phenocopies HBX19818 and P22077 in terms of selective inhibition of proliferation of mutant FLT3-expressing cells over null FLT3-expressing TF-1 cells, concomitant targeted induction of FLT3 degradation with no degradation of downstream effectors of FLT3 signaling, and USP10 target engagement (FIGS. 14B, 14D, 14J, 15C, and 15E).

Figure 16:
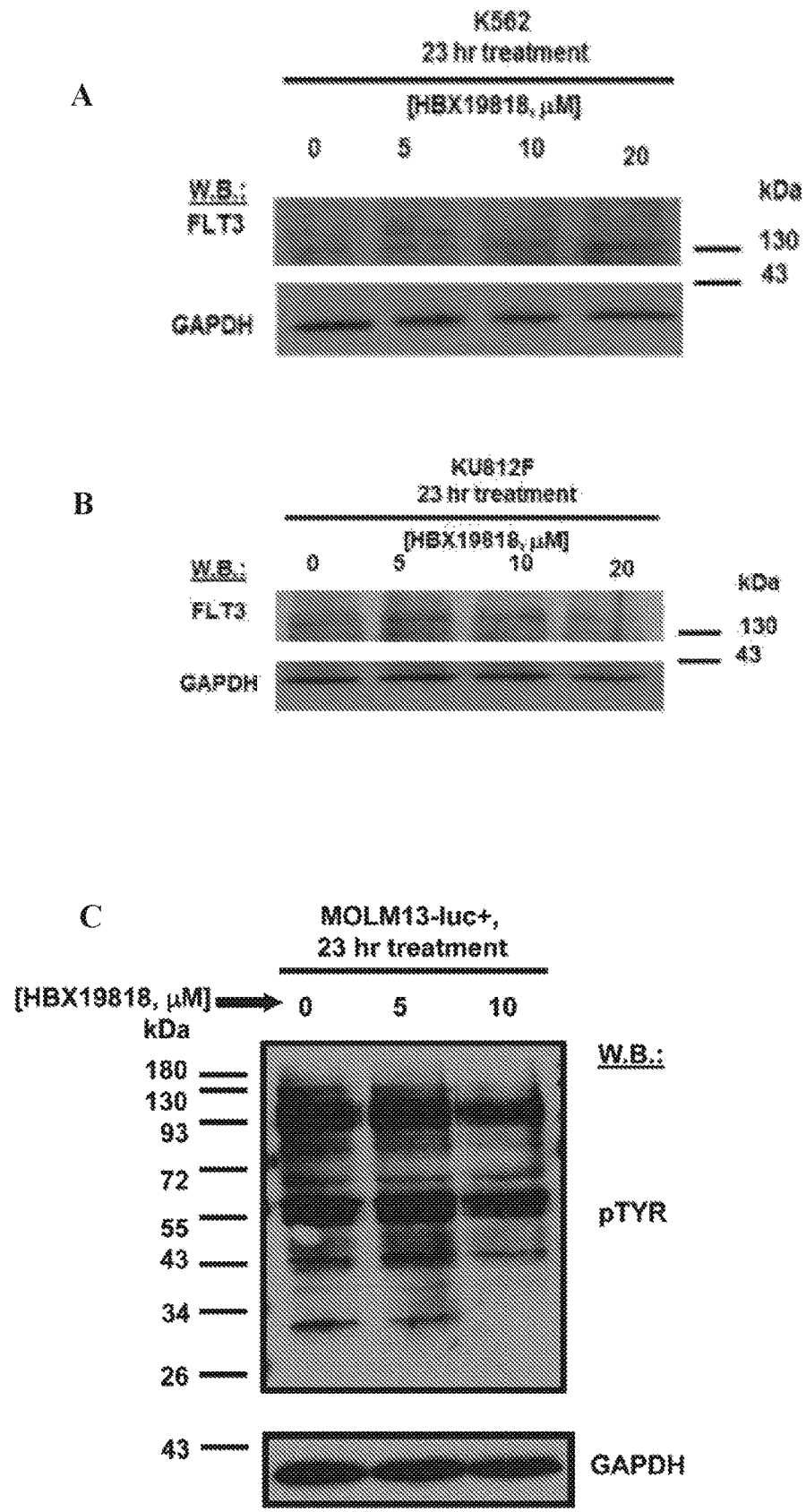
FIG. 16 includes 3 panels, identified as panels A, B, and C, which show the effects of HBX19818 on FLT3 protein and signaling. Panels A and B show the effect of HBX19818 treatment on FLT3 protein levels in K562 and KU812F cells after approximately 23 hours of treatment. Panel C shows the effects of approximately 23 hr treatment of MOLM13-luc+ cells with HBX19818 on total cellular tyrosine phosphorylation.

Importantly, degradation of mutant FLT3 by P22077, 1247825-37-1, and HBX19818, was observed to be selective, in that expression of signaling molecules downstream of FLT3, including AKT and ERK1/ERK2, was unchanged in drug-treated MOLM14 cells (FIG. 14I). Similar results were observed in drug-treated MOLM13-luc+ cells and MV4, 11 cells. Consistent with data in the Ba/F3 system, HBX19818 and P22077 have little to no impact on FLT3 protein in wt FLT3-expressing leukemia cell lines (FIG. 16A-B). Of note, inhibition of total cellular tyrosine phosphorylation was demonstrated in HBX19818-treated mutant FLT3-positive cells, which is consistent with drug-induced degradation of mutant FLT3 (FIG. 16C).

As with HBX19818, chloroquine rescued FLT3 degradation in P22077-treated cells and qPCR analysis confirmed the P22077 did not lead to a reduction in FLT3 transcript levels at concentrations that resulted in FLT3 protein degradation (FIGS. 6A-6B). Finally, similar to HBX19818 and its analogs, P22077 exhibited higher potency toward FLT3 mutant MOLM13, MOLM14, and MV4, 11 cell lines (0.4, 0.8, 2.9 µM) relative to a number of other leukemic cell lines not driven by FLT3, including TF-1 (10.2 µM), HEL (6.9 µM), K052 (5.7 µM), and K562 (10.6 µM) (Table 3). P22077 treatment also led to increased priming of mutant FLT3-expressing cells for apoptosis as compared to wt FLT3- or null FLT3-expressing cells (FIG. 3G). Identification of a second series of compounds (represented by P22077 and 1247825-37-1) that phenocopies the effects of HBX19818 further supports the notion that USP10 is the DUB-stabilizing FLT3-ITD in the system.

Example 5: USP10 Lead Inhibitors do not Degrade p53

USP10 has been reported as a regulator of tumor suppressor p53 localization and stability. Because a drug that degrades wt p53 could be undesirable, it was sought to elucidate whether pharmacological USP10 inhibition impacted p53 levels in AML cell lines expressing the transcription factor. Treatment of MOLM13 and MOLM14 cells with HBX19818 or P22077 did not result in a decrease of p53 levels and, in fact, if anything, a modest increase in p53 levels was observed (FIGS. 7C-7D and 14G). However, consistent with previous reports, hairpin KD of USP10 results in a reduction in p53 levels in both of the FLT3-ITD positive AML cell lines (FIGS. 7C-7D). HBX19818 and P22077 were both originally reported as USP7 inhibitors. USP7 stabilizes MDM2 leading to increased ubiquitylation and degradation of p53. As expected, pharmacological USP7 inhibition decreased MDM2 levels and increased p53 levels. The USP7 inhibitory activity of the inhibitors may counteract any potential effects on p53 degradation by USP10. Further development of selective USP10 inhibitors should help clarify the potentially opposing effects of inhibition of USP7 and USP10 deubiquitylating activity on p53 levels. Taken together, the small molecule and genetic KD results described above provide strong validation of USP10 as a novel target for FLT3-ITD mutant AML.

Figure 17:
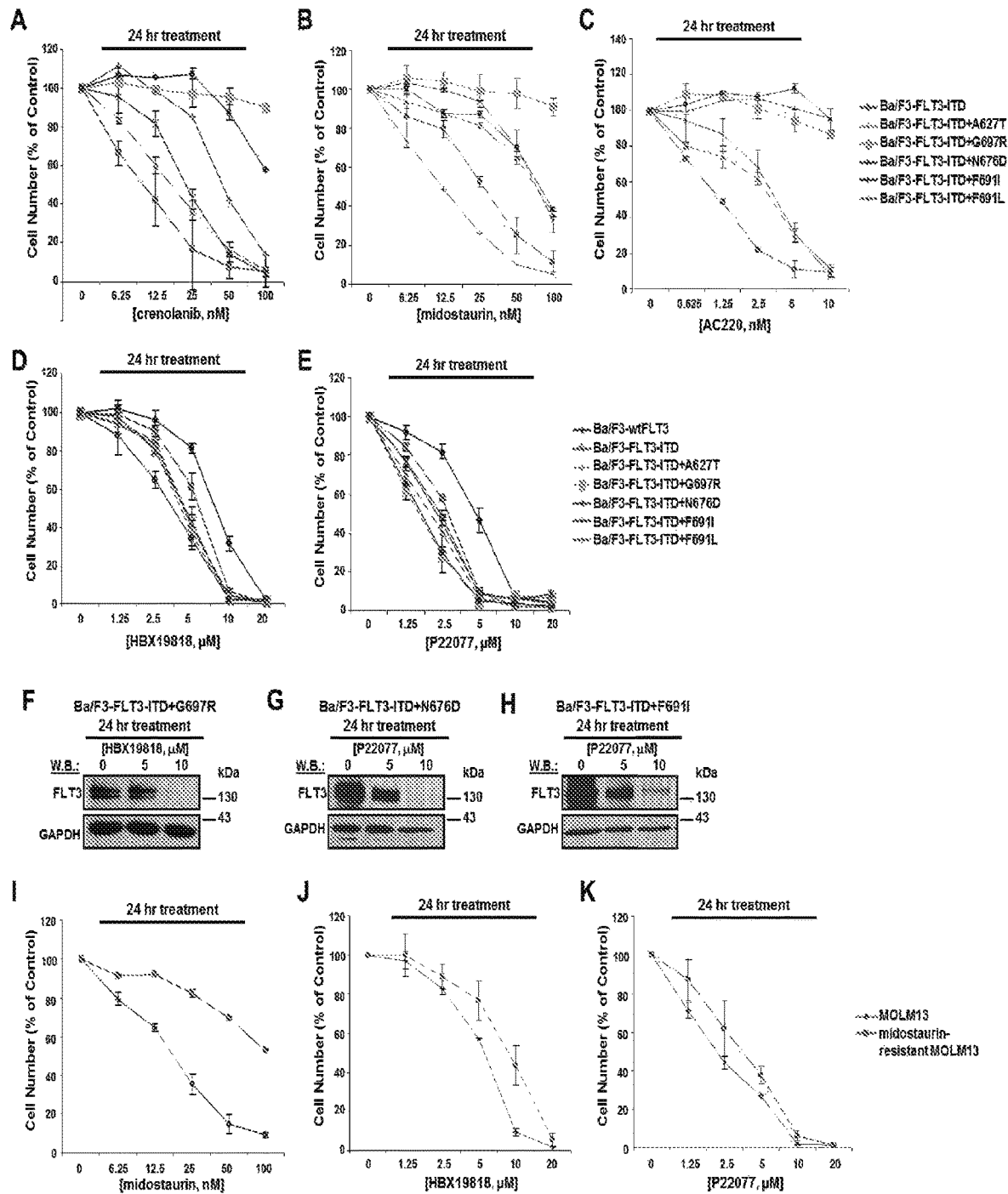
FIG. 17 includes 11 panels, identified as panels A, B, C, D, E, F, G, H, I, J, and K, which show the targeted effects of HBX19818 and P22077 on cells resistant to FLT3 kinase inhibitors. Approximately 24 hr treatment of Ba/F3-FLT3-ITD cells or Ba/F3-FLT3-ITD expressing TKD point mutants with crenolanib (Panel A), midostaurin (Panel B), AC220 (Panel C), HBX19818 (Panel D), or P22077 (Panel E). Error bars represent the standard deviation for samples set up in duplicate. Panels F-H show the effect of HBX19818 (Panel F) and P22077 (Panels G and H) on FLT3 expression in Ba/F3-FLT3-ITD cells expressing TKD point mutants. Panels I-K show the comparison of effects of midostaurin (Panel I), HBX19818 (Panel J), and P22077 (Panel K) on proliferation of MOLM13 and midostaurin-resistant MOLM13 cells. Error bars represent the standard deviation for samples set up in duplicate.
Figure 18:
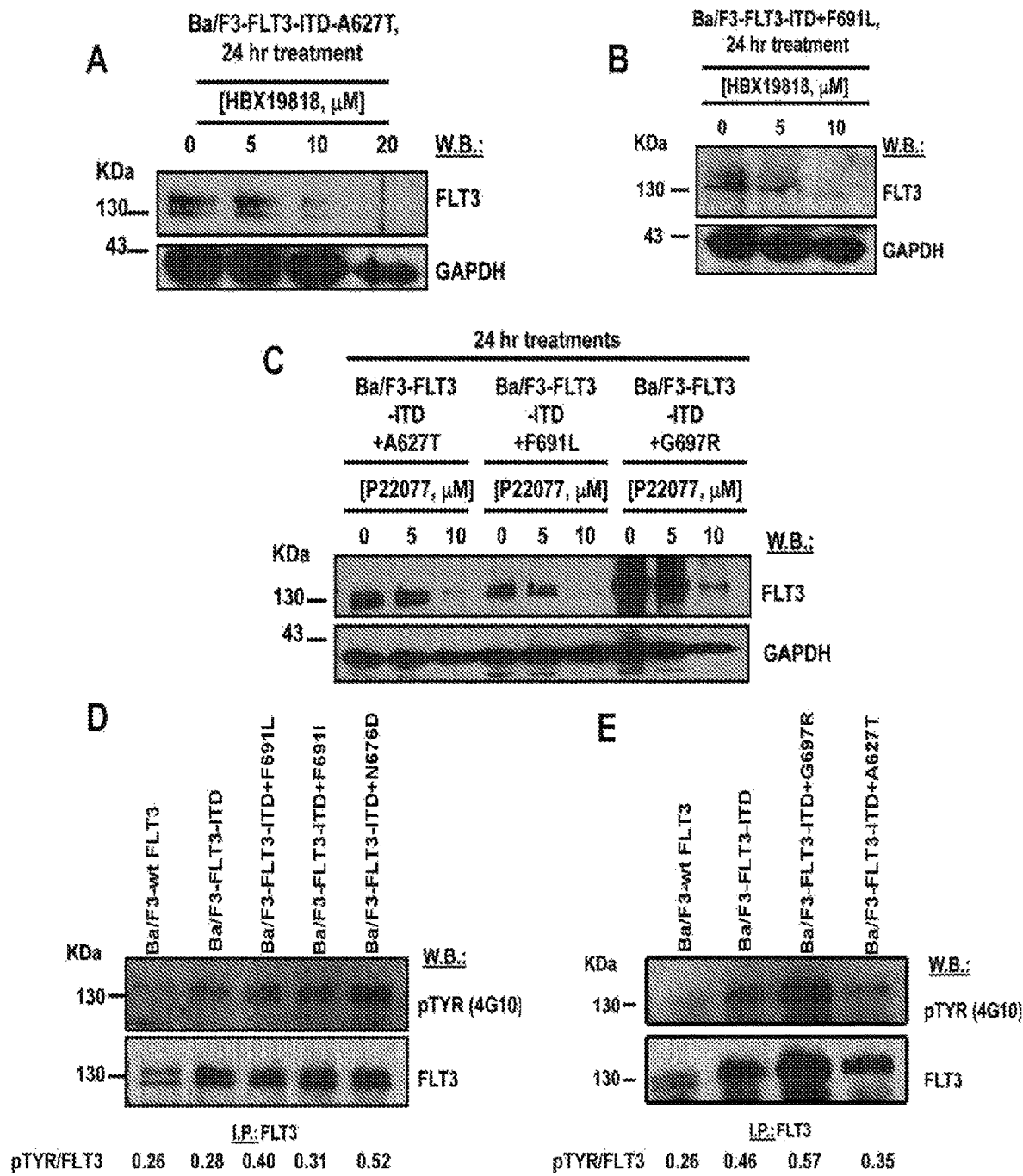
FIG. 18 includes 7 panels, identified as panels A, B, C, D, E, F, and G, which show that HBX19818 and P22077 induce degradation of constitutively active FLT3 in Ba/F3-FLT3-ITD cells expressing TKD point mutations. Panels A and B show that HBX19818 treatment leads to degradation of FLT3 in Ba/F3-FLT3-ITD cells expressing the A627T TKD mutant (Panel A) and Ba/F3-FLT3-ITD cells expressing the F691L mutant (Panel B). Panel C shows that P22077 treatment leads to degradation of FLT3 in Ba/F3-FLT3-ITD cells expressing the A627T, F691L, and G697R TKD mutants. Panels D and E shows the comparison of FLT3 phosphorylation status in Ba/F3-wt FLT3 cells, Ba/F3-FLT3-ITD cells, and Ba/F3-FLT3-ITD cells expressing TKD point mutants. Ba/F3-wt FLT3 cells and mutant FLT3-expressing cells were cultured in the presence of 10% FBS-containing RPMI media. Culture media for Ba/F3-wt FLT3 cells was supplemented with 15-20% WEHI, used as a source of IL-3 as the Ba/F3-wt FLT3 cells are growth factor-dependent. Panel F shows the effects of HBX19818 combined with PKC412 on proliferation of MOLM13-luc+ cells following approximately 3 days of treatment. Error bars represent the standard deviation for samples set up in duplicate. Panel G shows the combination indices corresponding to co-treatment of MOLM13-luc+ cells with midostaurin and HBX19818.
Figure 18:
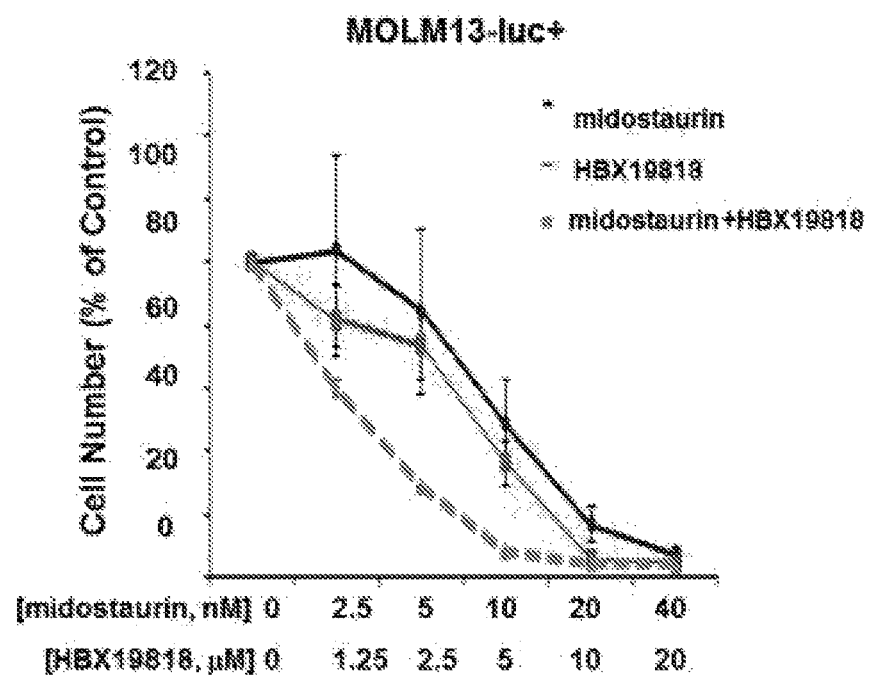
Figure 18:
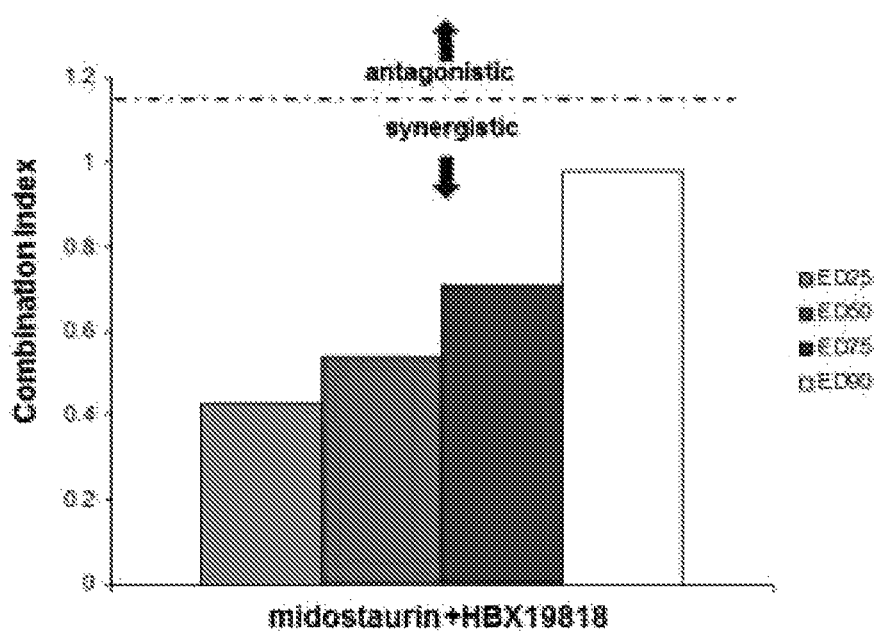

Example 6: Promoting Degradation of Mutant FLT3 Overcomes Resistance to Kinase Inhibition Further studies were performed to confirm that ubiquitin-mediated degradation is advantageous compared to FLT3 kinase inhibition in terms of overriding drug resistance. Treatment of Ba/F3-FLT3-ITD cells expressing TKD point mutations with the FLT3 kinase inhibitors led to rightward shifts in the dose-response curves (FIGS. 17A-17C), validating previously reported differential resistance to these inhibitors (Smith et al., 2014). In contrast, HBX19818 and P22077 treatments were equipotent against Ba/F3-FLT3-ITD cells versus Ba/F3-FLT3-ITD cells expressing the TKD point mutations, however less potent toward Ba/F3 cells engineered to over-express wt FLT3 (FIGS. 17D-17E).

Importantly, HBX19818 and P22077 induced degradation of FLT3 in the FLT3 kinase inhibitor-resistant cells at concentrations that were ineffective in promoting FLT3 degradation in Ba/F3-wt FLT3 cells (FIGS. 17F-17H, FIG. 2B, FIG. 1H, and FIGS. 18A-18C). All TKD point mutants were confirmed to express constitutively activated FLT3 (FIGS. 18D-18E). In addition, HBX19818 and P22077 showed similar potency toward parental MOLM13 cells and MOLM13 cells rendered resistant to midostaurin following prolonged culture in the presence of the drug (Weisberg et al., 2011) (FIGS. 17I-17K). The midostaurin-resistant MOLM13 cells were characterized as highly over-expressing FLT3 protein, believed to contribute to their resistance (Weisberg et al., 2011).

Example 7: HBX19818 Synergizes with FLT3 Kinase Inhibitors

Figure 19:
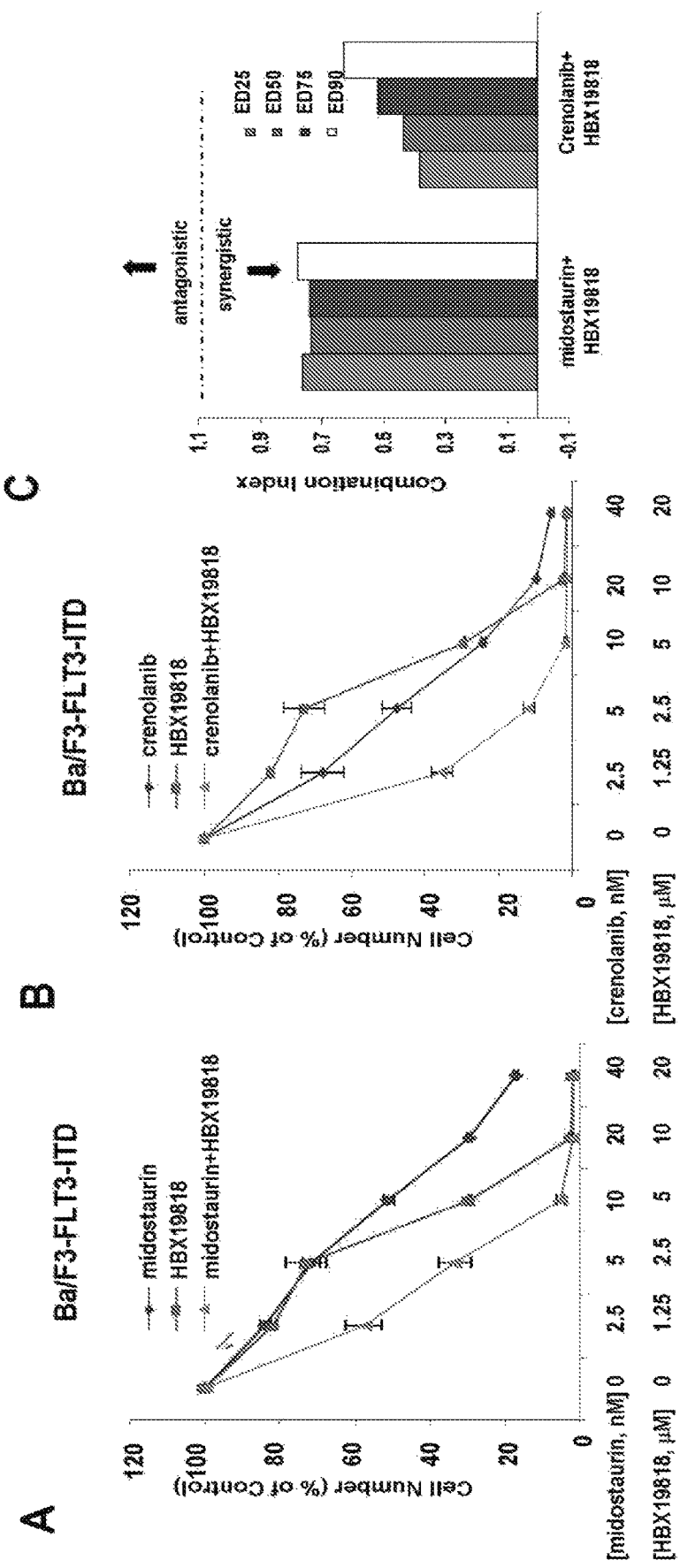
FIG. 19 includes 6 panels, identified as panels A, B, C, D, E, and F, which show the effects of the combination of HBX19818 with FLT3 inhibitors against mutant FLT3-expressing cells. Panels A-B show the effects of HBX19818 combined with midostaurin (Panel A) or crenolanib (Panel B) on proliferation of Ba/F3-FLT3-ITD cells following approximately 3 days of treatment. Panel C shows combination indices corresponding to the data shown in Panels A-B. Panel D shows the effects of HBX19818 combined with midostaurin (Panel D) or crenolanib (Panel E) on proliferation of MOLM14 cells. Panel F shows combination indices corresponding to the data shown in Panels D-E.
Figure 19:
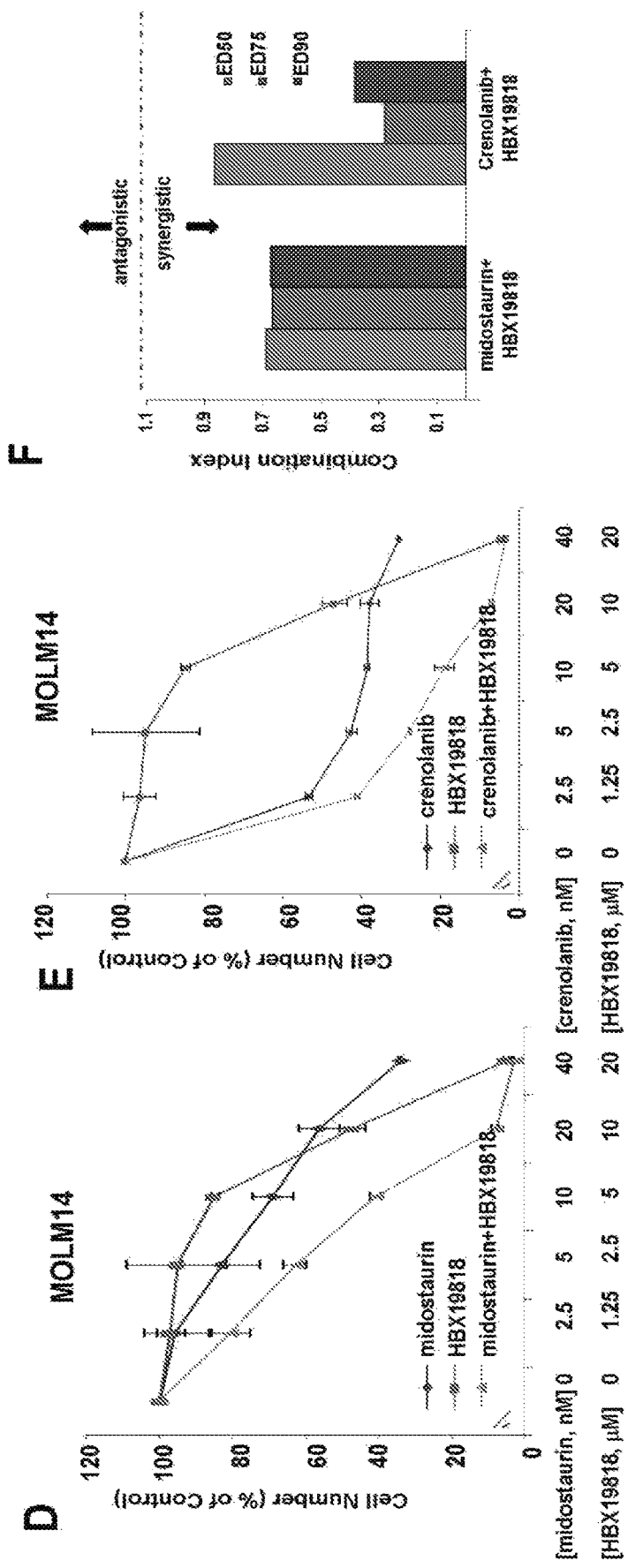

As further assessment of the therapeutic potential of USP10 inhibition, the ability of DUB inhibitors and FLT3 kinase inhibitors to interact synergistically was investigated. Specifically, a median-drug effect analysis was used, in which a combination index (CI) was calculated from growth inhibition curves using Calcusyn software (Biosoft, Cambridge, UK). Dual treatment of Ba/F3-FLT3-ITD, MOM13-luc+, and MOLM14 cells with HBX19818 and the FLT3 kinase inhibitors, midostaurin or crenolanib, at a fixed-ratio serial dilution resulted in decreased cell growth compared to single agent treatment (FIGS. 18F, 19B, and 19E). Combination index (CI) analysis indicated synergistic anti-proliferative effects (valued less than 1 indicate synergy) at 25%, 50%, 75% and 90% growth inhibition for MOLM13-luc+ cells and Ba/F3-FLT3-ITD cells and at 50%, 75%, and 90% growth inhibition for MOLM14 cells (FIGS. 18G, 19C, and 19F) upon treatment with either kinase inhibitor and concomitant HBX19818 treatment.

Figure 20:
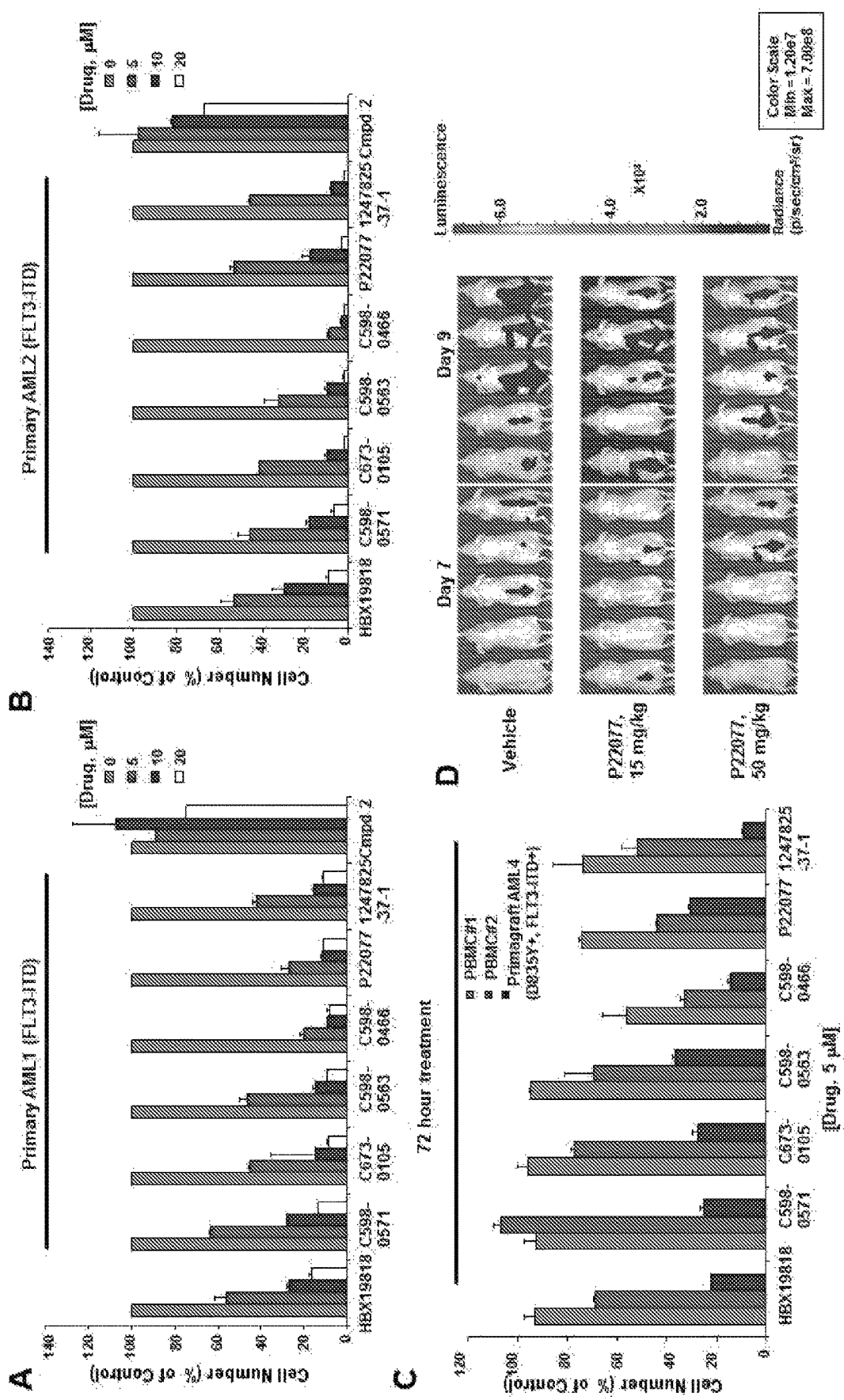
FIG. 20 includes 4 panels, identified as panels A, B, C, and D, which show targeted effects of USP10 inhibition on mutant FLT3-positive AML. Panels A-B show the effects of DUB inhibitors on FLT3-ITD-expressing primary AML patient cells following approximately 72 hrs of treatment. Primary AML 1: Female; 59 years old; <5% bone marrow blasts; 2.6K WBC count; crit: 30; 1% peripheral blasts; previous therapy: 3+7 chemotherapy; cytogenetics: normal; mutations: IDH2 (5%), RUNX1 (15%), SRSF2 (16.8%), FLT3-ITD (24 aa). Primary AML2: Male; 69 years old; 90% bone marrow blasts; 23K WBC count; crit: 24; 5% peripheral blasts; previous therapy: azacytidine, cytarabline, high dose Ara-c; cytogenetics: normal; mutations: SRSF2 (54%), ASXL1 (46%), RUNX1 (39.4%), TET2 (ins) (46%), TET2 (point mutation) (2.8%), TET2 (del) (3.5%), FLT3-ITD (51 aa). Panel C shows the effects of USP10 inhibitors on normal PBMCs versus mutant FLT3-expressing AML primagraft (D835Y+, FLT3-ITD+) cells following 72 hours. Panel D shows the effect of P22077 treatment on Ba/F3-FLT3-ITD-luc+ cell growth in a non-invasive in vivo bioluminescence model of leukemia.
Figure 21:
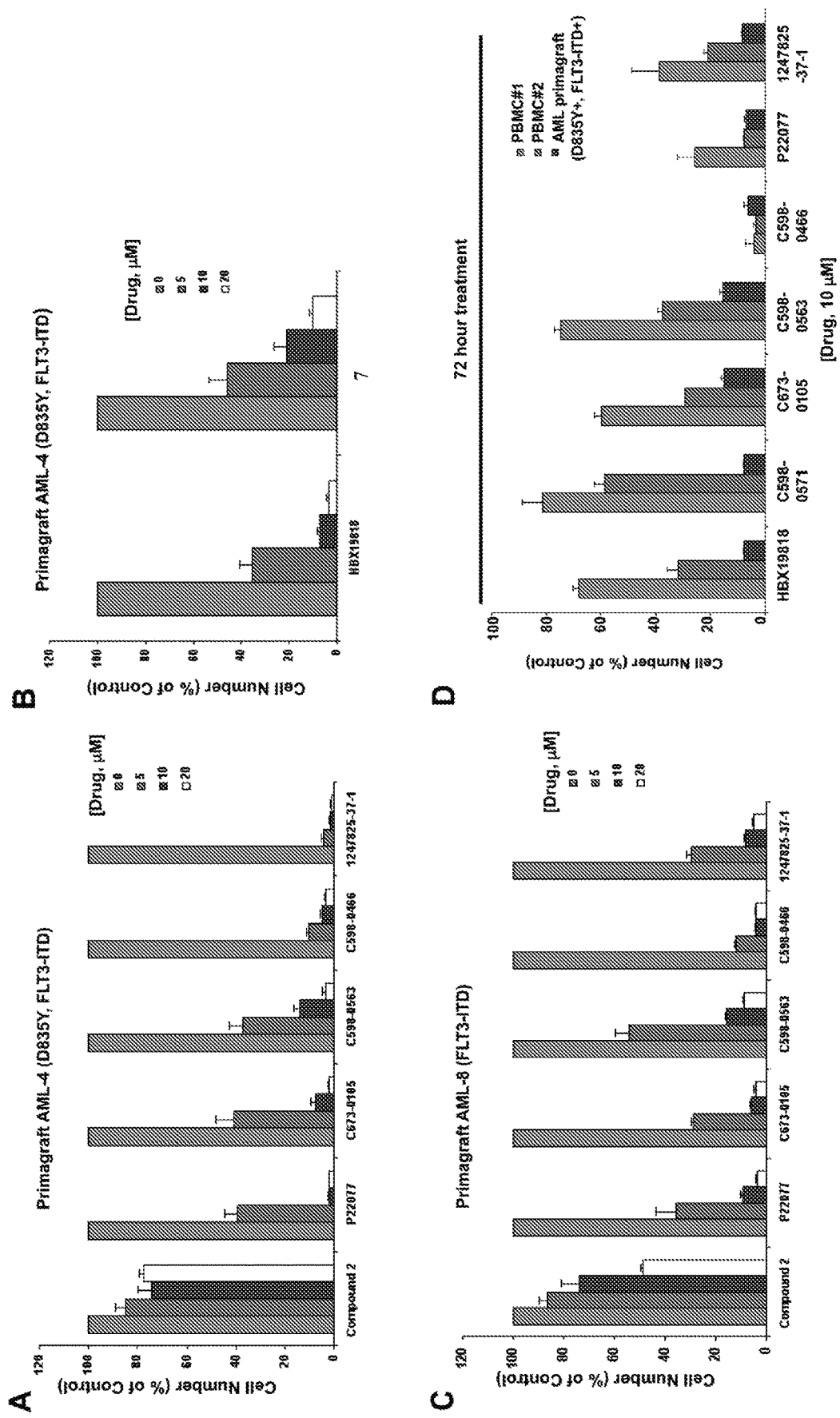
FIG. 21 includes 4 panels, identified as panels A, B, C, and D, which show the results of an analysis of USP10 inhibitor effects on mutant FLT3-expressing AML primagrafts. Panels A-C show the effects of DUB inhibitors on proliferation of mutant FLT3-expressing AML primagrafts following approximately 72 hrs of treatment ex vivo. Panel D shows the effects of USP10 inhibitors on normal PBMCs versus mutant FLT3-expressing AML primagraft (D835Y+, FLT3-ITD+) cells following 72 hours.
Figure 22:
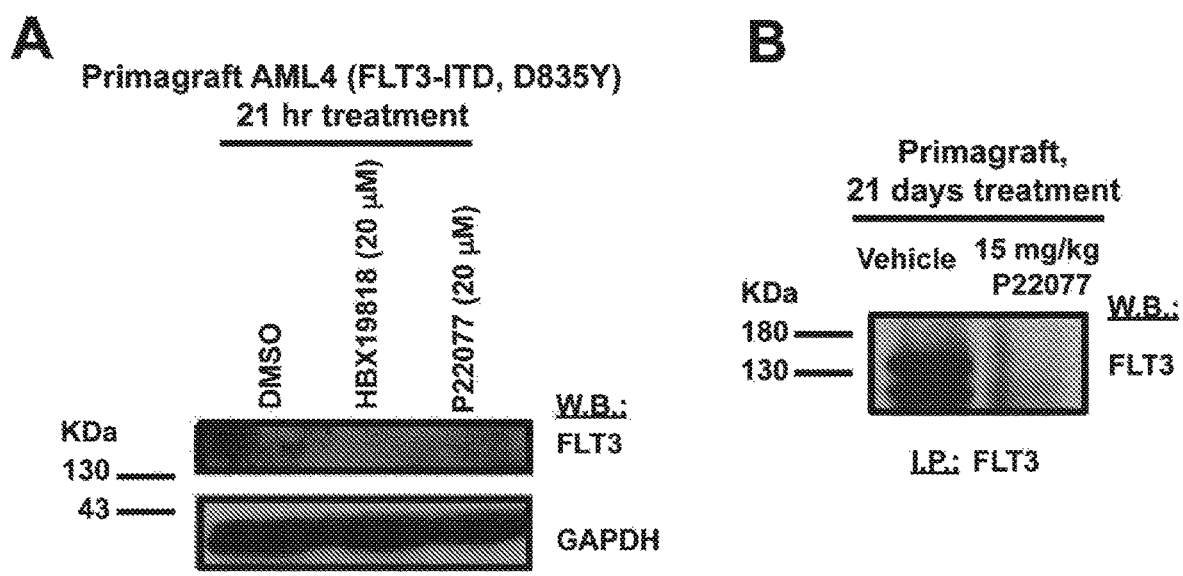
FIG. 22 includes 2 panels, identified as panels A and B, which show the effects of P22077 on FLT3 protein expression ex vivo and in vivo. Panel A shows the results of an analysis of FLT3 protein integrity in HBX19818- and P22077 ex vivo-treated FLT3-ITD-positive AML primagraft cells. Panel B shows the results of an analysis of FLT3 protein integrity in bone marrow cells extracted from 21-day vehicle (DMSO)-treated FLT3 mutant AML primagraft mice versus P22077 (15 mg/kg)-treated FLT3 mutant AML primagraft mice. FLT3 immunoprecipitation was performed on pooled protein lysate from 3 vehicle control mice versus pooled protein lysate from 3 P22077-treated mice.

Example 8: Pharmacological Inhibition of USP10 Inhibits Growth of FLT3 Mutant PDXs and Primary Tumor Samples and Leads to Anti-Leukemic Activity In Vivo It was also sought to further investigate the therapeutic potential of the lead USP10 inhibitor series by testing growth inhibitory effects on primary patient tumor samples and PDXs. HBX19818, selected HBX19818 analogs, P22077, 1247825-37-1, and Compound 2 were evaluated for ability to block growth of primary tumor cells isolated from two FLT3-ITD positive AML patients and two FLT3 mutant primagrafts. All USP10 inhibitors tested caused a dose-dependent reduction in survival against both patient samples and primagrafts (FIGS. 20A-20C and 21). HBX19818 was less potent toward two donor peripheral blood mononucleated cell (PBMC) samples from healthy donors while P22077 was less potent toward one of two PBMCs samples tested against (FIG. 20C, Tables 4-7, FIG. 21D). The selective USP7 inhibitor, Compound 2, had little to no effect on survival of these samples (FIGS. 20A-20C, 21A, and 21C). HBX19818, P22077, 1247825-37-1, and several of the HBX19818 analogs were evaluate for activity against PBMCs in order to assess the therapeutic window of USP10 inhibitors for FLT3-ITD positive tumor cells over peripheral blood mononucleated cells (PBMCs) from healthy donors. Mutant FLT3-expressing AML primagraft cells were more sensitive than two donor PBMC samples to all of the inhibitors following 24-72 hours of treatment (FIGS. 20C and 21D and Tables 4-7). Enough cells were obtained from one primagraft to enable analysis of FLT3 levels via immunoblotting. There was no trace of FLT3 following 21 hours of treatment with either HBX19818 or P22077 at a concentration of 20 indicating a strong reduction of FLT3 levels (FIG. 22A).

TABLE 4

IC50s (+/−S.D.) calculated for 24 hr treatment of PBMCs versus mutant FLT3-expressing primagraft cells with USP10-targeting inhibitors

| 24 hr assay | PBMC#1 | PBMC#2 | AML primagraft (D835Y+, FLT3-ITD+) |
|---|---|---|---|
| HBX19818 (IC50, μM) | 25.5 +/− 7 | 24.1 +/− 8 | 9.8 +/− 0.8 |
| C673-0105 (IC50, μM) | 17.2 +/− 0.3 | 17.4 +/− 1.3 | 8.5 +/− 0.4 |
| C598-0563 (IC50, μM) | 22.9 +/− 0.4 | 44.4 +/− 6.4 | 12.2 +/− 2 |
| C598-0466 (IC50,μM) | 10.5 +/− 1.3 | 10.5 +/− 1.6 | 4.1 +/− 0.5 |
| C598-0571 (IC50, μM) | 32.3 +/− 5.7 | 31.3 +/− 8.3 | 10.3 +/− 0.8 |
| P22077 (IC50, μM) | 10.6 +/− 1.1 | 7.8 +/− 0.7 | 6.9 +/− 1.5 |
| 1247825-37-1 (IC50, μM) | 14.9 +/− 2.1 | 16.6 +/− 3.6 | 2.5 +/− 0.4 |

TABLE 5

IC50s (+/−S.D.) calculated for 72 hr treatment of PBMCs versus mutant FLT3-expressing primagraft cells with USP10-targeting inhibitors

| 72 hr assay | PBMC#1 | PBMC#2 | AML primagraft (D835Y+, FLT3-ITD+) |
|---|---|---|---|
| HBX19818 (IC50, μM) | 12.4 +/− 0.9 | 7.3 +/− 0.3 | 1.9 +/− 0.1 |
| C673-0105 (IC50, μM) | 10 +/− 1 | 7.3 +/− 0.14 | 3.1 +/− 0.2 |
| C598-0563 (IC50, μM) | 15.6 +/− 0.14 | 7.9 +/− 1.2 | 2.8 +/− 0.1 |
| C598-0466 (IC50, μM) | 4.8 +/− 0.9 | 3.1 +/− 0.1 | 0.6 +/− 0.1 |
| C598-0571 (IC50, μM) | 16.6 +/− 1.8 | 14.8 +/− 0.2 | 1.4 +/− 0.1 |
| P22077 (IC50, μM) | 6.9 +/− 0.3 | 4.4 +/− 0 | 2.6 +/− 0.1 |

TABLE 6

Patient information for FLT3-ITD-positive AML primagraft "AML4"

Pathologic diagnosis: AML M4/M5
WHO classification: AML with recurrent gene mutations
Disease stage at time of sample acquisition: Relapsed post-allogeneic HSCT
Age, gender: 61, male
Percent tissue involvement: 71
Notable clinical features: Prior prostate cancer s/p prostatectomy/EBRT 26 months prior as well as papillary thyroid cancer for which he was being treated with RAI at the time of the AML diagnosis; of note the relapse AML now expresses CD19 which is atypical.
Patient clinical details: Relapsed following 6 + 3, consolidation HiDAC, allogeneic HSCT in CR1.
Source tumor karyotype: 47, X, -Y, del(6)(q15q21), +8, +14[15]/47, idem, t(1; 9)(q23; q34)[4]//46, XX[1]
Source karyotype simplified: Trisomies 8 and 14, deletion 6q, and loss of Y chromosome; 3 metaphases also contained t(1; 9).
FISH positive: nuc ish(DXZ1x1)[161/200]//(DXZ1x2)[39/200]
Immunophenotype positive: CD45(dim), HLA-DR, CD13, CD33, CD117 (subset), CD15 (subset), CD19 (aberrant) and CD7 (aberrant dim)
Immunophenotype negative: CD34, CD10, CD20, CD79a, cytoplasmic CD22, and other monocytic, B and T lymphoid markers

TABLE 6-continued

Patient information for FLT3-ITD-positive AML primagraft "AML4"

Presenting WBC: 260000
Molecular alterations (FLT3): FLT3-ITD
c.2503C > A p.D835Y-in 43.0% of 1767 reads
Molecular alterations (NMP1): c.859_860insTCTG
p.W288fs* > 9-in 38.1% of 412 reads

TABLE 7

Patient information for FLT3-ITD-positive AML primagraft "AML8"

Pathologic diagnosis: AML M5a
WHO classification: AML with recurrent gene mutations
Disease stage at time of sample acquisition: Primary refractory post-induction
Age, gender: pediatric, male
Percent tissue involvement: Not reported
Notable clinical features: None listed
Patient clinical details: M5 monoblastic AML w/FLT3-ITD; day 22 of induction I (refractory); WBC on presentation 0.72 (ANC: 0.05, Platelets 38); treated as per DFCI 04-172 w/daunorubicin, etoposide, and low dose Ara-C; bone marrow on Mar. 12, 2014 with 13% involvement by flow
Source tumor karyotype: 46, XY, add(6)(q21), add(9)(p24)[10]/46, XY[10]
Source karyotype simplified: 9p and 6q additional material
FISH negative: Rearrangement or loss/gain of MLL, CBFB rearrangement, RUNX1T1/RUN1 (ETO/AML1) rearrangement,

TABLE 7-continued

Patient information for FLT3-ITD-positive AML primagraft "AML8"

PML/RARA translocation. nuc ish(RUNX1T1, MLL, PML, CBFB, RARA, RUNX1)x2[500]
Immunophenotype positive: CD45 (intermediate), CD117, CD34 , CD13, and CD33
Immunophenotype negative: No report
Presenting WBC: 720
Molecular alterations (FLT3): FLT3-ITD
Molecular alterations (NMP1): None reported

TABLE 9

Anti-proliferation IC50s (+/−S.D.) calculated for 24 hr treatment of human AML cell lines with USP10-targeting inhibitors. MOLM13-luc+, MOLM14 and MV4, 11 express FLT3-ITD; the other cell lines shown are FLT3 wt or null.

| Compound | USP7 IC$_{50}$ +/− SEM (µM) |
|---|---|
| C598-0466 | 3.6 +/− 0.53 (2) |
| C598-0468 | >>100 (2) |
| C598-0515 | >>100 (2) |
| C598-0563 | 50 +/− 16 (2) |
| C598-0571 | 22 +/− 13 (2) |
| C598-0646 | >>100 (1) |
| C673-0105 | >>100 (1) |

TABLE 10

List of DUB inhibitors.
Table 1. Reported DUB inhibitors included in the primary screen.

| Reported target | Compound ID | Compound Structure | Reference |
|---|---|---|---|
| USP1 | SJB3-019A | $C_{16}H_8N_2O_3$ | Mistry, H., Hsieh, G., Buhrlage, S. J., Huang, M., Park, E., Cuny, G. D., Galinsky, I., Stone, R. M., Gray, N. S., D'Andrea, A.D., and Parmar, K. (2013) *Molecular cancer therapeutics* 12, 2651-2662 |
| | ML323 | $C_{23}H_{24}N_6$ | Liang, Q., Dexheimer, T. S., Zhang, P., Rosenthal, A. S., Villamil, M. A., You, C., Zhang, Q., Chen, J., Ott, C. A., Sun, H., Luci, D. K., Yuan, B., Simeonov, A., Jadhav, A., Xiao, H., Wang, Y., Maloney, D. J., and Zhuang, Z. (2014) *Nature chemical biology* 10, 298-304 |

TABLE 10-continued

List of DUB inhibitors.
Table 1. Reported DUB inhibitors included in the primary screen.

| Reported target | Compound ID | Compound Structure | Reference |
|---|---|---|---|
| | Pimozide | $C_{28}H_{29}F_2N_3O$ | Chen, J., Dexheimer, T. S., Ai, Y., Liang, Q., Villamil, M. A., Inglese, J., Maloney, D. J., Jadhav, A., Simeonov, A., and Zhuang, Z. (2011) *Chemistry & biology* 18, 1390-1400 |
| | GW7647 | $C_{29}H_{46}N_2O_3S$ | Chen, J., Dexheimer, T. S., Ai, Y., Liang, Q., Villamil, M. A., Inglese, J., Maloney, D. J., Jadhav, A., Simeonov, A., and Zhuang, Z. (2011) *Chemistry & biology* 18, 1390-1400 |
| | Trifluoperazine | $C_{21}H_{24}F_3N_3S$ | Chen, J., Dexheimer, T. S., Ai, Y., Liang, Q., Villamil, M. A., Inglese, J., Maloney, D. J., Jadhav, A., Simeonov, A., and Zhuang, Z. (2011) *Chemistry & biology* 18, 1390-1400 |
| USP2 | HY17541A | $C_{18}H_{14}N_4O$ | WO2007009715 |

TABLE 10-continued

List of DUB inhibitors.
Table 1. Reported DUB inhibitors included in the primary screen.

| Reported target | Compound ID | Compound Structure | Reference |
|---|---|---|---|
| | ML364 | 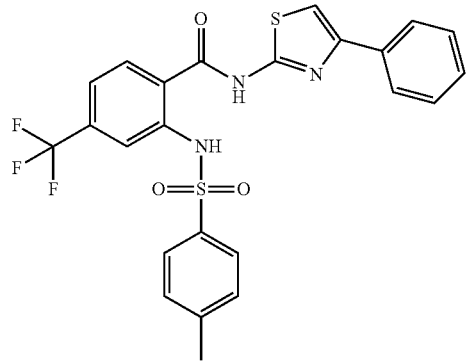<br>$C_{24}H_{18}F_3N_3O_3S_2$ | Journal of Biological Chemistry, 2016, 291, 24628-24640. |
| USP2, 7 | NSC632839 | 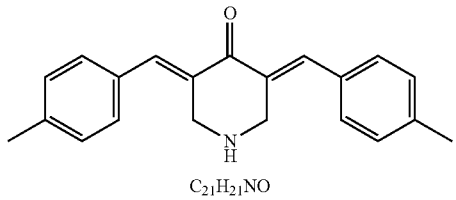<br>$C_{21}H_{21}NO$ | Nicholson B, et al. Protein Sci, 2008, 17(6), 1035-1043. |
| USP5, 9x, 14, UCHL5 | WP1130 | 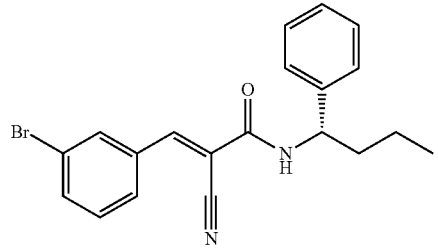<br>$C_{19}H_{18}BrN_3O$ | Barhtolomeusz, G., . . . Donato, N. J., Cancer Research (2007), 67, 3912-3918 |
| USP7 | HBX19818 | 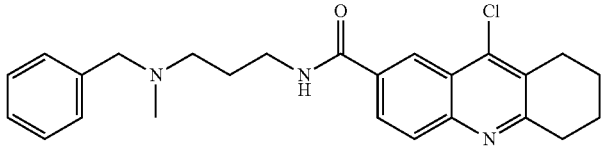<br>$C_{25}H_{28}ClN_3O$ | Reverdy, C. Conrath, S. Lopez, R., Planquette, C., Atmanene, C., Collura, V., Harpon, J., Battaglia, V., Vivat, V., Sippl, W., and Colland, F. (2012) Chemistry & biology 19, 467-477 |
| | HBX41108 | 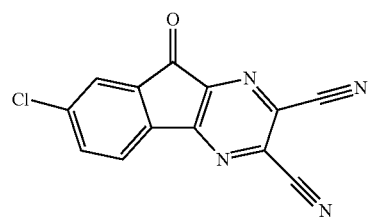<br>$C_{13}H_3ClN_4O$ | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |

TABLE 10-continued

List of DUB inhibitors.
Table 1. Reported DUB inhibitors included in the primary screen.

| Reported target | Compound ID | Compound Structure | Reference |
|---|---|---|---|
| | Compound 2 | 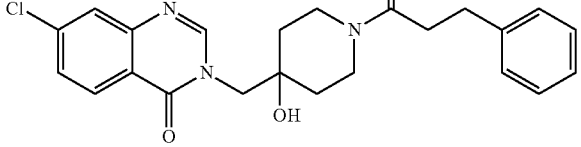<br>$C_{23}H_{24}ClN_3O_3$ | Compound 2 - WO2013030218; Analogs - WO20160185785, WO20160185786, WO2016126926, WO2016126929, WO2016126935. |
| USP7, 8 | HY50736/ Compound 16 | 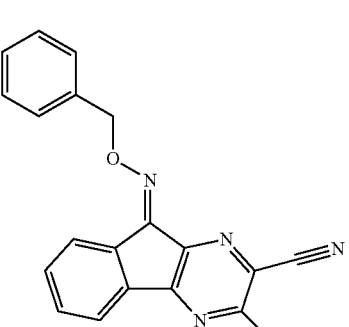<br>$C_{20}H_{11}N_5O$ | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| | HY-50737A | 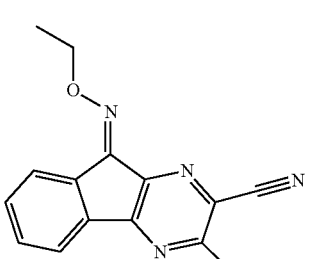<br>$C_{15}H_9N_5O$ | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| USP7, 47 | P22077 | 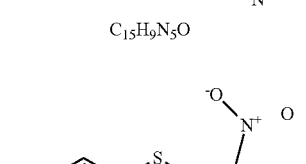<br>$C_{12}H_7F_2NO_3S_2$ | Tian X, et al. Assay Drug Dev Technol, 2011, 9(2), 165-173. |

TABLE 10-continued

List of DUB inhibitors.
Table 1. Reported DUB inhibitors included in the primary screen.

| Reported target | Compound ID | Compound Structure | Reference |
|---|---|---|---|
| | 1247825-37-1 | 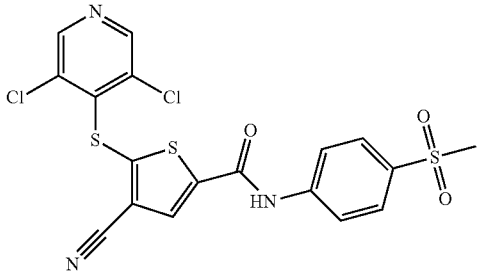<br>$C_{18}H_{11}Cl_2N_3O_3S_3$ | Weinstock, J., Wu, J., Cao, P., Kingsbury, W. D., McDermott, J. L., Kodrasov, M. P., McKelvey, D. M., Suresh Kumar, K. G., Goldenberg, S. J., Mattern, M. R., and Nicholson, B. (2012) *ACS medicinal chemistry letters* 3, 789-792 |
| USP10, 13 | Spautin-1 | 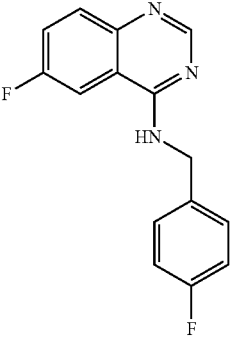<br>$C_{15}H_{11}F_2N_3$ | Liu, J., Xia, H., Kim, M., Xu, L., Li, Y., Zhang, L., Cai, Y., Norberg, H. V., Zhang, T., Furuya, T., Jin, M., Zhu, Z., Wang, H., Yu, J., Hao, Y., Choi, A., Ke, H., Ma, D., and Yuan, J. (2011) *Cell* 147, 223-234 |
| USP14 | IU1 | 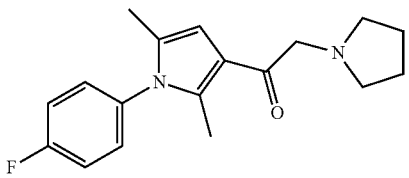<br>$C_{18}H_{21}FN_2O$ | Lee, B. H., Lee, M. J., Park, S., Oh, D. C., Elsasser, S., Chen, P. C., Gartner, C., Dimova, N., Hanna, J., Gygi, S. P., Wilson, S. M., King, R. W., and Finley, D. (2010) *Nature* 467, 179-184 |
| USP14, UCHL5 | b-AP15 | 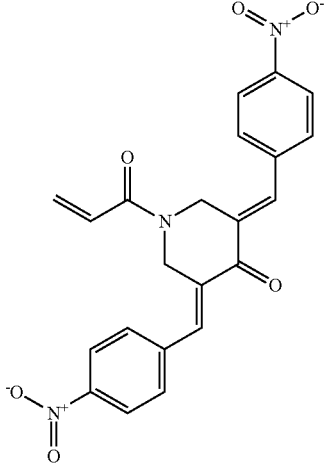<br>$C_{22}H_{17}N_3O_6$ | *Nature Medicine*, 2011, 17, 1636-1640. |

TABLE 10-continued

List of DUB inhibitors.
Table 1. Reported DUB inhibitors included in the primary screen.

| Reported target | Compound ID | Compound Structure | Reference |
|---|---|---|---|
| | Auranofin | 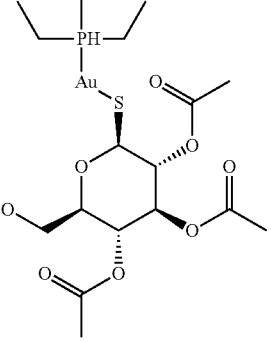<br>$C_{20}H_{35}AuO_9PS$ | Liu, N., Li, X., Huang, H., Zhao, C., Liao, S., Yang, C., Liu, S., Song, W., Lu, X., Lan, X., Chen, X., Yi, S., Xu, L., Jiang, L., Dong, X., Zhou, P., Li, S., Wang, S., Shi, X., Dou, P. Q., Wang, X., and Liu, J. (2014) *Oncotarget* 5, 5453-5471 |
| UCHL1 | LDN57444 | 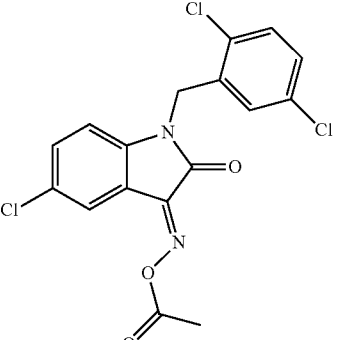<br>$C_{17}H_{11}Cl_3N_2O_3$ | Liu, Y., Lashuel, H. A., Choi, S., Xing, X., Case, A., Ni, J., Yeh, L. A., Cuny, G. D., Stein, R. L., and Lansbury, P. T., Jr. (2003) *Chemistry & biology* 10, 837-846 |
| | 5TK547622 | 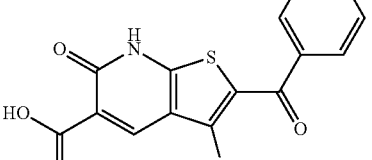<br>$C_{15}H_{10}N_2O_4S$ | Mermerian, A. H., Case, A., Stein, R. L., and Cuny, G. D. (2007) *Bioorganic & medicinal chemistry letters* 17, 3729-3732 |
| | Z-VAE(Ome)-fmk | 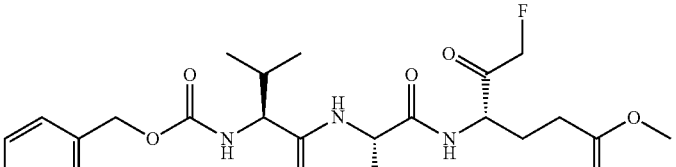<br>$C_{23}H_{32}FN_3O_7$ | Davies, C. W., Chaney, J., Korbel, G., Ringe, D., Petsko, G. A., Ploegh, H., and Das, C. (2012) *Bioorganic & medicinal chemistry letters* 22, 3900-3904 |

TABLE 10-continued

List of DUB inhibitors.
Table 1. Reported DUB inhibitors included in the primary screen.

| Reported target | Compound ID | Compound Structure | Reference |
|---|---|---|---|
| UCHL3 | R140309 | 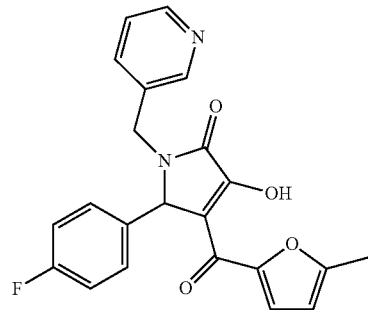 $C_{22}H_{17}FN_2O_4$ | WO2008127275 |
| | TCID | 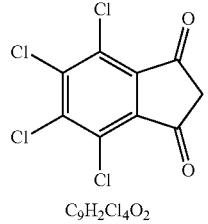 [SMILES: "C9H2Cl4O2" ; O=C1CC(=O)c2c(Cl)c(Cl)c(Cl)c(Cl)c21] $C_9H_2Cl_4O_2$ | Chemistry & Biology, 2012, 19(4), 467-477. |
| JAMM family | PB49673382 | 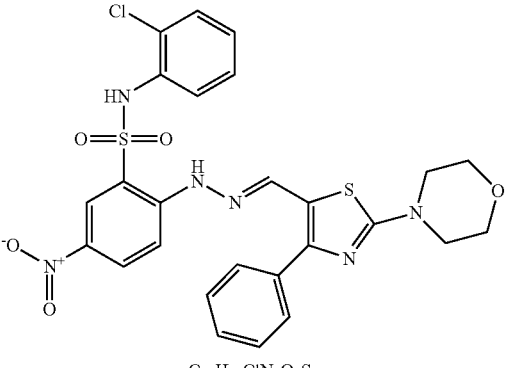 $C_{26}H_{23}ClN_6O_5S_2$ | WO2013123071 |
| | Z30529104 | 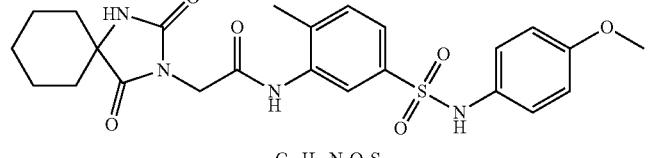 $C_{24}H_{28}N_4O_6S$ | commercial analog of inhibitor in WO2013123071 |
| SARS PLPro | HY-17542 | 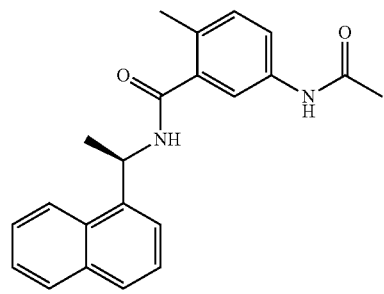 $C_{22}H_{22}N_2O_2$ | Ratia, K., Pegan, S., Takayama, J., Sleeman, K., Coughlin, M., Baliji, S., Chaudhuri, R., Fu, W., Prabhakar, B. S., Johnson, M. E., Baker, S. C., Ghosh, A. K., and Mesecar, A. D. (2008) *Proceedings of the National Academy of Sciences of the United States of America* 105, 16119-16124. |

TABLE 10-continued

List of DUB inhibitors.
Table 1. Reported DUB inhibitors included in the primary screen.

| Reported target | Compound ID | Compound Structure | Reference |
|---|---|---|---|
| pan | PR619 | $H_2N$, N, $NH_2$, N, S, S, N  $C_7H_5N_5S_2$ | Altun, M., et. al. Chem. Biol. 2011, 18(11), 1401-1412. |

These results inspired the testing of P22077 in vivo using the same FLT3-ITD+, D835Y+ AML primagraft that was observed to show P22077-induced FLT3 degradation ex vivo. Following the methodology for in vivo administration of P22077 outlined in Fan et al. (2013) *Cell Death Dis.* 4:e867, DMSO was administered as a vehicle to primagraft mice (n=3) and P22077 to primagraft mice (n=3) IP 1× daily for 21 days. Once established disease was observed by flow cytometry, treatment was initiated. Mice were sacrificed on day 21 of treatment and fixed spleen and liver samples were analyzed for the presence of disease. While there was little to no evident disease observed in mouse spleens and liver, immunoblot analysis of protein lysates from mouse bone marrow cells pooled, respectively, from each treatment group showed a strong FLT3 signal in vehicle control-treated mice that was undetectable in P22077-treated mice (FIG. 22B), suggesting drug-induced FLT3 degradation in vivo. It is important to note that P22077 at 15 mg/kg was generally well tolerated for the 21-day treatment period with little change in weight (approximately 2-3 g on average loss for both vehicle-treated and P22077-treated; none of the mice were below 15% weight loss).

Figure 23:
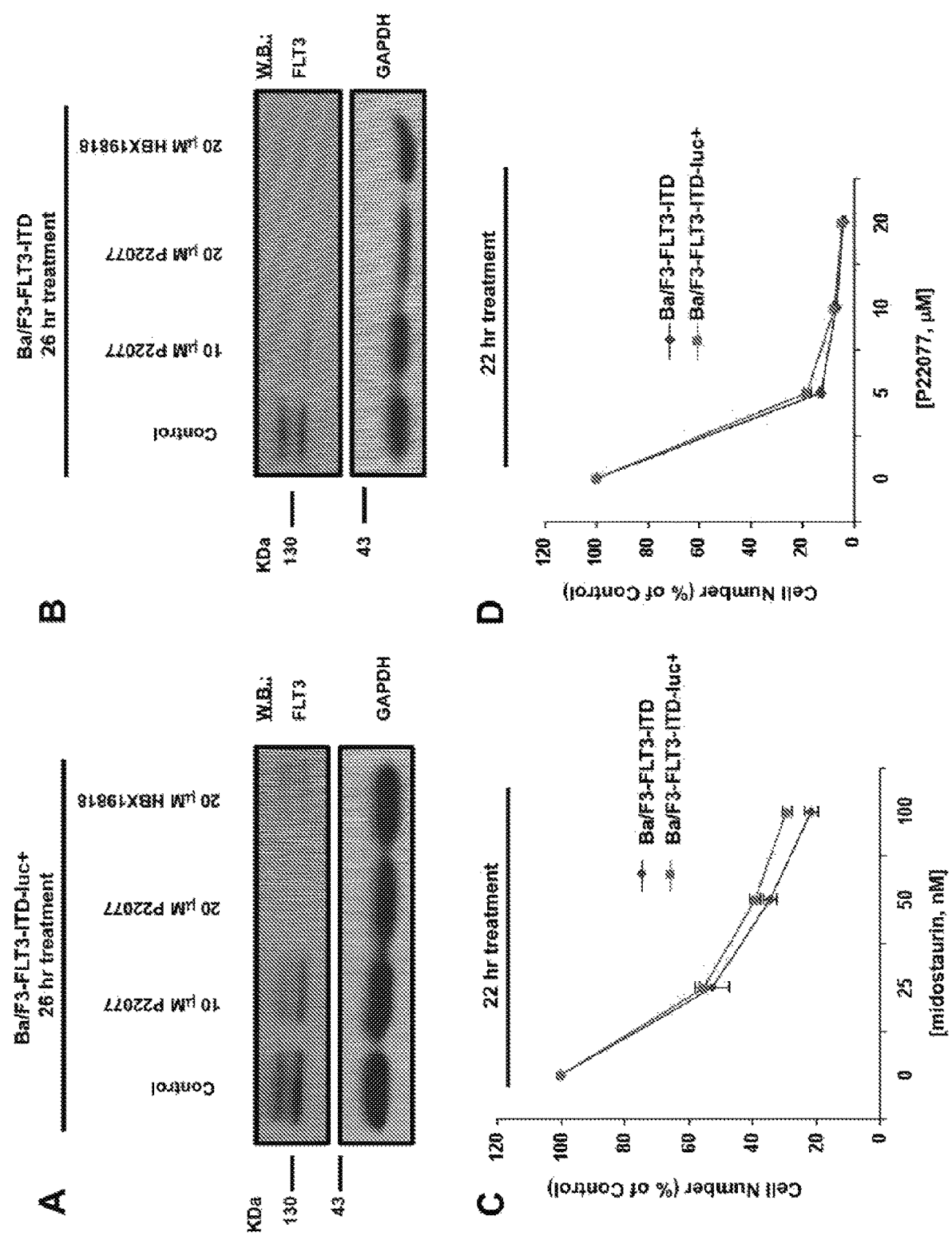
FIG. 23 includes 7 panels, identified as panels A, B, C, D, E, F, and G, which show in vitro DUB inhibitor-induced loss of FLT3 in luciferase-expressing Ba/F3-FLT3-ITD cells. Panels A-B show that HBX19818- and P22077-treatment of Ba/F3-FLT3-ITD-luc+ cells and Ba/F3-FLT3-ITD cells not expressing luciferase leads to FLT3 degradation in culture. Panels C-D show that midostaurin- and P22077-treatment (22 hr) of Ba/F3-FLT3-ITD-luc+ cells and Ba/F3-FLT3-ITD cells not expressing luciferase inhibits growth of cells to similar extents. Panel E shows that P22077 induced loss of FLT3 surface expression in Ba/F3-FLT3-ITD-luc+ cells following 24 hours of treatment. Panels F and G show the body weights (in grams (Panel F) or % (Panel G)) of mice treated for up to 11 days with vehicle or 50 mg/kg P22077, IP BID or 50 mg/kg P22077, PO QD.
Figure 23E:
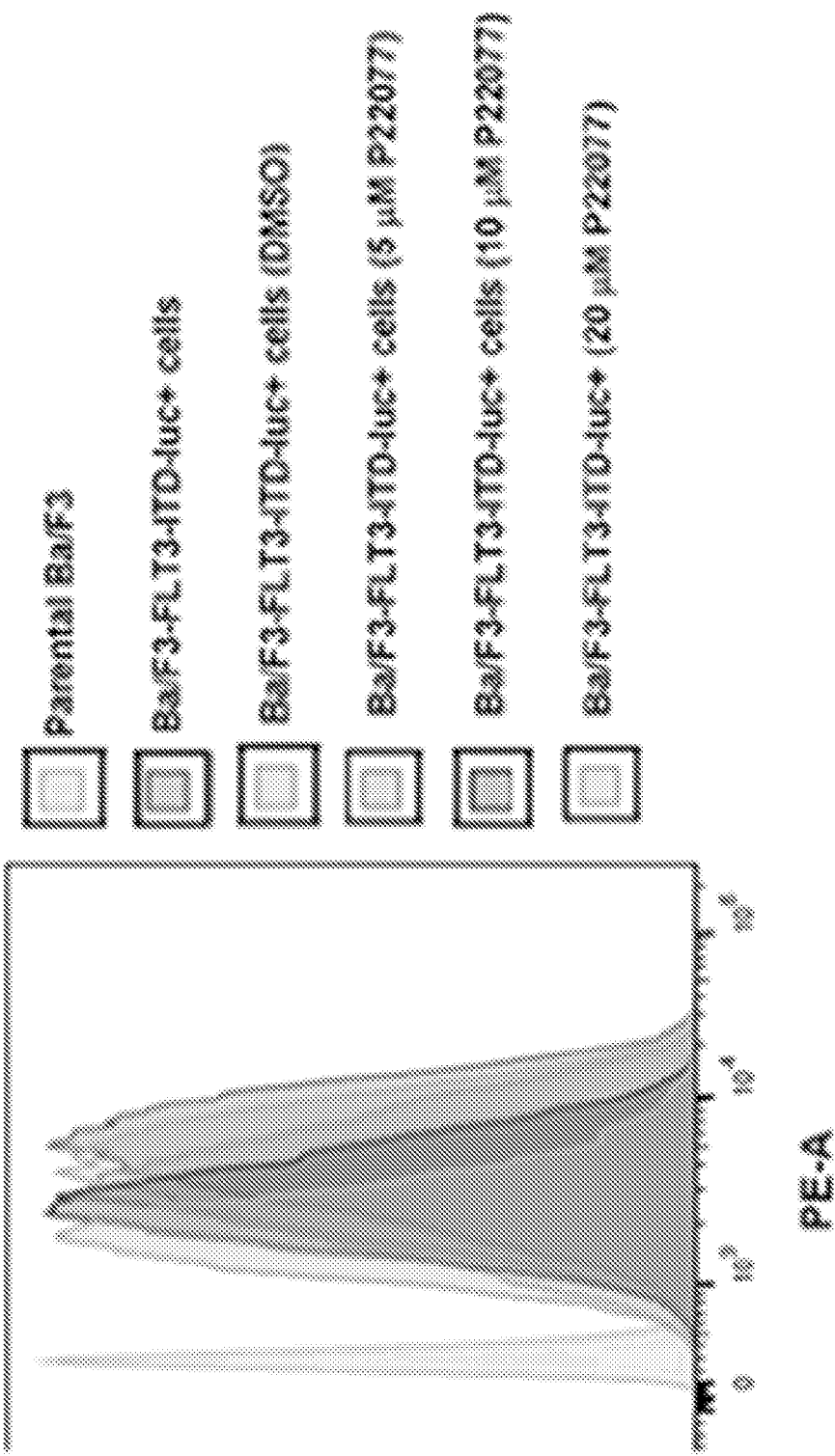
Figure 23F:
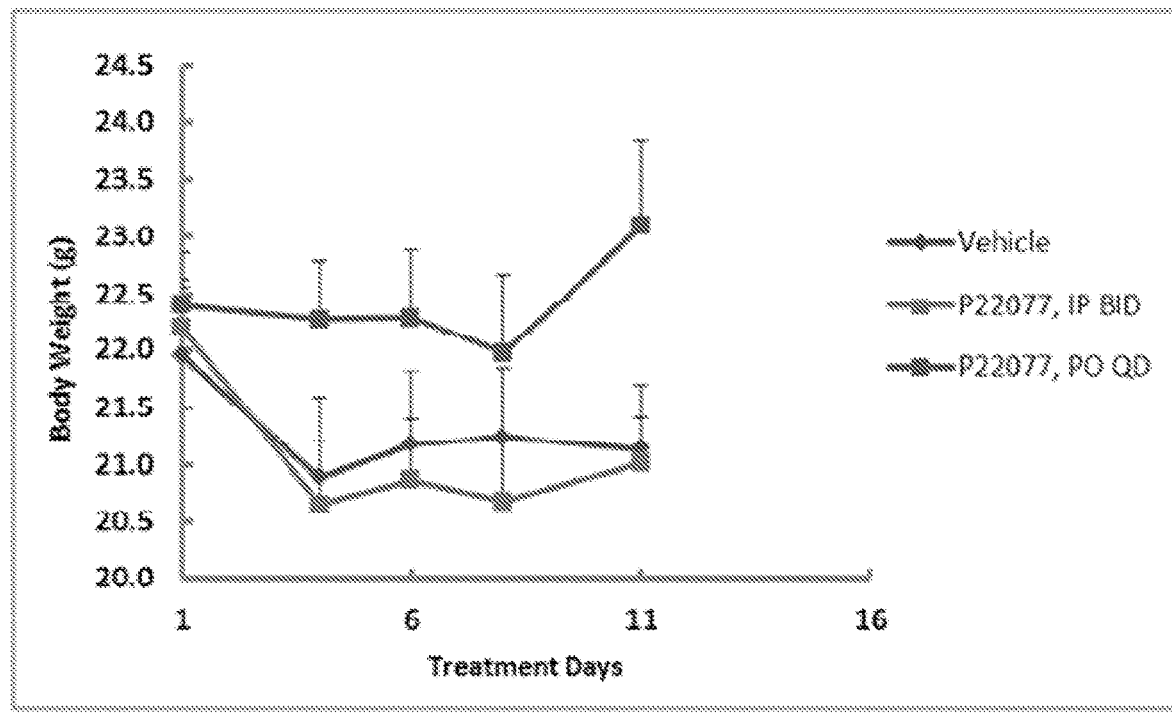
Figure 23G:
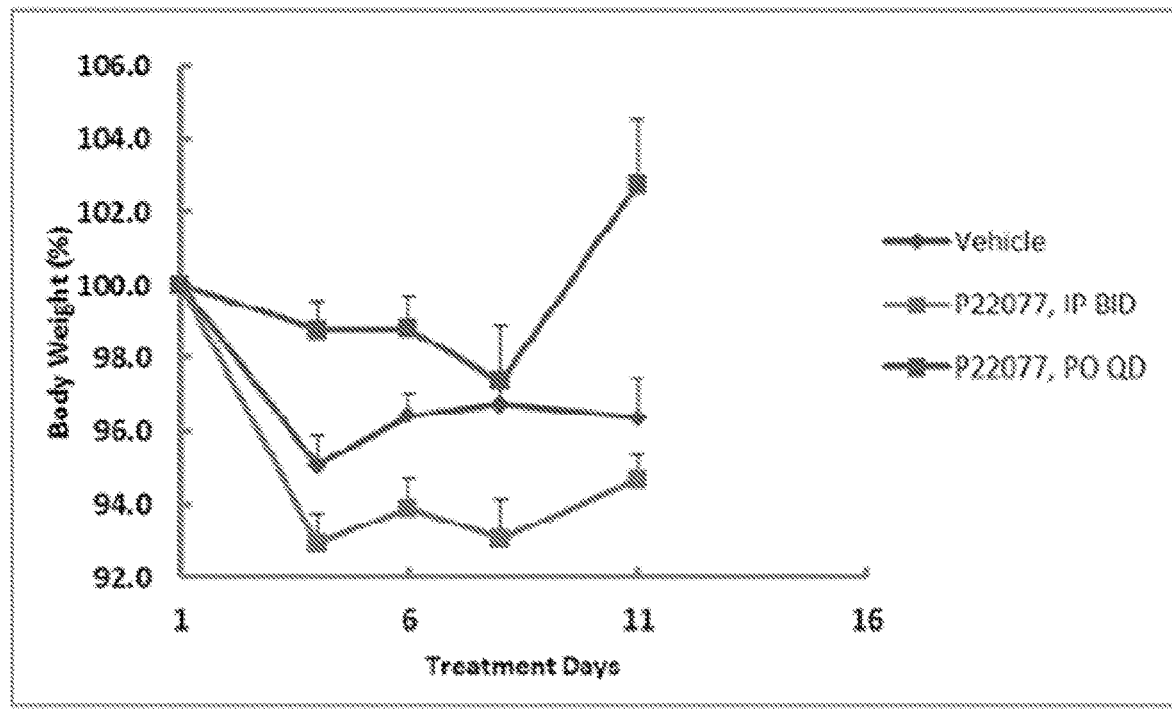
Figure 24:
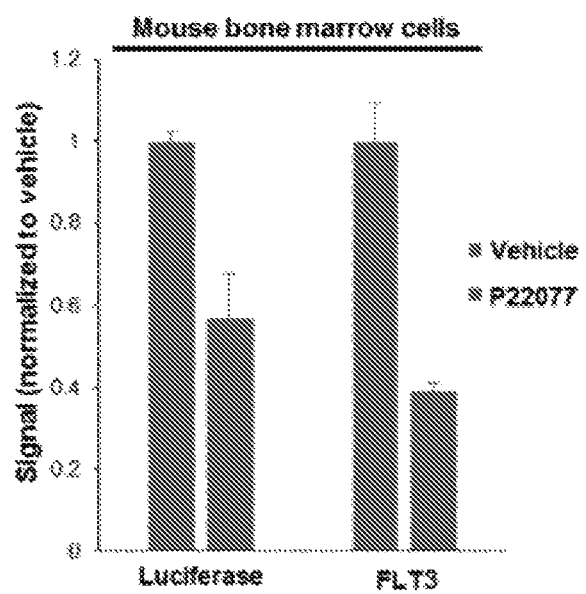
FIG. 24 includes 3 panels, identified as panels A, B, and C, which show effects of combination of HBX19818 with FLT3 kinase inhibitors and targeted effects of USP10 inhibition on mutant FLT3-positive AML, primary cells in vitro and in vivo. Panel A shows the correlation between luciferase-positive leukemia burden as measured by Bright Glo assay and luminoskan (left panel) and percent FLT3 as measured by flow cytometry using a CD135-PE conjugated antibody (right panel) in bone marrow samples from vehicle-versus P22077 (50 mg/kg, IP BID)-treated mice (pilot study, 4 day treatments). Error bars are representative of the standard error of the mean. Panels B and C show the effect of P22077 treatment on Ba/F3-FLT3-ITD-luc+ cell growth in a non-invasive in vivo bioluminescence model of leukemia. Panel B shows the total flux bioluminescence plotted as a graph. Error bars represent the standard error of the mean. Panel C shows bioluminescent images of representative mice with matched starting leukemia burden. Student t-test (two-sided): Vehicle vs IP BID: Day 4 (p=0.0069212), Day 6 (p=0.1033934). Vehicle vs PO QD: Day 4 (p=0.0034501), Day 6 (p=0.0425383).
Figure 24:
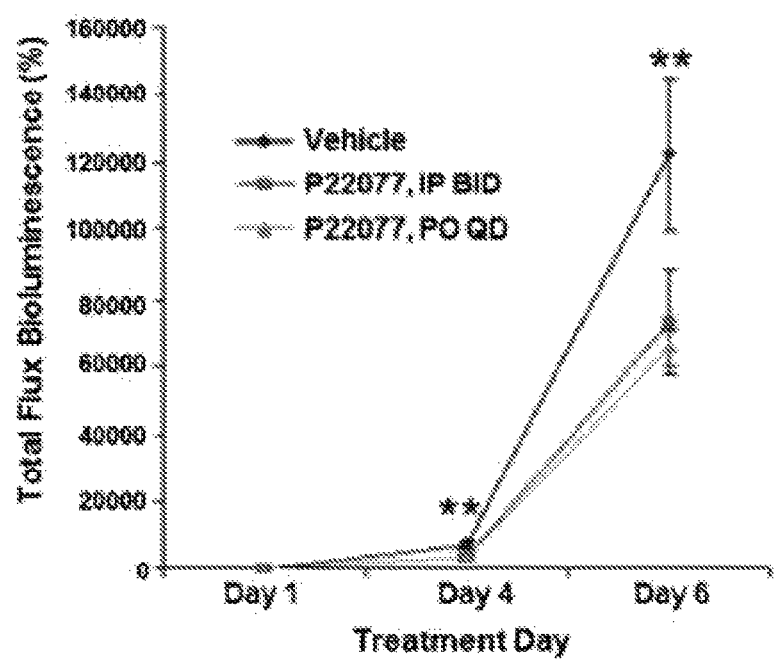
Figure 24:
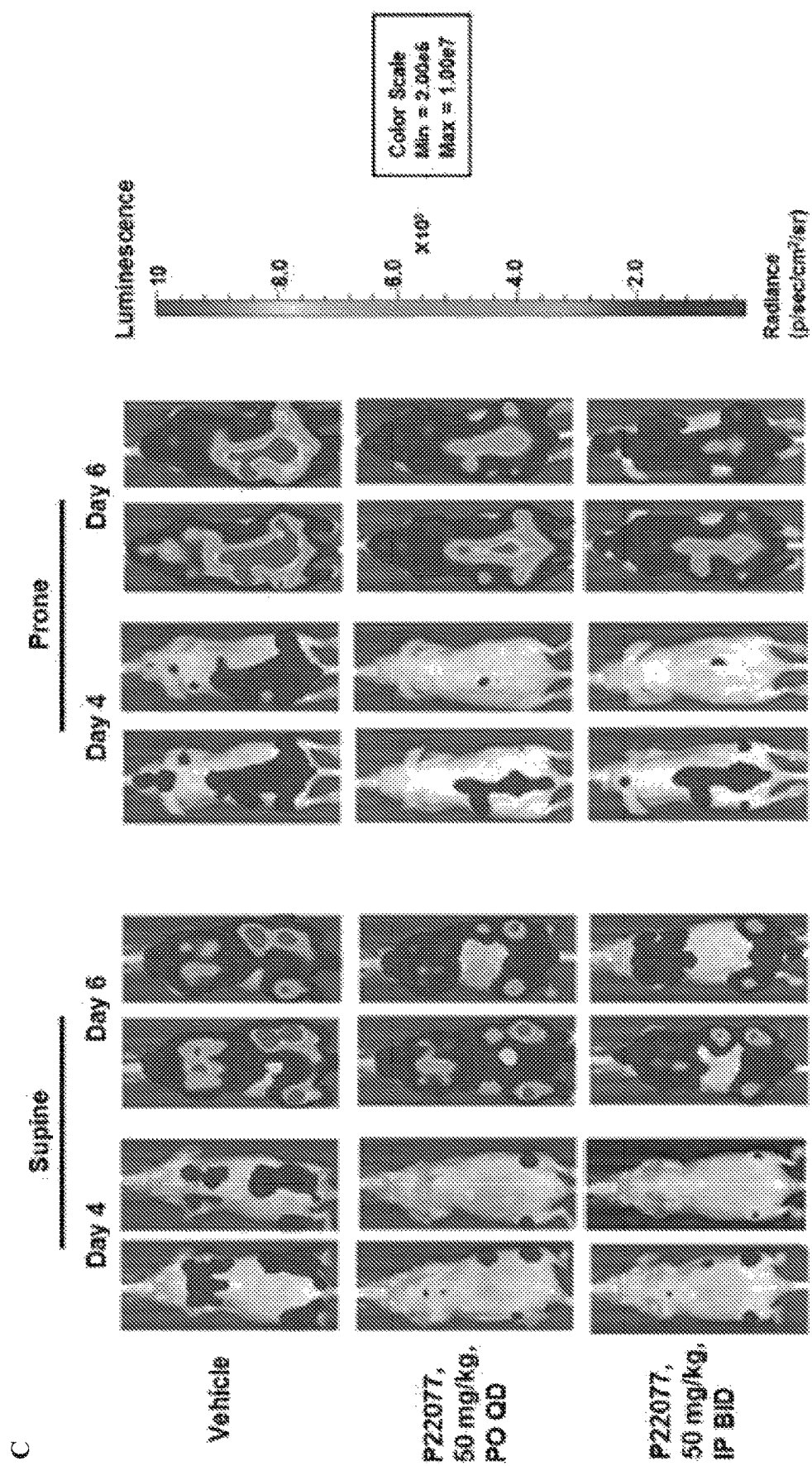
Figure 25:
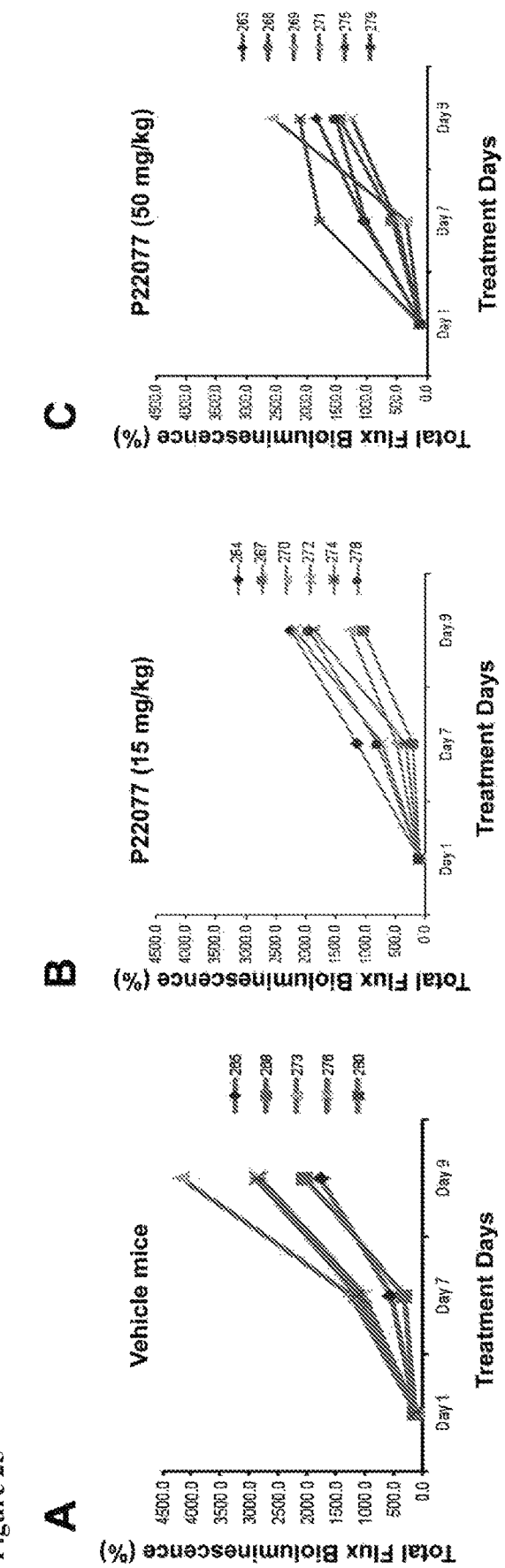
FIG. 25 includes 3 panels, identified as panels A, B, and C, which show the results of bioluminescence over time for individual mice in an in vivo bioluminescence study through treatment day 9.

In addition, the ability of P22077 to suppress the growth of mutant FLT3-positive cells using a non-invasive in vivo bioluminescence model was tested. HBX19818 and P22077 were first validated for their ability to induce FLT3 degradation in Ba/F3-FLT3-ITD-luc+ cells in vitro. It was found that Ba/F3-FLT3-ITD-luc+ cells respond to midostaurin and P22077 similar to non-luciferase-expressing cells in terms of growth suppression and FLT3 degradation (FIGS. 23A-23B) and DUB inhibitor-induced loss of FLT3 surface expression (FIG. 23E). In a small pilot study Ba/F3-FLT3-ITD-luc+ harboring female NCR nude mice treated with 50 mg/kg P22077 IP BID (n=4) for 4 days had a lower percentage (approximately 2-fold) of FLT3 expression in extracted bone marrow as measured by flow cytometry using a CD35-PE conjugated antibody in comparison to bone marrow extracted from vehicle control mice (n=4) (FIG. 24A). Aliquots of the bone marrow samples showed a similar approximately 2-fold reduction in luciferase-positive signal in P22077-treated mouse bone marrow samples as compared to vehicles (FIG. 24A). Taken together, these results suggest reduction in tumor burden via on-target effects. A larger 3-arm (n=8 per arm) study was then carried out, with administration of 50 mg/kg P22077 IP BID, P22077 PO QD, or vehicle to Ba/F3-FLT3-ITD-luc+ harboring female NCR nude mice. P22077 treatment was observed to lead to killing of mutant FLT3-ITD-expressing cells in vivo as measured by in vivo bioluminescence measurements, with a statistically significant decrease in leukemia burden compared to vehicle control mice noted following 4-6 days of treatment (FIGS. 24B-24C). In addition, Ba/F3-FLT3-ITD-luc+ cells, like Ba/F3-FLT3-ITD cells, were tested as a control for sensitivity to midostaurin and P22077. These controls were observed to respond similarly in terms of growth inhibition to both compounds (FIGS. 23C-23D). Fifteen mg/kg P22077 and 50 mg/kg P22077, administered once daily IP, visibly suppressed the growth of Ba/F3-FLT3-ITD-luc+ cells in mice compared to vehicle controls following 9 days of treatment (FIGS. 20D and 25). Importantly, there was no significant difference in weight observed between vehicle- and drug-treated mice treated for up to 11 days (FIGS. 23F-23G). There was also generally no evidence of vital organ toxicity in the mouse studies.

The five-year survival rate for AML patients is only 20% (De Kouchkovsky and Abdul-Hay, (2016) *Blood Cancer J,* 6, e441). The prognosis is especially poor for AML patients with FLT3-ITD mutations as these are associated with aggressive and lethal disease (Martelli et al., (2013) *Blood Rev,* 27, 13-22). Treatment with FLT3 kinase inhibitors unfortunately provides responses of only short duration due to emergence of drug resistance (Weisberg et al., (2010), *Mol Cancer Ther,* 9, 2468-77). Additionally, patients treated with FLT3 kinase inhibitors experience side-effects such as myelosuppression as a result of inhibition of wt FLT3 (Warkentin et al., (2014) *Elife,* 3). These limitations warrant the development of novel, targeted agents. Therapeutic targeting of mutant FLT3 by promoting its degradation as opposed to inhibition of its kinase activity is a novel approach that is potentially beneficial for overcoming resistance to current FLT3 kinase inhibitors and furthermore, may prove more efficacious than kinase inhibitors by simultaneously blocking both enzymatic and scaffolding functions of FLT3.

The DUB USP10 is shown herein as a critical effector enzyme of tumor growth and survival in FLT3-ITD mutant-positive AML. Two chemical classes of USP10 inhibitor that promote FLT3 degradation and confer an anti-proliferative effect in vitro and in vivo. Most studies aimed at identification of the DUB responsible for stabilization of a substrate of interest start with a genetic-based screen, typically knock-down or over-expression of individual DUBs, measuring protein levels. However, a novel approach, frequently utilized in the kinase field but not yet reported in the DUB field, is shown herein by a screen of small molecule DUB inhibitors for ability to selectively suppress growth of mutant FLT3-expressing cells over wt FLT3-expressing cells. This novel strategy was enabled by assembly of a DUB inhibitor library and annotation of the library for inhibitory activity across a large panel of DUBs. The top hit from exemplary screens, HBX19818, led to striking and selective anti-proliferative effects against mutant FLT3-positive cells, which results from inhibition of USP10, as a previously unreported target of the compound. The small moleculecentered approach discussed herein helped not only to identify a novel mechanism for regulation of FLT3-ITD but also to rapidly interrogate the translational potential of pharmacological inhibition of USP10 in mutant FLT3-driven AML, in preclinical models. The data generated across multiple models strongly supports the notion that USP10 inhibition may offer a novel strategy for targeting mutant FLT3 AML clinically and has the potential to overcome kinase inhibitor resistance mechanisms.

The observed selective degradation of mutant FLT3 may offer a significant clinical advantage over FLT3 kinase inhibitors that inhibit both wt and mutant enzyme by sparing wt FLT3 in normal hematopoietic cells. Phosphorylation of the FLT3 receptor has been shown to be necessary for FLT3 ubiquitination and degradation by the E3 ubiquitin ligase CBL (Lavagna-Se'venier et al., (1998) *Leukemia*, 12, 301-10; Sargin et al., (2007) *Blood* 110, 1004-12). Consistent with previous reports (Griffith et al., 2004), more significant phosphorylation of mutant FLT3 than wt FLT3 was observed in the absence of FLT3 ligand, with highest levels of autophosphorylation observed in cells expressing both FLT3-ITD and TKD mutations. Specifically, the half-life of FLT3-ITD following HBX19818 treatment is shorter than wt FLT3. The data are consistent with other reports showing that autophosphorylated FLT3-ITD, as compared to wt FLT3, undergoes more rapid degradation via proteasome- and lysosome-mediated pathways, where degradation was facilitated by the E3 ubiquitin ligases c-Cbl and c-Cbl-b (OSHIKAWA G., et. al., (2011) *J Biol Chem*, 286, 30263-73). Overall, the data indicate that mutant FLT3 exists in a state more prone to ubiquitination than wt FLT3, and this is believed to account for the observed selective degradation of mutant FLT3 compared to wt FLT3 by USP10 inhibition.

Figure 26:
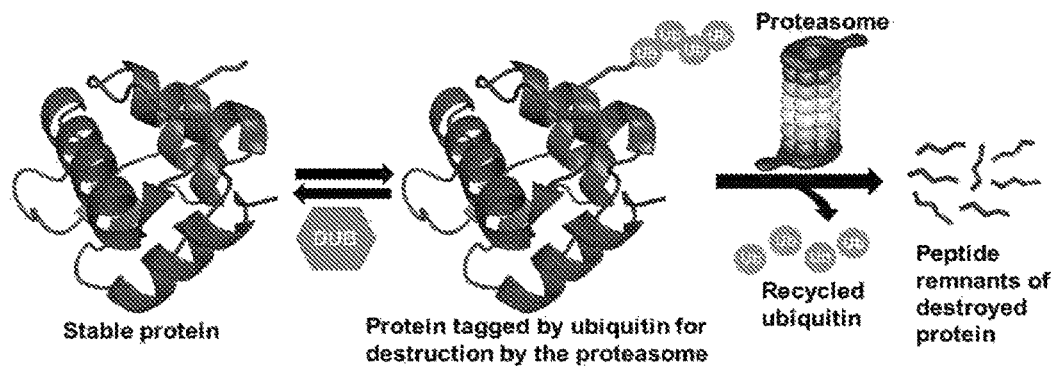
FIG. 26 includes 4 panels, identified as panels A, B, C, and D, which show provide a summary diagram providing data demonstrating that inhibition of USP10 induces degradation of oncogenic FLT3 and thereby providing a new approach to leukemia therapy. In each of the panels, the term USP10i-1 refers to HBX19818.
Figure 26:
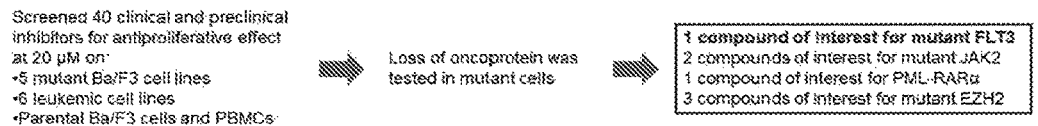
Figure 26:
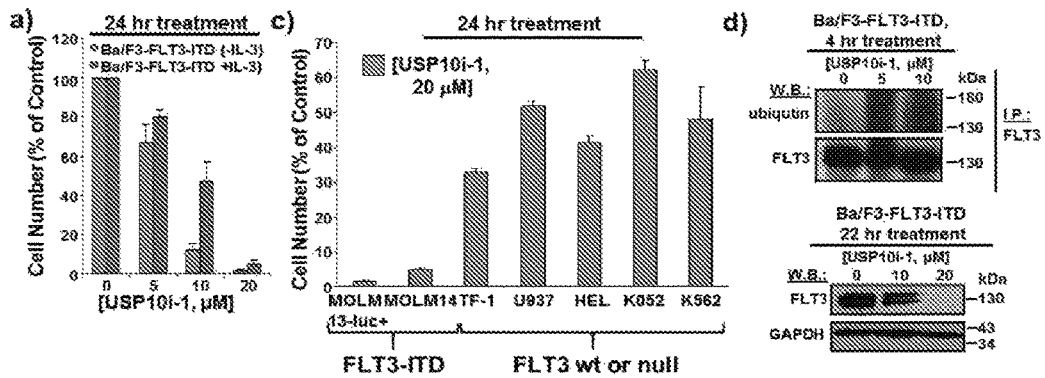
Figure 26:
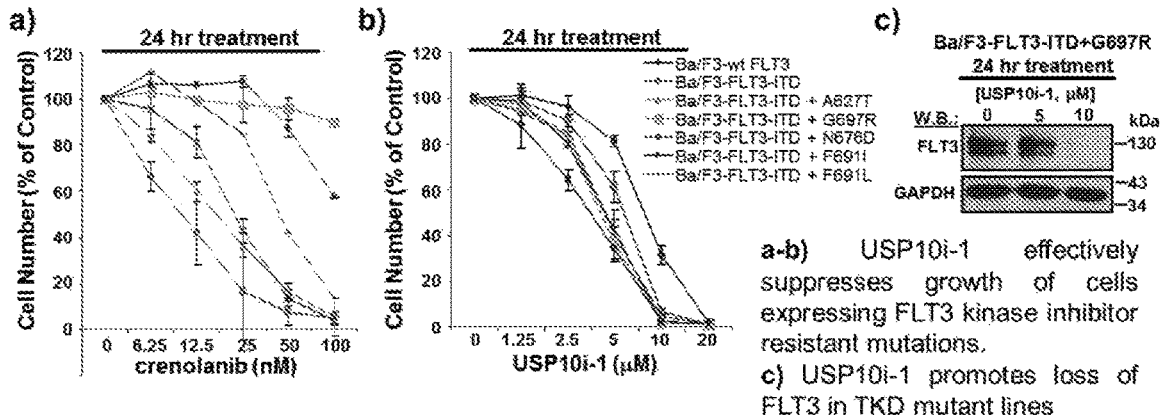
Figure 26:
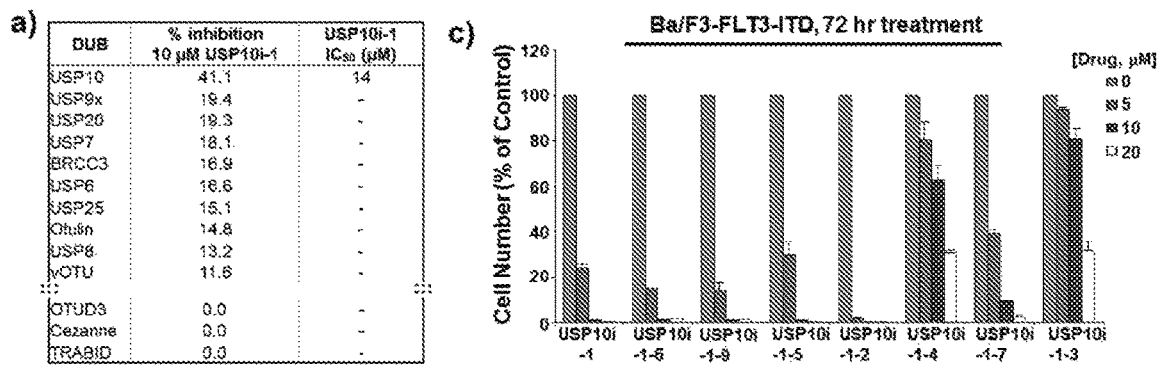
Figure 26:
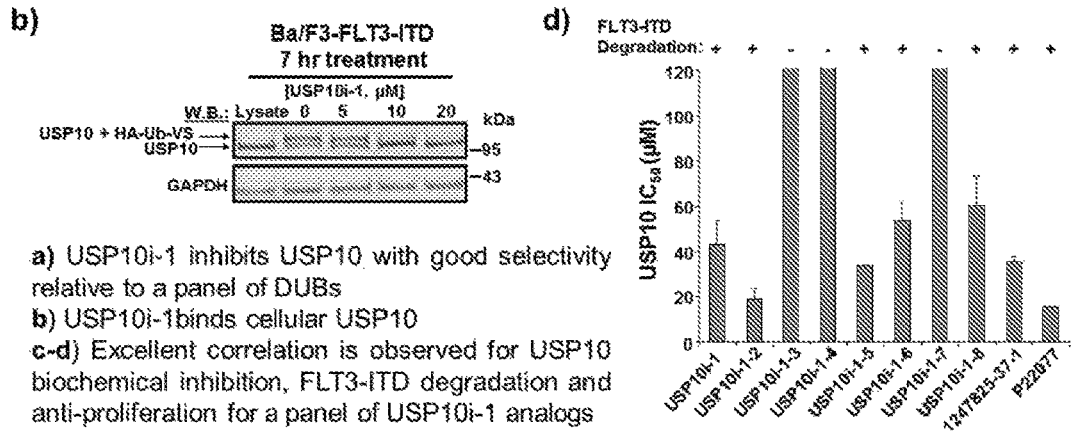

Taken together, the results described herein, such as those summarized at FIG. 26, demonstrate that USP10 is a critical effector enzyme of tumor growth and survival in FLT3-ITD mutant-positive AML, resulting from its deubiquitylation and stabilization of this mutant driver protein. Furthermore, two chemical classes of USP10 inhibitor were identified that promote degradation of mutant FLT3 in AML cell lines and confer an anti-proliferative effect in FLT3 mutant-positive AML cell lines and primary patient samples. The results further demonstrate that therapeutic targeting of USP10 has potent suppressive effects on FLT3-ITD positive AML, including kinase inhibitor resistant FLT3 mutants, and warrants further investigation as an alternative treatment strategy for this disease.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with activating FLT3 mutation-positive acute myeloblastic leukemia (AML), comprising administering to the subject a small molecule inhibitor of USP10 that binds to USP10, thereby treating the subject afflicted with the activating FLT3 mutation-positive AML, optionally wherein the USP10 is listed in Table 1.

2. The method of claim 1, wherein
   (i) the small molecule inhibitor of USP10 is administered in a pharmaceutically acceptable formulation; and/or
   (ii) the USP10 is human USP10.

3. The method of claim 1, further comprising administering at least one additional anti-cancer agent, optionally wherein the at least one additional anti-cancer agent inhibits the copy number, amount, and/or activity of at least one biomarker listed in Table 2.

4. A method of inhibiting hyperproliferative growth of activating FLT3 mutation-positive AML cells, the method comprising contacting the activating FLT3 mutation-positive AML cells with a small molecule inhibitor of USP10 that binds to USP10, thereby inhibiting hyperproliferative growth of the activating FLT3 mutation-positive AML cells, optionally wherein the USP10 is listed in Table 1.

5. The method of claim 4, wherein
   (i) the step of contacting occurs in vivo, ex vivo, or in vitro, optionally wherein the activating FLT3 mutation-positive AML cells die;
   (ii) the small molecule inhibitor of USP10 is administered in a pharmaceutically acceptable formulation; and/or
   (iii) the USP10 is human USP10.

6. The method of claim 4, further comprising administering at least one additional agent, optionally wherein the at least one additional anti-cancer agent inhibits the copy number, amount, and/or activity of at least one biomarker listed in Table 2.

7. The method of claim 1, wherein
   (a) the small molecule inhibitor of USP10 is selected from the group consisting of small molecules listed in FIGS. 1-22 and Table 8;
   (b) the small molecule inhibitor of USP10 also inhibits the activity or expression level of USP7;
   (c) the small molecule inhibitor of USP10 does not inhibit the activity or expression level of p53;
   (d) the activating FLT3 mutation-positive AML is adult activating FLT3 mutation-positive AML or pediatric activating FLT3 mutation-positive AML; and/or
   (e) the subject is a mammal, optionally wherein the mammal is an animal model of activating FLT3 mutation-positive AML or a human.

8. The method of claim 4, wherein
   (a) the small molecule inhibitor of USP10 is selected from the group consisting of small molecules listed in FIGS. 1-22 and Table 8;
   (b) the small molecule inhibitor of USP10 also inhibits the activity or expression level of USP7;
   (c) the small molecule inhibitor of USP10 does not inhibit the activity or expression level of p53;
   (d) the activating FLT3 mutation-positive AML is adult activating FLT3 mutation-positive AML or pediatric activating FLT3 mutation-positive AML; and/or
   (e) the contacting occurs in a subject and the subject is a mammal, optionally wherein the mammal is an animal model of activating FLT3 mutation-positive AML or a human.

\* \* \* \* \*

SEQUENCE LISTING

```
<160> NUMBER OF SEQ ID NOS: 9

<210> SEQ ID NO 1
<211> LENGTH: 3520
<212> TYPE: DNA
<213> ORGANISM: Homo sapiens

<400> SEQUENCE: 1
ctccccgcgc cccgcggcgc gcggccagtg cgcaggcgcg gcggccgatg cgagtgtgta      60
tgtgcgggcg agaagatggc ggcggcgggg gaagcagcgt gagcagccgg aggatcgcgg     120
agtcccaatg aaacgggcag ccatggccct ccacagcccg cagctcctgg gccatgatcc     180
cattttcatc agatgacttg agaacccaga agctctacca gcactgccat tctgtcccgt     240
cttgaaacat catgccctgg ttgccctctc ctggaatagg gcagtatatt tttggagatt     300
ttagccctga tgaattcaat caattctttg tgactcctcg atcttcagtt gagcttcctc     360
catacagtgg aacagttctg tgtggcacac aggctgtgga taaactacct gatggacaag     420
aatatcagag aattgagttt ggtgtcgatg aagtcattga acccagtgac actttgccga     480 gaaccccccag ctacagtatt tcaagcacac tgaaccctca ggcccctgaa tttattctcg     540
gttgtacagc ttccaaaata acccctgatg gtatcactaa agaagcaagc tatggctcca     600
tcgactgcca gtacccaggc tctgccctcg ctttggatgg aagttctaat gtggaggcgg     660 aagtttttgga aaatgatggt gtctcaggtg gtcttggaca aagggagcgt aaaaagaaga     720
```

```
aaaagcggcc acctggatat tacagctatt tgaaagatgg tggcgatgat agtatctcca    780
cagaagccct ggtcaatggc catgccaatt cagcagtccc gaacagtgtc agtgcagagg    840
atgcagaatt tatgggtgac atgccccgt cagttacgcc caggacttgt aacagccccc     900
agaactccac agactctgtc agtgacattg tgcctgacag tcctttcccc ggagcactcg    960
gcagtgacac caggactgca gggcagccag aggggggccc cggggctgat tttggtcagt   1020
cctgcttccc tgcagaggct ggcagagaca ccctgtcaag gacagctggg gctcagccct   1080
gcgttggtac cgatactact gaaaaccttg gagttgctaa tggacaaata cttgaatcct   1140
cgggtgaggg cacagctacc aacggggtgg agttgcacac cacggaaagc atagacttgg   1200
acccaaccaa acccgagagt gcatcacctc ctgctgacgg cacgggctct gcatcaggca   1260
cccttcctgt cagccagccc aagtcctggg ccagcctctt tcatgattct aagccctctt   1320
cctcctcgcc ggtggcctat gtggaaacta agtattcccc tcccgccata tctcccctgg   1380
tttctgaaaa gcaggttgaa gtcaagaag ggcttgttcc ggtttcagag gatcctgtag     1440
ccataaagat tgcagagttg ctggagaatg taaccctaat ccataaacca gtgtcgttgc   1500
aaccccgtgg gctgatcaat aaagggaact ggtgctacat taatgctaca ctgcaggcat   1560
tggttgcttg cccgccgatg taccacctga tgaagttcat tcctctgtat tccaaagtgc   1620
aaaggccttg tacgtcaaca cccatgatag acagctttgt tcggctaatg aatgagttca   1680
ctaatatgcc agtacctcca aaaccccgac aagctcttgg agataaaatc gtgagggata   1740
ttcgccctgg agctgccttt gagcccacat atatttacag actcctgaca gttaacaagt   1800
caagcctgtc tgaaagggt cgacaagaag atgctgagga atacttaggc ttcattctaa    1860
atggacttca tgaggaaatg ttgaacctaa agaagcttct ctcaccaagt aatgaaaaac   1920
ttacgatttc caacggcccc aaaaaccact cggtcaatga agaagagcag gaagaacaag   1980
gtgaaggaag cgaggatgaa tgggaacaag tgggcccccg gaacaagact tccgtcaccc   2040
gccaggcgga ttttgttcag actccaatca ccggcatttt tggtggacac atcaggtctg   2100
tggtttacca gcagagttca aaagaatctg ccactttgca gccatttttc acgttgcagt   2160
tggatatcca gtcagacaag atacgcacag tccaggatgc actggagagc ttggtggcaa   2220
gagaatctgt ccaaggttat accacaaaaa ccaaacaaga ggttgagata agtcgaagag   2280
tgactctgga aaaactccct cctgtcctcg tgctgcacct gaaacgattc gtttatgaga   2340
agactggtgg gtgccagaag cttatcaaaa atattgaata tcctgtggac ttggaaatta   2400
gtaaagaact gctttctcca ggggttaaaa ataagaattt taaatgccac cgaacctatc   2460
ggctctttgc agtggtctac catcacggca acagtgcgac gggcggccat tacactacag   2520
acgtcttcca gatcggtctg aatggctggc tgcgcatcga tgaccagaca gtcaaggtga   2580
tcaaccagta ccaggtggtg aaaccaactg ctgaacgcac agcctacctc ctgtattacc   2640
gccgagtgga cctgctgtaa accctgtgtg cgctgtgtgt gcgcccagtg cccgcttcgt   2700
aggacaccac ctcacactca cttcccgcct ctctttagtg gctctttaga gagaaactct   2760
ttctcccttt gcaaaaatgg gctagaatga aaggagatg ccttgggtt cgtgcacaac      2820
acagcttctg ttgactctaa cttccaaatc aaaatcattt ggttgaaaca gactgttgct   2880
tgattttaga aaatacacaa aaacccatat ttctgaaata atgctgattc ctgagataag   2940
aaagtggatt tgatccccag tctcattgct tagtagaata aatcctgcac cagcaacaac   3000
acttgtaaat ttgtgaaaat gaattttatc tttccttaaa aaagaaattt tttaatccat   3060
cacactttttc ttccctaccc tttagttttt gataaatgat aaaaatgagc cagttatcaa  3120
```

```
agaagaacta gttcttactt caaaagaaaa ataaacataa aaaataagtt gctggttcct    3180
aacaggaaaa attttaataa ttgtactgag agaaactgct tacgtacaca ttgcagatca    3240
aatatttgga gttaaaatgt tagtctacat agatgggtga ttgtaacttt attgccatta    3300
aaagatttca aattgcattc atgcttctgt gtacacataa tgaaaatgg gcaaataatg     3360 aagatctctc cttcagtctg ctctgtttaa ttctgctgtc tgctcttctc taatgctgcg    3420
tccctaattg tacacagttt agtgatatct aggagtataa agttgtcgcc catcaataaa    3480
aatcacaaag ttggtttaaa aaaaaaaaaa aaaaaaaaa                           3520
```

<210> SEQ ID NO 2
<211> LENGTH: 802
<212> TYPE: PRT
<213> ORGANISM: Homo sapiens

<400> SEQUENCE: 2

```
Met Pro Trp Leu Pro Ser Pro Gly Ile Gly Gln Tyr Ile Phe Gly Asp
1               5                   10                  15

Phe Ser Pro Asp Glu Phe Asn Gln Phe Phe Val Thr Pro Arg Ser Ser
            20                  25                  30

Val Glu Leu Pro Pro Tyr Ser Gly Thr Val Leu Cys Gly Thr Gln Ala
        35                  40                  45

Val Asp Lys Leu Pro Asp Gly Gln Glu Tyr Gln Arg Ile Glu Phe Gly
    50                  55                  60

Val Asp Glu Val Ile Glu Pro Ser Asp Thr Leu Pro Arg Thr Pro Ser
65                  70                  75                  80

Tyr Ser Ile Ser Ser Thr Leu Asn Pro Gln Ala Pro Glu Phe Ile Leu
                85                  90                  95

Gly Cys Thr Ala Ser Lys Ile Thr Pro Asp Gly Ile Thr Lys Glu Ala
            100                 105                 110

Ser Tyr Gly Ser Ile Asp Cys Gln Tyr Pro Gly Ser Ala Leu Ala Leu
        115                 120                 125

Asp Gly Ser Ser Asn Val Glu Ala Glu Val Leu Glu Asn Asp Gly Val
    130                 135                 140

Ser Gly Gly Leu Gly Gln Arg Glu Arg Lys Lys Lys Lys Arg Pro
145                 150                 155                 160

Pro Gly Tyr Tyr Ser Tyr Leu Lys Asp Gly Gly Asp Ser Ile Ser
                165                 170                 175

Thr Glu Ala Leu Val Asn Gly His Ala Asn Ser Ala Val Pro Asn Ser
            180                 185                 190

Val Ser Ala Glu Asp Ala Glu Phe Met Gly Asp Met Pro Pro Ser Val
        195                 200                 205

Thr Pro Arg Thr Cys Asn Ser Pro Gln Asn Ser Thr Asp Ser Val Ser
    210                 215                 220

Asp Ile Val Pro Asp Ser Pro Phe Pro Gly Ala Leu Gly Ser Asp Thr
225                 230                 235                 240

Arg Thr Ala Gly Gln Pro Glu Gly Gly Pro Gly Ala Asp Phe Gly Gln
                245                 250                 255

Ser Cys Phe Pro Ala Glu Ala Gly Arg Asp Thr Leu Ser Arg Thr Ala
            260                 265                 270

Gly Ala Gln Pro Cys Val Gly Thr Asp Thr Thr Glu Asn Leu Gly Val
        275                 280                 285

Ala Asn Gly Gln Ile Leu Glu Ser Gly Glu Gly Thr Ala Thr Asn
    290                 295                 300
```

```
Gly Val Glu Leu His Thr Thr Glu Ser Ile Asp Leu Asp Pro Thr Lys
305                 310                 315                 320

Pro Glu Ser Ala Ser Pro Ala Asp Gly Thr Gly Ser Ala Ser Gly
            325                 330                 335

Thr Leu Pro Val Ser Gln Pro Lys Ser Trp Ala Ser Leu Phe His Asp
                340                 345                 350

Ser Lys Pro Ser Ser Ser Pro Val Ala Tyr Val Glu Thr Lys Tyr
            355                 360                 365

Ser Pro Pro Ala Ile Ser Pro Leu Val Ser Glu Lys Gln Val Glu Val
        370                 375                 380

Lys Glu Gly Leu Val Pro Val Ser Glu Asp Pro Val Ala Ile Lys Ile
385                 390                 395                 400

Ala Glu Leu Leu Glu Asn Val Thr Leu Ile His Lys Pro Val Ser Leu
                405                 410                 415

Gln Pro Arg Gly Leu Ile Asn Lys Gly Asn Trp Cys Tyr Ile Asn Ala
            420                 425                 430

Thr Leu Gln Ala Leu Val Ala Cys Pro Pro Met Tyr His Leu Met Lys
        435                 440                 445

Phe Ile Pro Leu Tyr Ser Lys Val Gln Arg Pro Cys Thr Ser Thr Pro
450                 455                 460

Met Ile Asp Ser Phe Val Arg Leu Met Asn Glu Phe Thr Asn Met Pro
465                 470                 475                 480

Val Pro Pro Lys Pro Arg Gln Ala Leu Gly Asp Lys Ile Val Arg Asp
            485                 490                 495

Ile Arg Pro Gly Ala Ala Phe Glu Pro Thr Tyr Ile Tyr Arg Leu Leu
            500                 505                 510

Thr Val Asn Lys Ser Ser Leu Ser Glu Lys Gly Arg Gln Glu Asp Ala
            515                 520                 525

Glu Glu Tyr Leu Gly Phe Ile Leu Asn Gly Leu His Glu Glu Met Leu
        530                 535                 540

Asn Leu Lys Lys Leu Leu Ser Pro Ser Asn Glu Lys Leu Thr Ile Ser
545                 550                 555                 560

Asn Gly Pro Lys Asn His Ser Val Asn Glu Glu Glu Gln Glu Glu Gln
            565                 570                 575

Gly Glu Gly Ser Glu Asp Glu Trp Glu Gln Val Gly Pro Arg Asn Lys
        580                 585                 590

Thr Ser Val Thr Arg Gln Ala Asp Phe Val Gln Thr Pro Ile Thr Gly
            595                 600                 605

Ile Phe Gly Gly His Ile Arg Ser Val Val Tyr Gln Gln Ser Ser Lys
        610                 615                 620

Glu Ser Ala Thr Leu Gln Pro Phe Phe Thr Leu Gln Leu Asp Ile Gln
625                 630                 635                 640

Ser Asp Lys Ile Arg Thr Val Gln Asp Ala Leu Glu Ser Leu Val Ala
            645                 650                 655

Arg Glu Ser Val Gln Gly Tyr Thr Thr Lys Thr Lys Gln Glu Val Glu
            660                 665                 670

Ile Ser Arg Arg Val Thr Leu Glu Lys Leu Pro Pro Val Leu Val Leu
            675                 680                 685

His Leu Lys Arg Phe Val Tyr Glu Lys Thr Gly Gly Cys Gln Lys Leu
            690                 695                 700

Ile Lys Asn Ile Glu Tyr Pro Val Asp Leu Glu Ile Ser Lys Glu Leu
705                 710                 715                 720
```

```
Leu Ser Pro Gly Val Lys Asn Lys Asn Phe Lys Cys His Arg Thr Tyr
                725                 730                 735

Arg Leu Phe Ala Val Val Tyr His His Gly Asn Ser Ala Thr Gly Gly
            740                 745                 750

His Tyr Thr Thr Asp Val Phe Gln Ile Gly Leu Asn Gly Trp Leu Arg
        755                 760                 765

Ile Asp Asp Gln Thr Val Lys Val Ile Asn Gln Tyr Gln Val Val Lys
    770                 775                 780

Pro Thr Ala Glu Arg Thr Ala Tyr Leu Leu Tyr Tyr Arg Arg Val Asp
785                 790                 795                 800

Leu Leu

<210> SEQ ID NO 3
<211> LENGTH: 3399
<212> TYPE: DNA
<213> ORGANISM: Homo sapiens

<400> SEQUENCE: 3
ctccccgcgc cccgcggcgc gcggccagtg cgcaggcgcg gcggccgatg cgagtgtgta      60
tgtgcgggcg agaagatggc ggcggcgggg gaagcagcgt gagcagccgg aggatcgcgg     120
agtcccaatg aaacgggcag ccatggccct ccacagcccg cagtatattt ttggagattt     180
tagccctgat gaattcaatc aattctttgt gactcctcga tcttcagttg agcttcctcc     240
atacagtgga acagttctgt gtggcacaca ggctgtggat aaactacctg atggacaaga     300
atatcagaga attgagtttg tgtcgatga agtcattgaa cccagtgaca ctttgccgag     360 aaccccagc tacagtattt caagcacact gaaccctcag gcccctgaat ttattctcgg     420
ttgtacagct tccaaaataa cccctgatgg tatcactaaa gaagcaagct atggctccat     480
cgactgccag tacccaggct ctgccctcgc tttggatgga agttctaatg tggaggcgga     540
agttttggaa aatgatggtg tctcaggtgg tcttggacaa agggagcgta aaaagaagaa     600
aaagcggcca cctggatatt acagctattt gaaagatggt ggcgatgata gtatctccac     660
agaagccctg gtcaatggcc atgccaattc agcagtcccg aacagtgtca gtgcagagga     720
tgcagaattt atgggtgaca tgccccgtc agttacgccc aggacttgta acagccccca     780
gaactccaca gactctgtca gtgacattgt gcctgacagt cctttccccg gagcactcgg     840
cagtgacacc aggactgcag gcagccaga gggggcccc ggggctgatt ttggtcagtc     900
ctgcttccct gcagaggctg gcagagacac cctgtcaagg acagctgggg ctcagccctg     960
cgttggtacc gatactactg aaaaccttgg agttgctaat ggacaaatac ttgaatcctc    1020
gggtgagggc acagctacca acggggtgga gttgcacacc acggaaagca tagacttgga    1080
cccaaccaaa cccgagagtg catcacctcc tgctgacggc acgggctctg catcaggcac    1140
ccttcctgtc agccagccca gtcctgggc cagcctcttt catgattcta gccctcttc    1200 ctcctcgccg gtggcctatg tggaaactaa gtattccct cccgccatat ctcccctggt    1260
ttctgaaaag caggttgaag tcaaagaagg gcttgttccg gtttcagagg atcctgtagc    1320
cataaagatt gcagagttgc tggagaatgt aaccctaatc cataaaccag tgtcgttgca    1380
accccgtggg ctgatcaata aagggaactg gtgctacatt aatgctacac tgcaggcatt    1440
ggttgcttgc ccgccgatgt accacctgat gaagttcatt cctctgtatt ccaaagtgca    1500
aaggccttgt acgtcaacac ccatgataga cagctttgtt cggctaatga atgagttcac    1560
taatatgcca gtacctccaa aaccccgaca agctcttgga gataaaatcg tgagggatat    1620
```

| | | |
|---|---|---|
| tcgccctgga gctgcctttg agcccacata tatttacaga ctcctgacag ttaacaagtc | 1680 | |
| aagcctgtct gaaaagggtc gacaagaaga tgctgaggaa tacttaggct tcattctaaa | 1740 | |
| tggacttcat gaggaaatgt tgaacctaaa gaagcttctc tcaccaagta atgaaaaact | 1800 | |
| tacgatttcc aacggcccca aaaccactc ggtcaatgaa gagagcagg aagaacaagg | 1860 | |
| tgaaggaagc gaggatgaat gggaacaagt gggcccccgg aacaagactt ccgtcacccg | 1920 | |
| ccaggcggat tttgttcaga ctccaatcac cggcattttt ggtggacaca tcaggtctgt | 1980 | |
| ggtttaccag cagagttcaa aagaatctgc cactttgcag ccattttca cgttgcagtt | 2040 | |
| ggatatccag tcagacaaga tacgcacagt ccaggatgca ctggagagct tggtggcaag | 2100 | |
| agaatctgtc caaggttata ccacaaaaac caaacaagag gttgagataa gtcgaagagt | 2160 | |
| gactctggaa aaactccctc ctgtcctcgt gctgcacctg aaacgattcg tttatgagaa | 2220 | |
| gactggtggg tgccagaagc ttatcaaaaa tattgaatat cctgtggact tggaaattag | 2280 | |
| taaagaactg ctttctccag gggttaaaaa taagaatttt aaatgccacc gaacctatcg | 2340 | |
| gctcttttgca gtggtctacc atcacggcaa cagtgcgacg ggcggccatt acactacaga | 2400 | |
| cgtcttccag atcggtctga atggctggct gcgcatcgat gaccagacag tcaaggtgat | 2460 | |
| caaccagtac caggtggtga aaccaactgc tgaacgcaca gcctacctcc tgtattaccg | 2520 | |
| ccgagtggac ctgctgtaaa ccctgtgtgc gctgtgtgtg cgcccagtgc ccgcttcgta | 2580 | |
| ggacaccacc tcacactcac ttcccgcctc tctttagtgg ctcttagag agaaactctt | 2640 | |
| tctccctttg caaaaatggg ctagaatgaa aaggagatgc cttggggttc gtgcacaaca | 2700 | |
| cagcttctgt tgactctaac ttccaaatca aatcatttg gttgaaacag actgttgctt | 2760 | |
| gatttagaa aatacacaaa aacccatatt tctgaaataa tgctgattcc tgagataaga | 2820 | |
| aagtggattt gatccccagt ctcattgctt agtagaataa atcctgcacc agcaacaaca | 2880 | |
| cttgtaaatt tgtgaaaatg aattttatct ttccttaaaa agaaattttt ttaatccatc | 2940 | |
| acacttttct tccctaccct ttagttttg ataaatgata aaatgagcc agttatcaaa | 3000 | |
| gaagaactag ttcttacttc aaaagaaaaa taaacataaa aataagttg ctggttccta | 3060 | |
| acaggaaaaa ttttaataat tgtactgaga gaaactgctt acgtacacat tgcagatcaa | 3120 | |
| atatttggag ttaaaatgtt agtctacata gatgggtgat tgtaacttta ttgccattaa | 3180 | |
| aagatttcaa attgcattca tgcttctgtg tacacataat gaaaaatggg caaataatga | 3240 | |
| agatctctcc ttcagtctgc tctgtttaat tctgctgtct gctcttctct aatgctgcgt | 3300 | |
| ccctaattgt acacagttta gtgatatcta ggagtataaa gttgtcgccc atcaataaaa | 3360 | |
| atcacaaagt tggtttaaaa aaaaaaaaaa aaaaaaaa | 3399 | |

<210> SEQ ID NO 4
<211> LENGTH: 798
<212> TYPE: PRT
<213> ORGANISM: Homo sapiens

<400> SEQUENCE: 4

Met Ala Leu His Ser Pro Gln Tyr Ile Phe Gly Asp Phe Ser Pro Asp
1               5                   10                  15

Glu Phe Asn Gln Phe Phe Val Thr Pro Arg Ser Ser Val Glu Leu Pro
            20                  25                  30

Pro Tyr Ser Gly Thr Val Leu Cys Gly Thr Gln Ala Val Asp Lys Leu
        35                  40                  45

Pro Asp Gly Gln Glu Tyr Gln Arg Ile Glu Phe Gly Val Asp Glu Val
    50                  55                  60

```
Ile Glu Pro Ser Asp Thr Leu Pro Arg Thr Pro Ser Tyr Ser Ile Ser
 65                  70                  75                  80

Ser Thr Leu Asn Pro Gln Ala Pro Glu Phe Ile Leu Gly Cys Thr Ala
                 85                  90                  95

Ser Lys Ile Thr Pro Asp Gly Ile Thr Lys Glu Ala Ser Tyr Gly Ser
            100                 105                 110

Ile Asp Cys Gln Tyr Pro Gly Ser Ala Leu Ala Leu Asp Gly Ser Ser
        115                 120                 125

Asn Val Glu Ala Glu Val Leu Glu Asn Asp Gly Val Ser Gly Gly Leu
    130                 135                 140

Gly Gln Arg Glu Arg Lys Lys Lys Lys Arg Pro Pro Gly Tyr Tyr
145                 150                 155                 160

Ser Tyr Leu Lys Asp Gly Gly Asp Ser Ile Ser Thr Glu Ala Leu
                165                 170                 175

Val Asn Gly His Ala Asn Ser Ala Val Pro Asn Ser Val Ser Ala Glu
                180                 185                 190

Asp Ala Glu Phe Met Gly Asp Met Pro Pro Ser Val Thr Pro Arg Thr
            195                 200                 205

Cys Asn Ser Pro Gln Asn Ser Thr Asp Ser Val Ser Asp Ile Val Pro
    210                 215                 220

Asp Ser Pro Phe Pro Gly Ala Leu Gly Ser Asp Thr Arg Thr Ala Gly
225                 230                 235                 240

Gln Pro Glu Gly Gly Pro Gly Ala Asp Phe Gly Gln Ser Cys Phe Pro
                245                 250                 255

Ala Glu Ala Gly Arg Asp Thr Leu Ser Arg Thr Ala Gly Ala Gln Pro
                260                 265                 270

Cys Val Gly Thr Asp Thr Thr Glu Asn Leu Gly Val Ala Asn Gly Gln
            275                 280                 285

Ile Leu Glu Ser Ser Gly Glu Gly Thr Ala Thr Asn Gly Val Glu Leu
        290                 295                 300

His Thr Thr Glu Ser Ile Asp Leu Asp Pro Thr Lys Pro Glu Ser Ala
305                 310                 315                 320

Ser Pro Pro Ala Asp Gly Thr Gly Ser Ala Ser Gly Thr Leu Pro Val
                325                 330                 335

Ser Gln Pro Lys Ser Trp Ala Ser Leu Phe His Asp Ser Lys Pro Ser
            340                 345                 350

Ser Ser Ser Pro Val Ala Tyr Val Glu Thr Lys Tyr Ser Pro Pro Ala
        355                 360                 365

Ile Ser Pro Leu Val Ser Glu Lys Gln Val Glu Val Lys Glu Gly Leu
    370                 375                 380

Val Pro Val Ser Glu Asp Pro Val Ala Ile Lys Ile Ala Glu Leu Leu
385                 390                 395                 400

Glu Asn Val Thr Leu Ile His Lys Pro Val Ser Leu Gln Pro Arg Gly
                405                 410                 415

Leu Ile Asn Lys Gly Asn Trp Cys Tyr Ile Asn Ala Thr Leu Gln Ala
            420                 425                 430

Leu Val Ala Cys Pro Pro Met Tyr His Leu Met Lys Phe Ile Pro Leu
        435                 440                 445

Tyr Ser Lys Val Gln Arg Pro Cys Thr Ser Thr Pro Met Ile Asp Ser
    450                 455                 460

Phe Val Arg Leu Met Asn Glu Phe Thr Asn Met Pro Val Pro Pro Lys
465                 470                 475                 480
```

```
Pro Arg Gln Ala Leu Gly Asp Lys Ile Val Arg Asp Ile Arg Pro Gly
                    485                 490                 495

Ala Ala Phe Glu Pro Thr Tyr Ile Tyr Arg Leu Leu Thr Val Asn Lys
                500                 505                 510

Ser Ser Leu Ser Glu Lys Gly Arg Gln Glu Asp Ala Glu Glu Tyr Leu
            515                 520                 525

Gly Phe Ile Leu Asn Gly Leu His Glu Glu Met Leu Asn Leu Lys Lys
            530                 535                 540

Leu Leu Ser Pro Ser Asn Glu Lys Leu Thr Ile Ser Asn Gly Pro Lys
545                 550                 555                 560

Asn His Ser Val Asn Glu Glu Gln Glu Glu Gln Gly Glu Gly Ser
                565                 570                 575

Glu Asp Glu Trp Glu Gln Val Gly Pro Arg Asn Lys Thr Ser Val Thr
                580                 585                 590

Arg Gln Ala Asp Phe Val Gln Thr Pro Ile Thr Gly Ile Phe Gly Gly
                595                 600                 605

His Ile Arg Ser Val Val Tyr Gln Gln Ser Ser Lys Glu Ser Ala Thr
            610                 615                 620

Leu Gln Pro Phe Phe Thr Leu Gln Leu Asp Ile Gln Ser Asp Lys Ile
625                 630                 635                 640

Arg Thr Val Gln Asp Ala Leu Glu Ser Leu Val Ala Arg Glu Ser Val
                645                 650                 655

Gln Gly Tyr Thr Thr Lys Thr Lys Gln Glu Val Glu Ile Ser Arg Arg
                660                 665                 670

Val Thr Leu Glu Lys Leu Pro Pro Val Leu Val Leu His Leu Lys Arg
            675                 680                 685

Phe Val Tyr Glu Lys Thr Gly Gly Cys Gln Lys Leu Ile Lys Asn Ile
690                 695                 700

Glu Tyr Pro Val Asp Leu Glu Ile Ser Lys Glu Leu Leu Ser Pro Gly
705                 710                 715                 720

Val Lys Asn Lys Asn Phe Lys Cys His Arg Thr Tyr Arg Leu Phe Ala
                725                 730                 735

Val Val Tyr His His Gly Asn Ser Ala Thr Gly Gly His Tyr Thr Thr
            740                 745                 750

Asp Val Phe Gln Ile Gly Leu Asn Gly Trp Leu Arg Ile Asp Asp Gln
                755                 760                 765

Thr Val Lys Val Ile Asn Gln Tyr Gln Val Val Lys Pro Thr Ala Glu
            770                 775                 780

Arg Thr Ala Tyr Leu Leu Tyr Tyr Arg Arg Val Asp Leu Leu
785                 790                 795

<210> SEQ ID NO 5
<211> LENGTH: 2297
<212> TYPE: DNA
<213> ORGANISM: Homo sapiens

<400> SEQUENCE: 5
ctccccgcgc cccgcggcgc gcggccagtg cgcaggcgcg gcggccgatg cgagtgtgta      60
tgtgcgggcg agaagatggc ggcggcgggg gaagcagcgt gagcagccgg aggatcgcgg     120
agtcccaatg aaacgggcag ccatggccct ccacagcccg cagtatattt ttggagattt     180
tagccctgat gaattcaatc aattctttgt gactcctcga tcttcagttg agagttgctg     240
gagaatgtaa ccctaatcca taaaccagtg tcgttgcaac cccgtgggct gatcaataaa     300
gggaactggt gctacattaa tgctacactg caggcattgg ttgcttgccc gccgatgtac     360
```

```
cacctgatga agttcattcc tctgtattcc aaagtgcaaa ggccttgtac gtcaacaccc     420
atgatagaca gctttgttcg gctaatgaat gagttcacta atatgccagt acctccaaaa     480
ccccgacaag ctcttggaga taaaatcgtg agggatattc gccctggagc tgcctttgag     540
cccacatata tttacagact cctgacagtt aacaagtcaa gcctgtctga aagggtcga      600 caagaagatg ctgaggaata cttaggcttc attctaaatg gacttcatga ggaaatgttg     660
aacctaaaga agcttctctc accaagtaat gaaaaactta cgatttccaa cggccccaaa     720
aaccactcgg tcaatgaaga agagcaggaa gaacaaggtg aaggaagcga ggatgaatgg     780
gaacaagtgg gccccccggaa caagacttcc gtcacccgcc aggcggattt tgttcagact    840
ccaatcaccg gcattttgg tggacacatc aggtctgtgg tttaccagca gagttcaaaa      900
gaatctgcca ctttgcagcc attttcacg ttgcagttgg atatccagtc agacaagata      960
cgcacagtcc aggatgcact ggagagcttg gtggcaagag aatctgtcca aggttatacc    1020
acaaaaacca acaagaggt tgagataagt cgaagagtga ctctggaaaa actccctcct     1080
gtcctcgtgc tgcacctgaa acgattcgtt tatgagaaga ctggtgggtg ccagaagctt    1140
atcaaaaata ttgaatatcc tgtggacttg gaaattagta agaaactgct ttctccaggg    1200
gttaaaaata agaattttaa atgccaccga acctatcggc tctttgcagt ggtctaccat    1260
cacggcaaca gtgcgacggg cggccattac actacagacg tcttccagat cggtctgaat    1320
ggctggctgc gcatcgatga ccagacagtc aaggtgatca accagtacca ggtggtgaaa    1380
ccaactgctg aacgcacagc ctacctcctg tattaccgcc gagtggacct gctgtaaacc    1440
ctgtgtgcgc tgtgtgtgcg cccagtgccc gcttcgtagg acaccacctc acactcactt    1500
cccgcctctc tttagtggct ctttagagag aaactctttc tccctttgca aaaatgggct    1560
agaatgaaaa ggagatgcct tggggttcgt gcacaacaca gcttctgttg actctaactt    1620
ccaaatcaaa atcatttggt tgaaacagac tgttgcttga tttagaaaaa tacacaaaaa    1680
cccatatttc tgaaataatg ctgattcctg agataagaaa gtggatttga tccccagtct    1740
cattgcttag tagaataaat cctgcaccag caacaacact tgtaaatttg tgaaaatgaa    1800
ttttatcttt ccttaaaaaa gaatttttt aatccatcac acttttcttc cctacccttt      1860 agttttgat aaatgataaa aatgagccag ttatcaaaga agaactagtt cttacttcaa      1920 aagaaaata aacataaaaa ataagttgct ggttcctaac aggaaaaatt ttaataattg      1980
tactgagaga aactgcttac gtacacattg cagatcaaat atttggagtt aaaatgttag    2040
tctacataga tgggtgattg taactttatt gccattaaaa gatttcaaat tgcattcatg    2100
cttctgtgta cacataatga aaaatgggca aataatgaag atctctcctt cagtctgctc    2160
tgtttaattc tgctgtctgc tcttctctaa tgctgcgtcc ctaattgtac acagtttagt    2220
gatatctagg agtataaagt tgtcgcccat caataaaaat cacaaagttg gtttaaaaaa    2280
aaaaaaaaaa aaaaaaa                                                   2297

<210> SEQ ID NO 6
<211> LENGTH: 3136
<212> TYPE: DNA
<213> ORGANISM: Homo sapiens

<400> SEQUENCE: 6
ctccccgcgc cccgcggcgc gcggccagtg cgcaggcgcg gcggccgatg cgagtgtgta     60
tgtgcgggcg agaagatggc ggcggcgggg gaagcagcgt gagcagccgg aggatcgcgg    120
```

```
agtcccaatg aaacgggcag ccatggccct ccacagcccg cagtatattt ttggagattt      180
tagccctgat gaattcaatc aattctttgt gactcctcga tcttcagttg aggacaagaa      240
tatcagagaa ttgagtttgg tgtcgatgaa gtcattgaac ccagtgacac tttgccgaga      300 accccccagct acagtatttc aagcacactg aaccctcagg cccctgaatt tattctcggt     360
tgtacagctt ccaaaataac ccctgatggt atcactaaag aagcaagcta tggctccatc      420
gactgccagt acccaggctc tgccctcgct ttggatggaa gttctaatgt ggaggcggaa      480
gttttggaaa atgatggtgt ctcaggtggt cttggacaaa gggagcgtaa aaagaagaaa      540
aagcggccac ctggatatta cagctatttg aaagatggtg gcgatgatag tatctccaca      600
gaagccctgg tcaatggcca tgccaattca gcagtcccga acagtgtcag tgcagaggat      660
gcagaattta tgggtgacat gccccgtca gttacgccca ggacttgtaa cagcccccag       720
aactccacag actctgtcag tgacattgtg cctgacagtc cttccccgg agcactcggc       780 agtgacacca ggactgcagg gcagccagag gggggcccg gggctgattt tggtcagtcc       840
tgcttccctg cagaggctgg cagagacacc ctgtcaagga cagctgggc tcagccctgc       900 gttggtaccg atactactga aaaccttgga gttgctaatg gacaaatact gaatcctcg       960 ggtgagggca cagctaccaa cgggggtggag ttgcacacca cggaaagcat agacttggac     1020
ccaaccaaac ccgagagtgc atcacctcct gctgacggca cgggctctgc atcaggcacc     1080
cttcctgtca gccagcccaa gtcctgggcc agcctctttc atgattctaa gccctcttcc     1140
tcctcgccgg tggcctatgt ggaaactaag tattcccctc ccgccatatc tcccctggtt     1200
tctgaaaagc aggttgaagt caaagaaggg cttgttccgg tttcagagga tcctgtagcc     1260
ataaagattg cagtgttcgg ctaatgaatg agttcactaa tatgccagta cctccaaaac     1320
cccgacaagc tcttggagat aaaatcgtga gggatattcg ccctggagct gcctttgagc     1380
ccacatatat ttacagactc ctgacagtta acaagtcaag cctgtctgaa aagggtcgac     1440
aagaagatgc tgaggaatac ttaggcttca ttctaaatgg acttcatgag gaaatgttga     1500
acctaaagaa gcttctctca ccaagtaatg aaaaacttac gatttccaac ggccccaaaa     1560
accactcggt caatgaagaa gagcaggaag aacaaggtga aggaagcgag gatgaatggg     1620
aacaagtggg ccccggaac aagacttccg tcacccgcca ggcggatttt gttcagactc       1680
caatcaccgg cattttggt ggacacatca ggtctgtggt ttaccagcag agttcaaaag       1740
aatctgccac tttgcagcca ttttcacgt tgcagttgga tatccagtca gacaagatac       1800
gcacagtcca ggatgcactg gagagcttgg tggcaagaga atctgtccaa ggttataccc      1860
caaaaaccaa acaagaggtt gagataagtc gaagagtgac tctggaaaaa ctccctcctg     1920
tcctcgtgct gcacctgaaa cgattcgttt atgagaagac tggtgggtgc cagaagctta     1980
tcaaaaatat tgaatatcct gtggacttgg aaattagtaa agaactgctt tctccagggg     2040
ttaaaaataa gaattttaaa tgccaccgaa cctatcggct cttttgcagtg gtctaccatc     2100 acggcaacag tgcgacgggc ggccattaca ctacagacgt cttccagatc ggtctgaatg     2160
gctggctgcg catcgatgac cagacagtca aggtgatcaa ccagtaccag gtggtgaaac     2220
caactgctga acgcacagcc tacctcctgt attaccgccg agtggacctg ctgtaaaccc     2280
tgtgtgcgct gtgtgtgcgc ccagtgcccg cttcgtagga caccacctca cactcacttc     2340
ccgcctctct ttagtggctc tttagagaga aactctttct cccttgcaa aaatgggcta     2400 gaatgaaaag gagatgcctt ggggttcgtg cacaacacag cttctgttga ctctaacttc     2460
caaatcaaaa tcatttggtt gaaacagact gttgcttgat tttagaaaat acacaaaaac     2520
```

```
ccatatttct gaaataatgc tgattcctga gataagaaag tggatttgat ccccagtctc    2580
attgcttagt agaataaatc ctgcaccagc aacaacactt gtaaatttgt gaaaatgaat    2640
tttatctttc cttaaaaaag aaatttttta atccatcaca cttttcttcc ctacccttta    2700
gtttttgata aatgataaaa atgagccagt tatcaaagaa gaactagttc ttacttcaaa    2760
agaaaaataa acataaaaaa taagttgctg gttcctaaca ggaaaaattt taataattgt    2820
actgagagaa actgcttacg tacacattgc agatcaaata tttggagtta aaatgttagt    2880
ctacatagat gggtgattgt aactttattg ccattaaaag atttcaaatt gcattcatgc    2940
ttctgtgtac acataatgaa aaatgggcaa ataatgaaga tctctccttc agtctgctct    3000
gtttaattct gctgtctgct cttctctaat gctgcgtccc taattgtaca cagtttagtg    3060
atatctagga gtataaagtt gtcgcccatc aataaaaatc acaagttggg tttaaaaaaa    3120
aaaaaaaaaa aaaaaa                                                    3136

<210> SEQ ID NO 7
<211> LENGTH: 3848
<212> TYPE: DNA
<213> ORGANISM: Homo sapiens

<400> SEQUENCE: 7
acctgcagcg cgaggcgcgc cgctccaggc ggcatcgcag ggctgggccg gcgcggcctg      60
gggaccccgg gctccggagg ccatgccggc gttggcgcgc gacggcggcc agctgccgct     120
gctcgttgtt ttttctgcaa tgatatttgg gactattaca aatcaagatc tgcctgtgat     180
caagtgtgtt ttaatcaatc ataagaacaa tgattcatca gtggggaagt catcatcata     240
tcccatggta tcagaatccc cggaagacct cgggtgtgcg ttgagacccc agagctcagg     300
gacagtgtac gaagctgccg ctgtggaagt ggatgtatct gcttccatca cactgcaagt     360
gctggtcgac gccccaggga acatttcctg tctctgggtc tttaagcaca gctccctgaa     420
ttgccagcca cattttgatt tacaaaacag aggagttgtt tccatggtca tttttgaaaat     480 gacagaaacc caagctggag aatacctact ttttattcag agtgaagcta ccaattacac     540
aatattgttt acagtgagta taagaaatac cctgctttac acattaagaa gaccttactt     600
tagaaaaatg gaaaaccagg acgccctggt ctgcatatct gagagcgttc cagagccgat     660
cgtggaatgg gtgctttgcg attcacaggg ggaaagctgt aaagaagaaa gtccagctgt     720
tgttaaaaag gaggaaaaag tgcttcatga attatttggg acggacataa ggtgctgtgc     780
cagaaatgaa ctgggcaggg aatgcaccag gctgttcaca atagatctaa atcaaactcc     840
tcagaccaca ttgccacaat tatttcttaa agtagggaa cccttatgga taaggtgcaa     900
agctgttcat gtgaaccatg gattcgggct cacctgggaa ttagaaaaca agcactcga     960 ggagggcaac tactttgaga tgagtaccta ttcaacaaac agaactatga tacggattct    1020
gtttgctttt gtatcatcag tggcaagaaa cgacaccgga tactacactt gttcctcttc    1080
aaagcatccc agtcaatcag ctttggttac catcgtagaa aagggattta taaatgctac    1140
caattcaagt gaagattatg aaattgacca atatgaagag ttttgttttt ctgtcaggtt    1200
taaagcctac ccacaaatca gatgtacgtg gaccttctct cgaaaatcat ttccttgtga    1260
gcaaaagggt cttgataacg gatacagcat atccaagttt tgcaatcata agcaccagcc    1320
aggagaatat atattccatg cagaaaatga tgatgcccaa tttaccaaaa tgttcacgct    1380
gaatataaga aggaaacctc aagtgctcgc agaagcatcg gcaagtcagg cgtcctgttt    1440
```

```
ctcggatgga tacccattac catcttggac ctggaagaag tgttcagaca agtctcccaa    1500
ctgcacagaa gagatcacag aaggagtctg aatagaaag gctaacagaa aagtgtttgg     1560
acagtgggtg tcgagcagta ctctaaacat gagtgaagcc ataaaagggt tcctggtcaa    1620
gtgctgtgca tacaattccc ttggcacatc ttgtgagacg atccttttaa actctccagg    1680
ccccttccct ttcatccaag acaacatctc attctatgca acaattggtg tttgtctcct    1740
cttcattgtc gttttaaccc tgctaatttg tcacaagtac aaaaagcaat ttaggtatga    1800
aagccagcta cagatggtac aggtgaccgg ctcctcagat aatgagtact tctacgttga    1860
tttcagagaa tatgaatatg atctcaaatg ggagtttcca agagaaaatt tagagtttgg    1920
gaaggtacta ggatcaggtg cttttggaaa agtgatgaac gcaacagctt atggaattag    1980
caaaacagga gtctcaatcc aggttgccgt caaaatgctg aaagaaaaag cagacagctc    2040
tgaaagagag gcactcatgt cagaactcaa gatgatgacc cagctgggaa gccacgagaa    2100
tattgtgaac ctgctggggg cgtgcacact gtcaggacca atttacttga ttttgaata    2160
ctgttgctat ggtgatcttc tcaactatct aagaagtaaa agagaaaaat ttcacaggac    2220
ttggacagag attttcaagg aacacaattt cagtttttac cccactttcc aatcacatcc    2280
aaattccagc atgcctggtt caagagaagt tcagatacac ccggactcgg atcaaatctc    2340
agggcttcat gggaattcat ttcactctga agatgaaatt gaatatgaaa accaaaaaag    2400
gctggaagaa gaggaggact tgaatgtgct tacatttgaa gatcttcttt gctttgcata    2460
tcaagttgcc aaaggaatgg aatttctgga atttaagtcg tgtgttcaca gagacctggc    2520
cgccaggaac gtgcttgtca cccacgggaa agtggtgaag atatgtgact ttggattggc    2580
tcgagatatc atgagtgatt ccaactatgt tgtcagggc aatgcccgtc tgcctgtaaa    2640
atggatggcc cccgaaagcc tgtttgaagg catctacacc attaagagtg atgtctggtc    2700
atatggaata ttactgtggg aaatcttctc acttggtgtg aatccttacc ctggcattcc    2760
ggttgatgct aacttctaca aactgattca aatggattt aaaatggatc agccatttta    2820
tgctacagaa gaaatataca ttataatgca atcctgctgg gcttttgact caaggaaacg    2880
gccatccttc cctaatttga cttcgttttt aggatgtcag ctggcagatg cagaagaagc    2940
gatgtatcag aatgtggatg gccgtgtttc ggaatgtcct cacacctacc aaaacaggcg    3000
acctttcagc agagagatgg atttggggct actctctccg caggctcagg tcgaagattc    3060
gtagaggaac aatttagttt taaggacttc atccctccac ctatccctaa caggctgtag    3120
attaccaaaa caagattaat ttcatcacta aaagaaaatc tattatcaac tgctgcttca    3180
ccagactttt ctctagaagc tgtctgcgtt tactcttgtt ttcaaaggga cttttgtaaa    3240
atcaaatcat cctgtcacaa ggcaggagga gctgataatg aactttattg gagcattgat    3300
ctgcatccaa ggccttctca ggctggcttg agtgaattgt gtacctgaag tacagtatat    3360
tcttgtaaat acataaaaca aaagcatttt gctaaggaga agctaatatg attttttaag    3420
tctatgtttt aaaataatat gtaaattttt cagctattta gtgatatatt ttatgggtgg    3480
gaataaaatt tctactacag aattgcccat tattgaatta tttacatggt ataattaggg    3540
caagtcttaa ctggagttca cgaacccct gaaattgtgc acccatagcc acctacacat    3600
tccttccaga gcacgtgtgc ttttacccca agatacaagg aatgtgtagg cagctatggt    3660
tgtcacagcc taagatttct gcaacaacag gggttgtatt ggggaagtt tataatgaat    3720
aggtgttcta ccataaagag taatacatca cctagacact ttggcggcct tcccagactc    3780
agggccagtc agaagtaaca tggaggatta gtattttcaa taaagttact cttgtcccca    3840
```

-continued

```
caaaaaaa                                                        3848

<210> SEQ ID NO 8
<211> LENGTH: 993
<212> TYPE: PRT
<213> ORGANISM: Homo sapiens

<400> SEQUENCE: 8

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365
```

```
Phe Ser Val Arg Phe Lys Ala Tyr Pro Gln Ile Arg Cys Thr Trp Thr
    370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
        435                 440                 445
Gln Ala Ser Cys Phe Ser Asp Gly Tyr Pro Leu Pro Ser Trp Thr Trp
    450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
            500                 505                 510
Lys Cys Cys Ala Tyr Asn Ser Leu Gly Thr Ser Cys Glu Thr Ile Leu
        515                 520                 525
Leu Asn Ser Pro Gly Pro Phe Pro Phe Ile Gln Asp Asn Ile Ser Phe
    530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
                565                 570                 575
Gln Met Val Gln Val Thr Gly Ser Ser Asp Asn Glu Tyr Phe Tyr Val
            580                 585                 590
Asp Phe Arg Glu Tyr Glu Tyr Asp Leu Lys Trp Glu Phe Pro Arg Glu
        595                 600                 605
Asn Leu Glu Phe Gly Lys Val Leu Gly Ser Gly Ala Phe Gly Lys Val
    610                 615                 620
Met Asn Ala Thr Ala Tyr Gly Ile Ser Lys Thr Gly Val Ser Ile Gln
625                 630                 635                 640
Val Ala Val Lys Met Leu Lys Glu Lys Ala Asp Ser Ser Glu Arg Glu
                645                 650                 655
Ala Leu Met Ser Glu Leu Lys Met Met Thr Gln Leu Gly Ser His Glu
            660                 665                 670
Asn Ile Val Asn Leu Leu Gly Ala Cys Thr Leu Ser Gly Pro Ile Tyr
        675                 680                 685
Leu Ile Phe Glu Tyr Cys Cys Tyr Gly Asp Leu Leu Asn Tyr Leu Arg
    690                 695                 700
Ser Lys Arg Glu Lys Phe His Arg Thr Trp Thr Glu Ile Phe Lys Glu
705                 710                 715                 720
His Asn Phe Ser Phe Tyr Pro Thr Phe Gln Ser His Pro Asn Ser Ser
                725                 730                 735
Met Pro Gly Ser Arg Glu Val Gln Ile His Pro Asp Ser Asp Gln Ile
            740                 745                 750
Ser Gly Leu His Gly Asn Ser Phe His Ser Glu Asp Glu Ile Glu Tyr
        755                 760                 765
Glu Asn Gln Lys Arg Leu Glu Glu Glu Glu Asp Leu Asn Val Leu Thr
    770                 775                 780
```

```
Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
            805                 810                 815

Val Leu Val Thr His Gly Lys Val Lys Ile Cys Asp Phe Gly Leu
        820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
            885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
            915                 920                 925

Asp Ser Arg Lys Arg Pro Ser Phe Pro Asn Leu Thr Ser Phe Leu Gly
930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 9
<211> LENGTH: 3980
<212> TYPE: DNA
<213> ORGANISM: Homo sapiens

<400> SEQUENCE: 9
acctgcagcg cgaggcgcgc cgctccaggc ggcatcgcag ggctgggccg gcgcggcctg      60
gggaccccgg gctccggagg ccatgccggc gttggcgcgc gacggcggcc agctgccgct     120
gctcgttgtt ttttctgcaa tgatatttgg gactattaca aatcaagatc tgcctgtgat     180
caagtgtgtt ttaatcaatc ataagaacaa tgattcatca gtggggaagt catcatcata     240
tcccatggta tcagaatccc cggaagacct cgggtgtgcg ttgagacccc agagctcagg     300
gacagtgtac gaagctgccg ctgtggaagt ggatgtatct gcttccatca cactgcaagt     360
gctggtcgac gccccaggga acatttcctg tctctgggtc tttaagcaca gctcccctgaa   420 ttgccagcca cattttgatt tacaaaacag aggagttgtt tccatggtca tttttgaaaat   480 gacagaaacc caagctggag aatacctact ttttattcag agtgaagcta ccaattacac     540 aatatattgttt acagtgagta taagaaatac cctgctttac acattaagaa gaccttactt    600
tagaaaaatg gaaaaccagg acgccctggt ctgcatatct gagagcgttc cagagccgat     660
cgtggaatgg gtgctttgcg attcacaggg ggaaagctgt aaagaagaaa gtccagctgt     720
tgttaaaaag gaggaaaaag tgcttcatga attatttggg acggacataa ggtgctgtgc     780
cagaaatgaa ctgggcaggg aatgcaccag gctgttcaca atagatctaa atcaaactcc    840
tcagaccaca ttgccacaat tatttcttaa agtagggaa cccttatgga taaggtgcaa     900
```

```
agctgttcat gtgaaccatg gattcgggct cacctgggaa ttagaaaaca aagcactcga    960
ggagggcaac tactttgaga tgagtaccta ttcaacaaac agaactatga tacggattct   1020
gtttgctttt gtatcatcag tggcaagaaa cgacaccgga tactacactt gttcctcttc   1080
aaagcatccc agtcaatcag ctttggttac catcgtagaa aagggattta taaatgctac   1140
caattcaagt gaagattatg aaattgacca atatgaagag ttttgttttt ctgtcaggtt   1200
taaagcctac ccacaaatca gatgtacgtg gaccttctct cgaaaatcat ttccttgtga   1260
gcaaagggt cttgataacg gatacagcat atccaagttt tgcaatcata agcaccagcc   1320
aggagaatat atattccatg cagaaaatga tgatgcccaa tttaccaaaa tgttcacgct   1380
gaatataaga aggaaacctc aagtgctcgc agaagcatcg gcaagtcagg cgtcctgttt   1440
ctcggatgga tacccattac catcttggac ctggaagaag tgttcagaca agtctcccaa   1500
ctgcacagaa gagatcacag aaggagtctg gaatagaaag gctaacagaa aagtgtttgg   1560
acagtgggtg tcgagcagta ctctaaacat gagtgaagcc ataaaagggt tcctggtcaa   1620
gtgctgtgca tacaattccc ttggcacatc ttgtgagacg atccttttaa actctccagg   1680
cccctccct ttcatccaag acaacatctc attctatgca acaattggtg tttgtctcct   1740
cttcattgtc gttttaaccc tgctaatttg tcacaagtac aaaaagcaat ttaggtatga   1800
aagccagcta cagatggtac aggtgaccgg ctcctcagat aatgagtact tctacgttga   1860
tttcagagaa tatgaatatg atctcaaatg ggagtttcca agagaaaatt tagagtttgg   1920
gaaggtacta ggatcaggtg cttttggaaa agtgatgaac gcaacagctt atggaattag   1980
caaaacagga gtctcaatcc aggttgccgt caaaatgctg aaagaaaaag cagacagctc   2040
tgaaagagag gcactcatgt cagaactcaa gatgatgacc cagctgggaa gccacgagaa   2100
tattgtgaac ctgctggggg cgtgcacact gtcaggacca atttacttga tttttgaata   2160
ctgttgctat ggtgatcttc tcaactatct aagaagtaaa agagaaaaat ttcacaggac   2220
ttggacagag attttcaagg aacacaattt cagttttac cccactttcc aatcacatcc   2280
aaattccagt aaaagaaat gagctttaca aaggcaaact ggaaaaaaga aggatggtga   2340
aacgcttacg ggactctcgg gaagatctgt attatgtgag ggaaagtggg ctgagttcag   2400
aaaccaaaga atgagatcga tcatgcctgg ttcaagagaa gttcagatac acccggactc   2460
ggatcaaatc tcagggcttc atgggaattc atttcactct gaagatgaaa ttgaatatga   2520
aaaccaaaaa aggctggaag aagaggagga cttgaatgtg cttacatttg aagatcttct   2580
ttgctttgca tatcaagttg ccaaaggaat ggaattctg gaatttaagt cgtgtgttca   2640
cagagacctg gccgccagga acgtgcttgt cacccacggg aaagtggtga gatatgtga   2700
ctttggattg gctcgagata tcatgagtga ttccaactat gttgtcaggg gcaatgcccg   2760
tctgcctgta aaatggatgg cccccgaaag cctgtttgaa ggcatctaca ccattaagag   2820
tgatgtctgg tcatatggaa tattactgtg ggaaatcttc tcacttggtg tgaatccta   2880
ccctggcatt ccggttgatg ctaacttcta caaactgatt caaatggat ttaaaatgga   2940
tcagccattt tatgctacag aagaaatata cattataatg caatcctgct gggcttttga   3000
ctcaaggaaa cggccatcct tccctaattt gacttcgttt ttaggatgtc agctggcaga   3060
tgcagaagaa gcgatgtatc agaatgtgga tggccgtgtt tcggaatgtc ctcacaccta   3120
ccaaaacagg cgacctttca gcagagagat ggatttgggg ctactctctc gcaggctca   3180
ggtcgaagat tcgtagagga acaatttagt tttaaggact tcatccctcc acctatccct   3240
aacaggctgt agattaccaa aacaagatta atttcatcac taaaagaaaa tctattatca   3300
```

```
actgctgctt caccagactt ttctctagaa gctgtctgcg tttactcttg tttcaaagg    3360 gacttttgta aaatcaaatc atcctgtcac aaggcaggag gagctgataa tgaactttat    3420
tggagcattg atctgcatcc aaggccttct caggctggct tgagtgaatt gtgtacctga    3480
agtacagtat attcttgtaa atacataaaa caaaagcatt ttgctaagga gaagctaata    3540 tgattttta agtctatgtt ttaaaataat atgtaaattt ttcagctatt tagtgatata    3600
ttttatgggt gggaataaaa tttctactac agaattgccc attattgaat tatttacatg    3660
gtataattag ggcaagtctt aactggagtt cacgaacccc ctgaaattgt gcacccatag    3720
ccacctacac attccttcca gagcacgtgt gcttttaccc caagatacaa ggaatgtgta    3780
ggcagctatg gttgtcacag cctaagattt ctgcaacaac aggggttgta ttgggggaag    3840
tttataatga ataggtgttc taccataaag agtaatacat cacctagaca ctttggcggc    3900
cttcccagac tcagggccag tcagaagtaa catggaggat tagtattttc aataaagtta    3960
ctcttgtccc cacaaaaaaa                                                3980
```